(12) United States Patent
Jackson et al.

(10) Patent No.: US 8,246,655 B2
(45) Date of Patent: Aug. 21, 2012

(54) INTERVERTEBRAL IMPLANT DEVICES AND METHODS FOR INSERTION THEREOF

(75) Inventors: Michael R. Jackson, Hancock, MI (US); Russell M. Pietila, Hancock, MI (US); Qi-Bin Bao, Marquette, MI (US); Wade DePas, Ishpeming, MI (US); Jeffrey L. Trudeau, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 171 days.

(21) Appl. No.: 12/685,618

(22) Filed: Jan. 11, 2010

(65) Prior Publication Data

US 2010/0179595 A1    Jul. 15, 2010

Related U.S. Application Data

(60) Provisional application No. 61/143,652, filed on Jan. 9, 2009, provisional application No. 61/155,102, filed on Feb. 24, 2009.

(51) Int. Cl.
*A61B 17/70* (2006.01)

(52) U.S. Cl. .................................. 606/248; 606/249
(58) Field of Classification Search .......... 606/246–249, 606/263, 276, 277, 279, 86 A; 623/17.11–17.16
See application file for complete search history.

(56) References Cited

U.S. PATENT DOCUMENTS

| 7,879,104 | B2 * | 2/2011 | Dewey et al. | 623/17.16 |
| 2006/0271194 | A1 * | 11/2006 | Zucherman et al. | 623/17.11 |
| 2008/0183211 | A1 * | 7/2008 | Lamborne et al. | 606/249 |

* cited by examiner

*Primary Examiner* — Eduardo C Robert
*Assistant Examiner* — Christina Negrelli
(74) *Attorney, Agent, or Firm* — Fitch, Even, Tabin & Flannery, LLP

(57) ABSTRACT

Implant apparatuses are provided for being inserted between adjacent vertebral bone portions and maintaining mechanical engagement with the vertebral bone portions. The implant apparatuses are generally constructed to be inserted in an insertion orientation and pivoted between the vertebral bone portions to an implanted orientation. The implant apparatuses are further secured in the implanted orientation to maintain engagement with the adjacent vertebral bone portions.

16 Claims, 123 Drawing Sheets

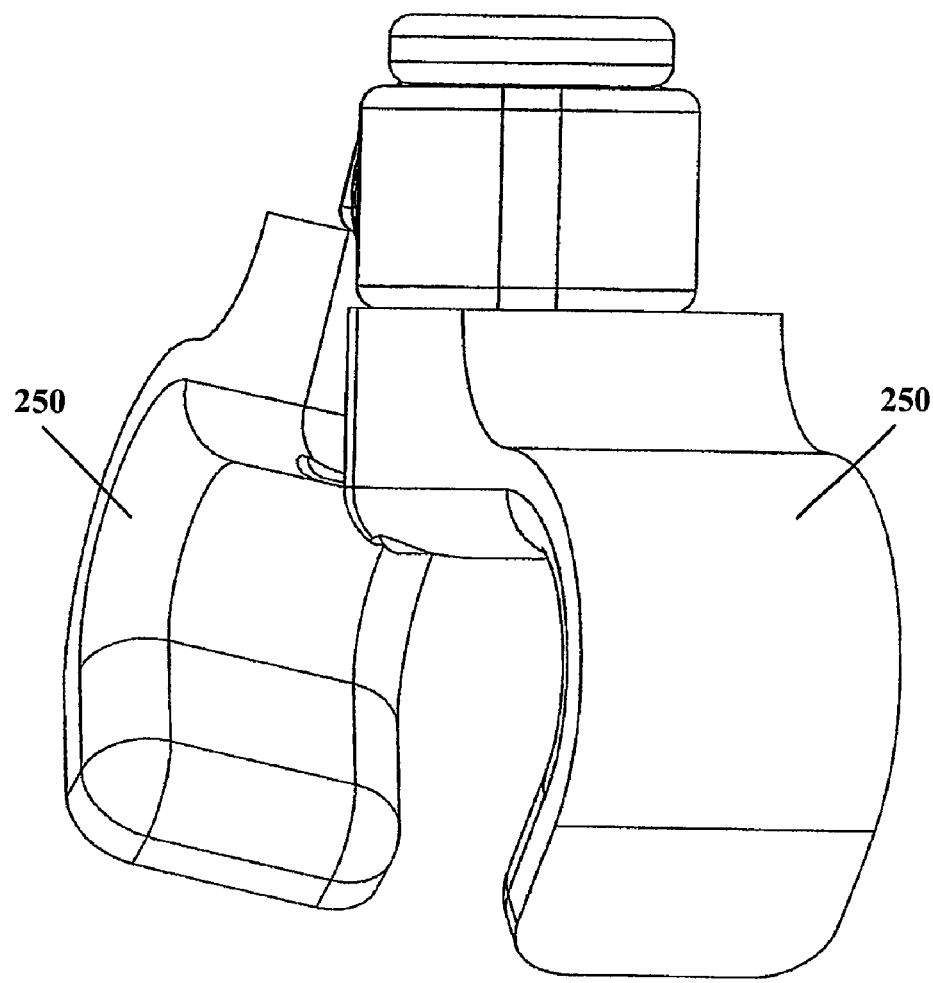
FIG. 62

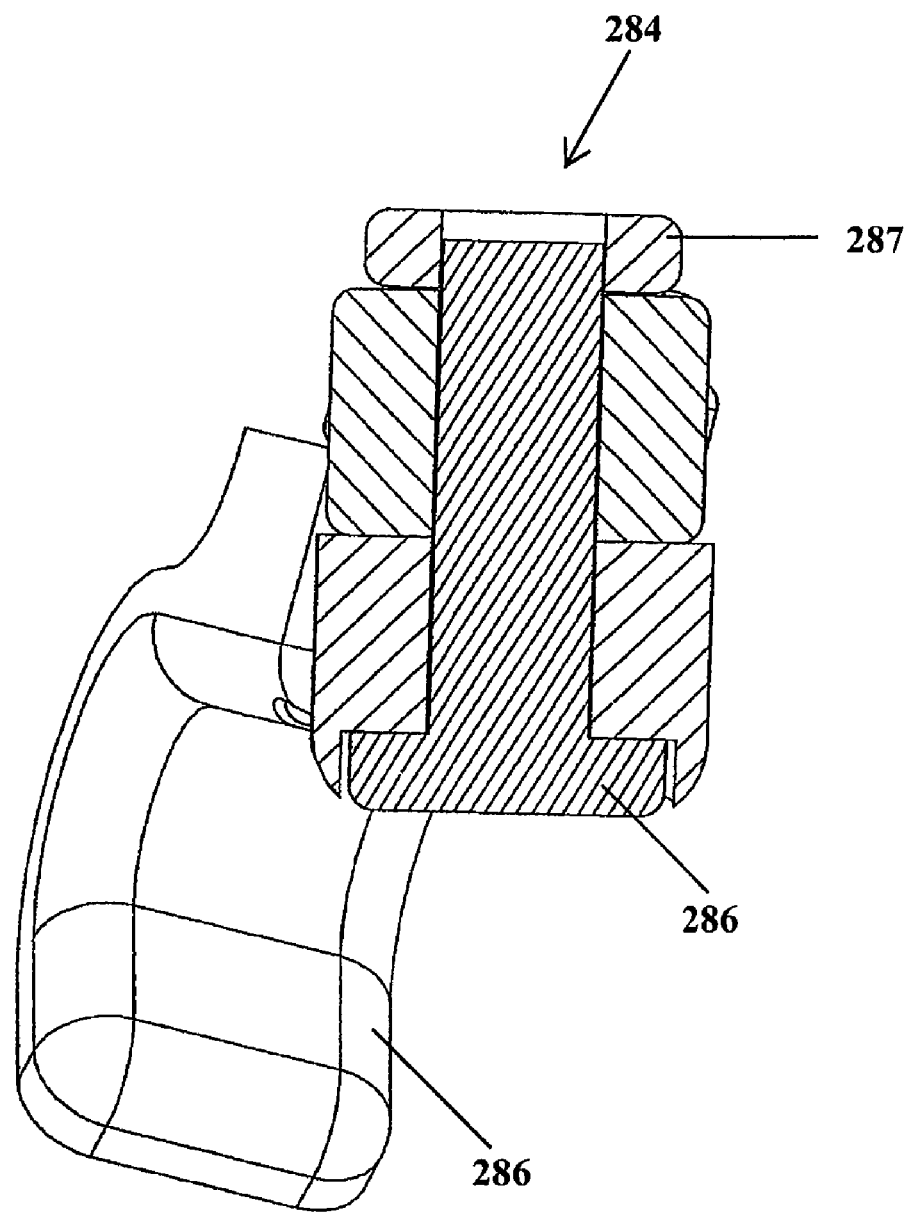
FIG. 63

38   38
322   FIG. 88

INTERVERTEBRAL IMPLANT DEVICES AND METHODS FOR INSERTION THEREOF

CROSS REFERENCE TO RELATED APPLICATIONS

This application is a non-provisional application claiming the benefit of U.S. Provisional Application No. 61/143,652 filed Jan. 9, 2009, and U.S. Provisional Application No. 61/155,102 filed Feb. 24, 2009, both of which are hereby incorporated in their entirety herein.

FIELD OF THE INVENTION

The invention relates to implant devices for implantation between adjacent vertebrae and, in particular, to implant devices positionable between spinous processes of adjacent vertebrae for both distracting and securing the adjacent vertebrae, and to methods for the implantation of such devices.

BACKGROUND OF THE INVENTION

A person may experience pain or limited mobility as a result of a variety of spinal conditions including trauma, deformity, disease, or other degenerative conditions. Existing methods of treating these conditions include surgical decompression of the affected area of the spine. One such technique employs the use of an interspinous implant device which is inserted between adjacent spinous processes to distract and maintain the desired spatial relationship of the adjacent vertebrae. In coordination with the interspinous device, a securing mechanism, such as a cable or strap, is used to further maintain the position of the spinous processes relative to the interspinous device.

There are a number of limitations of existing interspinous implant devices used in conjunction with a securing mechanism, including the inability to be inserted through minimally invasive surgical procedures and the inability to accommodate the distinct anatomical structures of the spine.

For example, U.S. Pat. No. 6,582,433 to Yun discloses a spacer which does not have a reduced profile insertion orientation, thereby requiring the spinous processes to be distracted further prior to insertion. Similarly, U.S. Patent Publication No. 2007/0233082 to Chin et al. disclose having an insertion profile larger than the desired final distraction spacing of the adjacent spinous process. Further, Chin et al. disclose the use of tools to engage the adjacent spinous processes to aid in insertion of the fixation device.

Alternatively, while some prior art implants include a reduced insertion profile they do not include a means of securing the implant device after insertion. For example, U.S. Patent Publication No. 2009/0149886 to Zentes et al. discloses an implant device which is pivotable between an insertion profile and an operable profile. To provide easier insertion of the implant between the adjacent spinous processes, the size and configuration of the tool engagement end of the implant is limited. Based on these restrictions, the implant includes an integral latch which locks the implant in place once shifted to the operable profile. However, by locking the implant automatically upon being pivoted to the operable profile, the implant cannot be easily repositioned, removed or replaced.

Accordingly, there is a need for an implant device which can be inserted with minimal trauma to the spinous processes and the surrounding tissues and can maintain the desired spatial relationship of the spinous processes after insertion.

SUMMARY OF THE INVENTION

In accordance with one aspect of the invention, an implant apparatus is provided that is configured to minimize trauma during insertion between spinous processes and securely space the adjacent spinous processes after insertion. In this regard, inserting and securing the implant apparatus reduces any pre-insertion distraction of the adjacent spinous processes and provides and maintains the predetermined spinous processes spacing.

In a preferred form, the implant apparatus includes an implant member which is pivotable between an insertion profile and an implanted profile. Additionally, the implant apparatus includes a locking mechanism to keep the implant member in the implanted orientation and in secure engagement with the adjacent vertebral bone portions.

In accordance with another aspect of the invention, an implant device is provided that allows for a plate member to be shifted along a spacer member and into engagement with adjacent spinous processes. In this regard, shifting the entire plate member allows a higher proportion of a surface of the plate member to be engaged with the spinous processes.

The configuration of the prior art implant devices, in particular pivoted connection of the "plates" for engaging a side of a spinous process, presented obstacles in securely engaging the spinous process. While the "plates" may in fact engage a side of the spinous process, the actual engagement area is limited by the location of the pivoted connection, the actual "plate" area potentially available to engage a spinous process, and the size of the predetermined seat portion relative to the size of the spinous processes to be seated. Further, by pivoting the "plates" into engagement with the spinous processes, the distal ends of the plates engage the spinous processes before the rest of the plate. As a result, a disproportionate amount of the frictional resistance to movement of the spinous processes relative to the implant device occurs at the distal ends of the "plates" instead of being distributed along the entire surface area of the "plate".

In another aspect, a method of securing adjacent spinous processes is provided. The method includes inserting an implant device between adjacent spinous processes which has been previously pivoted to an insertion orientation. After the implant device has been inserted, the implant device is pivoted to an implanted orientation. With the implant device in the implanted orientation, the implant device is secured in place to resist further pivoting of the implant device from the implanted orientation.

There are several advantages of inserting an implant device in an insertion orientation and securing the device after the device has been shifted to the implanted orientation. The first advantage is a reduction in the distraction distance of the spinous processes which must be achieved prior to insertion. As a result, movement of the spinous processes and the ligaments around the insertion site is reduced and, with reference to the ligaments, the opening therethrough for receiving the implant device is not larger than necessary. In addition, by securing the implant device after the device has been pivoted to the implanted orientation, the implant device can be pivoted from the implanted orientation so that the device can be repositioned to accommodate the spinal geometries of the implantation site without having to remove or disarm any automatically engaging securing mechanisms.

BRIEF DESCRIPTION OF THE DRAWINGS

FIG. 62 is a bottom view of the hooks and telescoping rod of FIG. 55;

FIG. 63 is a bottom sectional view of one of the hooks and the rod of the implant of FIG. 55 showing the pin and cap connecting the hook to the rod;

FIG. 119 is a right side elevational view of the implant of FIG. 113;

FIG. 120 is a left side elevational view of the implant of FIG. 113;

FIG. 121 is a bottom view of the implant of FIG. 113 showing the hook connecting member connected to the spanning member; and FIG. 122 is a bottom sectional side view of the implant of FIG. 113 showing the set screw for securing the hook connecting member in a given orientation relative to the spanning member.

DETAILED DESCRIPTION OF THE PREFERRED EMBODIMENTS

Figure 1:
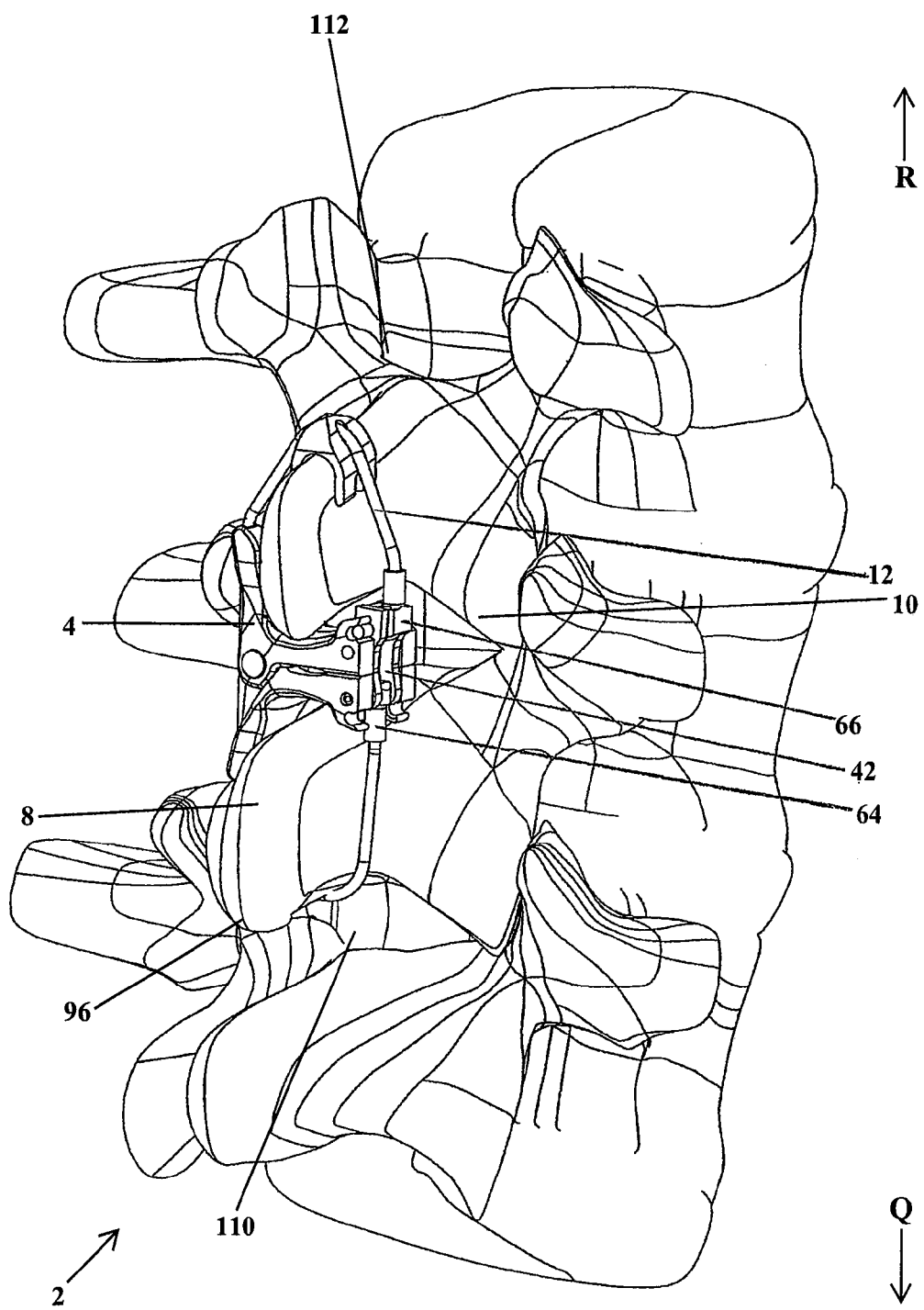
FIG. 1 is a posterior aspect prospective view of an implant in accordance with one aspect of the invention showing an interspinous insertion member positioned between adjacent spinous processes and a cable extending about the spinous processes and connected to the insertion member.

In FIG. 1, an implant apparatus 2 is shown having an interspinous spacing member 4 positioned between adjacent vertebral bodies 6 and 8 and secured or locked in place by a locking mechanism 10. The locking mechanism 10 is configured to secure engagement between the implant spacer 4 and the adjacent vertebral bone portions 6 and 8. As shown in FIG. 1 the locking mechanism 10 includes a flexible member 12 secured to and extending from the implant spacer 4, about the adjacent vertebral bone portions 6 and 8, and secured again to the implant spacer 4.

As shown in FIGS. 1-32, the interspinous spacing member includes an upper implant engaging member 14 for being positioned adjacent to and engaging an upper vertebral bone portion 6. Further, the spacing member 4 includes a lower implant engaging member 16 for being positioned adjacent to and engaging a lower vertebral bone portion 8. An exemplary interspinous spacing member 4 is disclosed in U.S. patent application Ser. No. 12/026,895, which is hereby incorporated in its entirety herein. Further, the upper and lower implant engaging members 14 and 16 can be identical to one another.

As shown in FIGS. 3, 5, 8 and 9, the spacer member 4 includes a pivot connection 18 between the upper and lower implant members 14 and 16. The pivot connection 18, as shown, allows the upper and lower implant members 14 and 16 to be pivoted between an insertion orientation 20 and an implanted orientation 22. In the insertion orientation 20, wherein leading arm portions 24 of the implant members 14 and 16 are pivoted toward one another, the leading arms portions 24 are inserted between the adjacent spinous processes 6 and 8 a specified distance, such as when the implant member seats 26 or tool engagement arms 28 and 30 engage a side 32 of the vertebral bone members 6 and 8. As such, the leading arms 24 are configured to ease their insertion between the bone portions 6 and 8 while minimizing or eliminating the need for preinsertion distraction of the bone portions 6 and 8. In particular, the leading arms 24 have a reduced insertion profile 32 and are tapered 34 at the leading edge 36 thereof to ease insertion.

Figure 5:
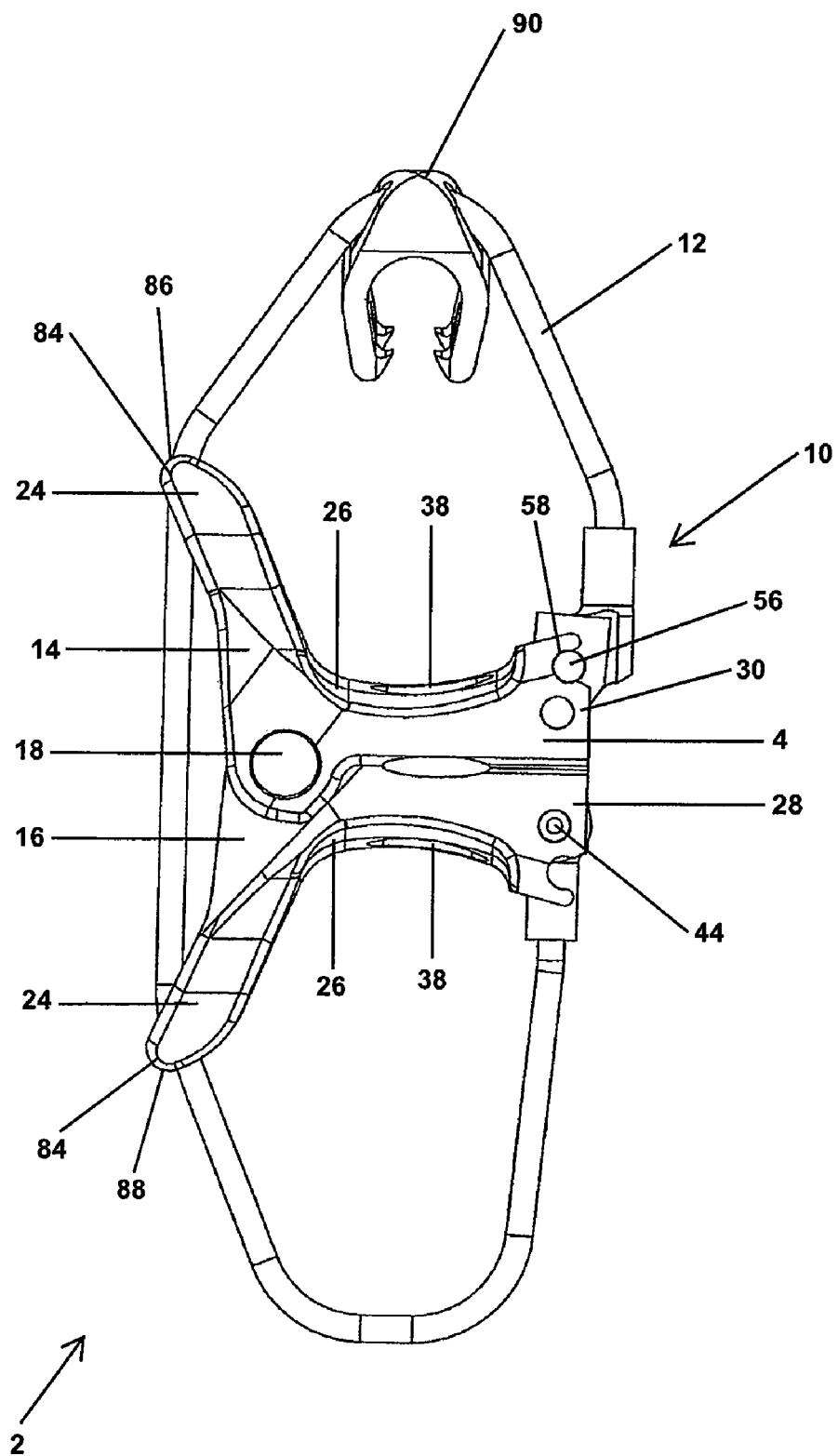
FIG. 5 is a front elevational view of the implant of FIG. 1.
Figure 6:
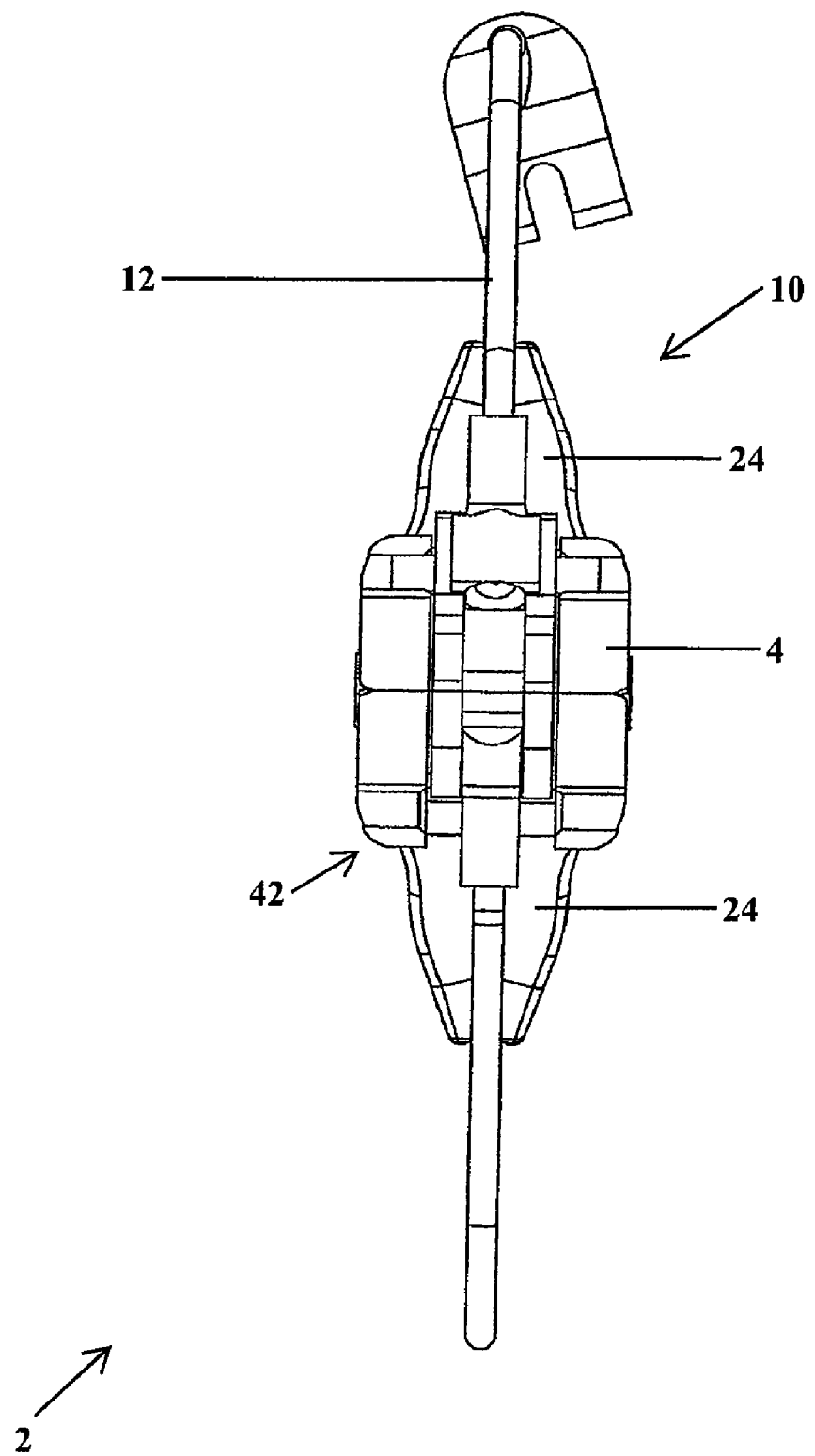
FIG. 6 is a right side elevational view of the implant of FIG. 1.
Figure 7:
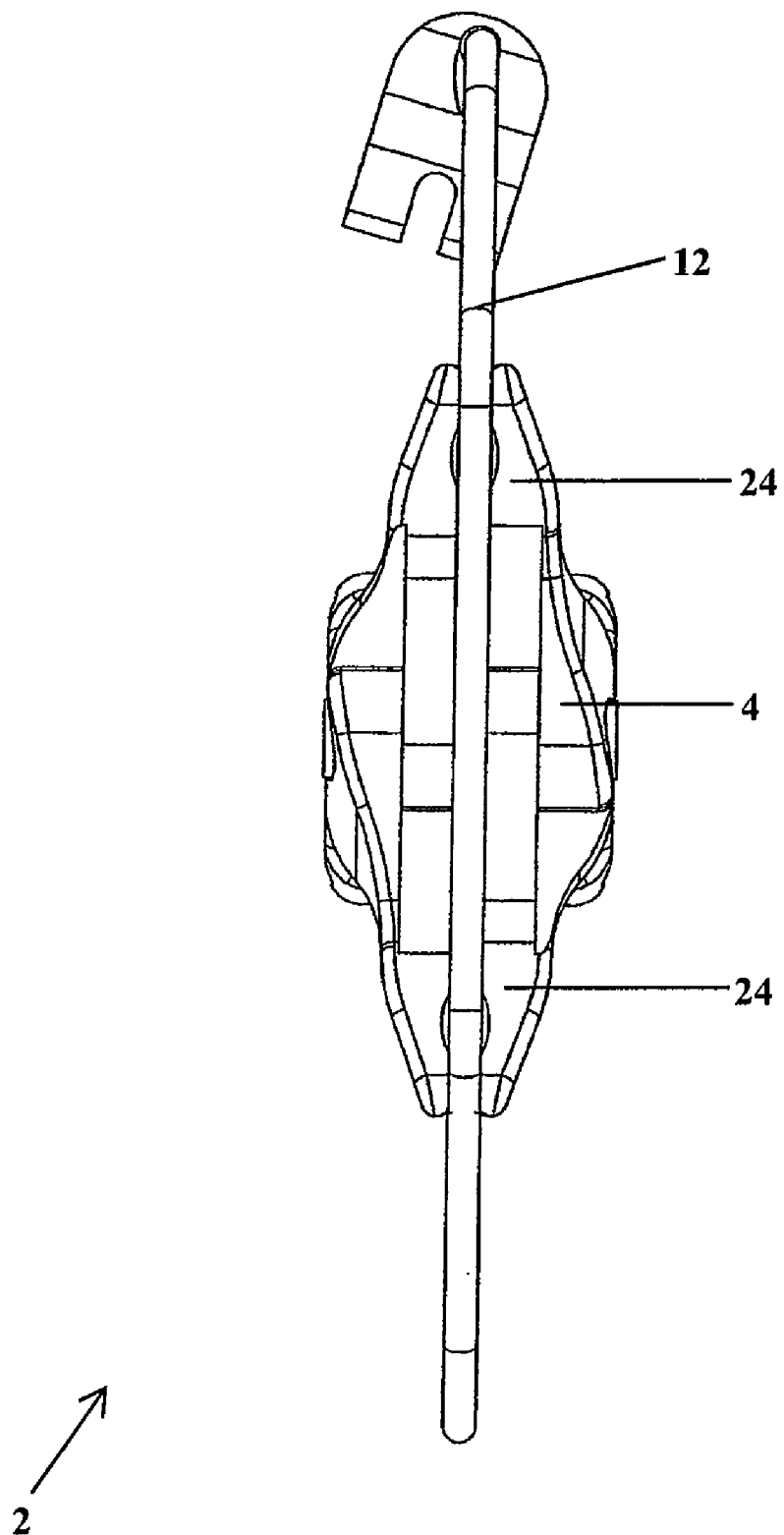
FIG. 7 is a left side elevational view of the implant of FIG. 1.
Figure 8:
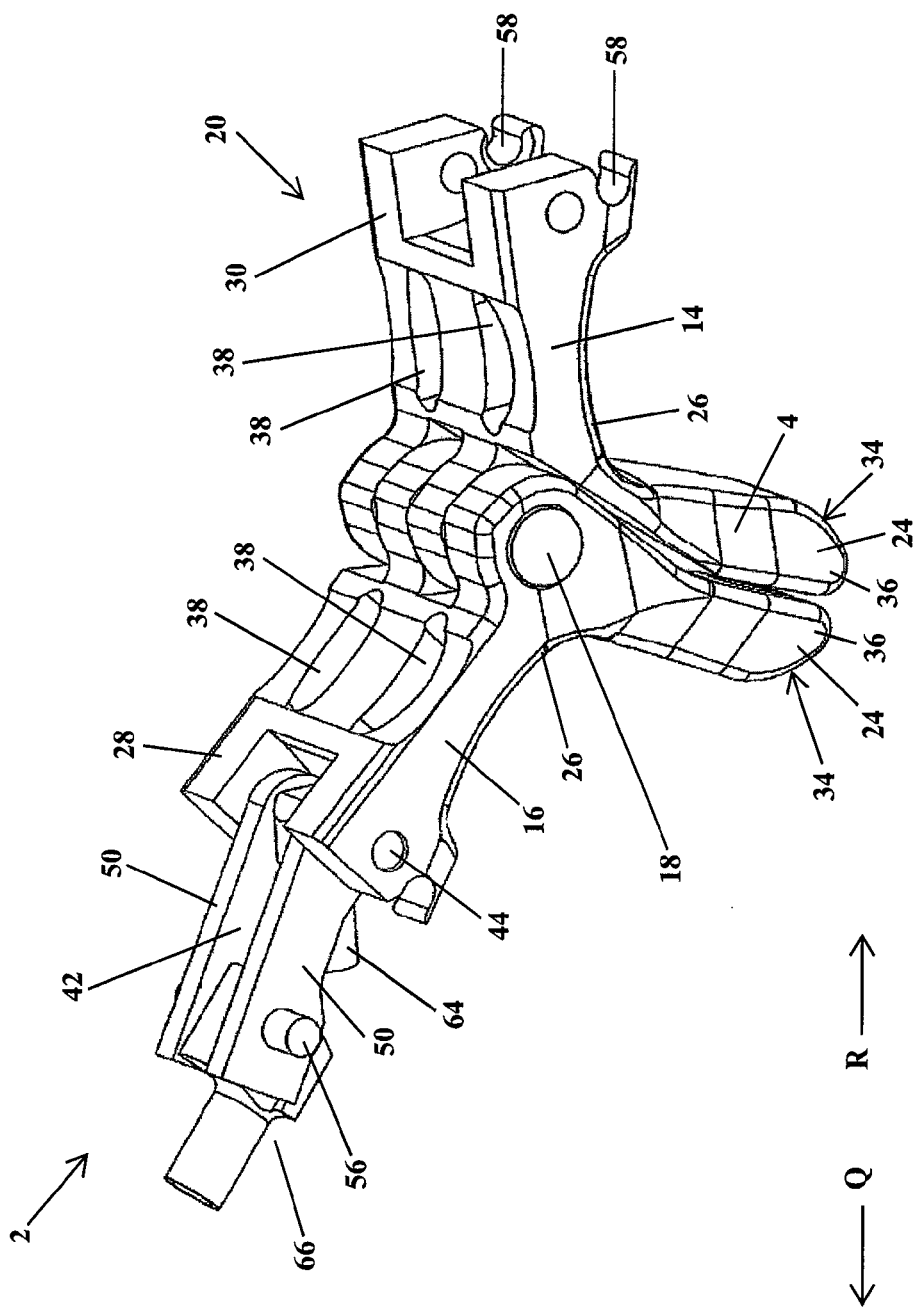
FIG. 8 is a perspective view of the interspinous insertion member of FIG. 1 showing the insertion member in the insertion orientation.
Figure 9:
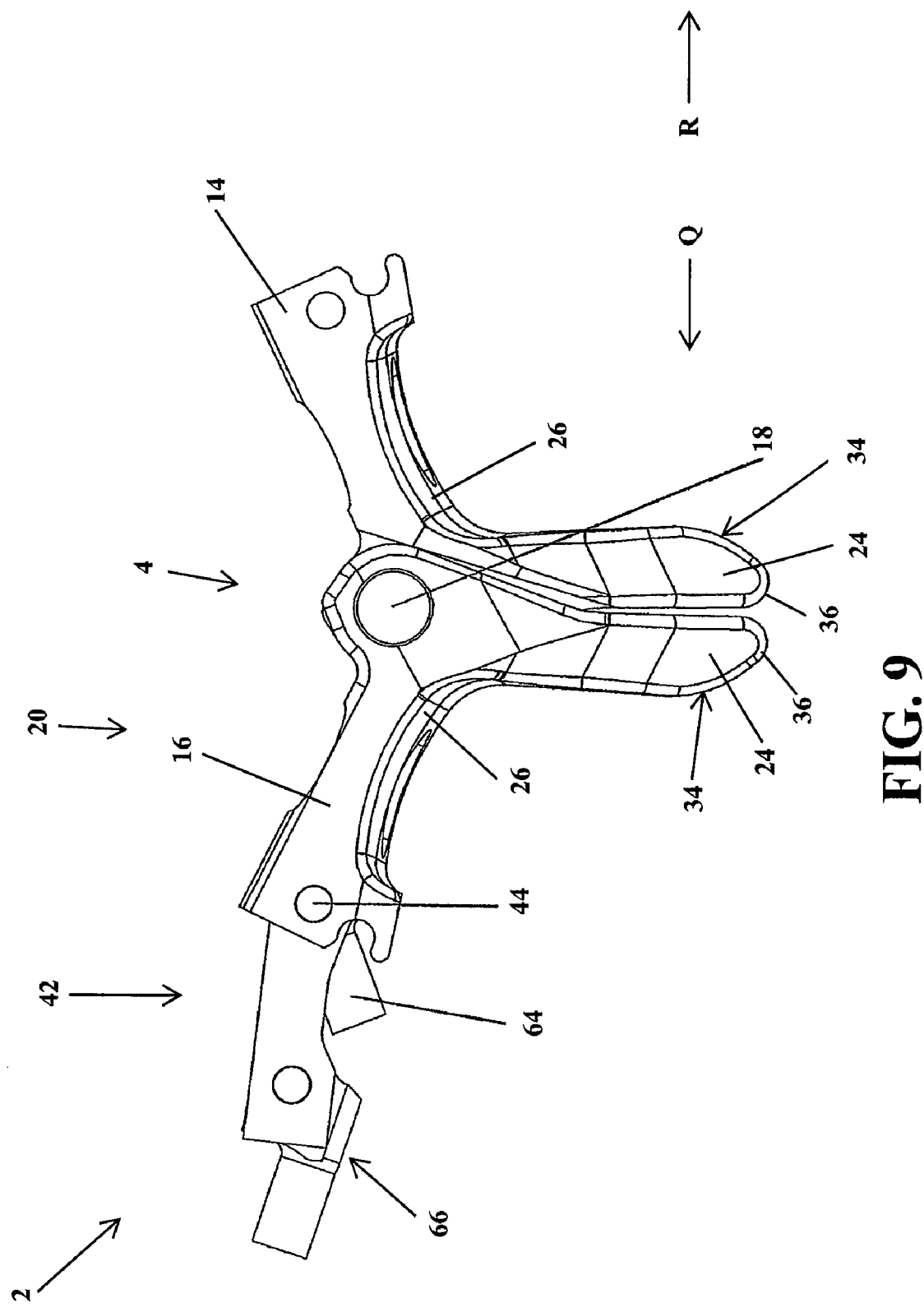
FIG. 9 is a front elevational view of the interspinous insertion member of FIG. 1 showing the insertion member in the insertion orientation.
Figure 10:
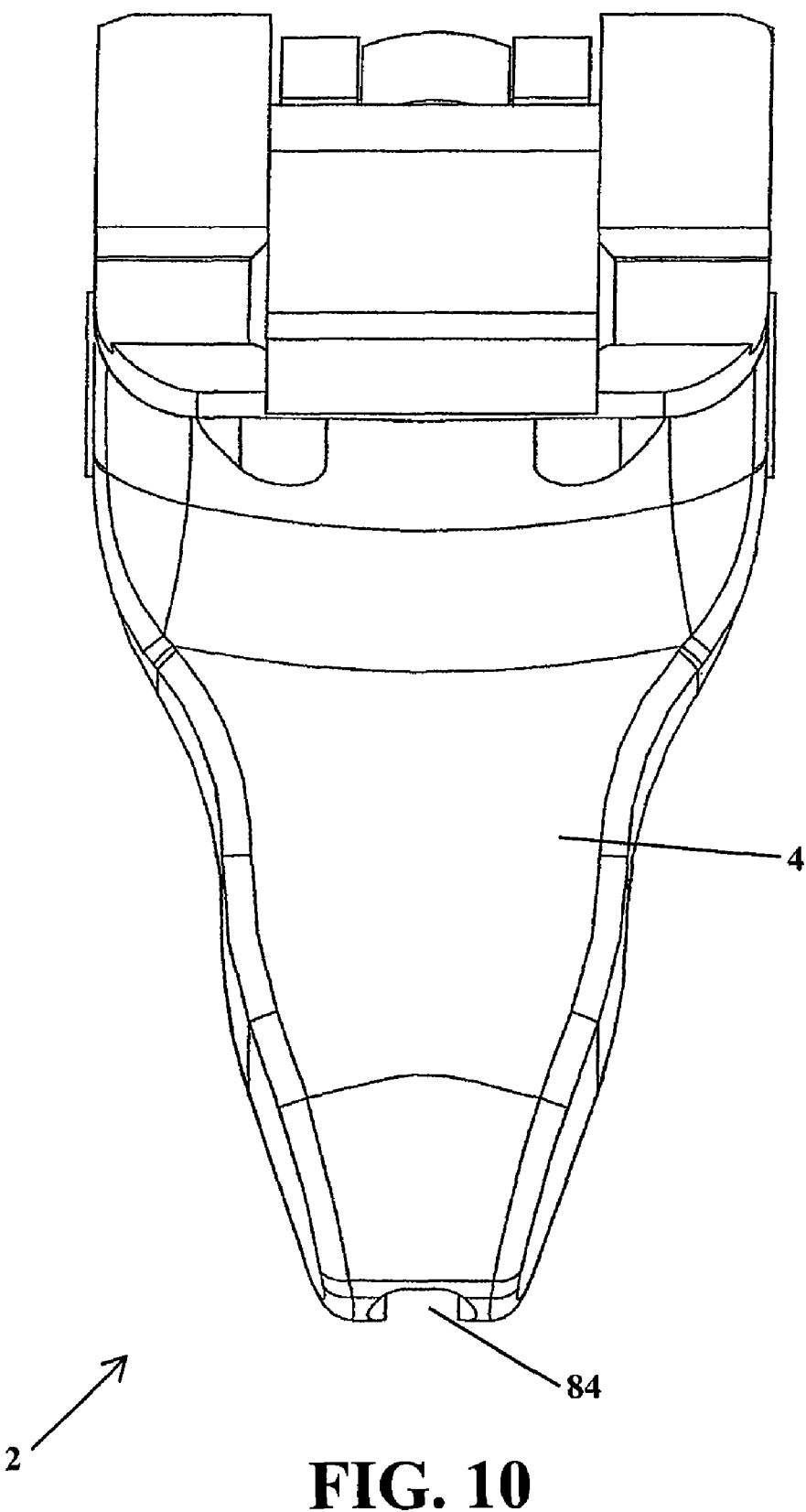
FIG. 10 is a right side view of the interspinous insertion member of FIG. 1 showing the insertion member in the insertion orientation.
Figure 11:
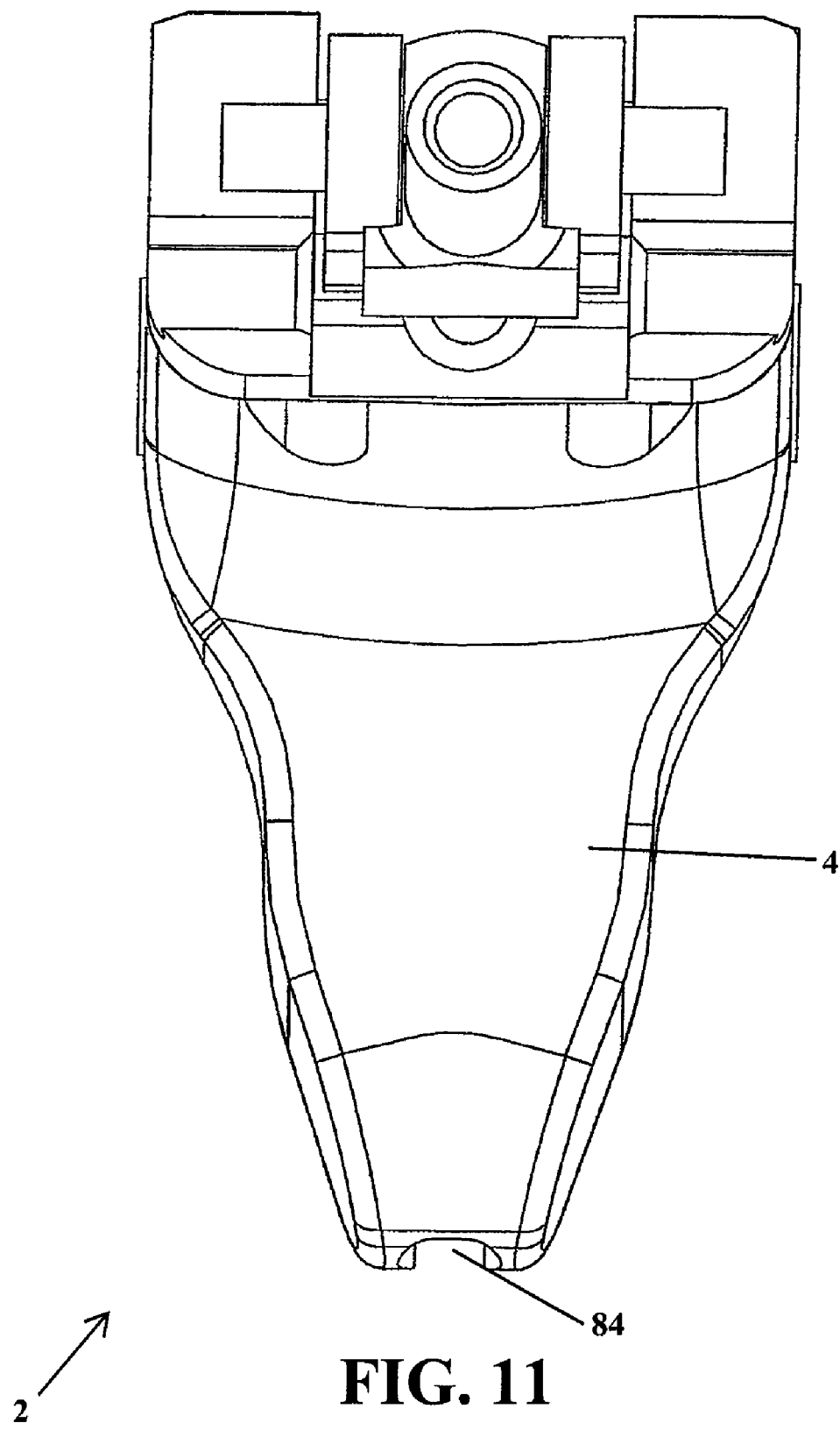
FIG. 11 is a left side view of the interspinous insertion member of FIG. 1 showing the insertion member in the insertion orientation.
Figure 12:
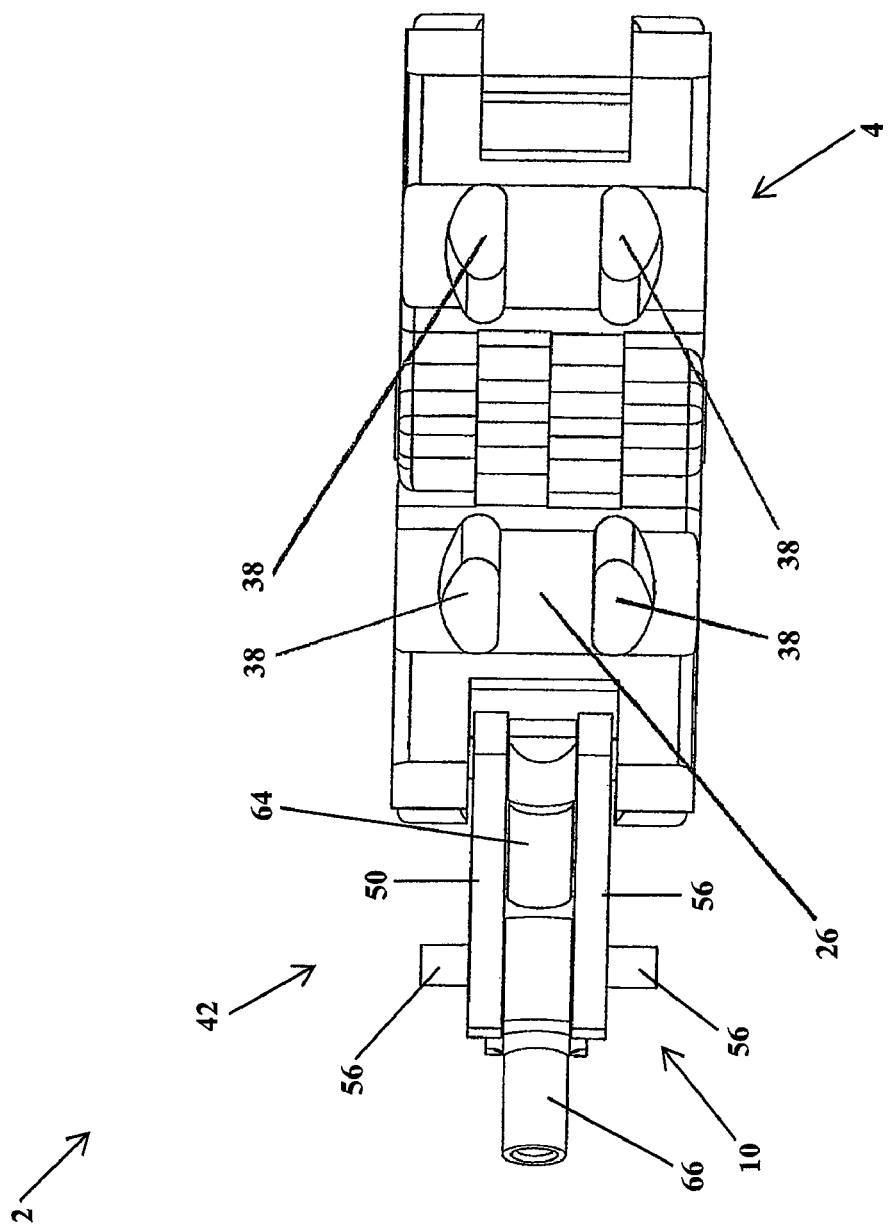
FIG. 12 is a top view of the interspinous insertion member of FIG. 1 showing the insertion member in the insertion orientation.
Figure 13:
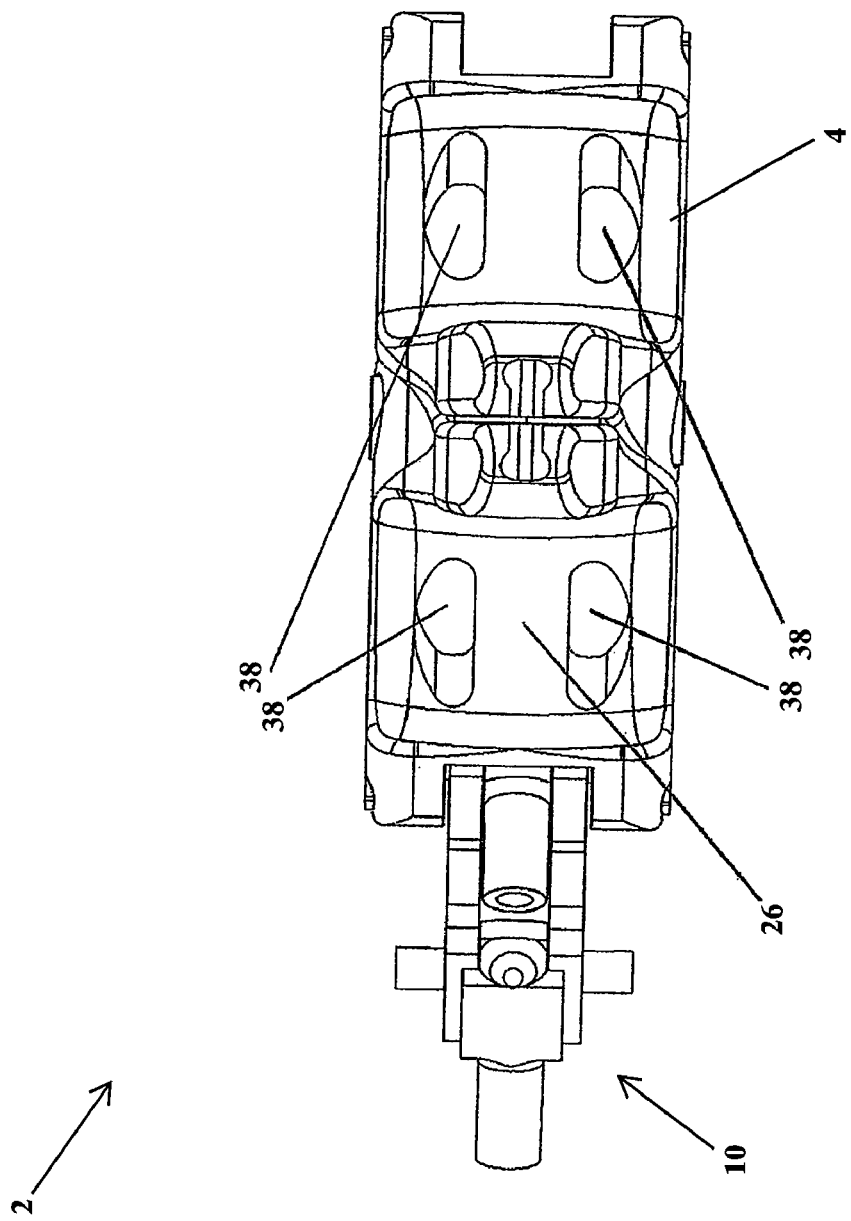
FIG. 13 is a bottom view of the interspinous insertion member of FIG. 1 showing the insertion member in the insertion orientation.
Figure 14:
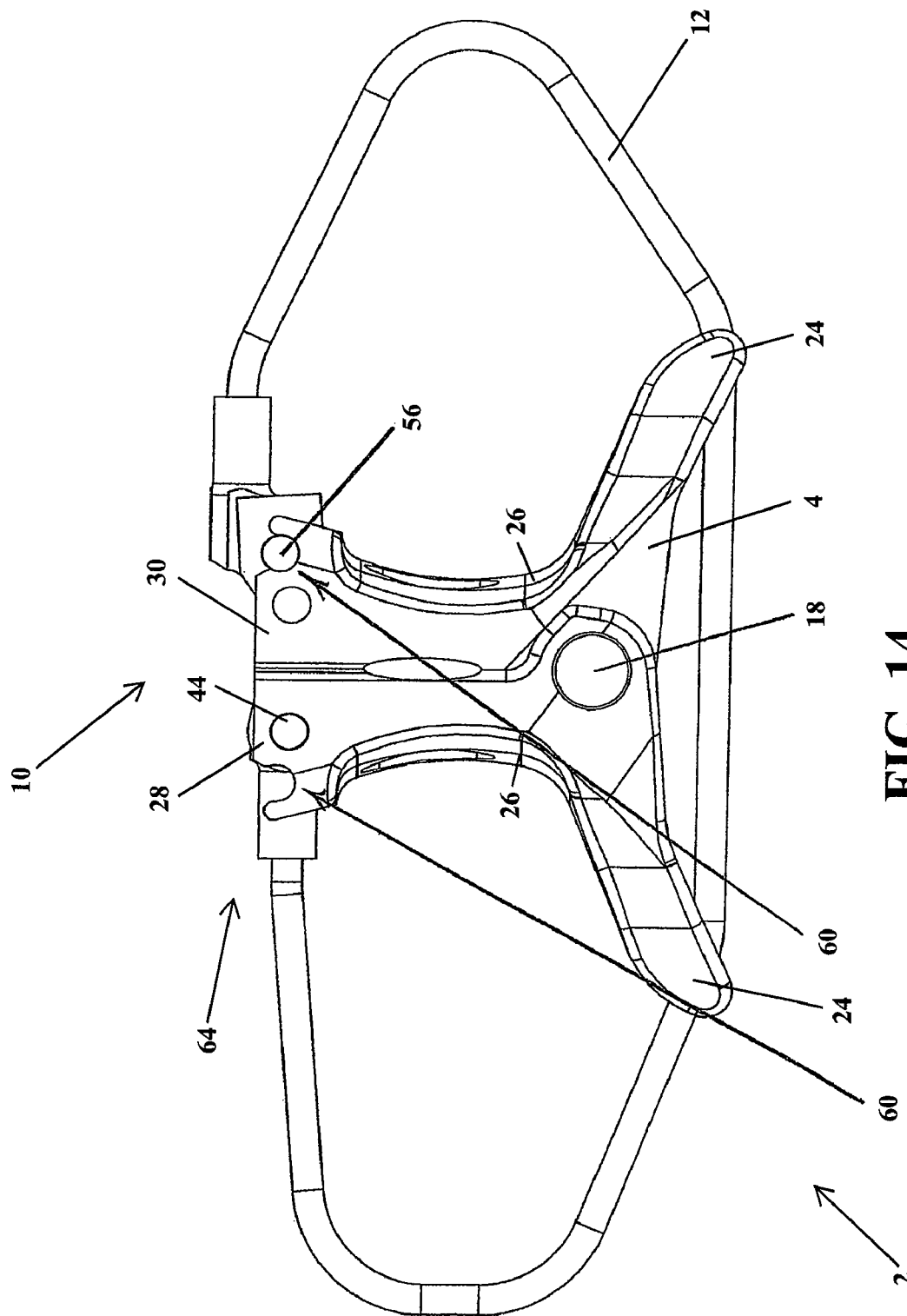
FIG. 14 is a front elevational view of the implant of FIG. 1.
Figure 15:
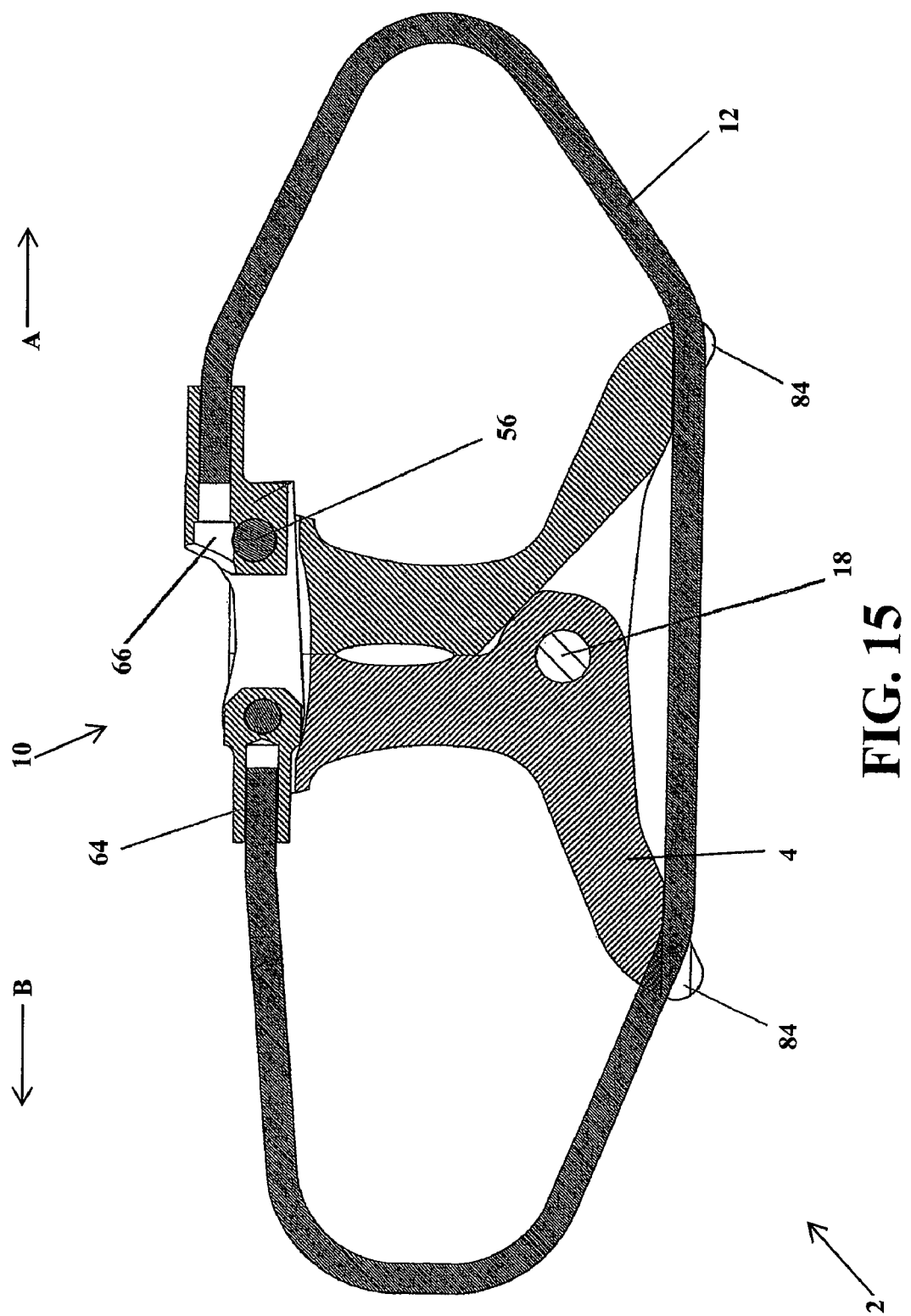
FIG. 15 is a front elevational sectional view of the implant of FIG. 1 showing the cable positioned in grooves of the arms of the insertion member.
Figure 16:
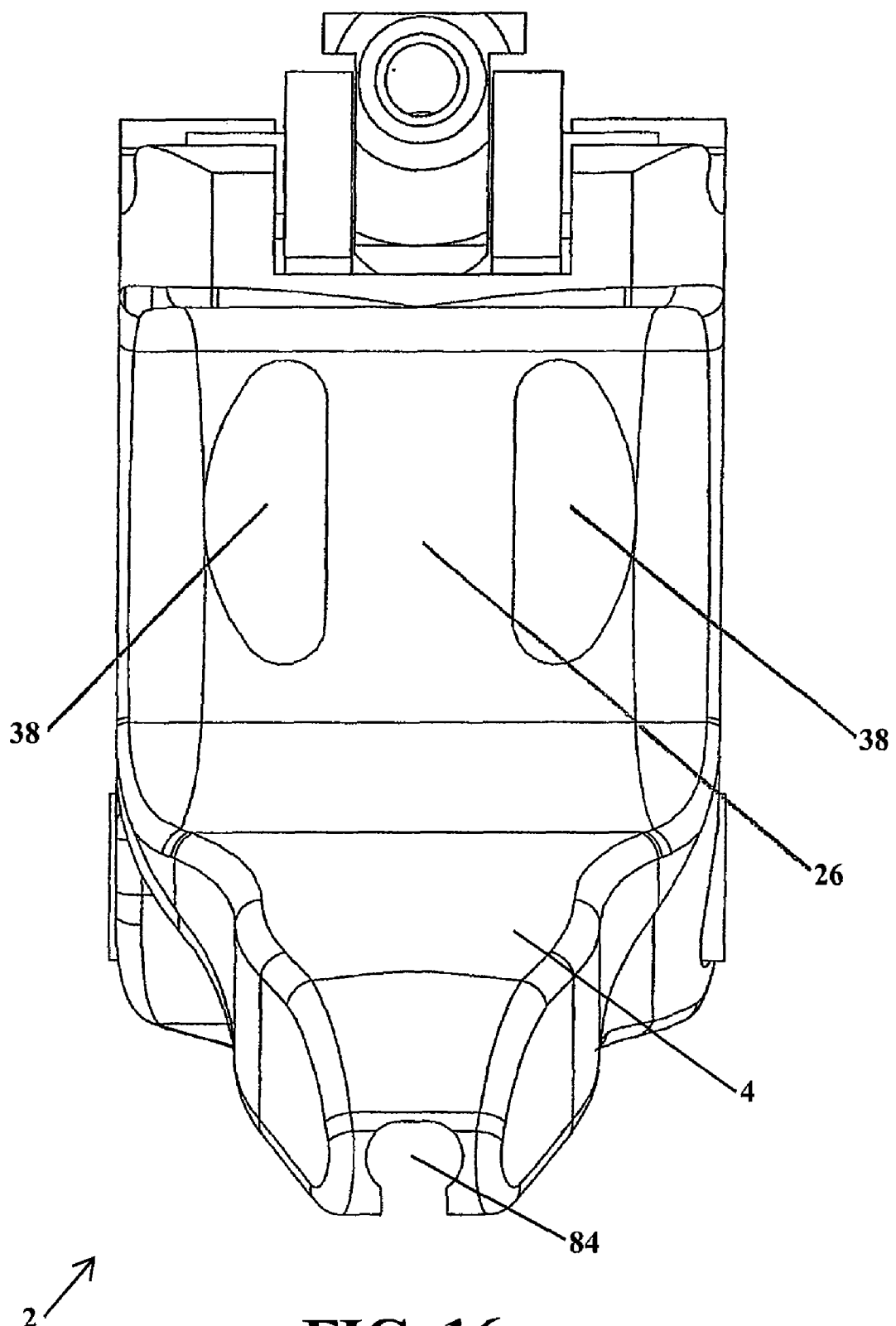
FIG. 16 is a right side view of the interspinous insertion member of FIG. 1 showing the insertion member in the implanted orientation.
Figure 17:
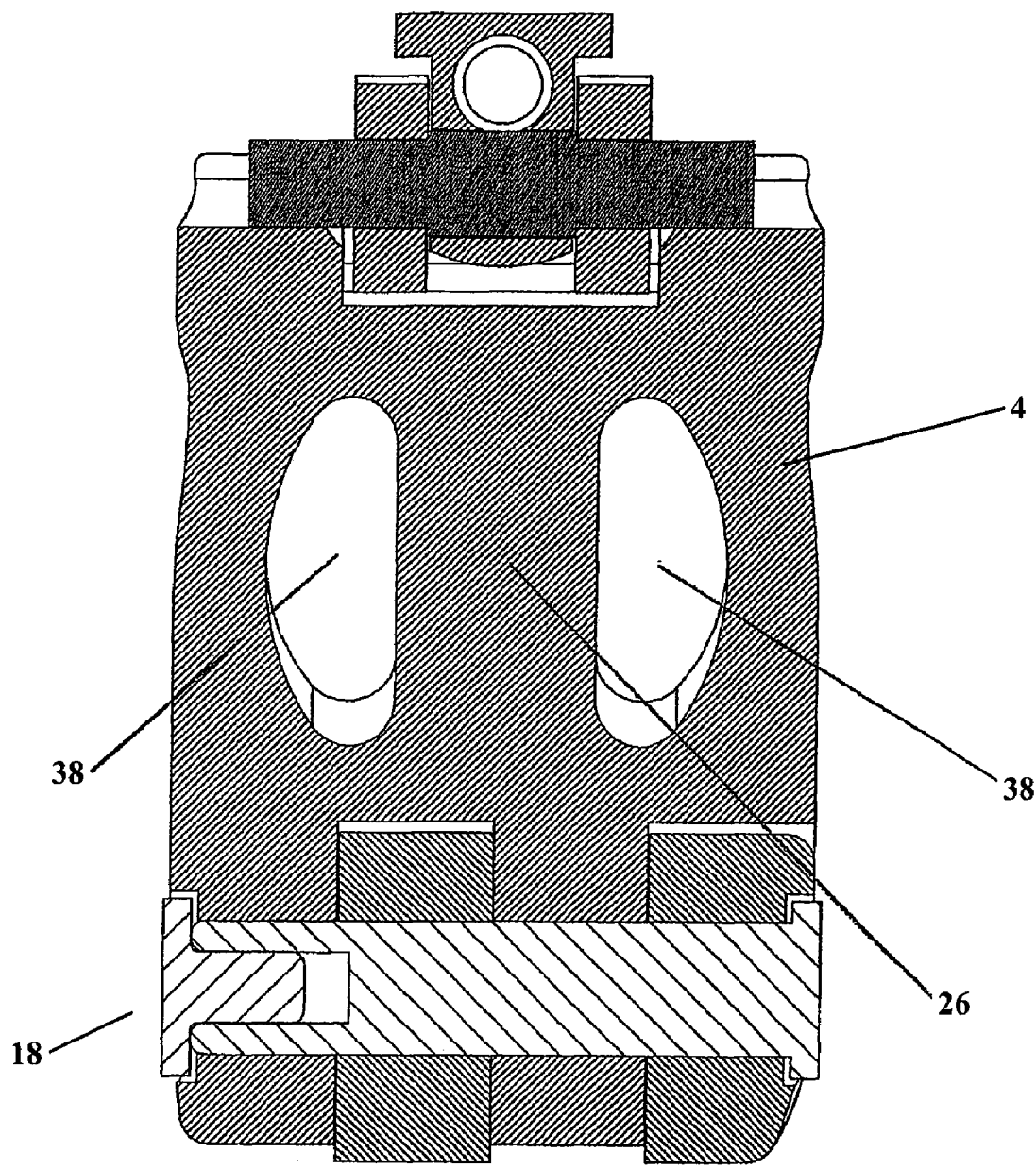
FIG. 17 is a right side sectional view of the interspinous insertion member of FIG. 1 showing the insertion member in the implanted orientation showing the pivot pin insertion member and the pivot pin of the locking mechanism.

The seat portions 26 of the implant members 14 and 16 are configured for engagement with the bone portions 6 and 8 with the implant members 14 and 16 in the implanted orientation 22. As shown in FIGS. 5 and 9, the orientation of the seats 26 relative to one another changes as the implant members 14 and 16 are pivoted about the pivot connection 18. More particularly, in the implanted orientation 22, the seat portions 26 are positioned directly adjacent one another and face in generally opposite direction. While in the insertion orientation 20, the seat portions 26 are spaced from one another as shown in FIGS. 8 and 9 and face in generally the same direction transverse to the upward and downward directions Q and R. As shown in FIGS. 8 and 9, as the implant members 14 and 16 are pivoted from the insertion orientation to the implanted orientation the seat portions are each reoriented at least approximately 40 degrees each. The seat portions 26 of the implant members 14 and 16 can include corresponding openings or cavities 38 extending therethrough to allow for bone void material or growth material to be positioned therein. Further, bone growth can occur through the openings 38 and extend between the two bone portions 6 and 8.

The trailing or tool engagement ends 28 and 30 of the implant members 14 and 16 are configured to be engaged by a tool 40 so that the implant members 14 and 16 can be pivoted about the pivot connection 18 to the implanted orientation 22, as shown in FIG. 5.

The locking assembly 10 of the implant apparatus 2 is configured to keep the implant members 14 and 16 from pivoting back about the pivot connection 18 toward the insertion orientation 20. As shown in FIGS. 1-4, the locking mechanism includes a linkage 42 pivotably connected to one of the upper and lower implant member tool engagement ends 28 and receivable by the other tool engagement end 30 with the implant members 14 and 16 in the implanted orientation 22. As shown in FIGS. 1-4, the locking mechanism 10 can further include a flexible elongate member 12, such as a strap or cable, extending about the vertebral bone portions 6 and 8 and secured to the tool engagement ends 28 and 30 of the upper and lower implant members 14 and 16.

The linkage or spanning member 42 is connected to one of the implant member tool engagement ends 28 and 30 by a pin member 44. The tool engagement ends 28 and 30 include grooves 46 for receiving the linkage member 42 therein and a pair of throughbores 48 for pivotably receiving the pin member 44 therein. Further connected to the pivot pin 44, and positioned within the tool engagement end groove 46, is a pair of linkage members 50. The spaced linkage members 50 extend from the pivot pin 44 and are connected to a pin member 52 at a distal end 54 of the linkage members 50. The pin member 52 extends between the linkage members 50 and includes head portions 56 extending beyond each of the linkage members 50. The head portions 56 are configured to be received by slots 58 defined by hooks 60 of the implant member tool engagement end 30 which to which the linkage 42 is not pivotably connected. Further, the linkage 42 acts as an extension of the tool engagement end 28 of the implant member 14. As a result, the head portions 56 and the hook slots 58 are further configured to be engaged by the insertion tool 40 for inserting the implant members 14 and 16 between the adjacent bone members 6 and 8 and pivoting the implant members 14 and 16 to the implanted orientation 22.

Figure 3:
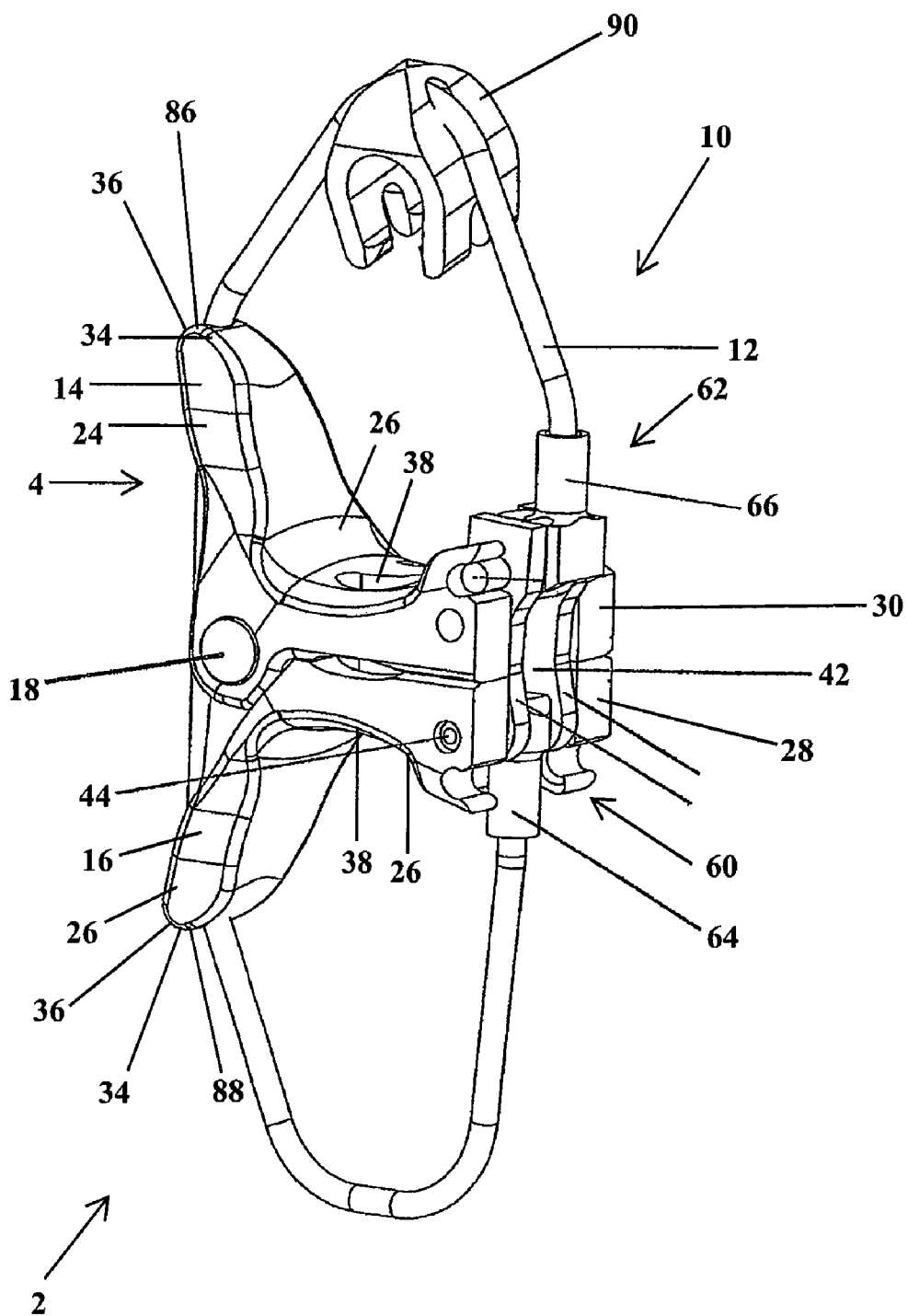
FIG. 3 is a perspective view of the implant of FIG. 1 showing the first tool engagement portion engaged with the second tool engagement portion.
Figure 4:
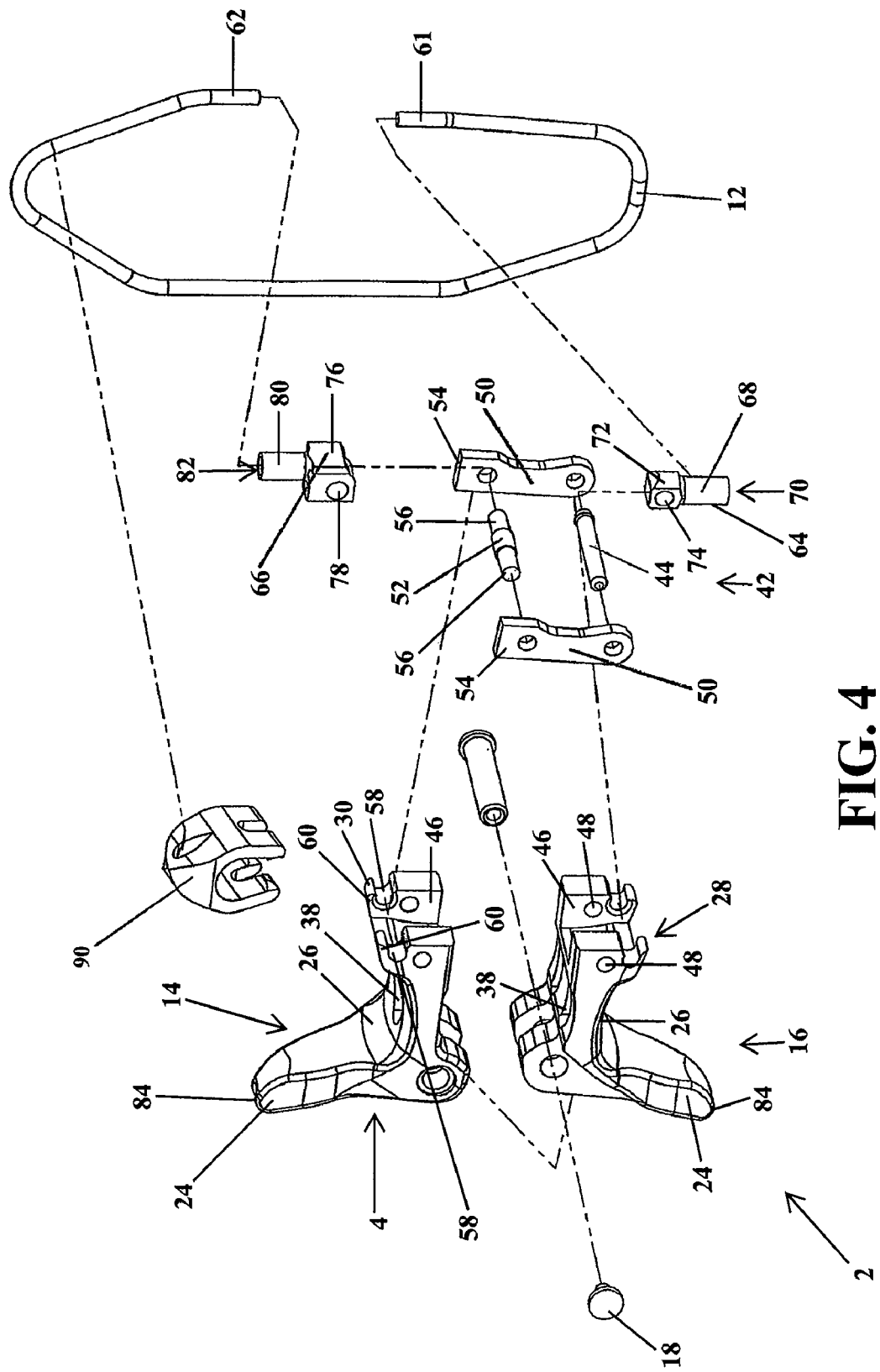
FIG. 4 is an exploded view of the implant of FIG. 1.

As a result, after the implant body members 14 and 16 are shifted from the insertion orientation 20 to the implanted orientation 22, the linkage 42 can act to secure the implant body members 14 and 16 in the implanted orientation 22. As discussed above and as shown in FIGS. 4 and 8-9, the implant member tool engagement end 30 which is not pivotably connected to the linkage 42 includes a groove 46 therein for receiving the linkage 42, similar to the groove 46 in the other implant member tool engagement end 28. As such, when the linkage 42 is pivoted about the pivot pin 44, the linkage 42 is received in the grooves 46 of the implant member tool ends 28 and 30. Further, the linkage pin heads 56 are received in hook slots 58 of the implant member 30 to which the linkage 42 is not pivotably connected, thereby acting to resist pivoting of the implant members 14 and 16 from the implanted orientation 22. As shown in FIGS. 3 and 5, the hooks slots 58 can be configured to further secure the pin heads 56 therein, such as by configuring the slots 58 to be inclined relative to the spinous processes 6 and 8.

The locking mechanism cable 12 is configured to extend from the implant member tool engagement ends 28 and 30 and about the bone members 6 and 8. The cable 12 is secured at a specified tension to urge the upper and lower vertebral bone portions 6 and 8 into engagement with the seats 26 of the implant members 14 and 16.

The cable 12 preferably is comprised of braided stainless steel, titanium, or cobalt chrome cable as described in U.S. Pat. No. 6,605,091 with Ser. No. 09/608,536 filed Jun. 30, 2000 and titled SURGICAL CABLE ASSEMBLY AND METHOD which is incorporated herein by reference in its entirety. Alternatively, the cable 12 can be made from other biocompatible materials such as synthetic polymer fibers such as polyglycolic acid (P.G.A.) or polydioxanone (PDS) in monofilament or braided configurations. Further, gut sutures could be used.

An alternative cable 12 is described in U.S. Pat. No. 5,456,722 with Ser. No. 100,458 filed Jul. 30, 1993 and titled LOAD BEARING POLYMERIC CABLE which is incorporated herein by reference in its entirety. The disclosed cable 12 is a braided high strength radiolucent ultra-high molecular weight polyethylene (UHMWPE) fiber. The disclosed cable 12 further avoids many of the potential complications caused by implantation of metal wires and metal cables, including wire/cable breakage, hemorrhage, contusion, laceration and interference with magnetic resonance and x-ray imagery. Furthermore, the cable 12 is sufficiently flexible for looping about bone tissue and may be secured relative to bone tissue through knotting procedures. The apparatuses and methods for the disclosed cable are described in U.S. Pat. No. 5,540,703 with Ser. No. 346,852 filed Nov. 30, 1994 and titled KNOTTED CABLE ATTACHMENT APPARATUS FORMED OF BRADED POLYMERIC FIBERS which is also incorporated herein by reference in its entirety. Further apparatuses and methods for the disclosed cable are described in U.S. Pat. No. 5,628,756 with Ser. No. 681,697 filed Jul. 29, 1996 and titled KNOTTED CABLE ATTACHMENT APPARATUS FORMED OF BRAIDED POLYMERIC FIBERS which is incorporated herein by reference in its entirety. Finally, the disclosed cable tensioning apparatus as described in U.S. Pat. No. 6,689,140 B2 with Ser. No. 09/968,694 filed Oct. 1, 2001 and titled SYSTEM AND METHOD OF SPINAL RECONSTRUCTION is incorporated herein by reference in its entirety.

As shown in FIGS. 1 and 3, the linkage 42 is configured to provide securing locations for the cable ends 61 and 62. An attachment member 64, such as crimping body 64 is positioned between the linkage members on the pivot pin 44 for securing a cable 12 therein. Further disposed on the second pin member 52 is an offset crimping body 66 for receiving and securing the cable 12 therein.

The first crimping body 64 includes a crimping portion 68 having an opening 70 for receiving the cable 12 therein. Adjacent the crimping portion 68 is a head portion 72, having a throughbore 74 for pivotably receiving the pivot pin 44 of the linkage 42 therein. The crimping portion 68 is configured so as to receive a first end 61 of the cable 12 and secure the cable first end 61 therein. The first end 61 of the cable 12 can be secured before or after the cable 12 is positioned about the adjacent vertebral bone portions 6 and 8. Further, given that the first crimping body 64 is pivotably connected to the pivot pin 44, the first crimping body 64 can be adjusted or self adjust to accommodate the angle at which the cable 12 approaches the first crimping body 64.

The offset crimping body 66 includes a head portion 76 through which a throughbore 78 is configured to pivotably receive the second pin member 52 and be positioned between the adjacent linkage members 50. Similar to the first crimping body 64, the pivotable connection allows the offset crimping body 66 to be pivoted or self pivot to accommodate the approach angle of the cable 12 to the crimping body 66. A crimp portion 80 of the crimping body 66 is offset from the head portion 76, such that a crimp throughbore 82 extends perpendicular to the head portion throughbore 78 but does not intersect the head portion throughbore 78. As such, the cable 12 can be threaded through the crimp throughbore 82 and pulled to provide the desired cable tension so as to mechanically engage the adjacent spinous processes 6 and 8 and apply a force thereto thereby limiting or preventing flexion of the mechanically engaged vertebrae 6 and 8. At that point, the crimp portion 80 is deformed to secure the cable 12 in place maintain the cable tension. Any excess cable 12 extending beyond the crimp throughbore 82 can be trimmed or otherwise removed.

In the preferred embodiment shown in FIGS. 1 through 6, the crimps 68 and 80 utilized are those described in U.S. Pat. No. 6,605,091 with Ser. No. 09/608,536 filed Jun. 30, 2000 and titled SURGICAL CABLE ASSEMBLY AND METHOD which is incorporated herein by reference in its entirety. The cable tensioner used with the preferred embodiments crimps is described in U.S. Pat. No. 7,452,360 with application Ser. No. 09/994,088 filed Nov. 14, 2001 and titled METHOD AND APPARATUS FOR CLAMPING SURGICAL WIRES OR CABLES which is incorporated herein by reference in its entirety.

Alternatively, the shape and configuration of the first crimp 64 and offset crimp 66 can be varied to allow use of different cable tensioning apparatuses. Alternatively, a crimp as described in U.S. Pat. No. 5,415,658 with application number 167,542 filed Dec. 14, 1993 and titled "Surgical Cable Loop Connector," which is incorporated herein by reference in its entirety, can be used. The cable tensioner used with the alternative crimp is described in U.S. Pat. No. 5,788,697 with application number Ser. No. 616,687 filed Mar. 15, 1996 and titled CABLE TENSIONING DEVICE, which is incorporated herein by reference in its entirety.

One method of inserting the cable 12 includes threading the cable 12 into the first crimp body 64 and securing the cable 12 therein. This can be done prior to or after implantation of the implant members 14 and 16 between the adjacent bone portions 6 and 8, in the implanted or insertion orientations 20 and 22. The cable 12 is then shifted about the adjacent bone portions 6 and 8 and threaded into the crimping throughbore 82 of the offset crimping body 66. After being tensioned to the desired cable tension, the crimp 80 of the offset crimping body 66 secures the cable 12 in place, after which excess cable is removed.

Figure 2:
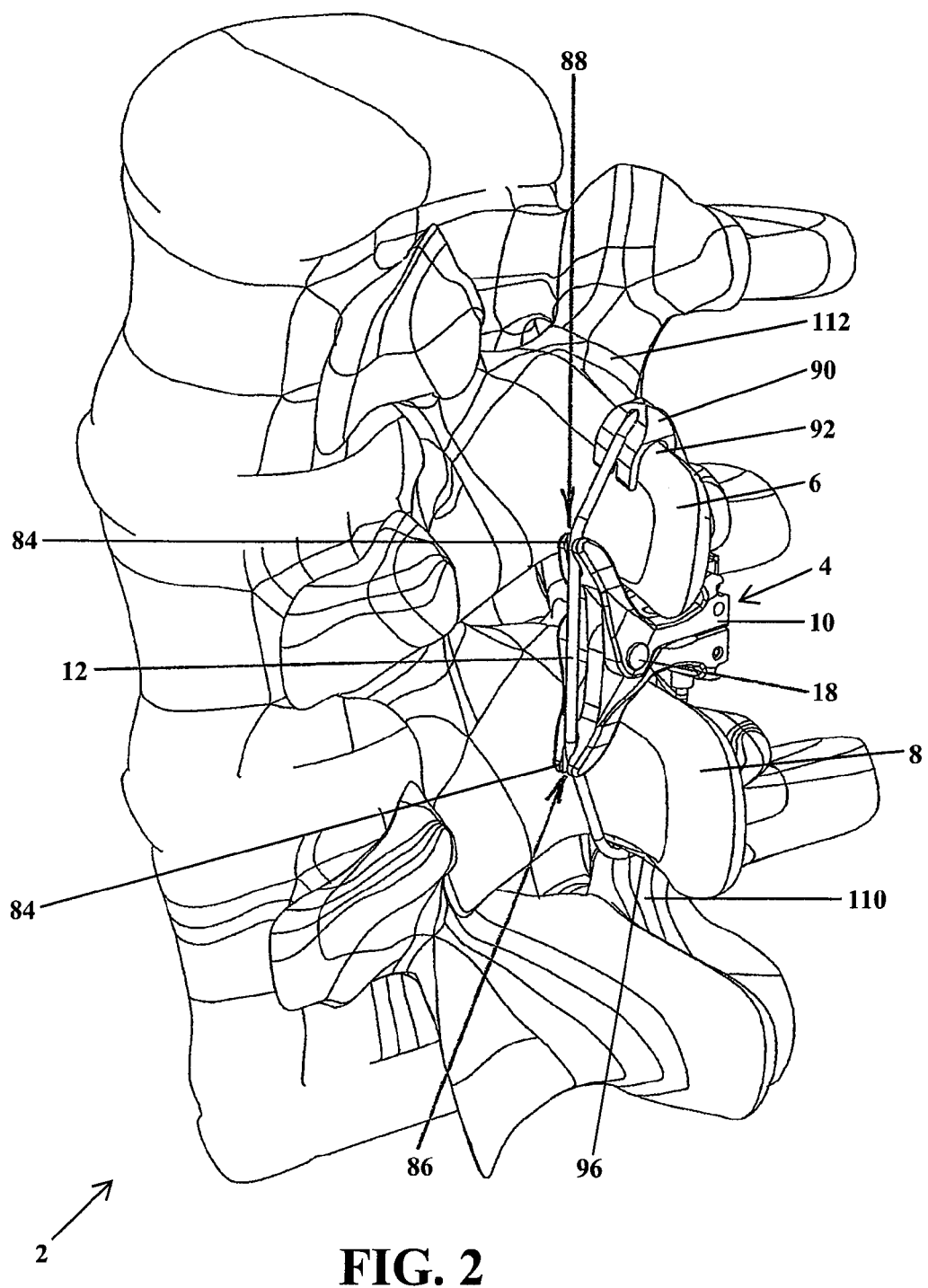
FIG. 2 is an alternative posterior aspect prospective view of the implant of FIG. 1 showing a grommet positioned on the upper spinous process.

To aid in securing the bone portions 6 and 8 and the implant spacer 4, the lead arms 24 of the upper and lower implant members 14 and 16 can include grooves 84 to receive and guide the cable 12, as shown in FIG. 2. This engagement provides two additional points 86 and 88 of mechanical engagement between the implant members 14 and 16 and the cable 12, thereby aiding in securing the implant members 14 and 16 in the implanted orientation 22. Further, the guides 84 act to reduce the contact area and any friction that may occur between the bone portions 6 and 8 and the cable 12 by providing contact points 86 and 88 for the cable 12 away from the spinous processes 6 and 8.

To further reduce or eliminate contact between the cable 12 and the bone portions 6 and 8, a gripping member 90 can be attached to the superior surface 92 of the upper bone portion 6. A second gripping member 94 can be further attached to the inferior surface 96 of the lower bone portion 8.

Figure 18:
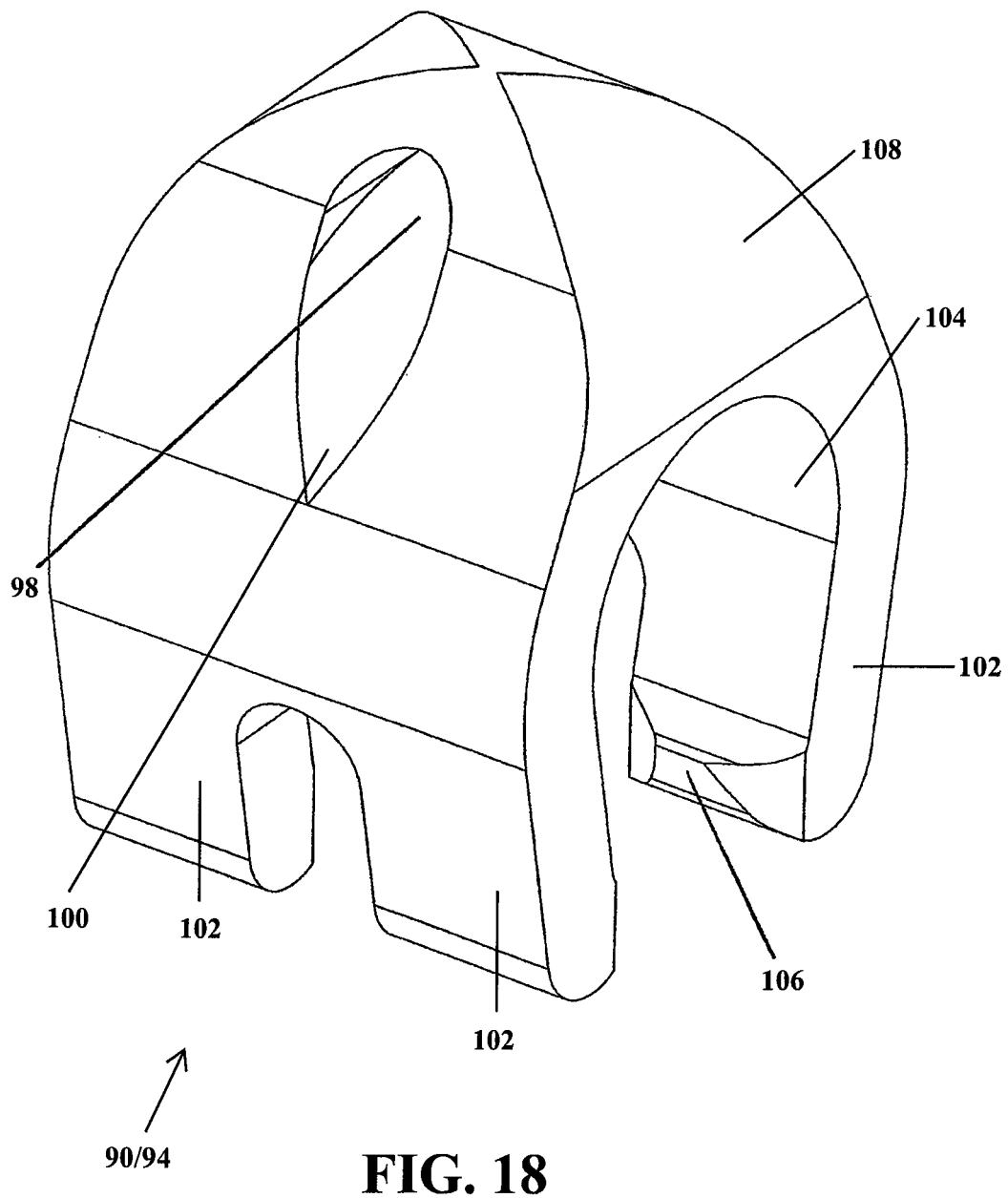
FIG. 18 is a perspective view of the grommet of the implant of FIG. 1.
Figure 19:
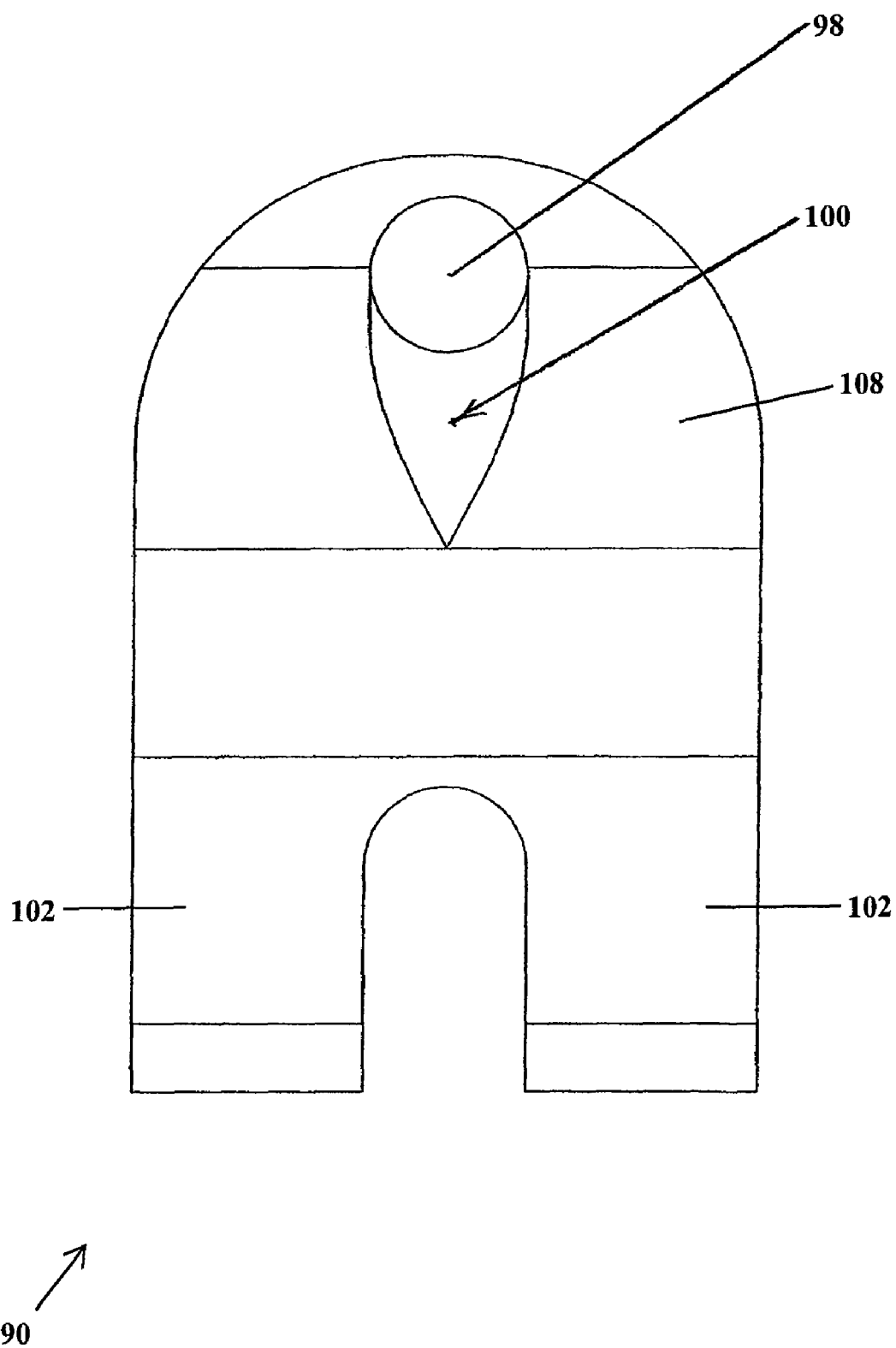
FIG. 19 is a front elevational view of the grommet of the implant of FIG. 1 showing the cable guide opening.

An exemplary gripping member 90 is shown in greater detail in FIGS. 1-3 and 18-22. The gripping member 90 is configured to limit or prevent the cable 12 from cutting or wearing against the thin structure of the superior edge 92 of the spinous process 6. As shown in FIG. 18, the gripping member 90 includes an eyelet or guide 98 throughbore configured to permit the cable 12 to pass though and mechanically engage the cable 12. The guide throughbore 98 is configured to be located a predetermined distance from the spinous process 6. As shown in FIG. 19, the gripping member also includes a guide channel 100 adjacent the guide throughbore 98 configured to seat the cable 12 therein and to resist movement of the cable 12 and slippage of the gripping member 90 on the spinous process 6.

Figure 20:
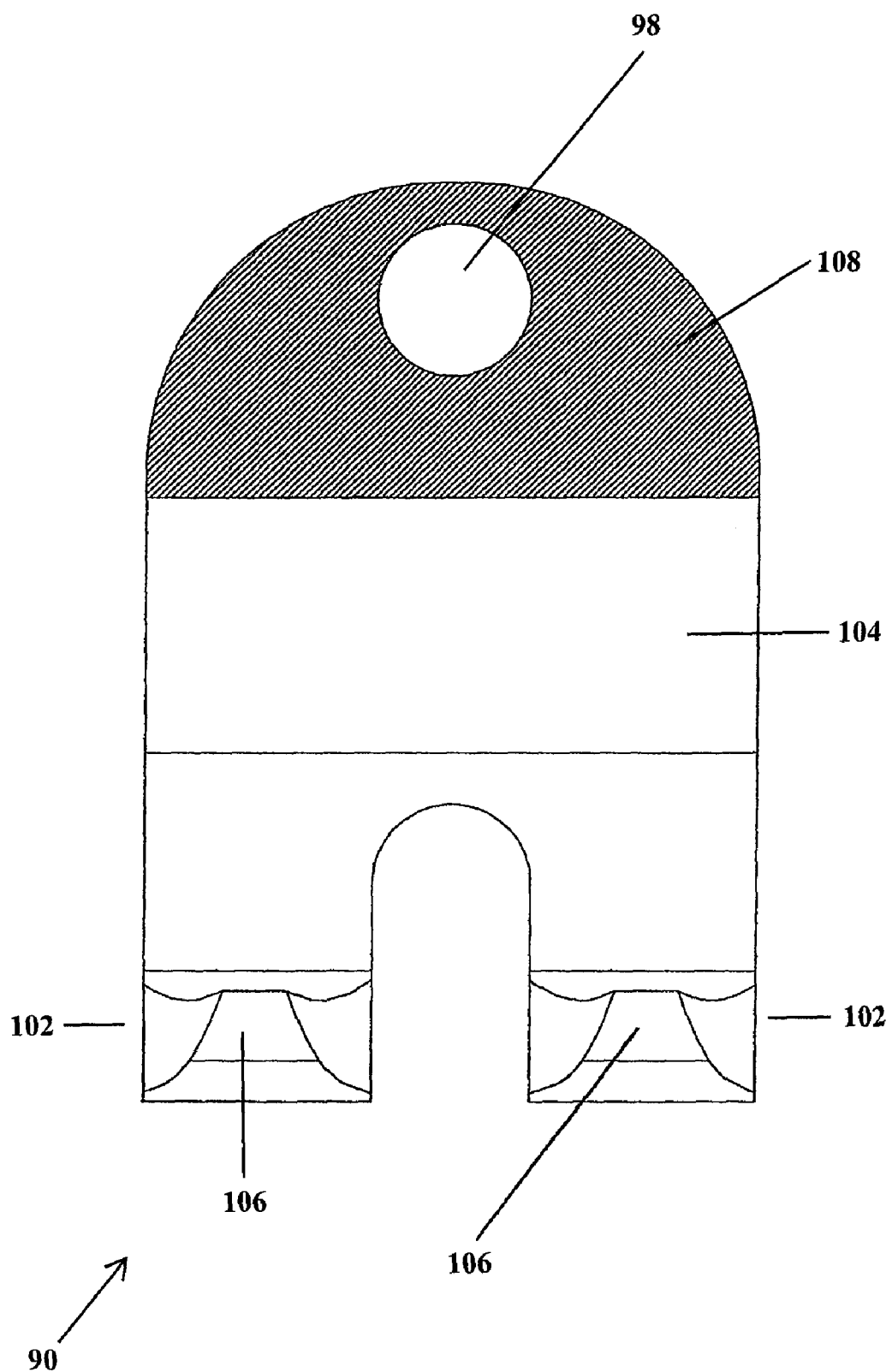
FIG. 20 is a front sectional view of the grommet of the implant of FIG. 1.
Figure 21:
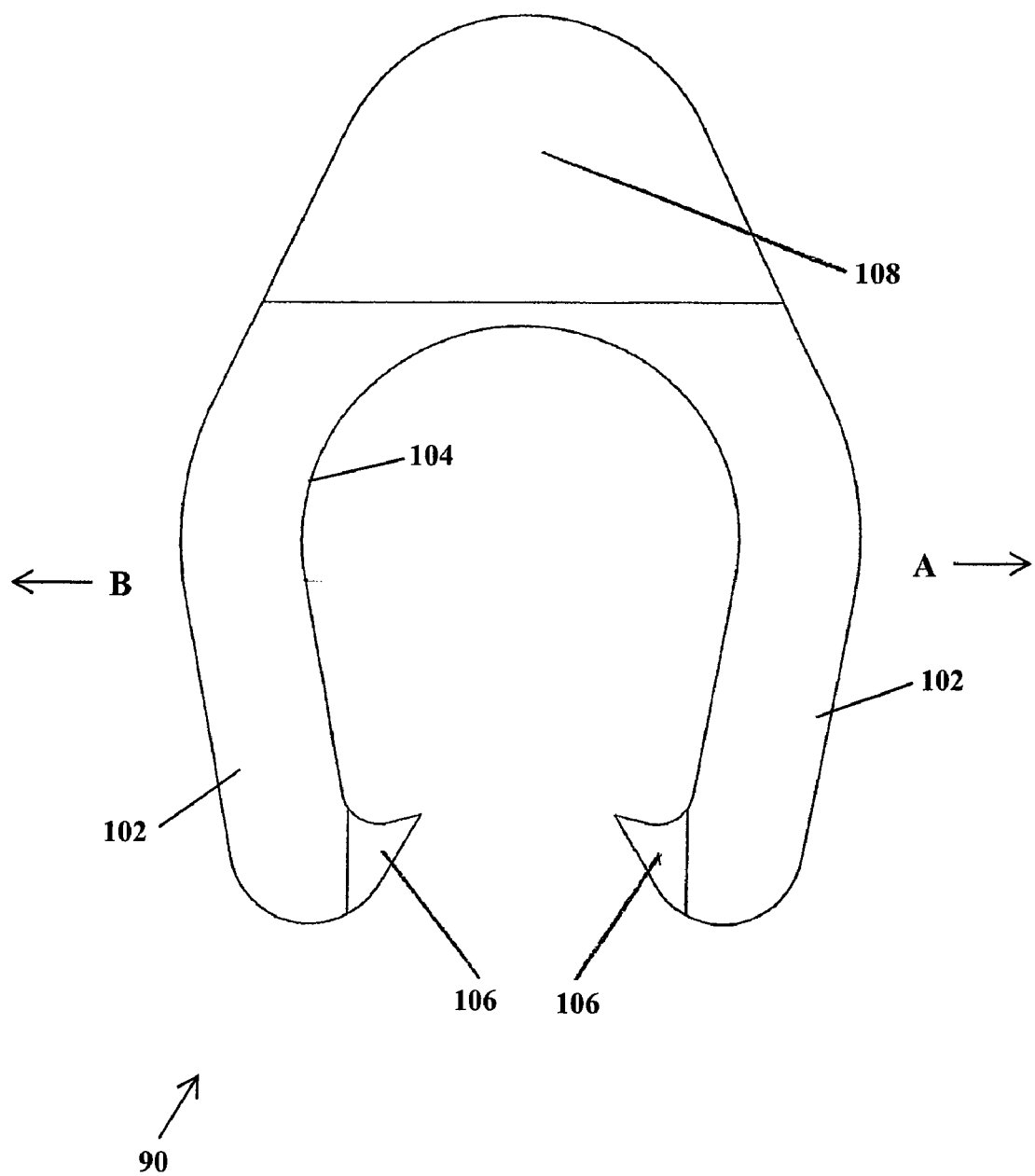
FIG. 21 is a right side view of the grommet of the implant of FIG. 1.
Figure 22:
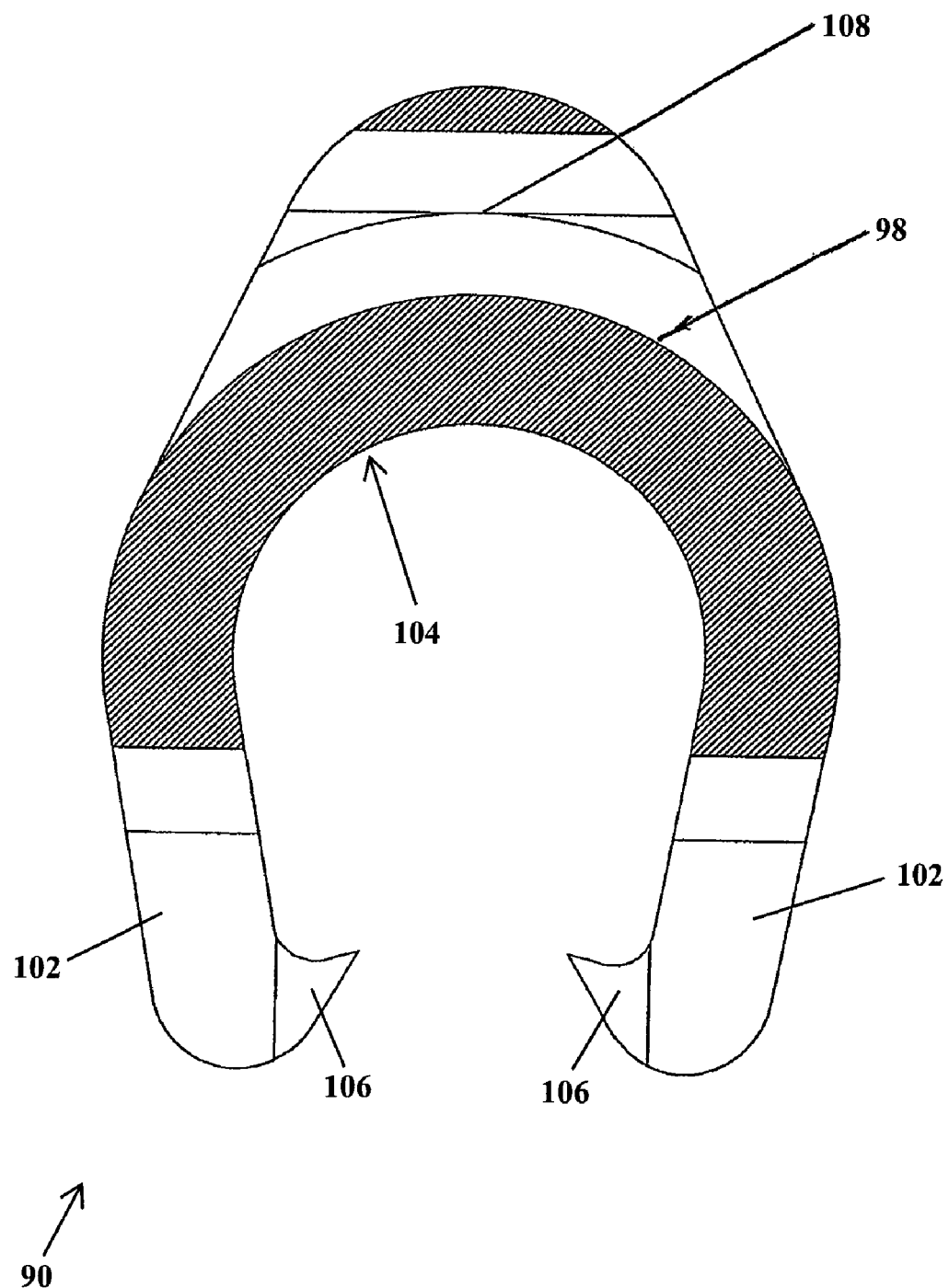
FIG. 22 is a right side sectional view of the grommet of the implant of FIG. 1 showing the cable guide opening.
Figure 23:
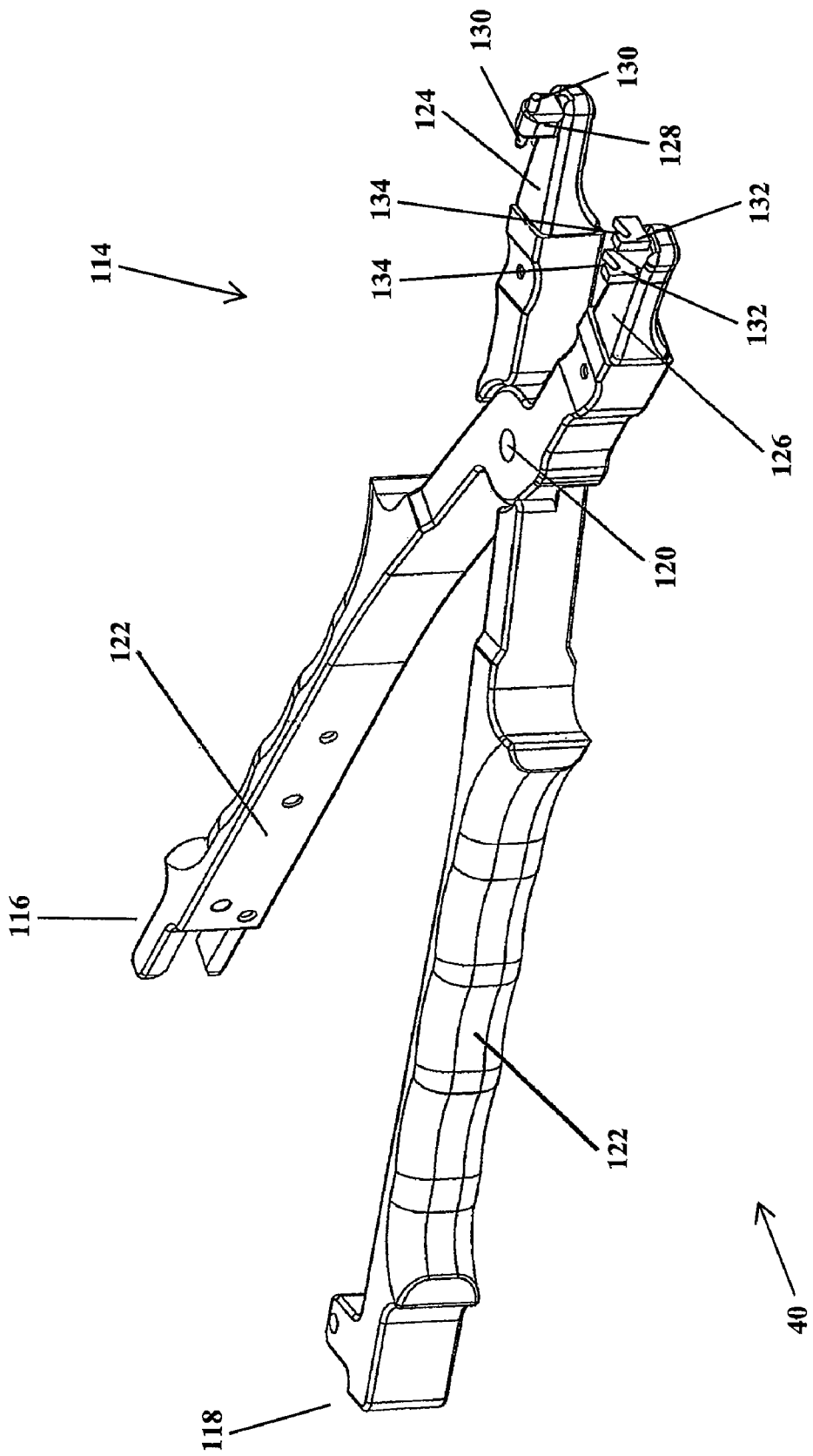
FIG. 23 is a perspective view of an insertion tool for the implant of FIG. 1 showing a handle portion, and a first implant engaging portion and a second implant engaging portion.

The gripping member 90 includes a pair of spaced arms 102 that are configured to elastically deflect in direction A and B when the upper gripping member 90 engages the bone of the spinous process 6. The inner surfaces 104 of the arms 102 the gripping member 90 further includes barbs 106 to limit or prevent slippage of the gripping member 90 on the spinous process 6 as shown in FIGS. 20-22. The arms 102 are configured to spring outward in direction A and B as the gripping member 90 is urged downwardly on to the bone 6 until the barbs 106 penetrate the bone 6 and secure the upper gripping member 90 into position. The function of the barbs 106 is to restrict the movement of the gripping member 90 once located on the edge 92 of the spinous process 6.

The body 108 of the gripping member 90 is not configured to elastically deflect like the arms 102 of the upper gripping member 90, but to remain substantially rigid and non-deformable. The rigid body 108 of the gripping member 90 is configured to limit or prevent the cable 12 from cutting into the bone 6 and to distribute the tensile load of the cable 12 over the interior surface 104 of the gripping member 90. Alternatively, the location and dimensions of the guide throughbore 98 of the gripping member 90 can be modified to allow the cable 12 to cut into the spinous process 6 to a controlled depth to provide greater mechanical engagement by the cable 12 with the spinous process 6.

The gripping member 90 is preferably made of a biocompatible material such as PEEK or stainless steel to limit or prevent the gripping member 90 from plastically deforming. Alternatively, the gripping member 90 can be made from materials such as titanium or other biocompatible materials.

Prior to insertion of the spacer member 4, the ligaments and tissue surrounding the spinous processes 6 and 8 are punctured with a dilator and expanded, if necessary, at the targeted interspinous process space. The ligaments and tissue at the inferior adjacent interspinous process space 110 and superior adjacent interspinous process space 112 are also punctured so that the cable 12 can be threaded through the adjacent interspinous process spaces 110 and 112.

Figure 27:
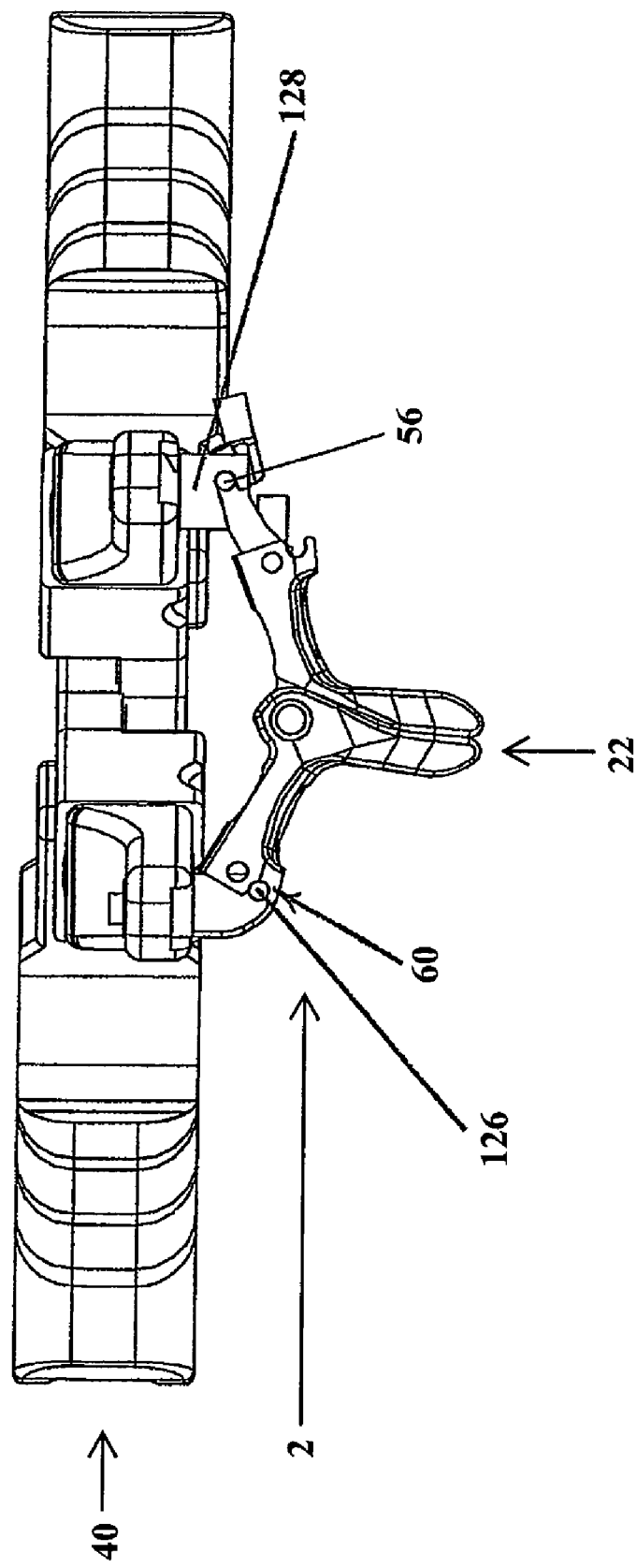
FIG. 27 is a front view of the implant of FIG. 1 showing the first and second tool engagement portions of the interspinous insertion member engaged with the first and second implant engaging portions of the tool with the interspinous insertion member in the compact insertion orientation.
Figure 28:
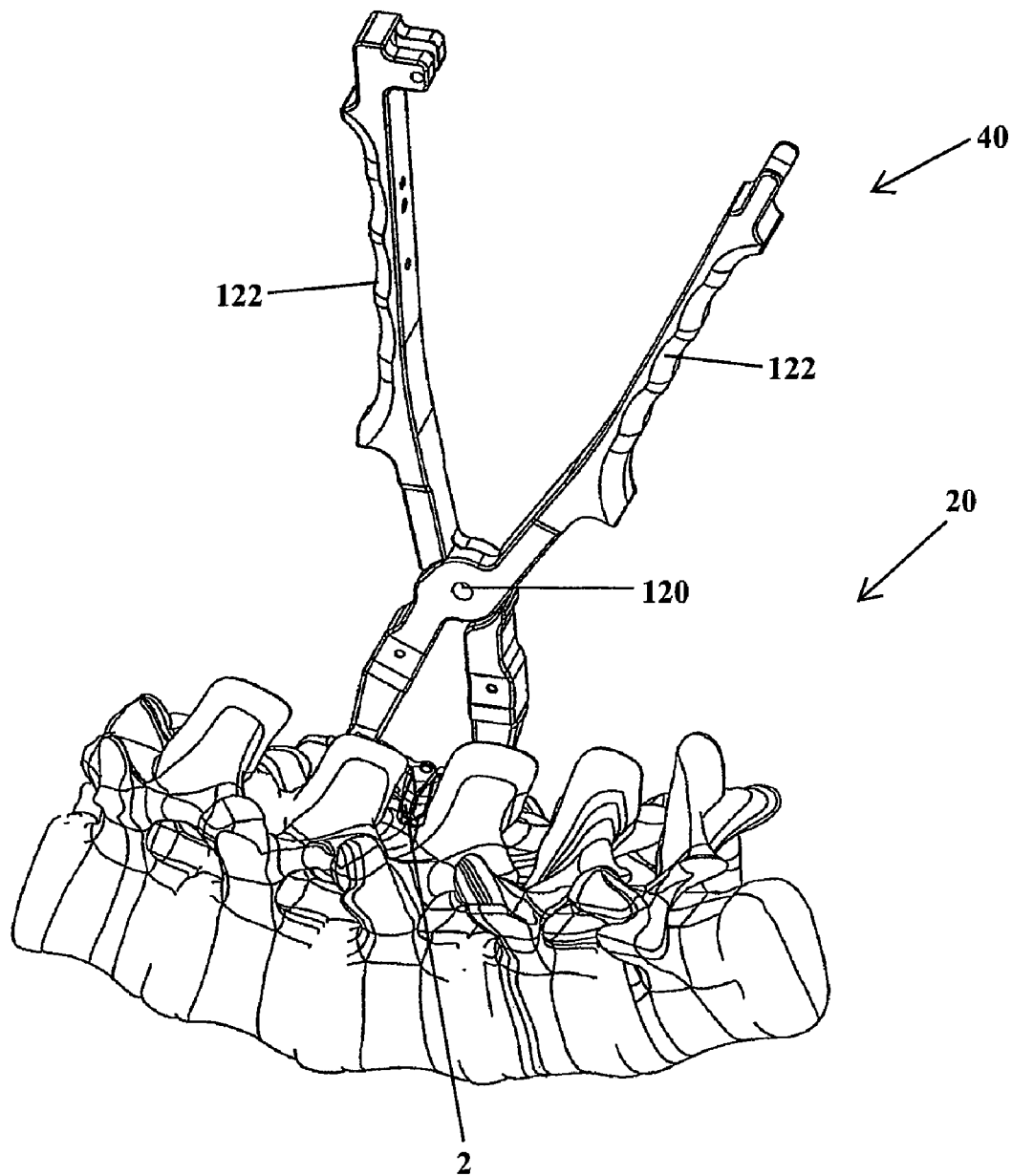
FIG. 28 is a front perspective view of the implant of FIG. 1 showing the interspinous insertion member being inserted between adjacent vertebrae by the tool with the interspinous insertion member in the insertion orientation.
Figure 29:
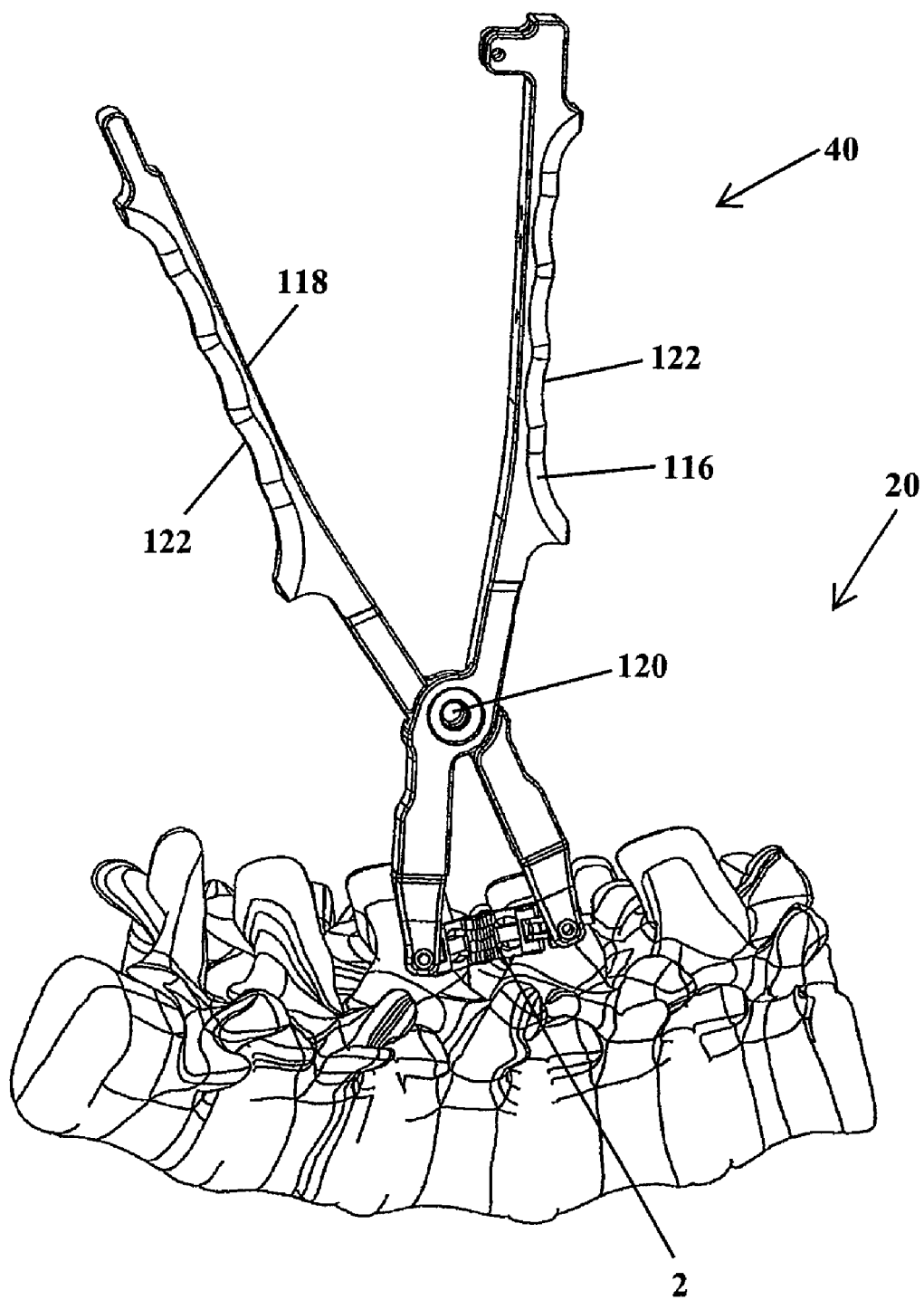
FIG. 29 is a rear perspective view of the implant of FIG. 1 showing the interspinous insertion member being inserted between adjacent vertebrae by the tool with the interspinous insertion member in the insertion orientation.
Figure 30:
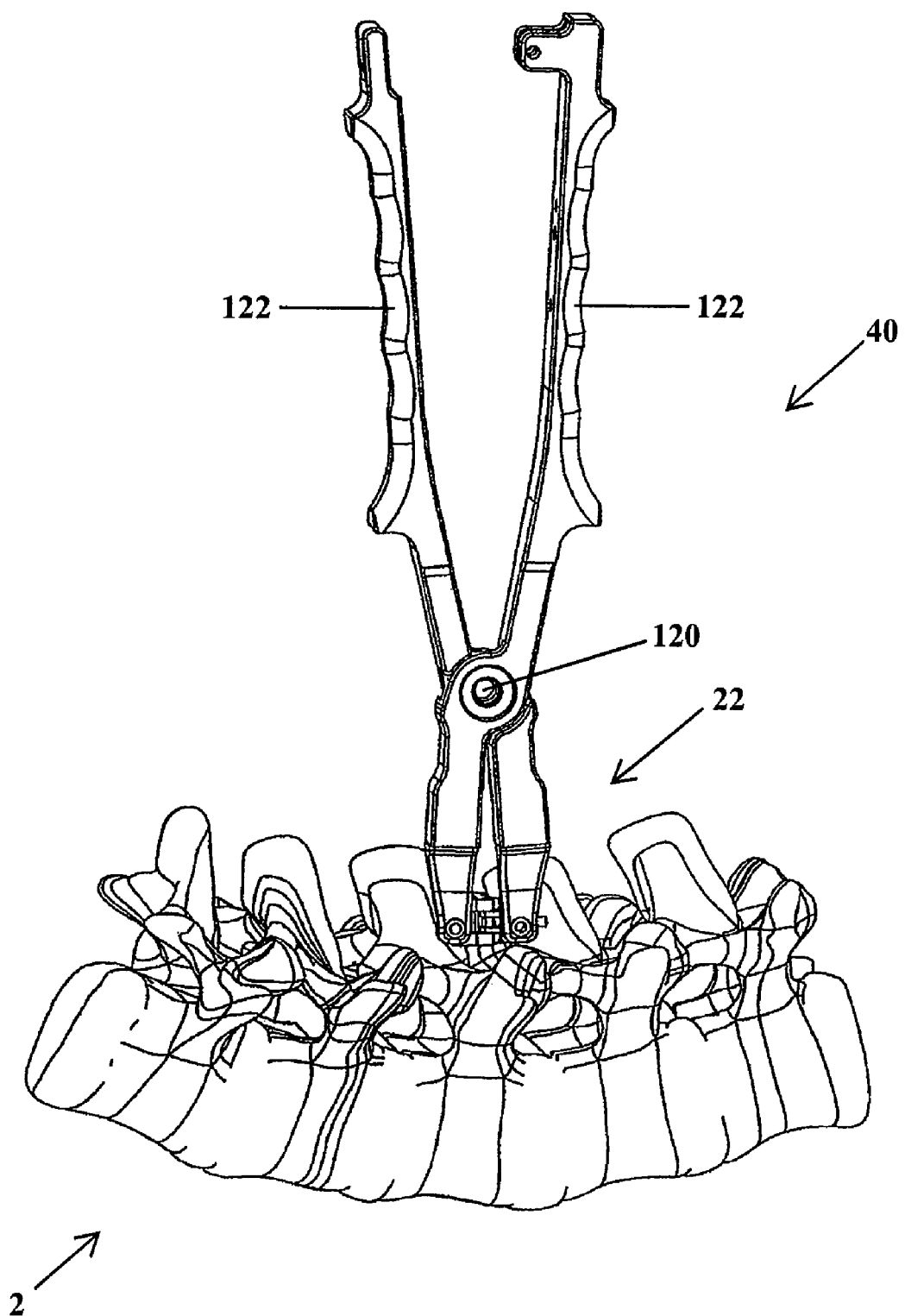
FIG. 30 is a rear perspective view of the implant of FIG. 1 showing the interspinous insertion member being inserted between adjacent vertebrae by the tool with the interspinous insertion member in the implanted orientation.
Figure 31:
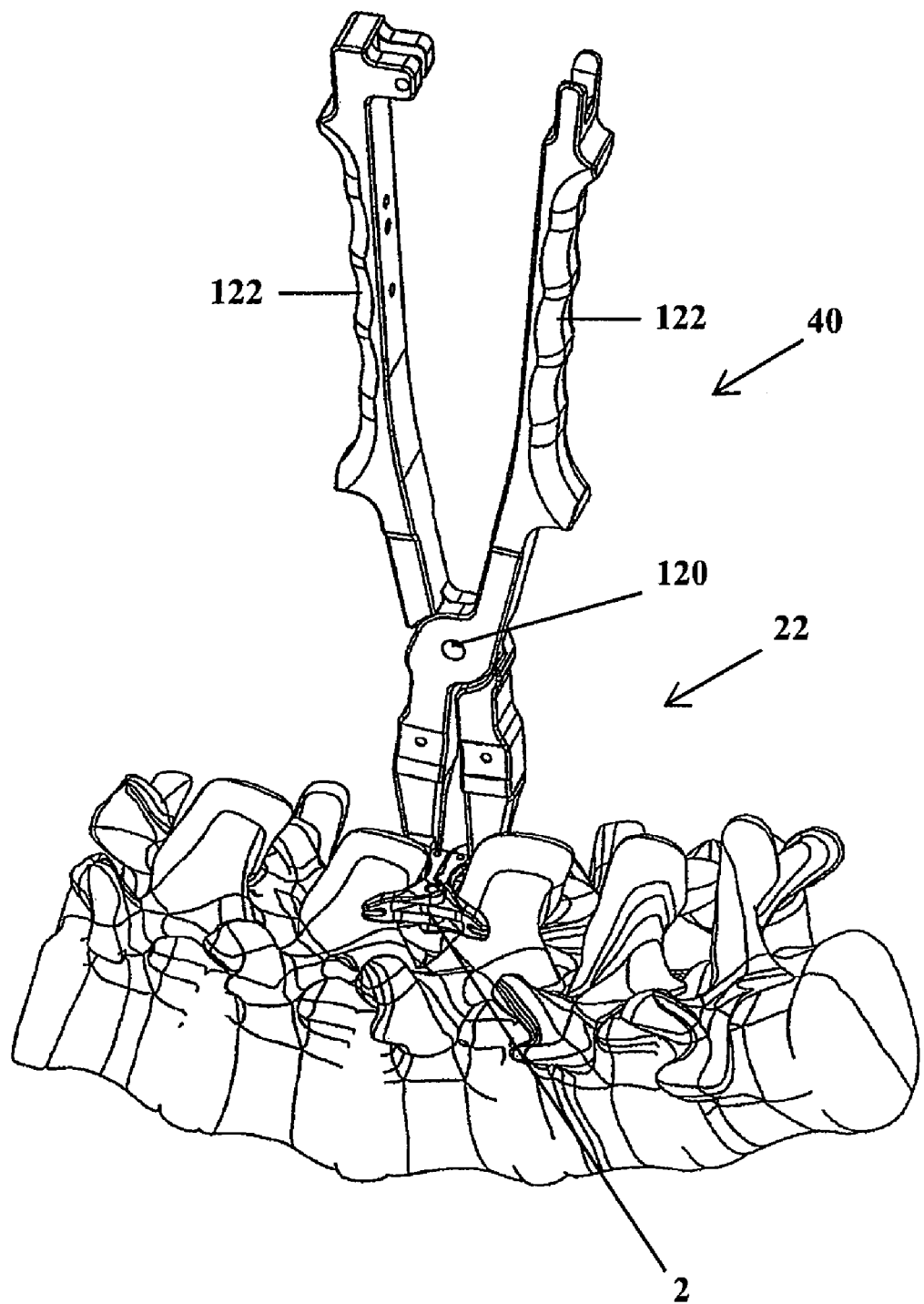
FIG. 31 is a front perspective view of the implant of FIG. 1 showing the interspinous insertion member being inserted between adjacent vertebrae by the tool with the interspinous insertion member in the implanted orientation.
Figure 32:
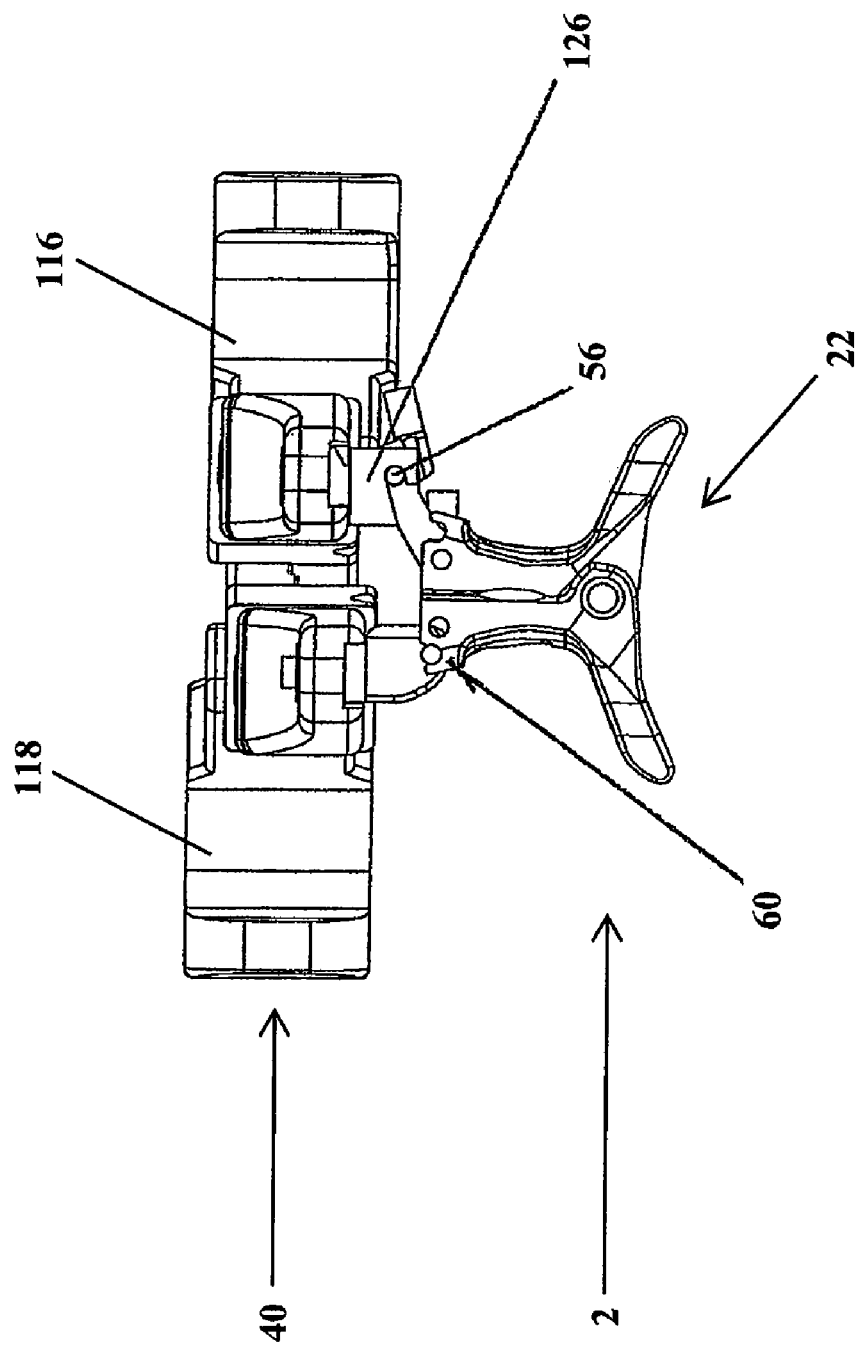
FIG. 32 is a front view of the implant of FIG. 1 showing the interspinous insertion member engaged by the tool with the interspinous insertion member in the implanted orientation.

As described above, the implant spacer 4 is inserted in the insertion orientation 20. A tool 40, such as shown in FIGS. 23-32, can be used to both insert the implant spacer 4 (as shown in FIGS. 27-28) and shift the implant spacer 4 from the insertion orientation 20 to the implanted orientation 22 (as shown in FIGS. 29-31).

As shown in FIG. 23 through 26, the insertion tool 40 includes a scissor-like configuration 114 with first and second lever arms 116 and 118 connected at an adjustable pivot connection 120. The first and second lever arms 116 and 118 include gripping end portions 122 to provide a handle for a surgeon to operate the tool 40. Implant engaging end portions 124 and 126 of the lever arms 116 and 118 are positioned opposite the gripping end portions 122. As shown, the lever arms 116 and 118 are configured such that shifting the gripping end portions 122 toward or away from one another causes a corresponding relative movement of the implant engaging end portions 124 and 126 toward or away from one another.

Figure 24:
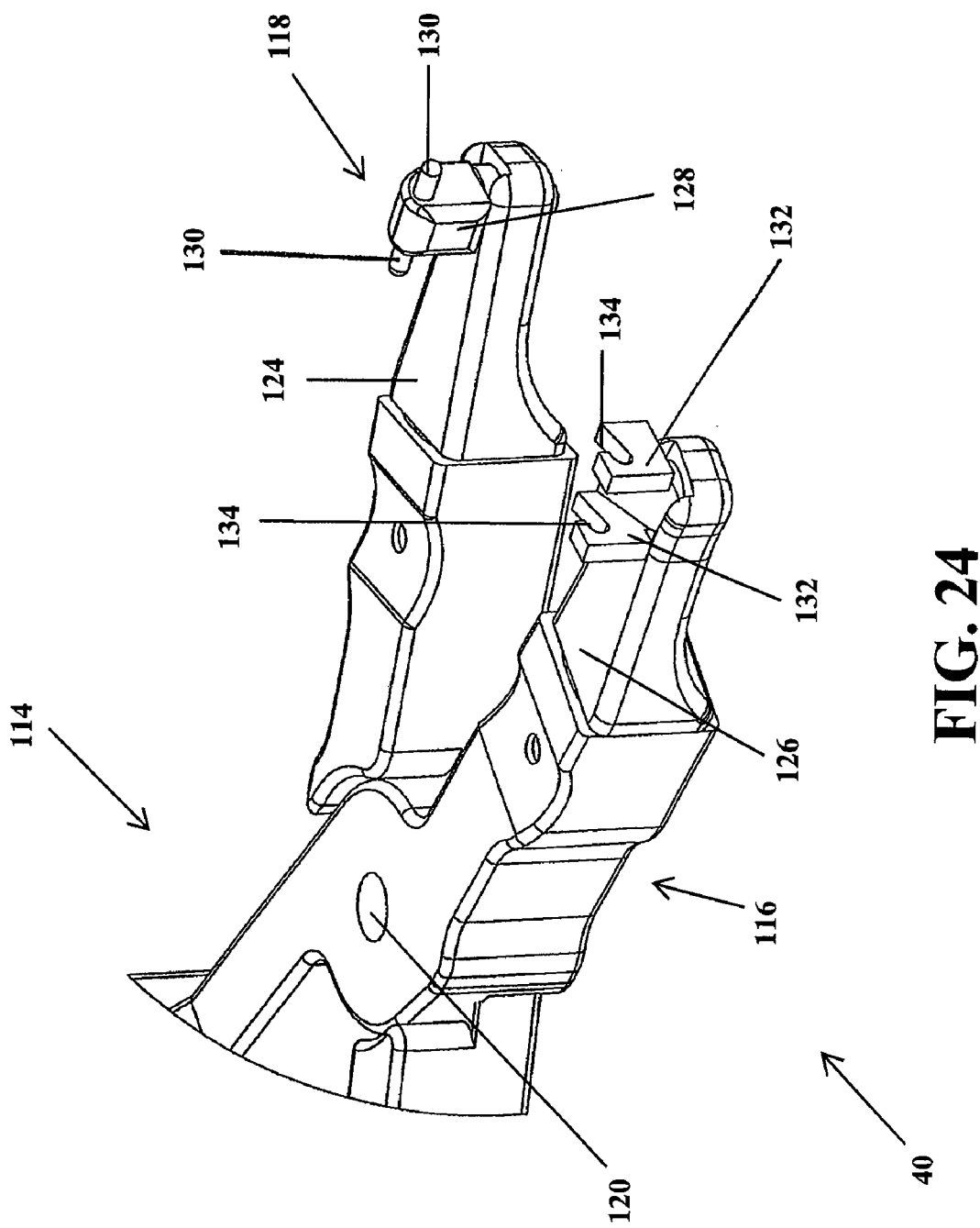
FIG. 24 is an enlarged perspective view of the insertion tool for the implant of FIG. 1 showing the first and second implant engaging portions.
Figure 25:
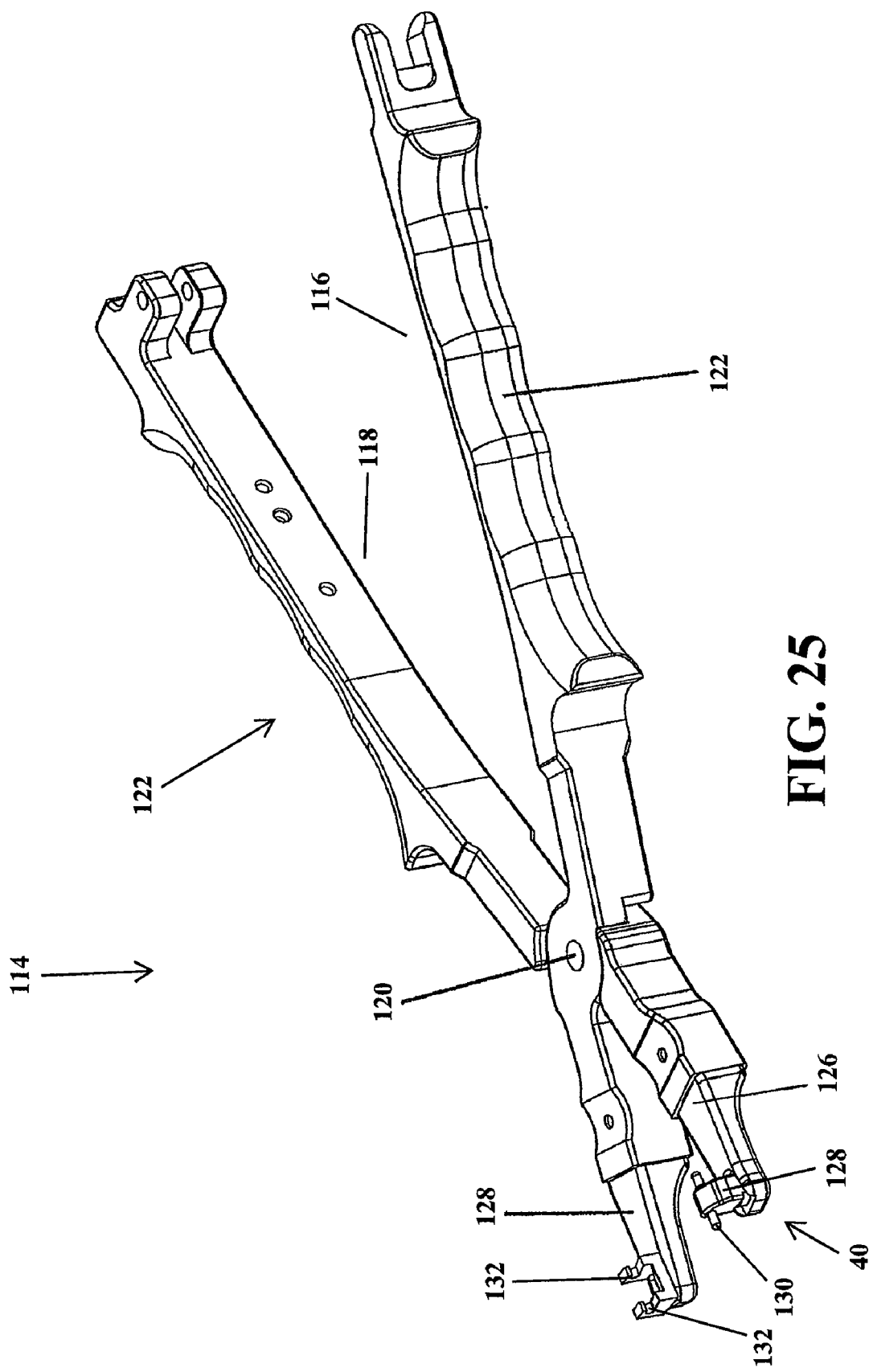
FIG. 25 is an alternative perspective view of the insertion tool for the implant of FIG. 1.
Figure 26:
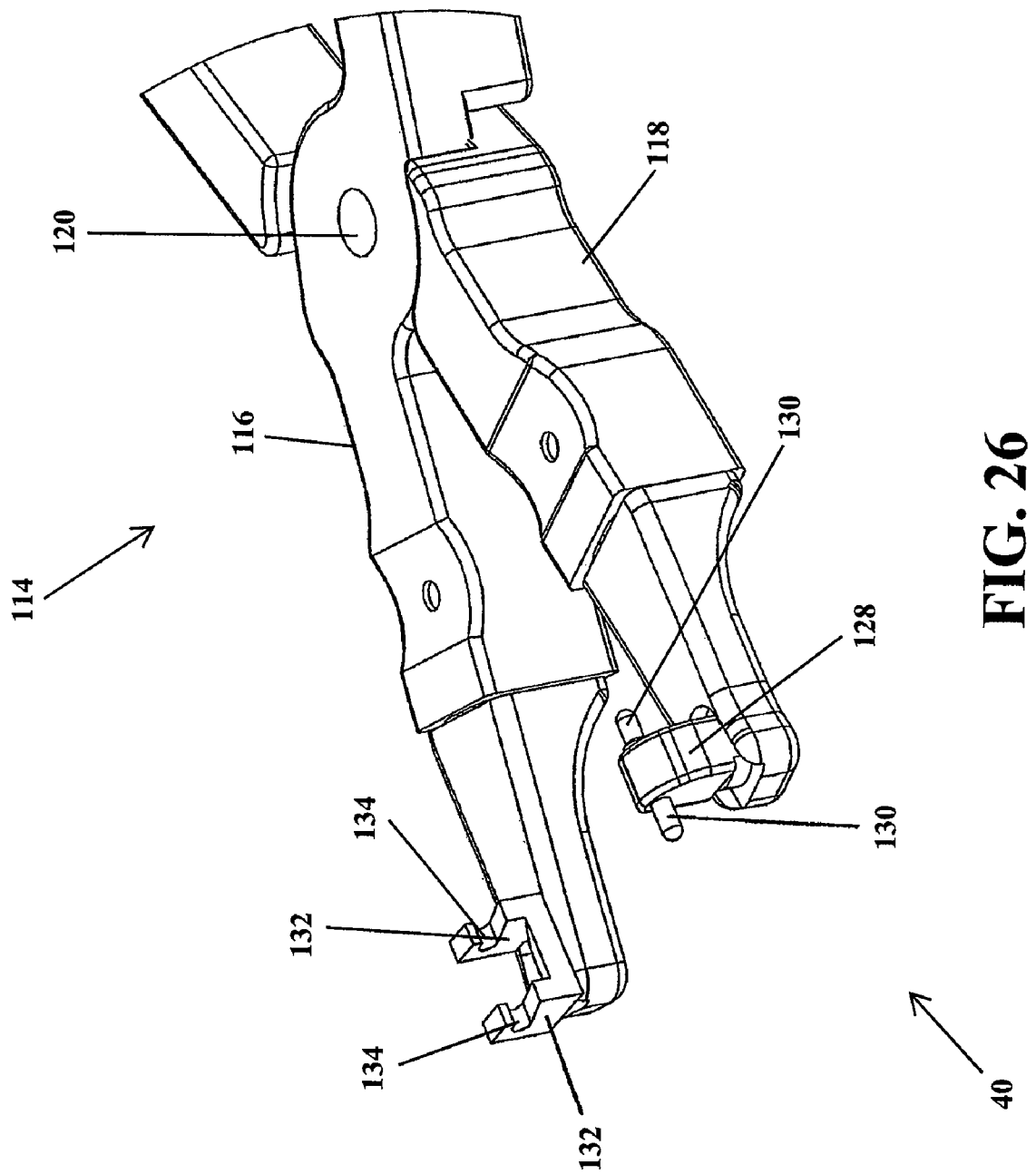
FIG. 26 is an enlarged alternative perspective view of the insertion tool for the implant of FIG. 1 showing the first and second implant engaging portions.

The implant engaging end portions 124 and 126 are configured to engage the spacer member 4, more particularly the pin head portions 56 of the linkage member 42 and hooks slots 58 of the implant member 16 to which the linkage member is not pivotably connected. As shown in FIG. 24, one implant engaging end portion 124 includes a lug 128 having a pair of bosses 130 extending outwardly therefrom. The lug 128 is configured to be received within the groove portion 46 of the implant member 16, with the bosses 130 configured to be received in the hooks slots 58 of the implant member 16. Further, the other implant engaging end portion 126 includes a pair of spaced brackets 132 positioned to receive the linkage therebetween. The spaced brackets 132 further include slots 134 formed therein corresponding to and configured to receive the pin head portions 56 therein.

With the implant engaging end portions 124 and 126 engaged with the spacer member 4 in the insertion orientation 20, the leading arms 24 of the implant members 14 and 16 are shifted between the adjacent spinous processes 6 and 8. Once positioned in the desired location, the gripping end portions 122 are shifted toward one another, causing a corresponding movement of the implant engaging end portions 124 and 126, resulting in the implant members 14 and 16 being pivoted to the implanted orientation 22. After the implant members 14 and 16 are in the implanted orientation 22, the tool 40 is disengaged therefrom and the spacer member 4 can be secured in the implanted orientation 22 by shifting the linkage 42 into engagement with the hooks slots 58 and positioning, tensioning and securing the cable member 12.

Figure 33:
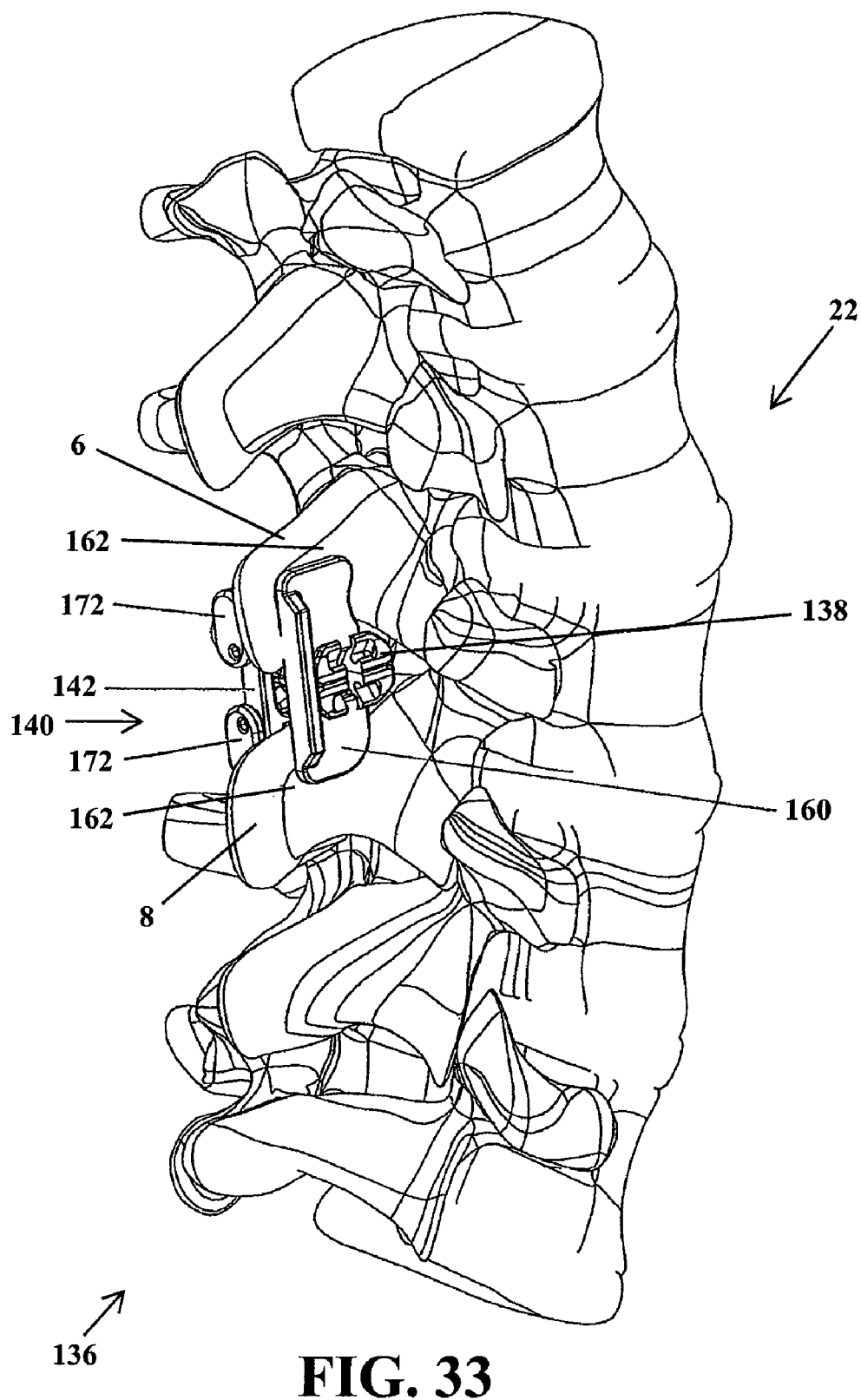
FIG. 33 is a posterior aspect prospective view of an implant in accordance with another aspect of the invention showing the implant secured between two adjacent spinous processes.
Figure 34:
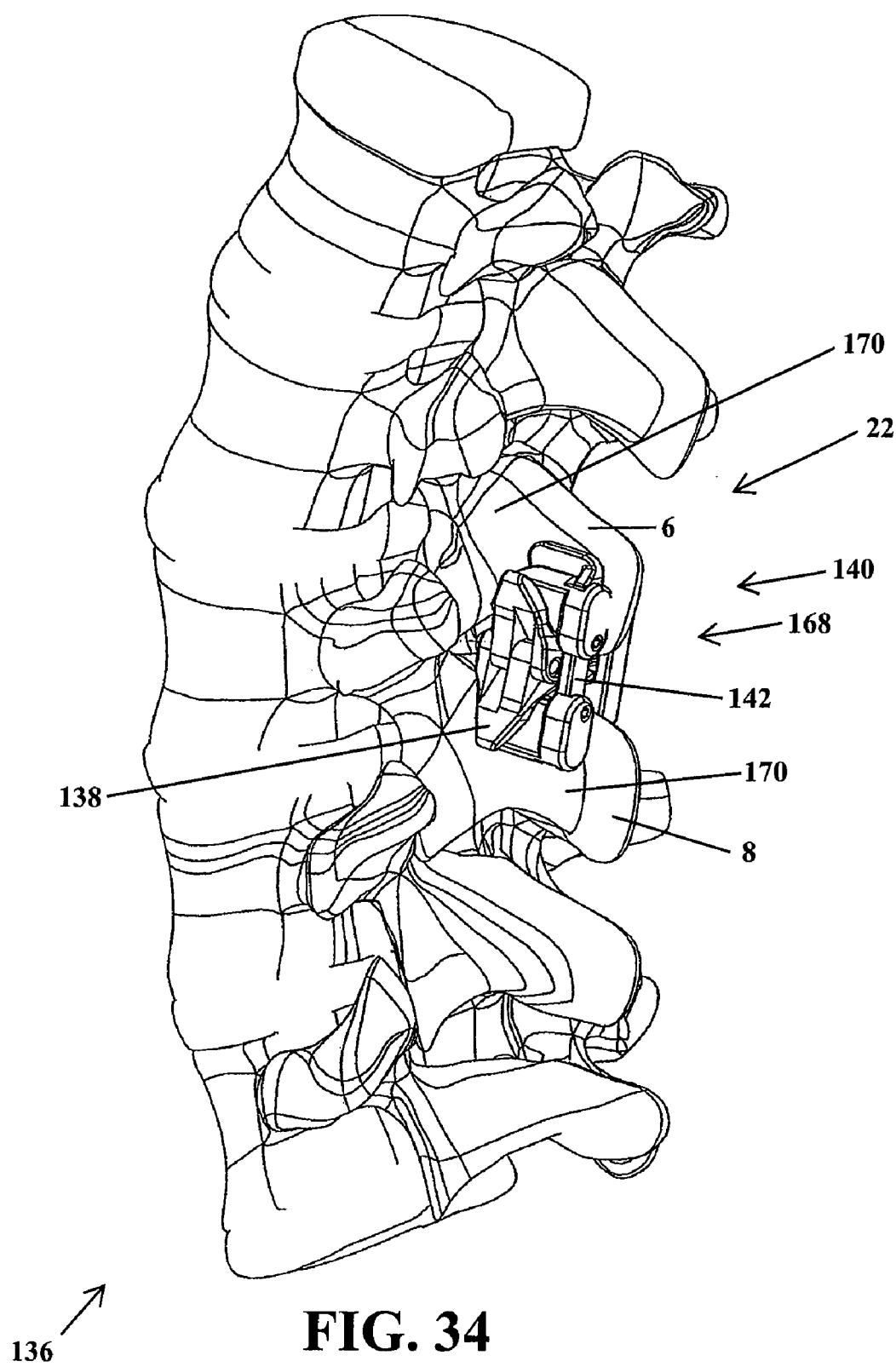
FIG. 34 is a posterior aspect prospective view of the implant of FIG. 33.

An implant 136 in accordance with another aspect of the invention is shown in FIGS. 33-41. As shown in FIG. 33, the implant device 136 includes an interspinous spacer 138 configured to be positioned between adjacent vertebrae 6 and 8. While other interspinous spacers can be utilized, the interspinous spacer 138 as shown in FIGS. 33-41 is similar to the interspinous spacer 4 described above, with any differences discussed below.

Figure 35:
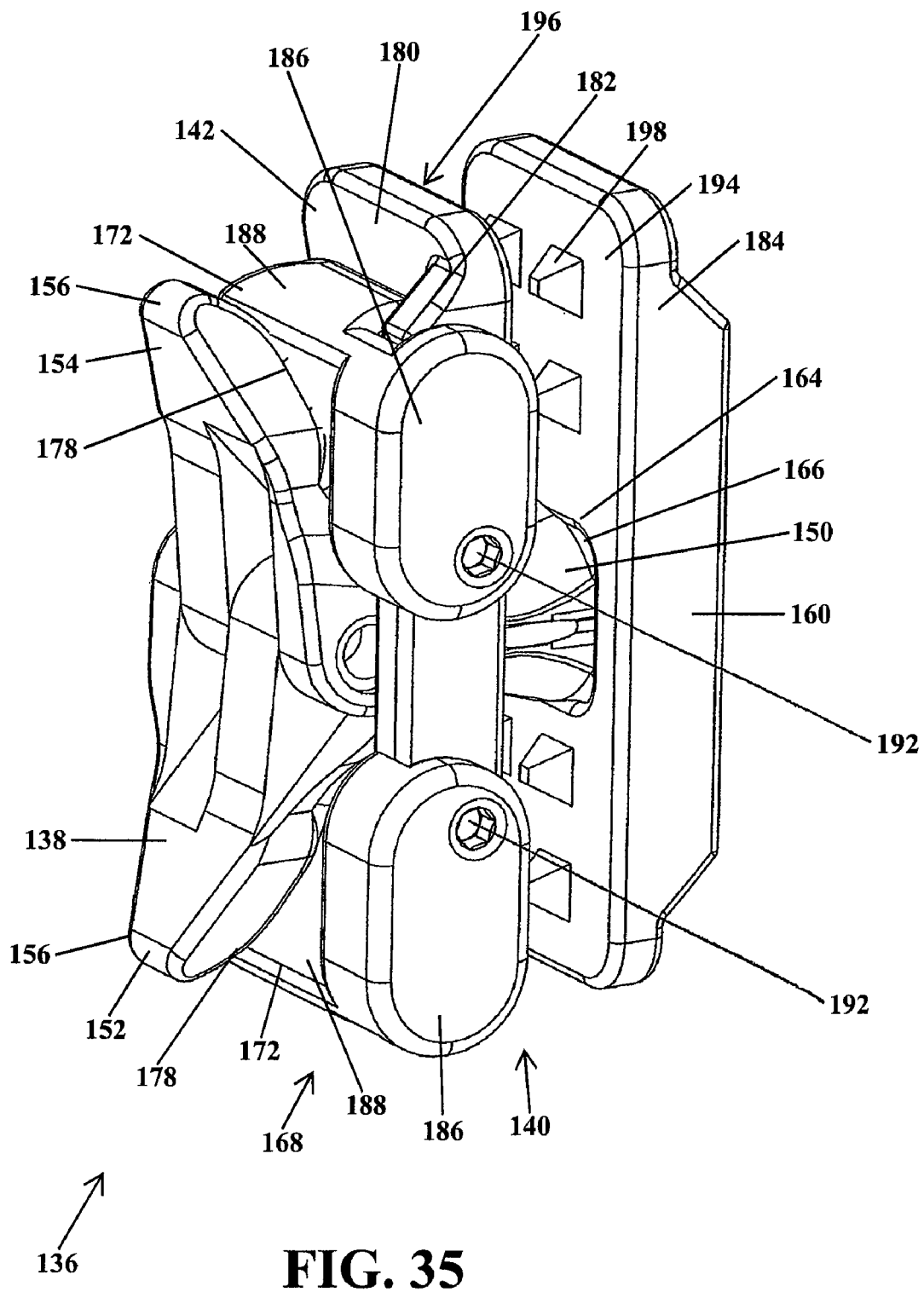
FIG. 35 is a perspective view of the implant of FIG. 33 showing the interspinous insertion member and spinous processes engaging walls.
Figure 36:
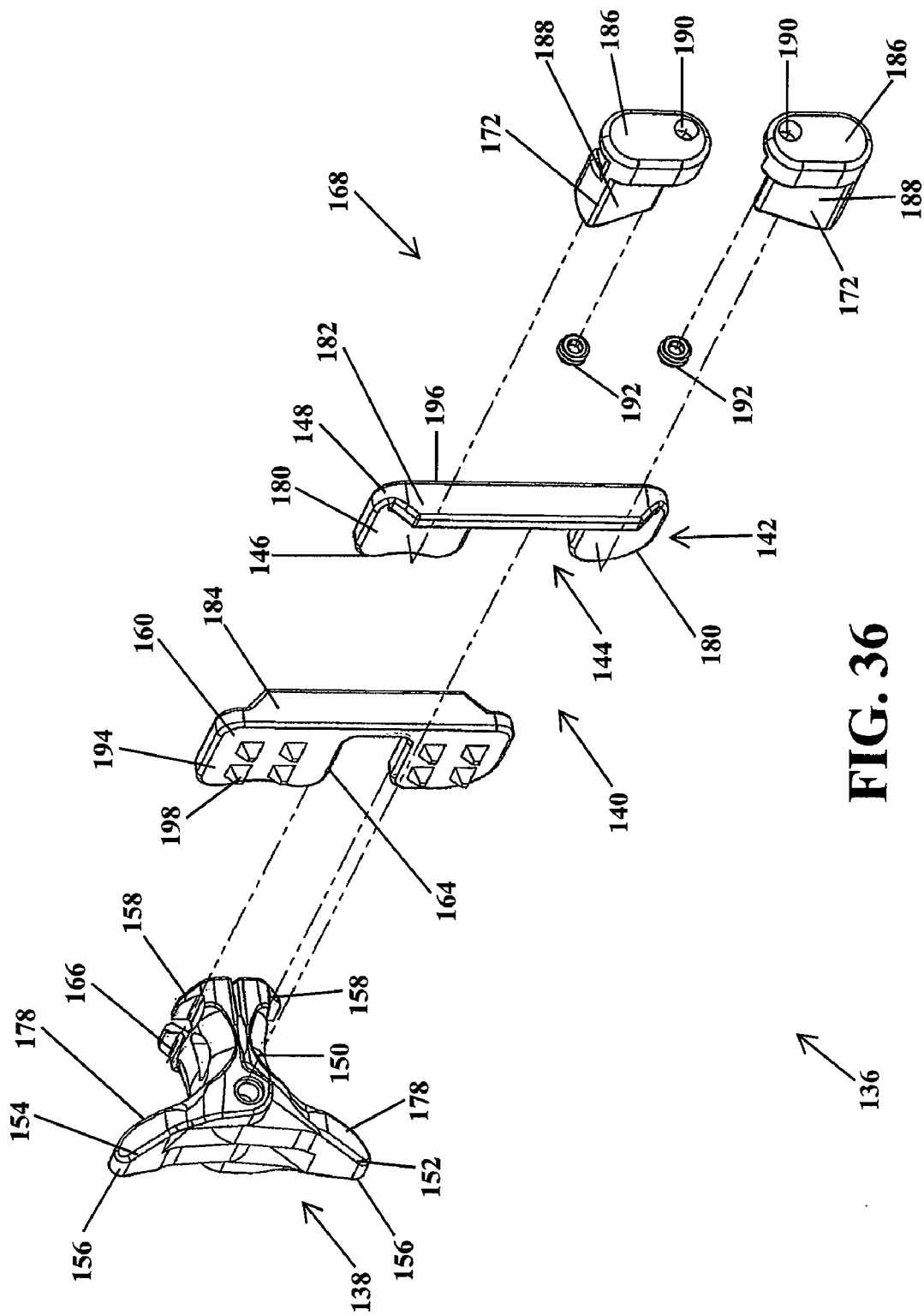
FIG. 36 is an exploded view of the implant of FIG. 33.
Figure 37:
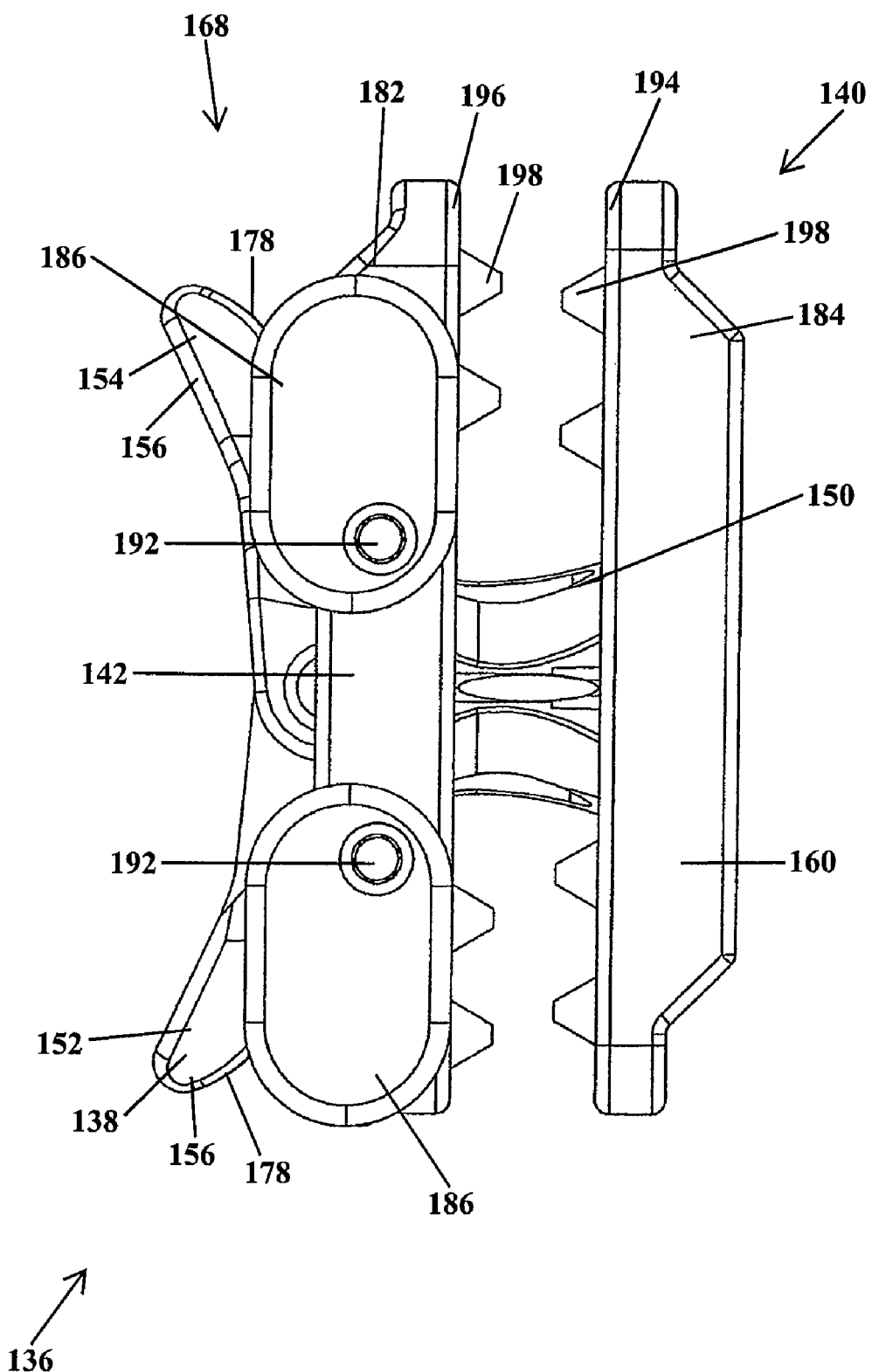
FIG. 37 is a front elevational view of the implant of FIG. 33 showing a space between the engaging walls for the spinous processes to be secured.
Figure 38:
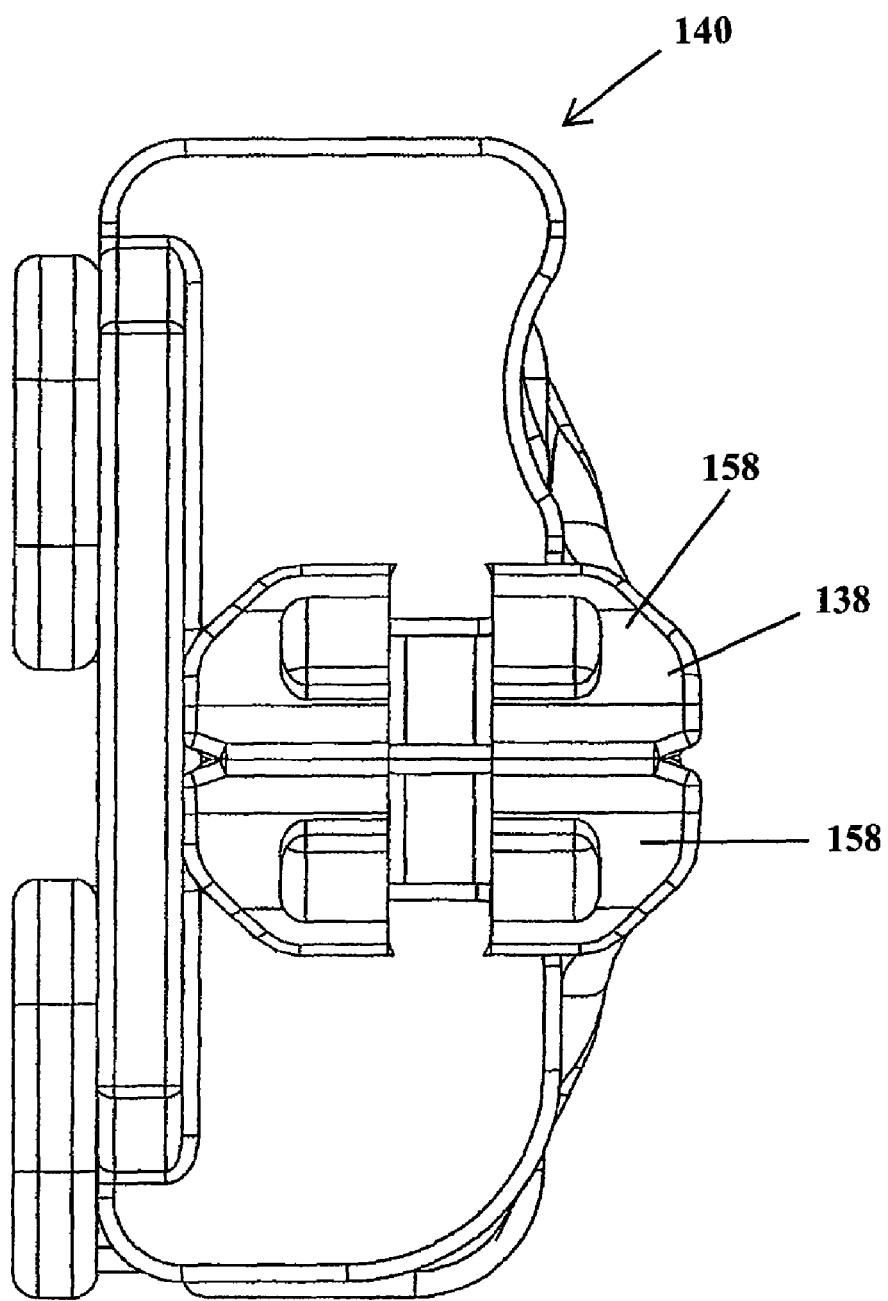
FIG. 38 is a right side elevational view of the implant of FIG. 33.
Figure 39:
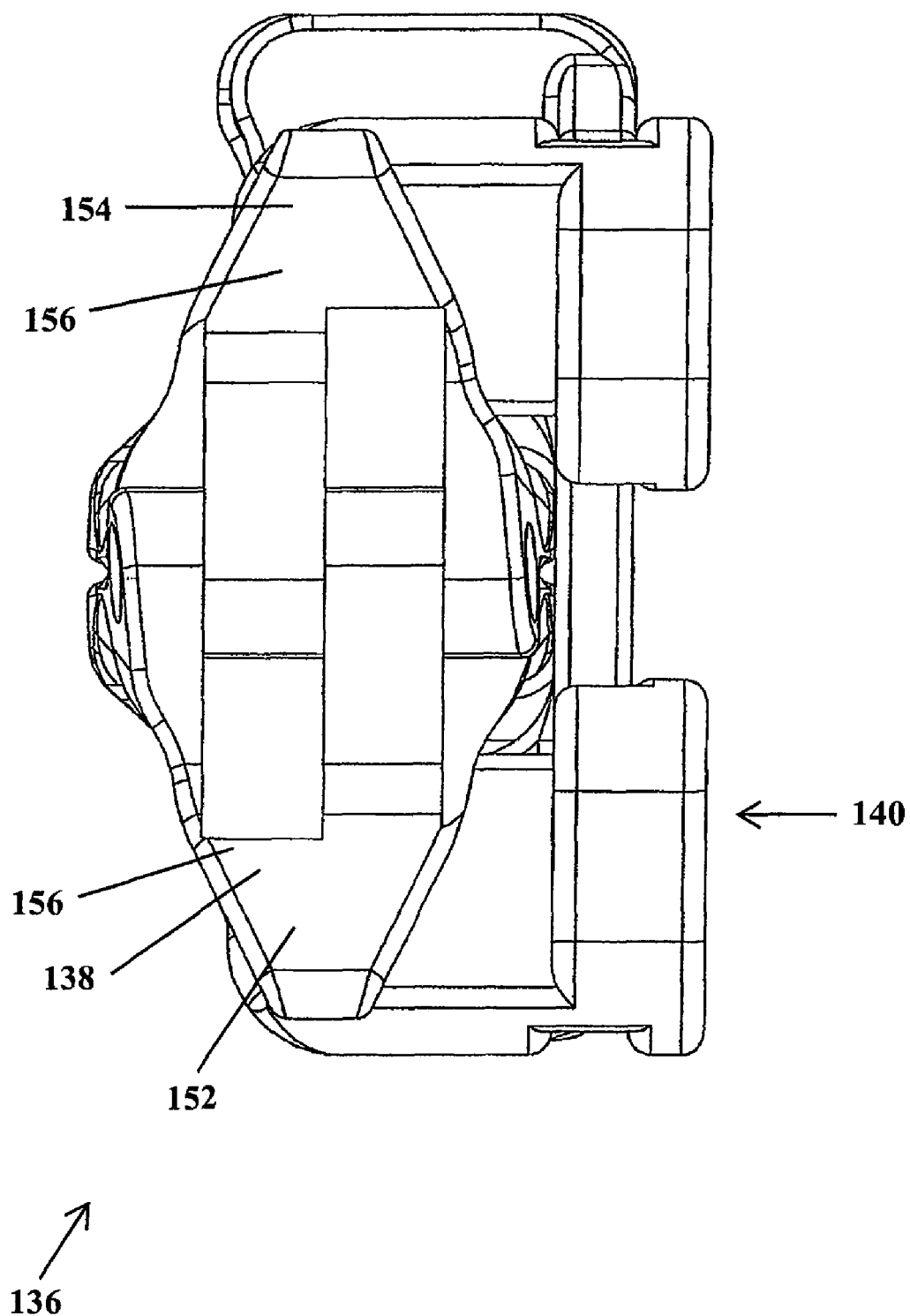
FIG. 39 is a left side elevational view of the implant of FIG. 33.
Figure 40:
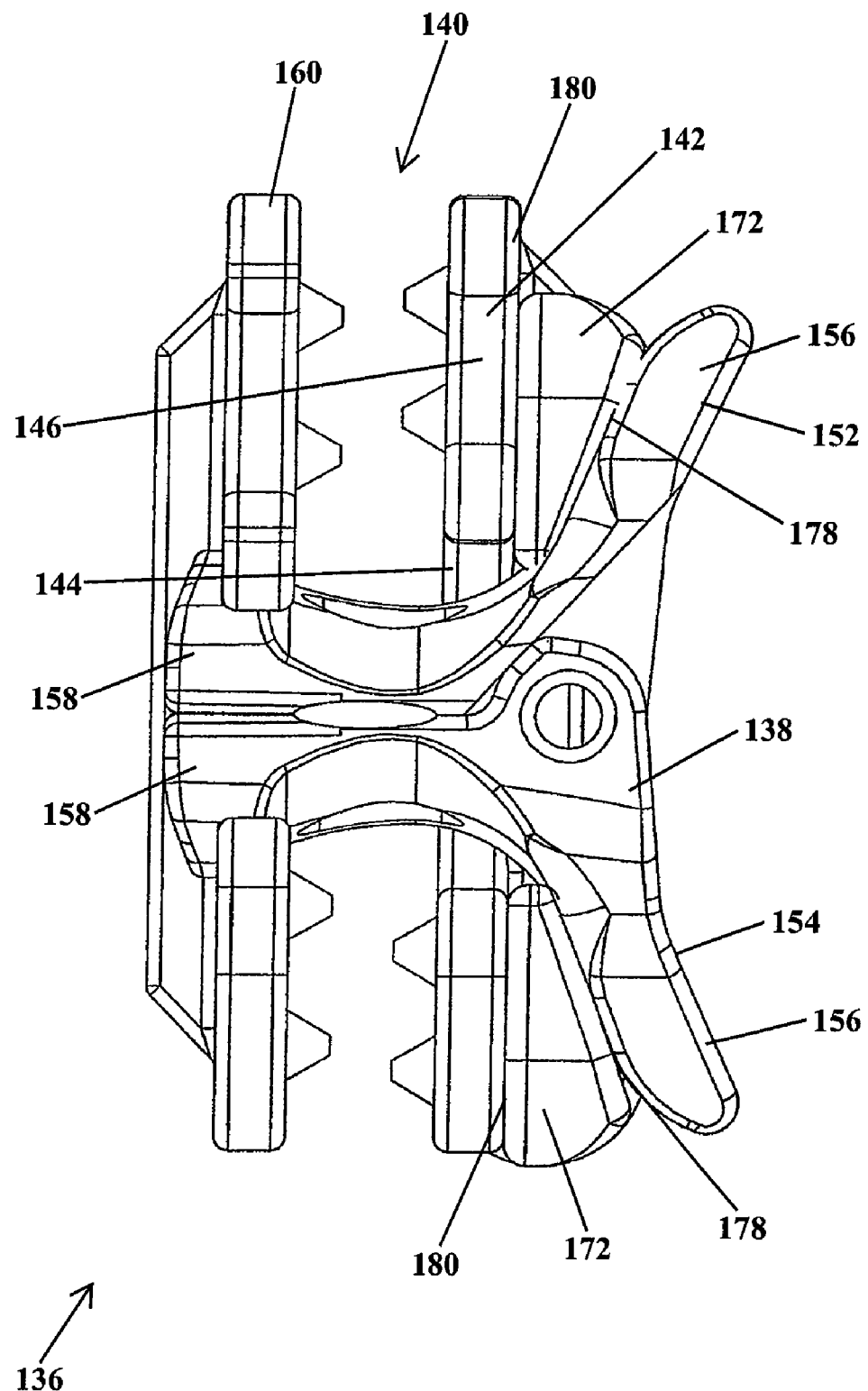
FIG. 40 is a back elevational view of the implant of FIG. 33 showing the engaging walls extending about the seat of the interspinous insertion member.
Figure 41:
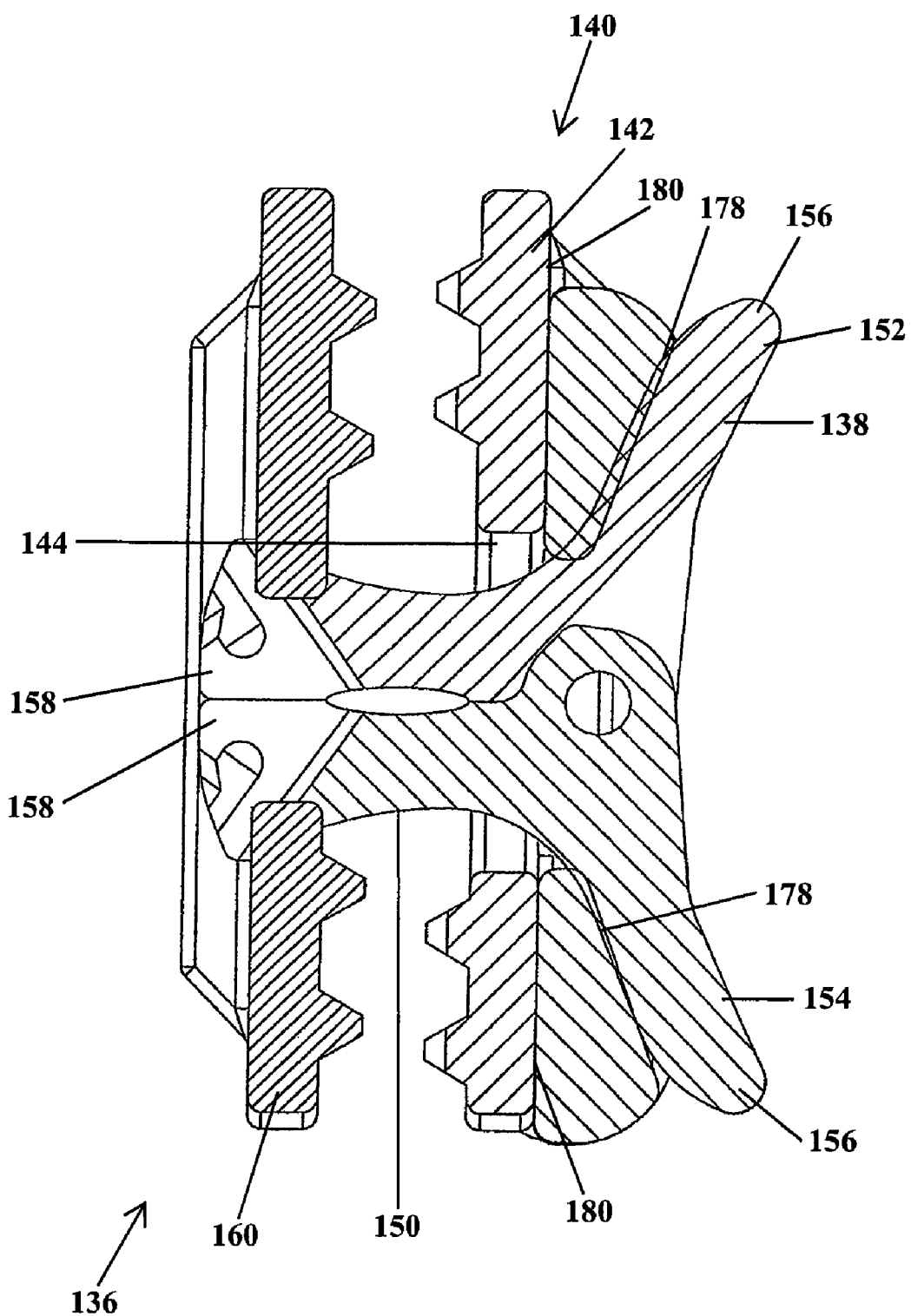
FIG. 41 is a back sectional view of the implant of FIG. 33 showing the stationary engaging wall being secured in a slot of the insertion member seat.

As shown in FIGS. 35-37, a locking mechanism 140 of the implant device 136 includes a plate member 142. The plate member 142 includes a cut-out opening 144 extending from one longitudinal side 146 of the plate member 142 toward an opposite longitudinal side 148. The cut-out opening 144 includes interior upper and lower edges spaced from one another a distance sufficient to receive the seat portions 150 of the upper and lower implant members 152 and 154 of the interspinous member 138 therein with the implant members 152 and 154 in the implanted orientation 22. Further, the cut-out opening 144 is configured to permit the plate member 142 to shift along the seat portion 150 between the insertion arms 156 and tool engagement arms 158 of the implant members 152 and 154 into tight engagement with the upper and lower spinous processes.

As shown in FIGS. 35-37, the implant device 136 can further include a second plate member 160 for being positioned adjacent a side 162 of the spinous processes 6 and 8 opposite the first plate member 142. The second plate member 160 includes a cut-out opening 164 formed therein configured to snugly receive a grooved seat portion 166 of the implant members 152 and 154 therein. The size and configuration of the grooved seat portion 166 is selected to minimize the slot or cut-out portion 164 of the second plate member 160, thereby increasing the available plate area to engage the adjacent spinous processes 6 and 8. As such, the second plate member 160 is secured along the groove 166 and restricts movement of the second plate member 160 along the seat 150 of the implant members 152 and 154. Further, the second plate member 160 acts to lock the implant members 152 and 154 in the implanted orientation 22 and resist pivoting of the implant members 152 and 154 from the implanted orientation 22.

The implant device 136 further includes an adjustment mechanism 168 for shifting the plate member 142 along the implant member seats 150 after the seats 150 have been received in the plate member cut-out opening 144. The adjustment mechanism 168 is configured to shift the plate 142 relative to the implant members 152 and 154 so that the plate member 142 engages a side 170 of the spinous processes 6 and 8. Further, the implant members 152 and 154 may be shifted between the spinous processes 6 and 8 so that the adjacent spinous processes 6 and 8 are engaged on either side 162 and 170 by plate portions 142 and 160, the second plate 160 portion being secured in the seat groove 166 of the implant members 152 and 154. By shifting the plate 142 independently of the implant members 152 and 154 the plates 142 and 160 can be positioned according to the size and geometry of the spinous processes 6 and 8 to ensure a secure engagement therebetween.

As shown in FIGS. 35-37, the adjustment mechanism 168 of the implant device 136 is a wedge member portion 172, however other adjustment mechanisms are contemplated, such as a ratcheted connection between the cut-out opening 144 and the seat portions 150 or a ratcheted connection between a wedge portion 172 and either the plate 142 or a facing surface of the implant spacer member.

As shown in FIGS. 35-37, in the implanted orientation the implant spacer members 152 and 154 include an arm portion 174 and 176 extending from each of the upper and lower implant members 152 and 154. The arms 174 and 176 each include a surface portion 178 facing the plate member 142. As shown in FIG. 36, the facing surface 178 of the arms 174 and 176 may be inclined relative to the plate member facing surface 180. As the wedge 172 shifted into the space between the facing surface 180 of the plate member 142 and the facing surface portions 178 of the arms 174 and 176, the increased width of the wedge 172 causes the plate member 142 and arms 174 and 176 to be urged away from one another, resulting in the plate member 142 being shifted toward the spinous processes 6 and 8. As discussed above, inserting the wedge 172 can further cause the implant members 152 and 154 to be shifted between the spinous processes 6 and 8 until the second plate member 160, which is secured on the seat groove portion 166 of the implant members 152 and 154 and shifts with the implant members 152 and 154, engages the spinous processes 6 and 8 opposite the first plate member 142.

As shown in FIGS. 35-37, the plates 142 and 160 can include transverse shelf portions 182 and 184 extending from the plates 142 and 160. The shelf portions 182 and 184 are configured to aid in insertion of the plates 142 and 160. Further, plate shelf 182 can be configured to secure the wedge portion 172 in the desired location. As shown in FIGS. 35-37, the wedge portion 172 can include a securing portion 186 extending from the wedge body 188 and extending about the plate shelf 182 and in contact with an outer surface 188 of the plate shelf 182. The securing portion 186 further includes an aperture 190 therein for securing the wedge 172 to the plate 142. More particularly, the aperture 190 is threaded and a set screw 192 is threaded into the aperture 190 and into contact with the outer surface 188 of the plate shelf 182, thereby securing the wedge 172 in the desired location relative to the plate 142.

As shown in FIGS. 35-37, the adjustment mechanism 168 preferably includes a pair of wedges 172, one positioned on either side of the generally central slot 144. As a result, the orientation of the plate member 142 can be adjusted to accommodate the spinal geometries of the insertion location, such as by inserting one of the wedges 172 between the plate 142 and the facing surface 180 further than the other wedge 172.

The plate member surfaces 194 and 196 facing the spinous processes 6 and 8 can be configured to reduce or resist movement of the spinous processes 6 and 8 relative to the plate members 142 and 160 engaged therewith. In one form, the plate members 142 and 160 can include a roughed surface to provide a frictional engagement with the spinous processes. Alternatively, as shown in FIGS. 36 and 37, the facing surfaces 194 and 196 can include projections 198 extending from the surfaces 194 and 196 to engage the spinous processes 6 and 8. These projections 198 are configured to resist movement of the spinous processes 6 and 8 without compromising the structural integrity of the bone.

Figure 42:
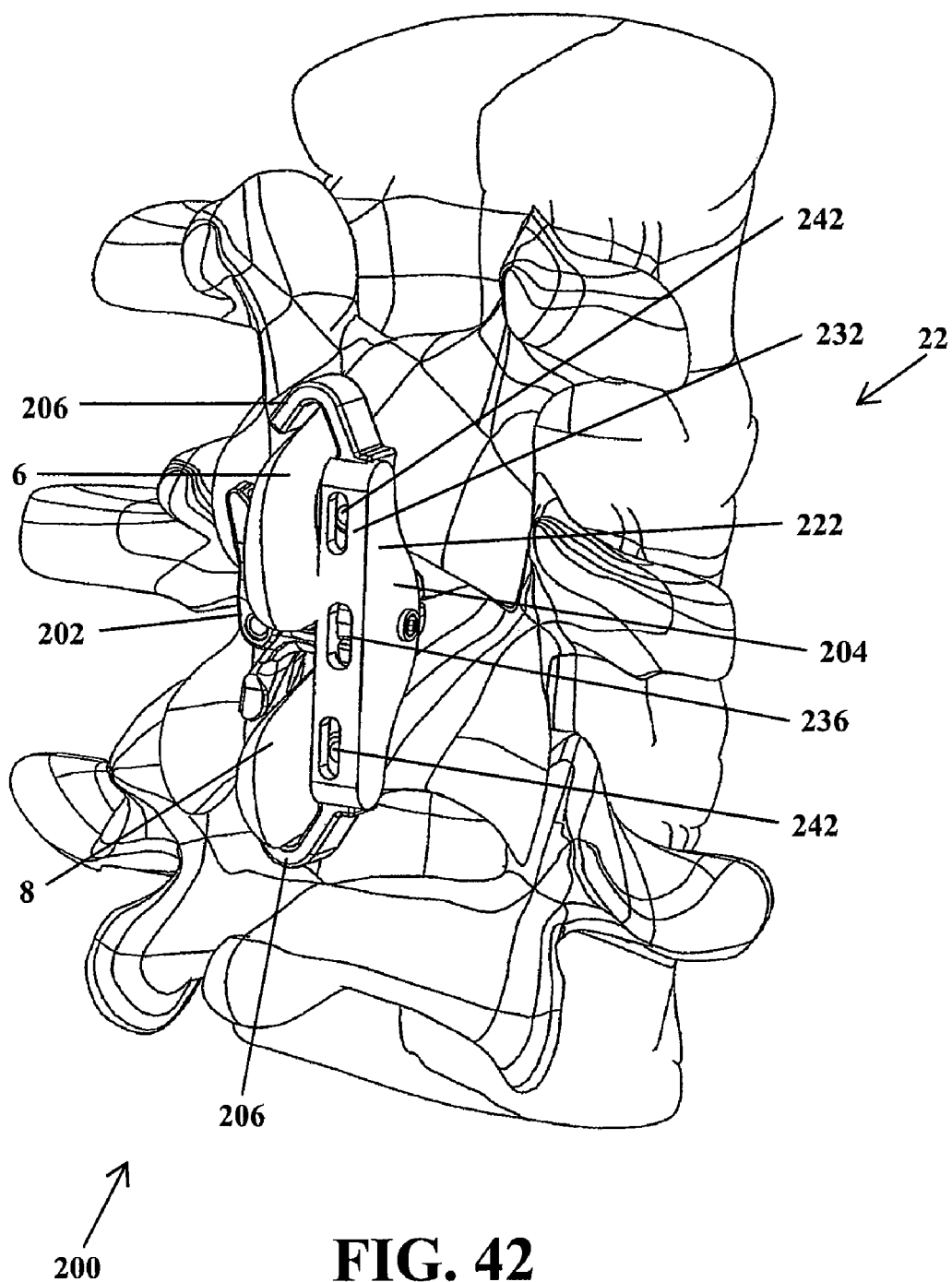
FIG. 42 is a posterior aspect prospective view of an implant in accordance with another aspect of the invention.
Figure 43:
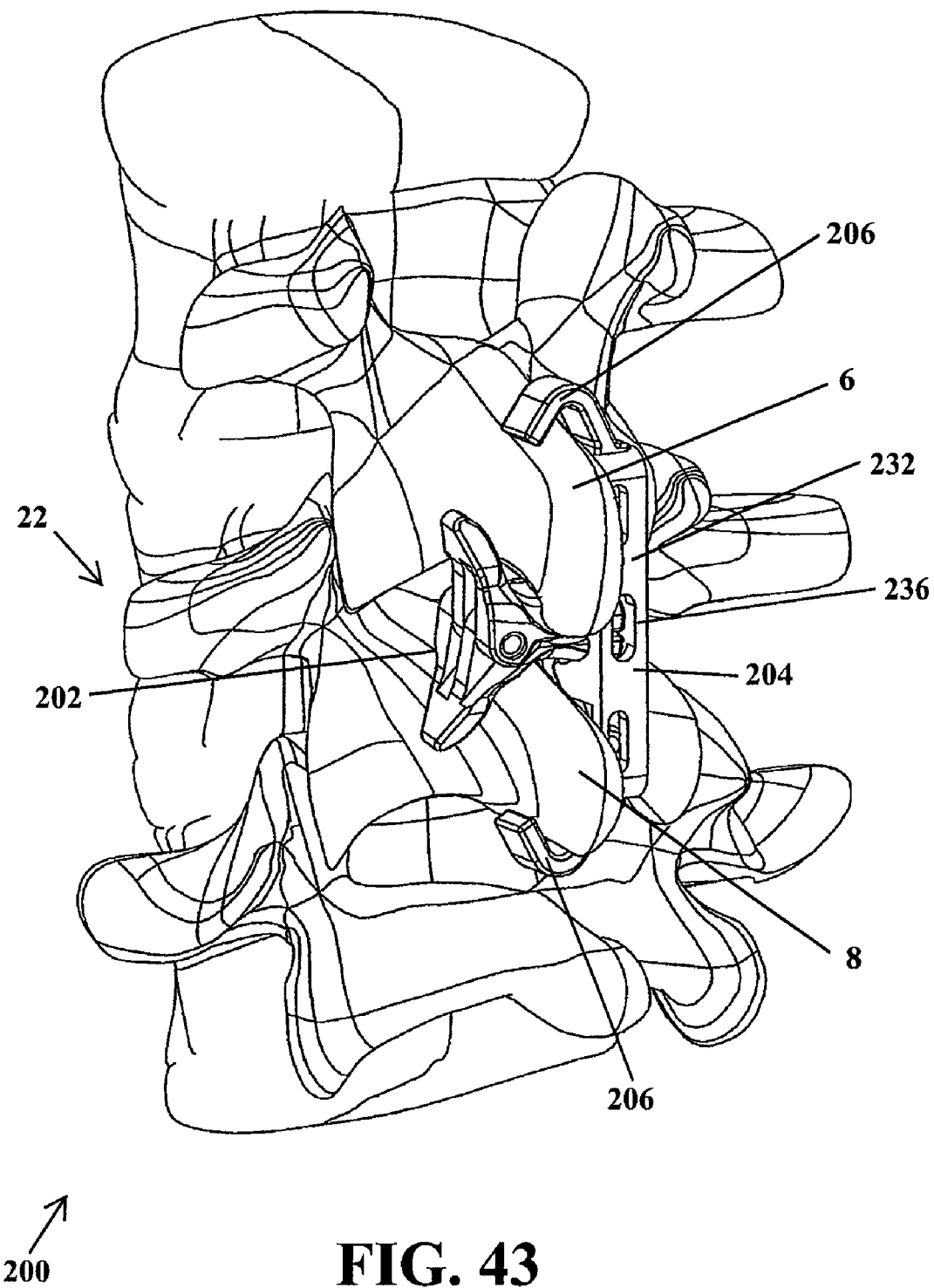
FIG. 43 is a posterior aspect prospective view of the implant of FIG. 42 showing the hooks engaging the upper and lower surfaces of the spinous processes.

An implant 200 in accordance with another aspect of the invention is shown in FIGS. 42-54. As shown in FIGS. 42-43, the implant device 200 includes an interspinous spacer 202 configured to be positioned between adjacent vertebrae 6 and 8. While other interspinous spacers can be utilized, the interspinous spacer 202 as shown in FIGS. 74-86 is similar to the interspinous spacers described above, with any differences discussed below.

As shown in FIGS. 42-46, the implant device 200 includes a spanning or sheath member 204 configured to engage the interspinous implant member 202 and extend alongside the adjacent spinous processes 6 and 8. The sheath member 204 includes a pair of hook connection members 206, one extending from either end 208 and 210 of the sheath member 204 for engaging a spinous process 6 and 8. The connection members 206 include hooks 212 configured to extend about and engage one of the upper and lower surfaces 92 and 96 of the adjacent spinous processes 6 and 8 generally opposite to the corresponding upper and lower seat portions 218 and secure the spinous processes 6 and 8 in engagement with the interspinous insertion member 202.

Figure 45:
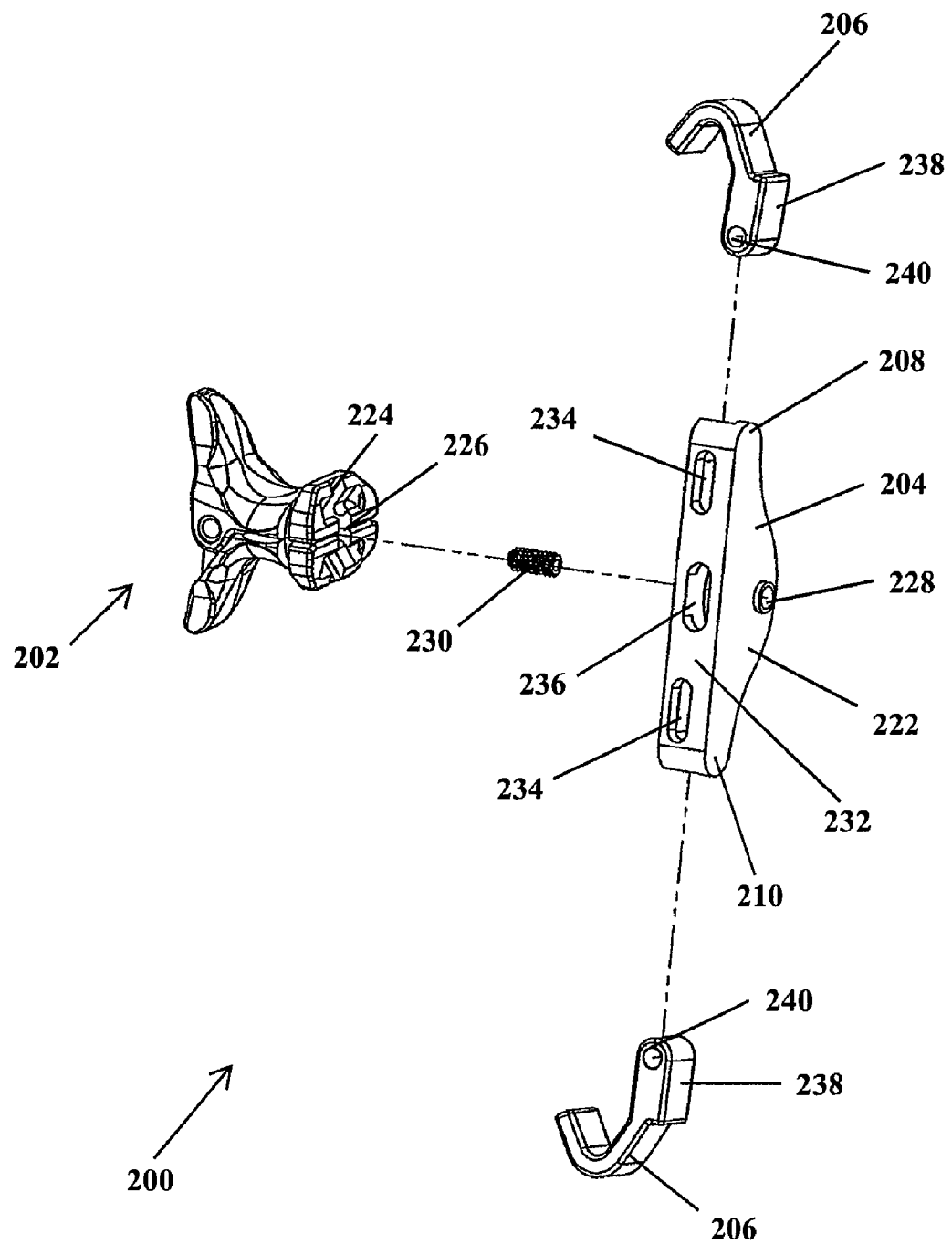
FIG. 45 is an exploded view of the implant of FIG. 42 showing the set screw for connecting the plate to the interspinous implant member.
Figure 49:
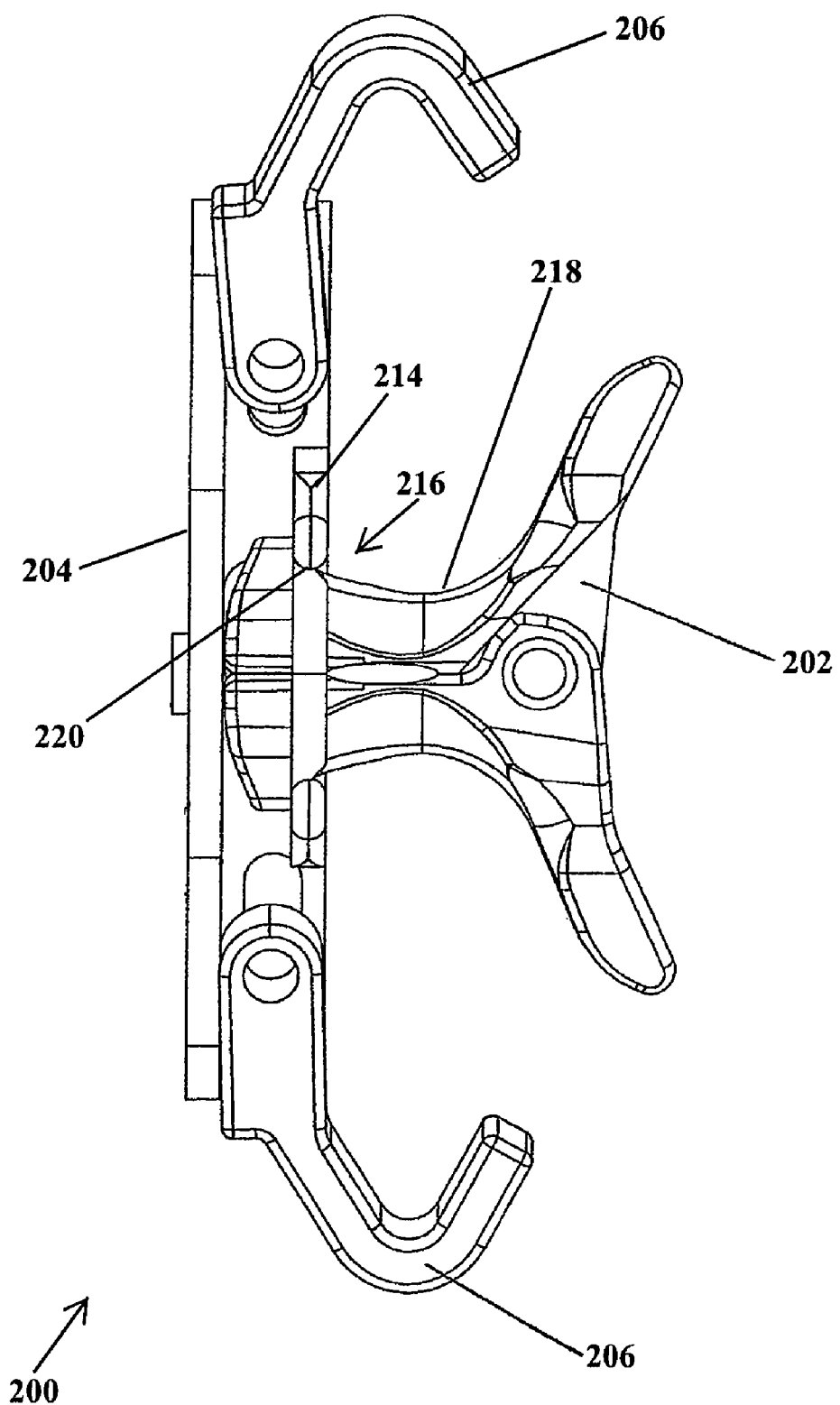
FIG. 49 is a back side view of the implant of FIG. 42 showing the plate positioned about the seat of the implant member and arms of the implant member disposed within a chamber of the plate.
Figure 50:
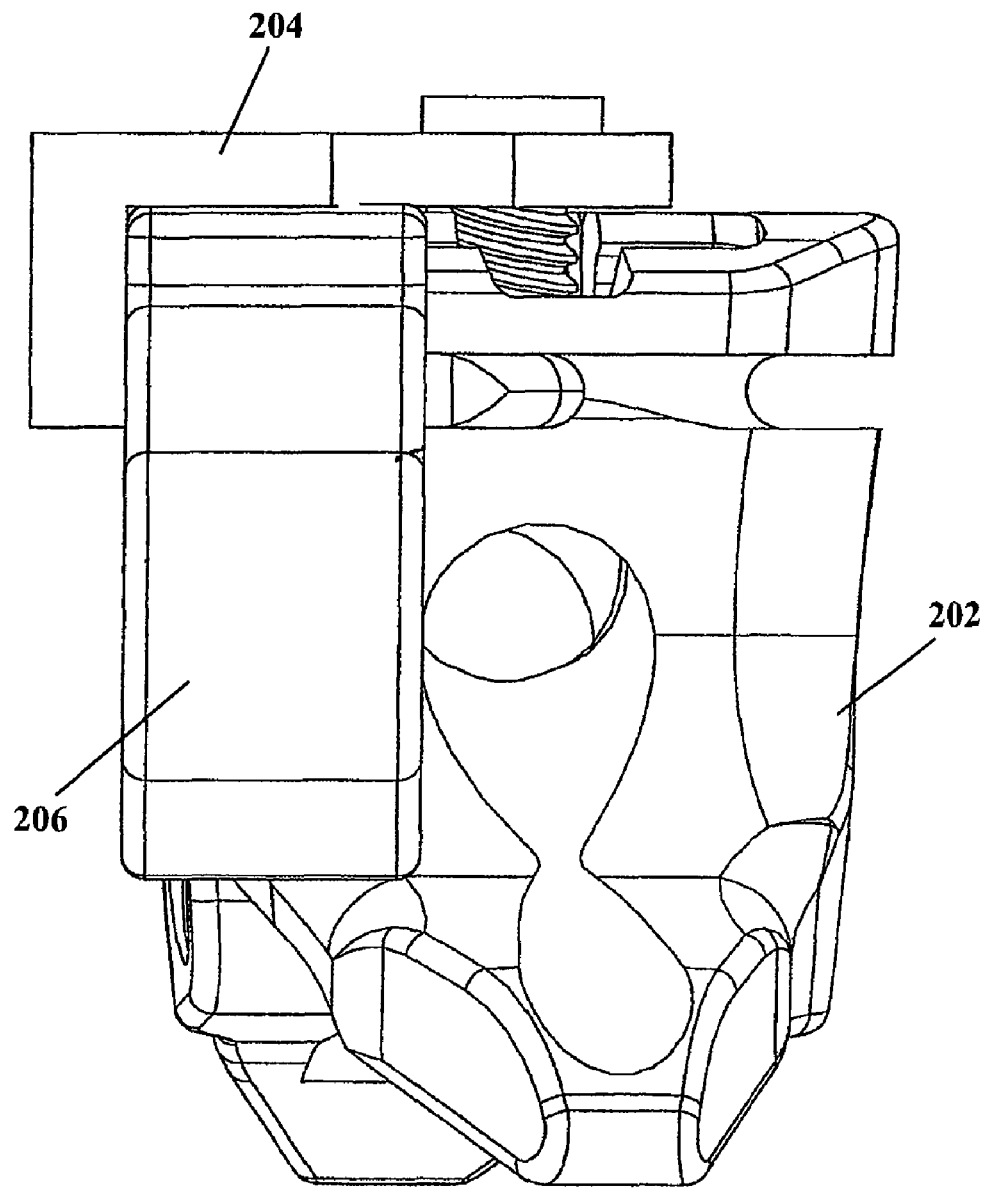
FIG. 50 is a bottom view of the implant of FIG. 42.
Figure 51:
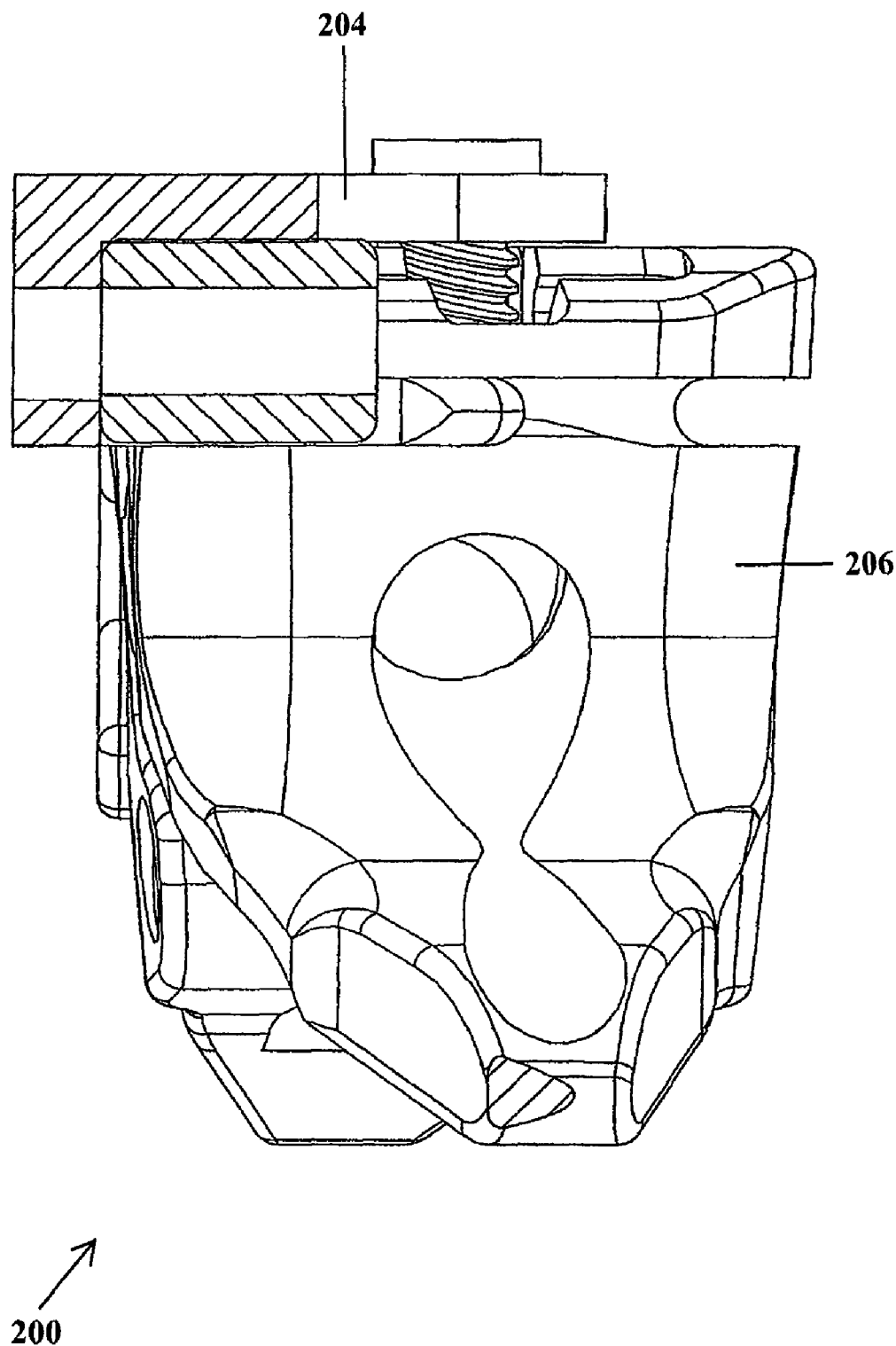
FIG. 51 is a bottom sectional view of the implant of FIG. 42.
Figure 52:
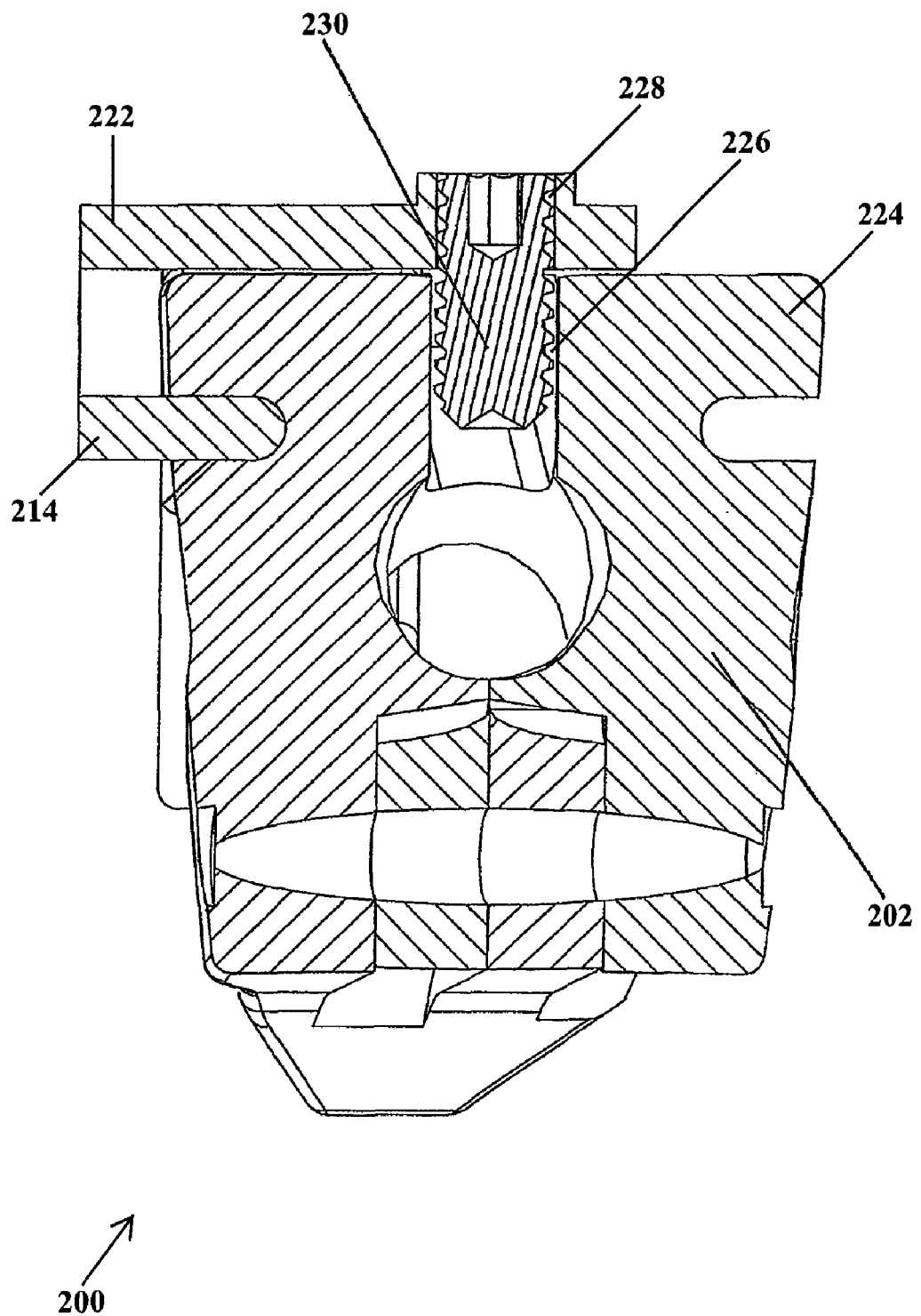
FIG. 52 is a bottom sectional view of the implant of FIG. 42 showing the set screw extending from the plate into the interspinous member.
Figure 53:
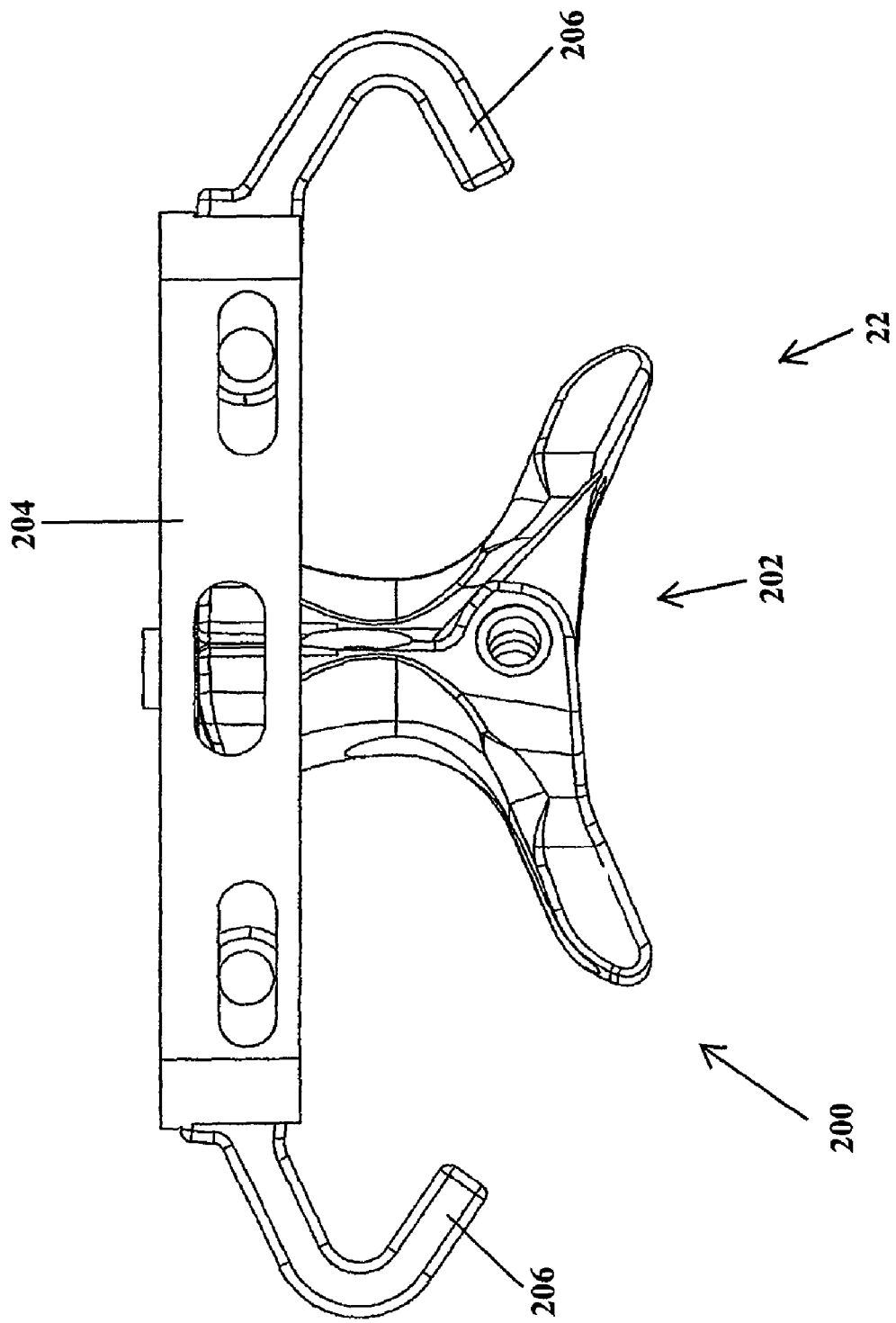
FIG. 53 is a front view of the implant of FIG. 42.
Figure 54:
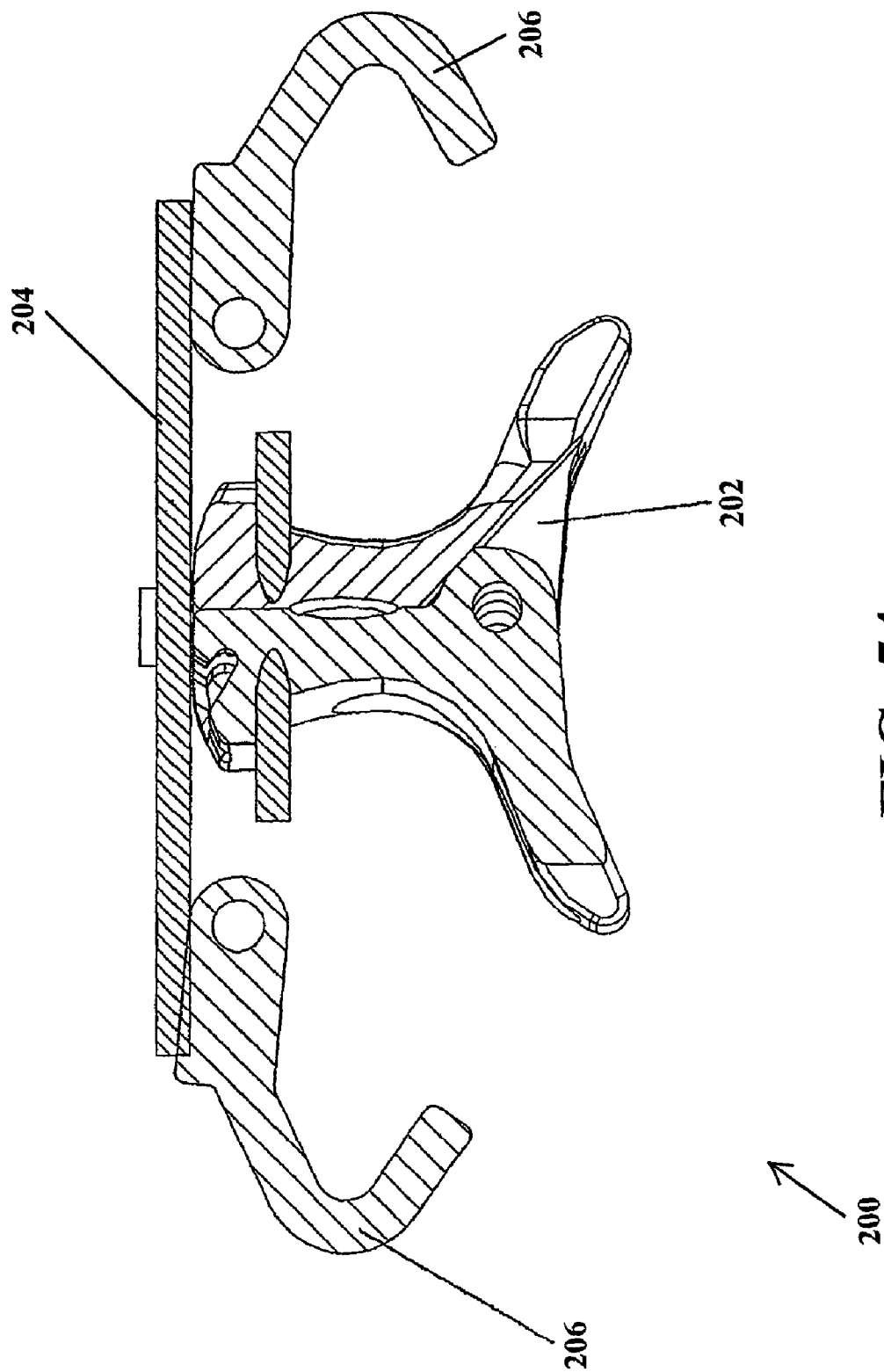
FIG. 54 is a front sectional view of the implant member of FIG. 42.

As shown in FIGS. 43 and 49, the sheath member 204 includes an inner wall 214 positioned adjacent to and extending along the adjacent spinous processes 6 and 8. The inner wall 214 includes a slot 216 opening configured to extend about the seat portion 218 of the interspinous insertion member 202. As shown in FIGS. 45 and 49, the seat 218 of the interspinous insertion member 202 can include a groove 220 for guiding the sheath member 204 to the appropriate insertion location. The size and configuration of the wall slot opening 216 and the insertion member seat groove 220 are predetermined to secure or lock the insertion member 202 in the implanted orientation 22 as the insertion member seat 218 is received in the wall slot opening 216. Further, the size and configuration of the grooved seat portion 220 are selected to minimize the slot or cut-out portion 216 of the sheath member 204, thereby increasing the available plate area to engage the adjacent spinous processes 6 and 8.

Figure 44:
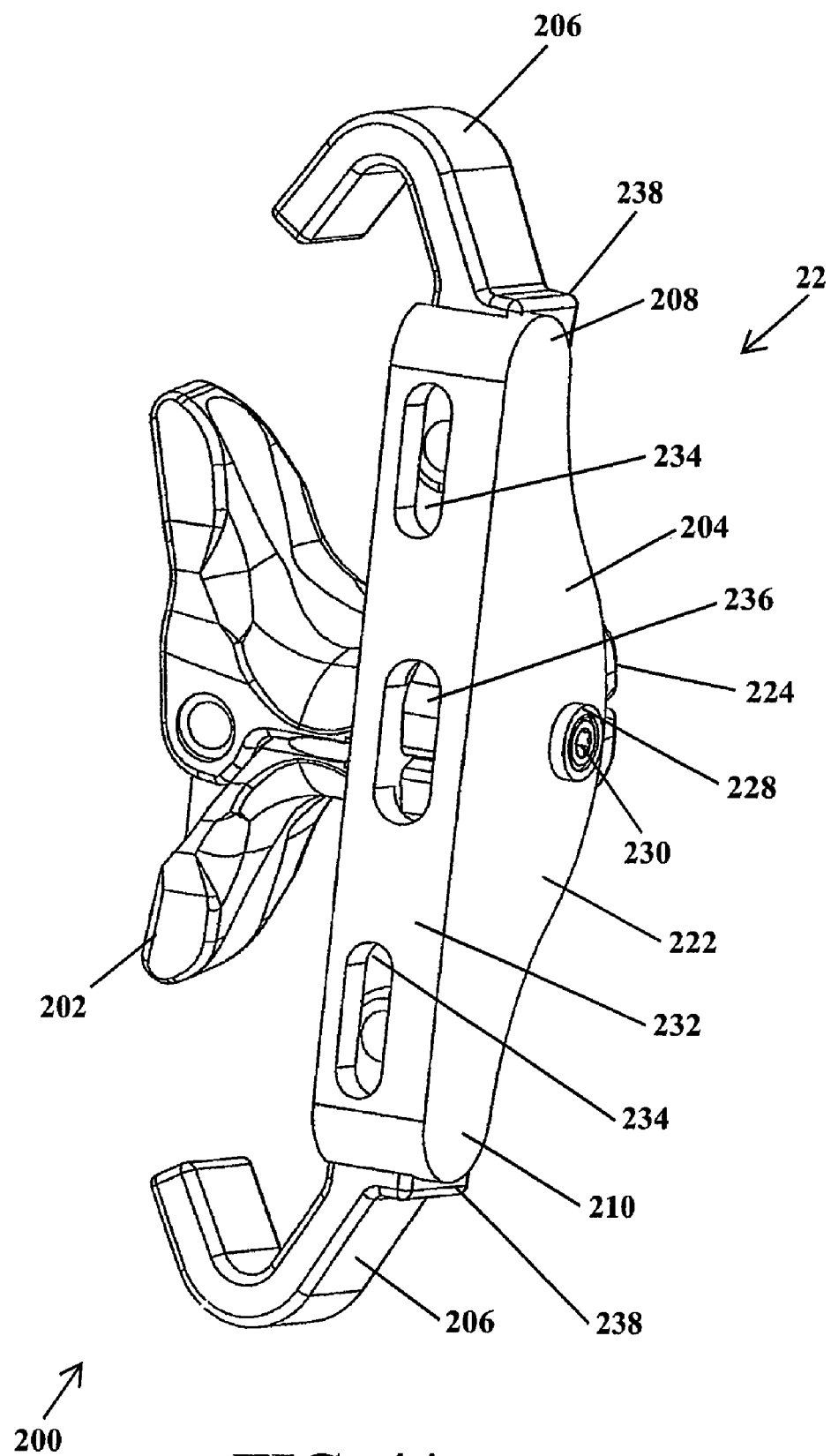
FIG. 44 is a perspective view of the implant of FIG. 42.

An outer sheath wall 222 is spaced from the inner wall 214 and extends generally parallel to the inner wall 214. As shown in FIG. 44, the outer wall 222 is positioned adjacent to and connected to an end of the interspinous member 202. As shown in FIGS. 45, 47, 50 and 51, the end 224 of the interspinous spacer 202 can include a threaded opening 226 corresponding to an opening 228 of the outer wall 22 into which a set screw 230 can be secured.

As shown in FIGS. 42-45, the sheath member 204 includes a sidewall 232 extending between the inner and outer wall portions 214 and 222. The sidewall 232 includes at least two slots 234 formed therein to provide a connection for the hook connection members 206. As shown in FIGS. 42 and 43, the side wall 232 can includes a third slot 236, located generally centrally along the sidewall 232 to provide a window for locating the interspinous insertion member 202 to ease in connecting the sheath member 204 to the interspinous insertion member 202.

Figure 46:
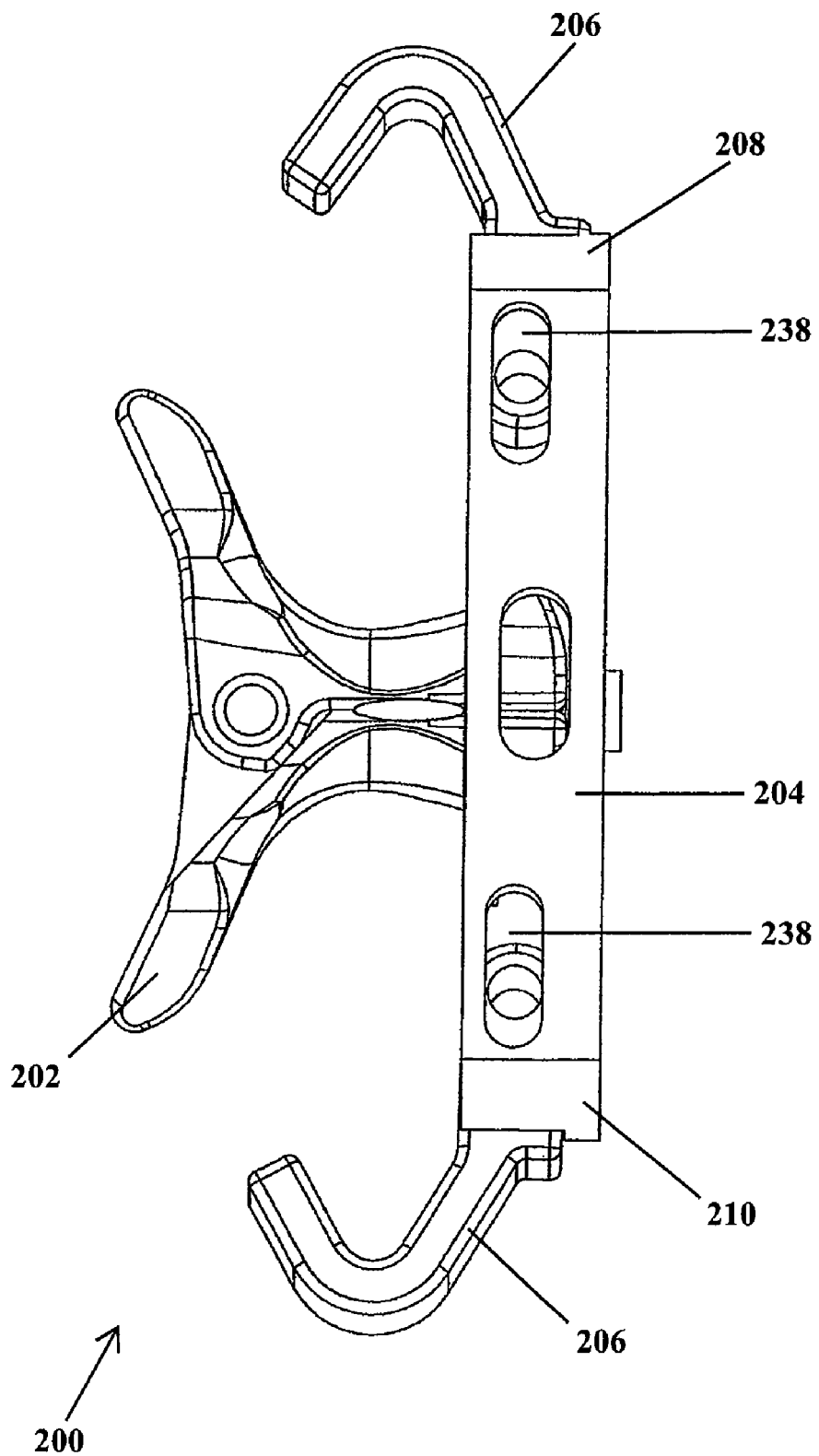
FIG. 46 is a front elevational view of the implant of FIG. 42.

As shown in FIGS. 44-46, the hook connection members 206 each include a hook body portion 238 extending into the sheath member 204 and connected thereto. A throughbore 240 of the hook member 206 corresponding to the slot 234 of the sheath sidewall 232. A securing member 242, such as a pin, extends through the hook body throughbore 240 and the sheath sidewall slot 232. The pin securing member 242 is configured to be translatable along the slot 232 and secured at the desired location wherein the hook portions 212 of the connecting member 206 engage the adjacent spinous processes 6 and 8.

Figure 47:
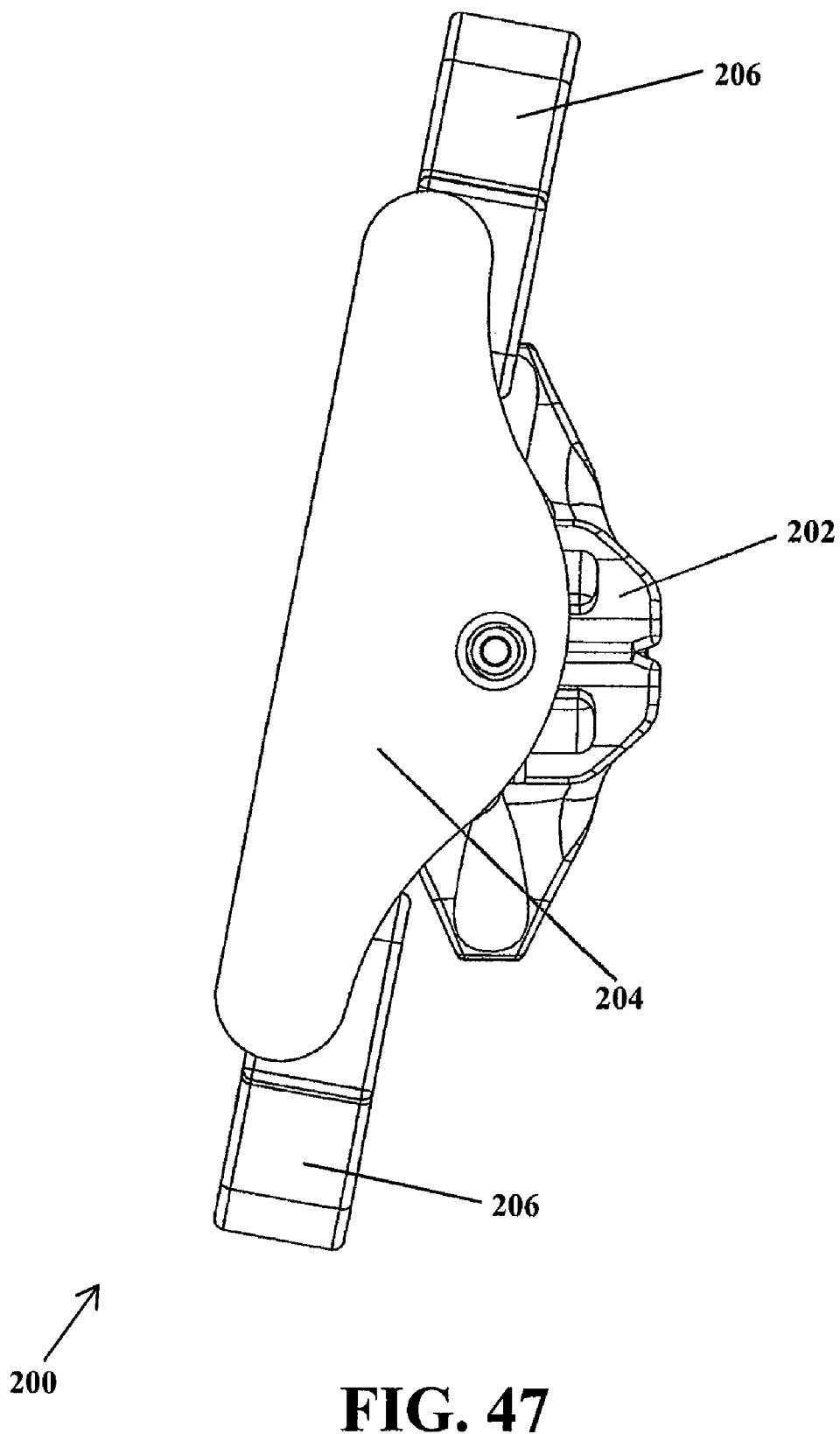
FIG. 47 is a right side elevational view of the implant of FIG. 42 showing an offset orientation of the plate relative to the interspinous implant member.
Figure 48:
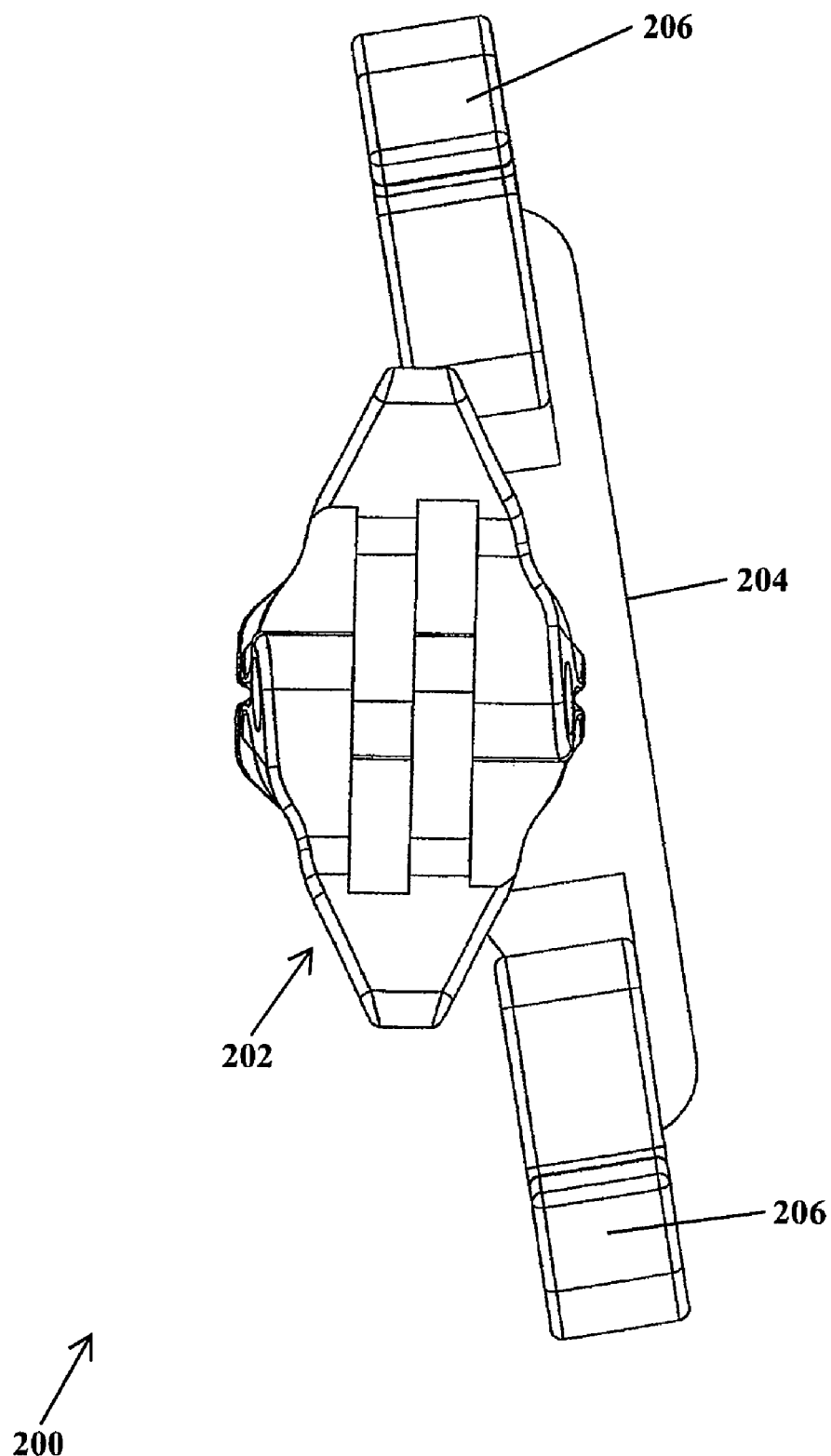
FIG. 48 is a left side elevational view of the implant of FIG. 42.

As shown in FIGS. 45, 47 and 48, the inner wall slot 216 is configured to permit the sheath member 204 to be positioned at various angles relative to the interspinous insertion member 202 based on the spinal geometry at the insertion site. As a result, the geometry of the upper and lower surfaces of the adjacent spinous processes 6 and 8 does not interfere with positioning the seat 218 of the interspinous insertion member 202 and the hooks 206 of the spanning member 204 so as to fully engage the spinous processes 6 and 8.

As shown, the interspinous implant member 202 and the sheath member 204 can be inserted using a unilateral posterior approach.

Figure 55:
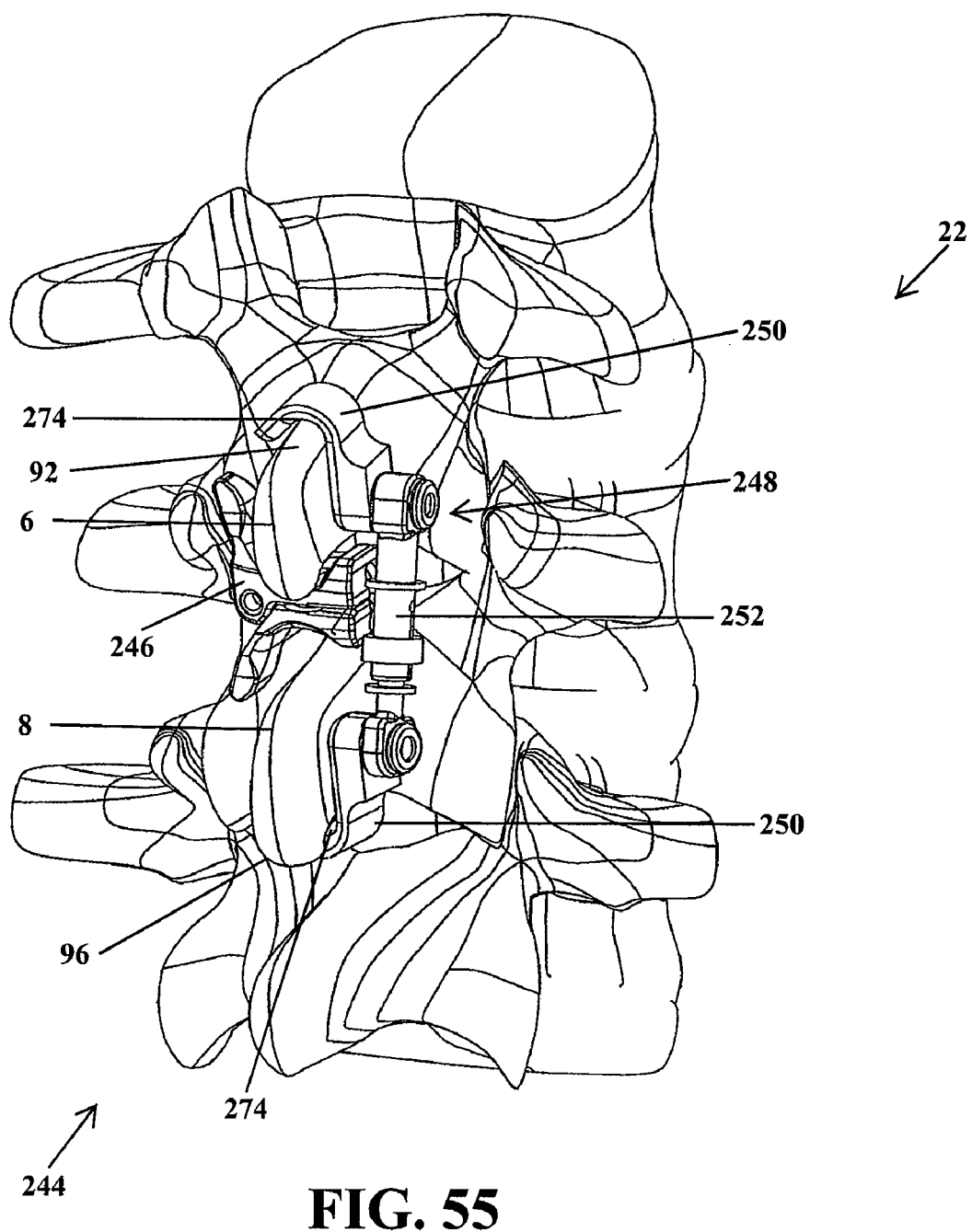
FIG. 55 is a posterior aspect prospective view of an implant in accordance with another aspect of the invention.

An implant 244 in accordance with another aspect of the invention is shown in FIGS. 55-65. As shown in FIG. 55, the implant device 244 includes an interspinous spacer 246 configured to be positioned between adjacent vertebrae 6 and 8. While other interspinous spacers can be utilized, the interspinous spacer 246 as shown in FIGS. 55-65 is similar to the interspinous spacers described above, with any differences discussed below.

Figure 56:
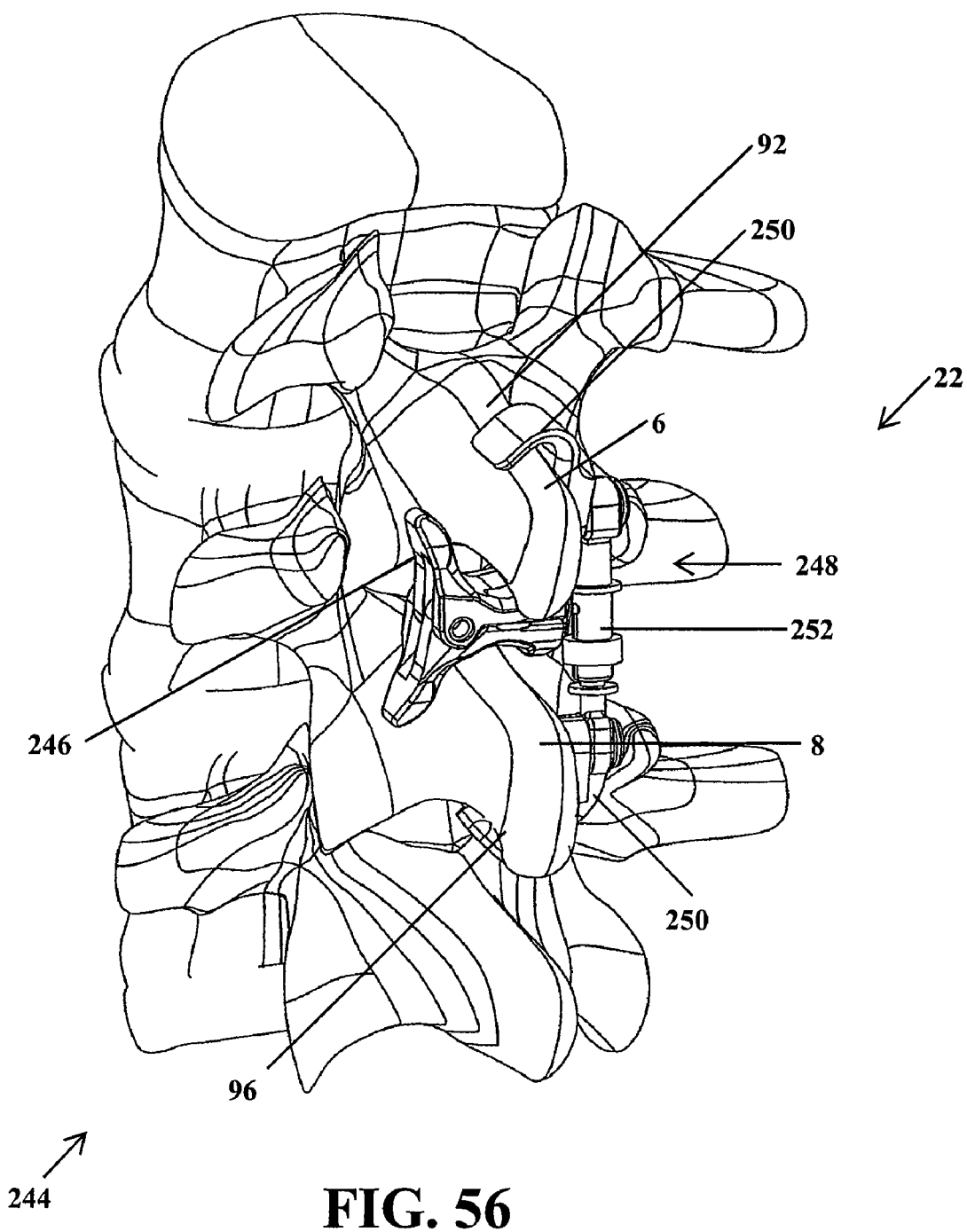
FIG. 56 is a posterior aspect prospective view of the implant of FIG. 55 showing hooks extending about the upper and lower surfaces of the spinous processes.
Figure 57:
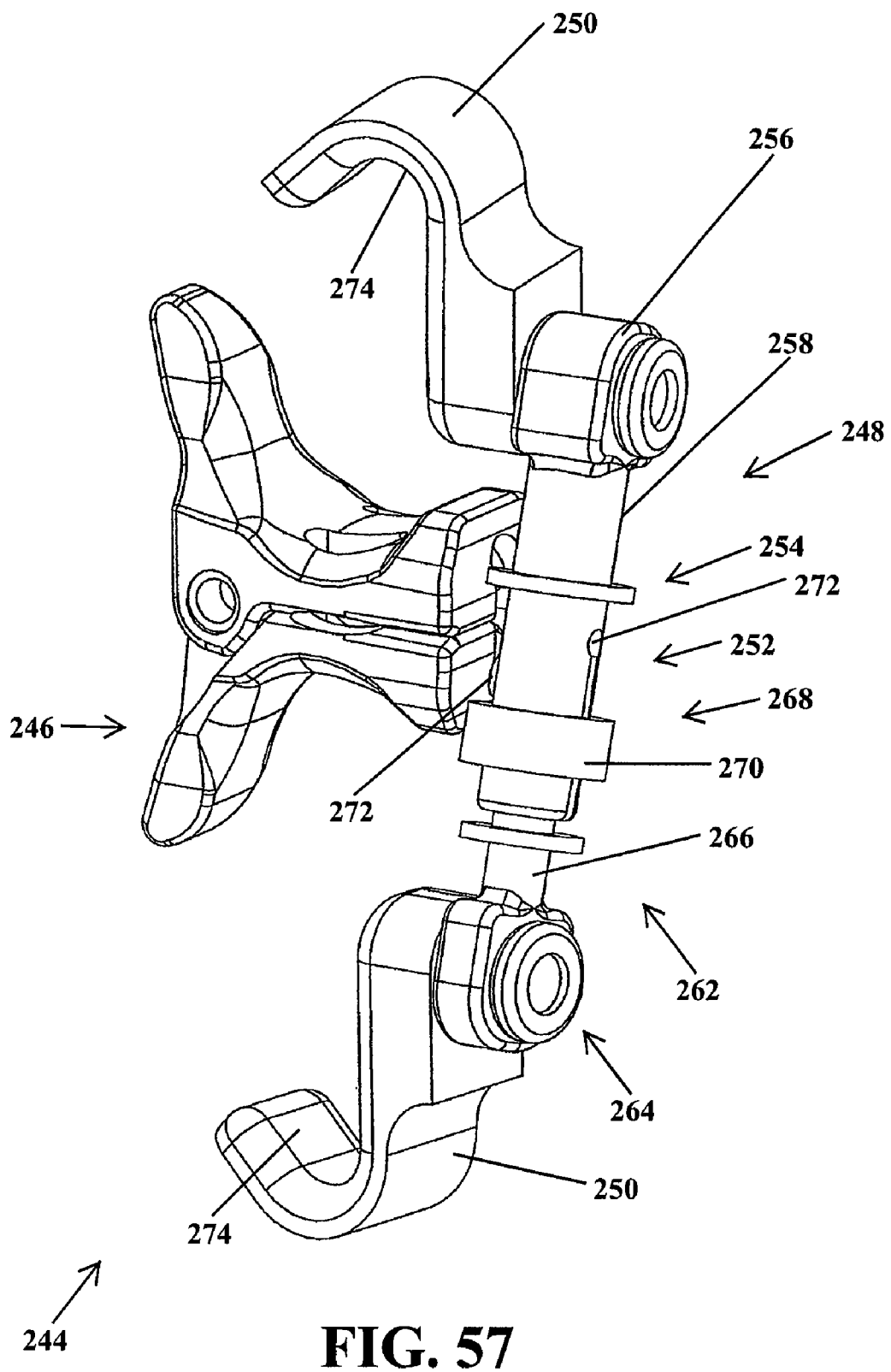
FIG. 57 is a perspective view of the implant of FIG. 55 showing an interspinous implant member, a telescoping rod of the spanning member and connecting members or hooks connected to the telescoping rod.

As shown in FIGS. 55-57, the implant device 244 includes the interspinous implant spacer 246 and a spanning or locking member 248. The spanning member 248 includes a pair of hooks 250 configured to engage about and secure the spinous processes 6 and 8 distracted by the interspinous spacer 246. Further, the hooks 250 act to maintain the engagement between the spinous processes 6 and 8 and the interspinous spacer 246 thereby securing or locking the spacer 246 in the implanted orientation 22. A telescoping rod member 252 extends between and is connected to the hooks 250. As shown in FIG. 57, the spanning member 248 need not be connected to the interspinous implant spacer 246.

Figure 58:
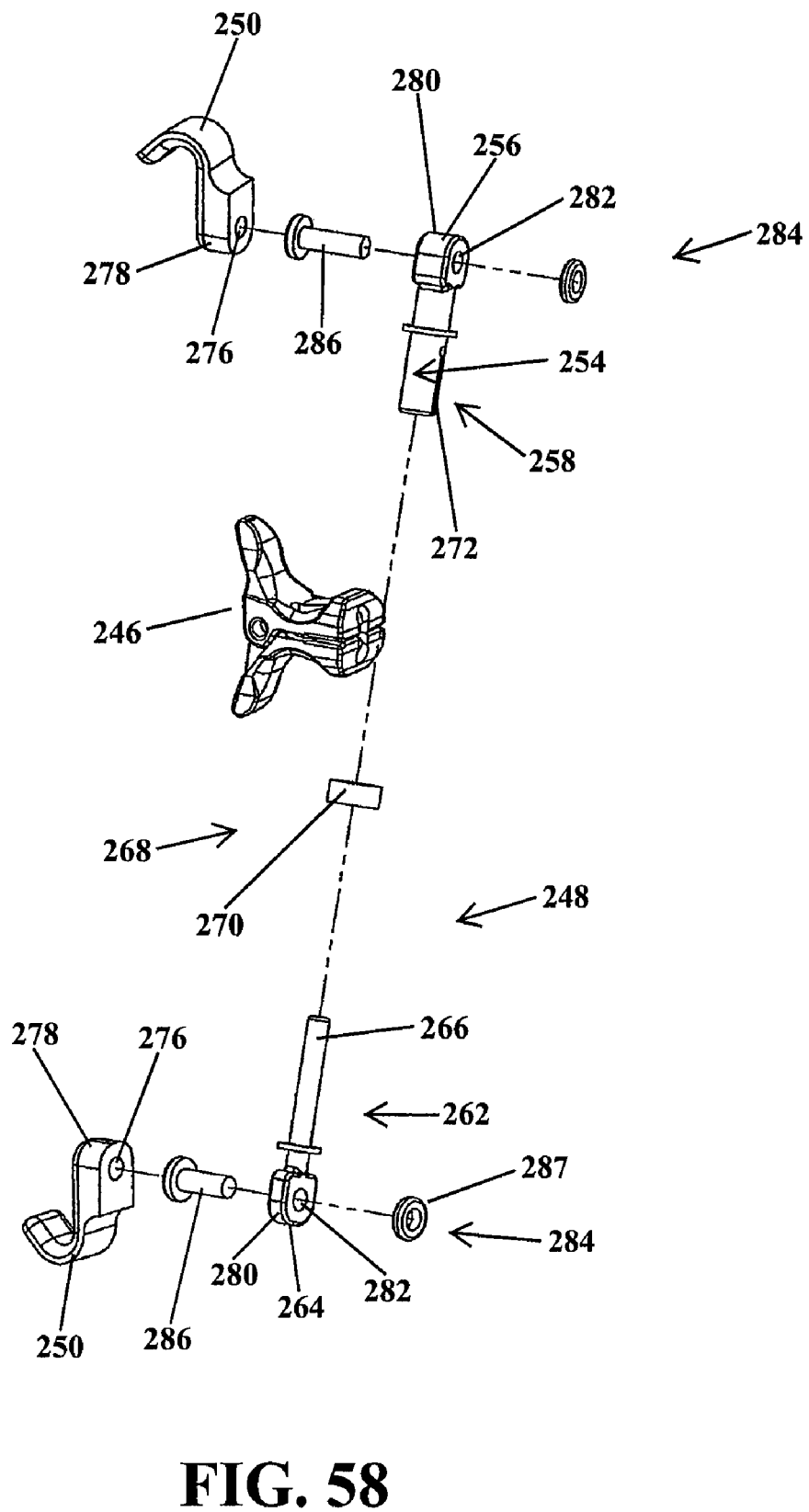
FIG. 58 is an exploded view of the implant of FIG. 55.

As shown in FIGS. 57 and 58, the rod 252 includes an outer member 254 which includes a head portion 256 and a hollow sheath 258 extending from the head portion 260. The rod 252 further includes an inner member 262 which includes a head portion 264 and a shaft 266 extending from the head portion 264, the shaft 266 configured to be slidably received within the hollow sheath 258 of the outer member 254.

Figure 59:
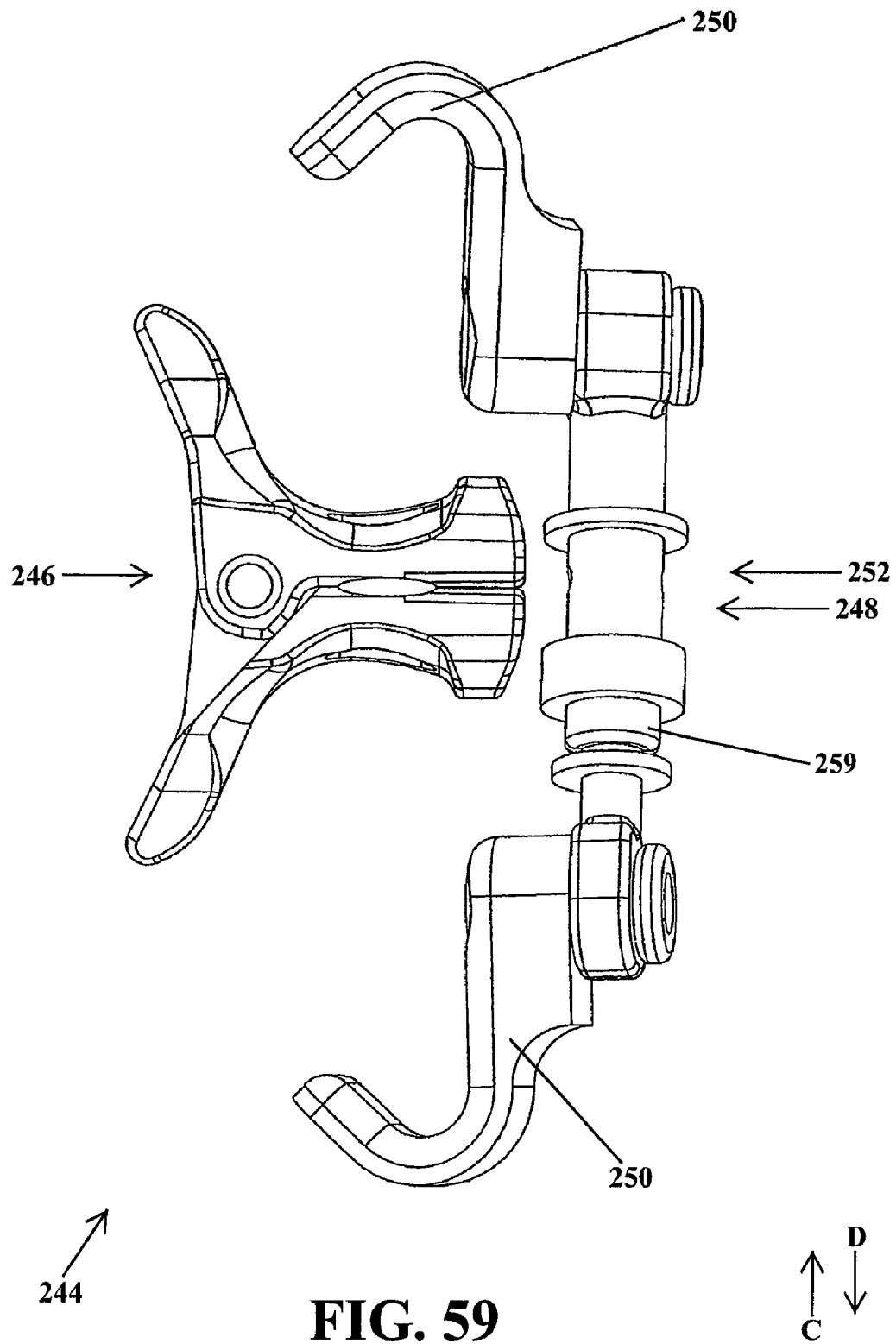
FIG. 59 is a front view of the implant of FIG. 55 showing the interspinous implant member and spanning member being independent from one another.
Figure 60:
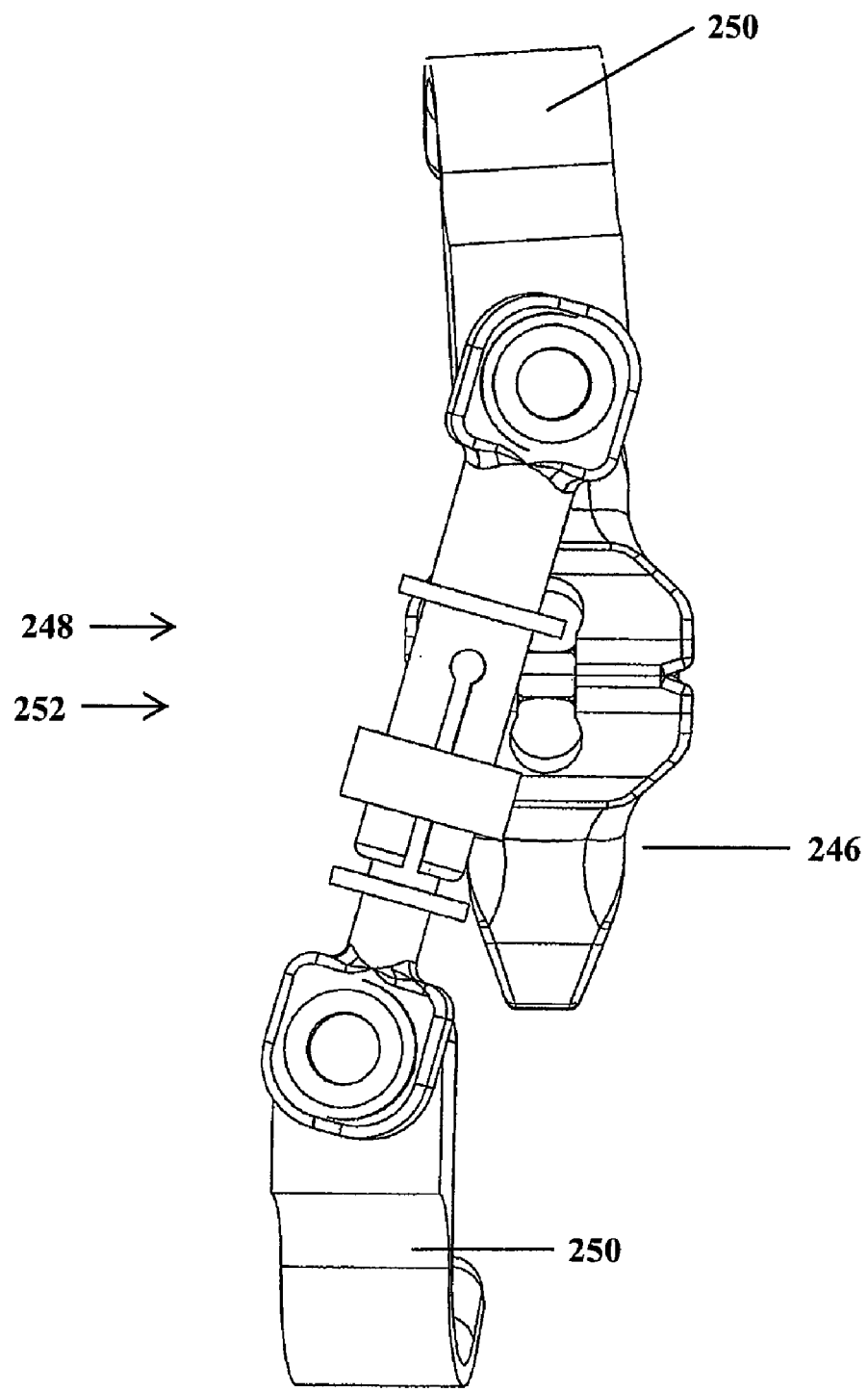
FIG. 60 is a right side view of the implant of FIG. 55 showing the hooks offset from one another.
Figure 61:
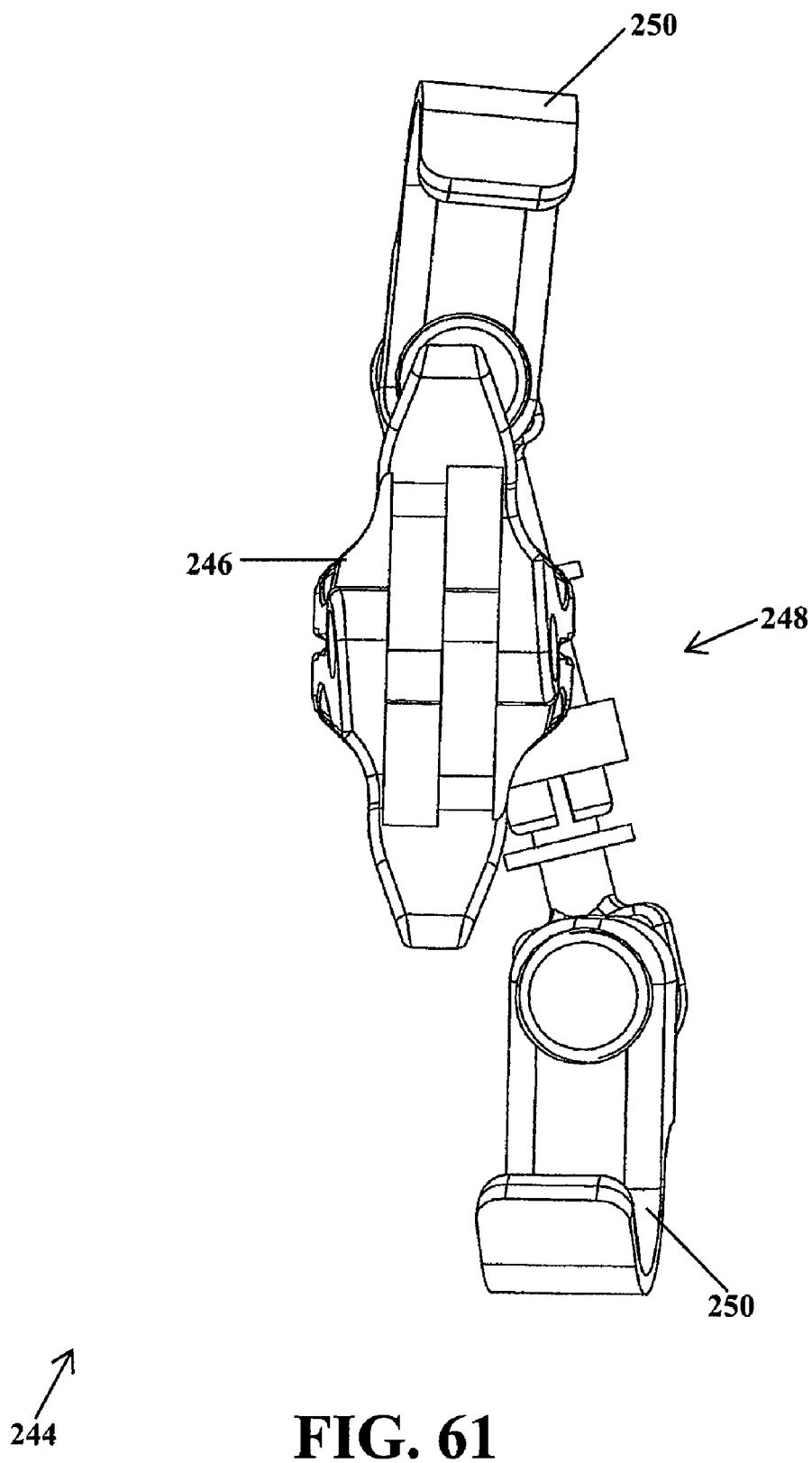
FIG. 61 is a left side view of the implant of FIG. 55.
Figure 64:
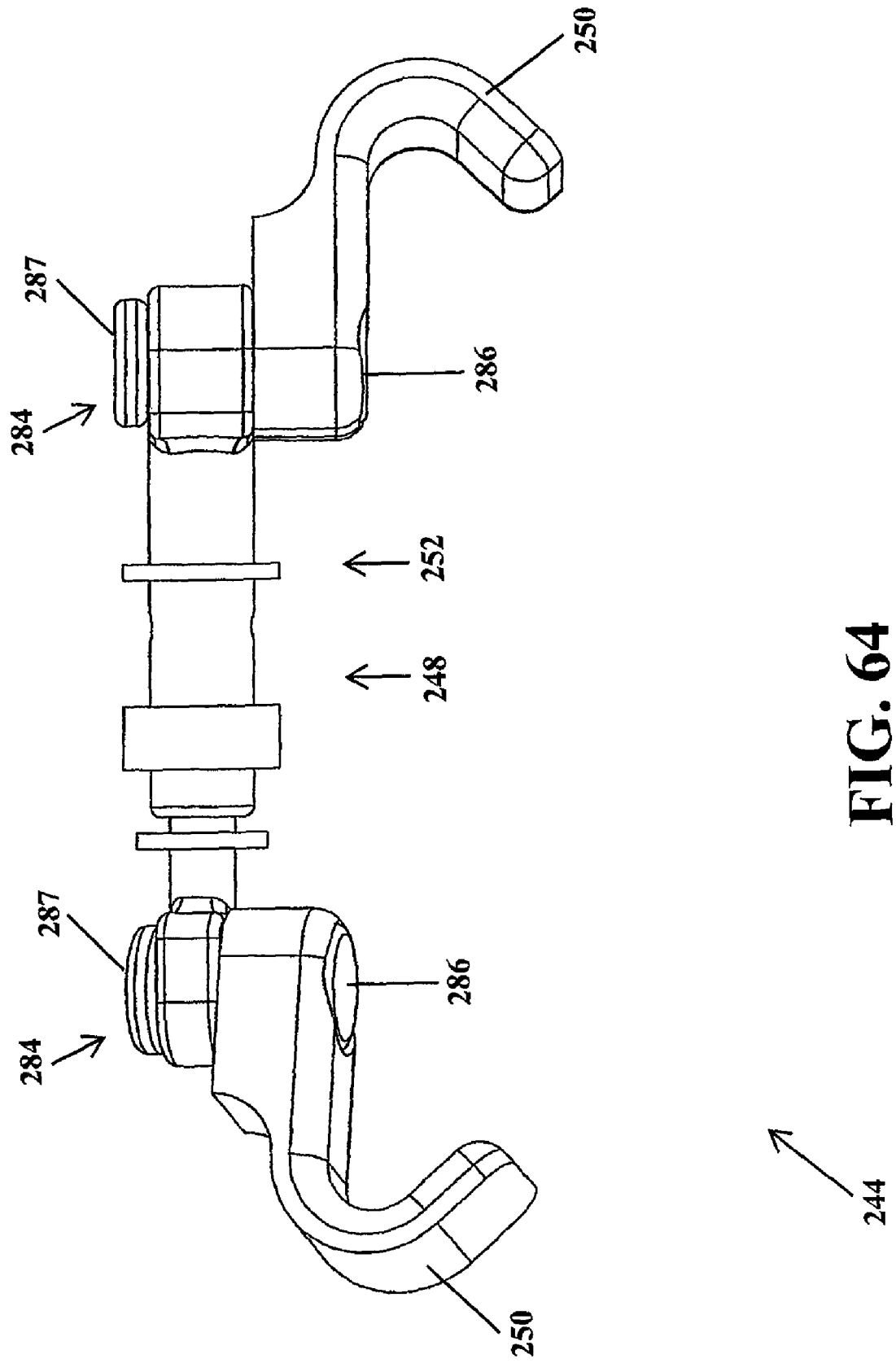
FIG. 64 is a front elevational view of the spanning and connecting members of the implant of FIG. 55.
Figure 65:
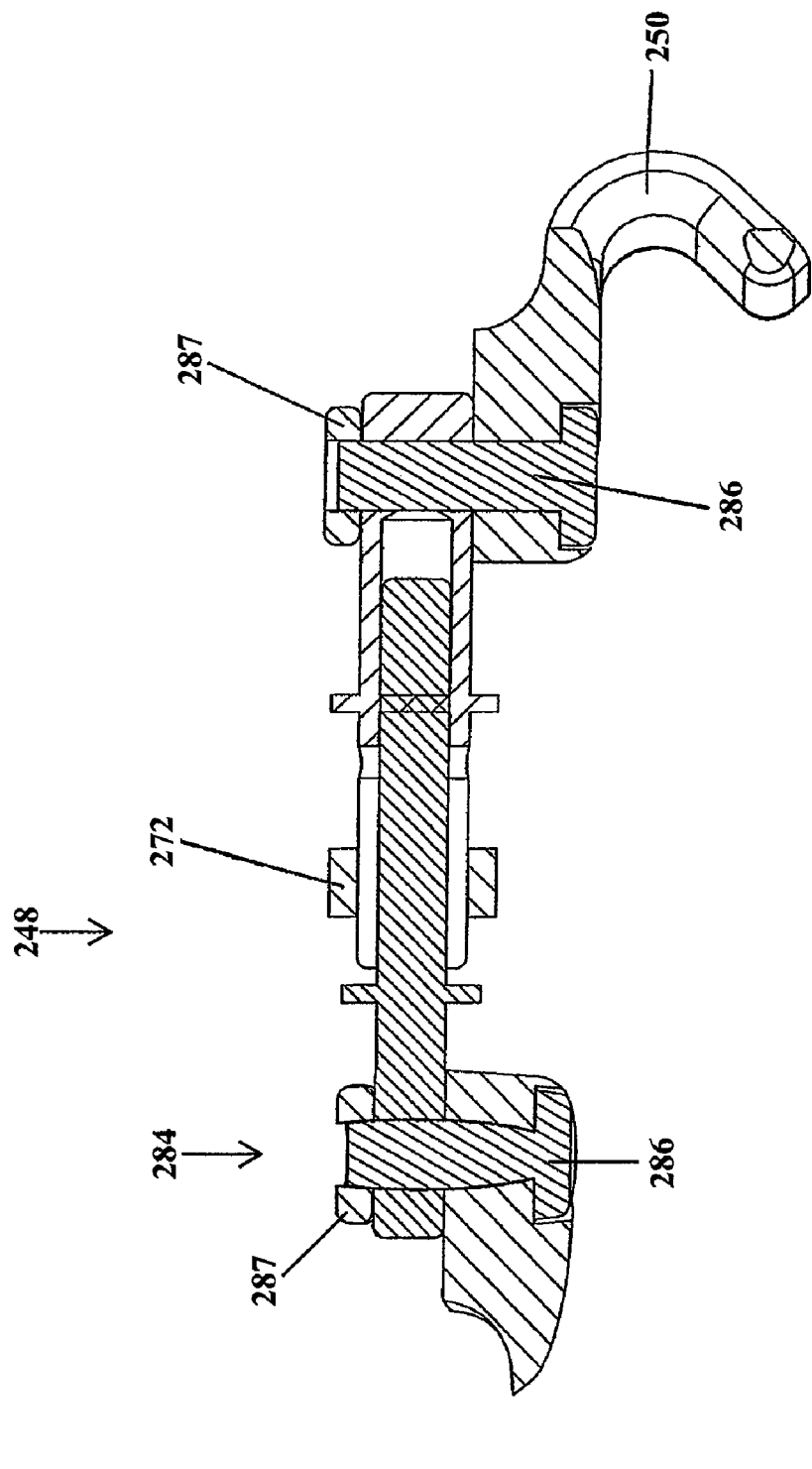
FIG. 65 is a front sectional view of the spanning and connecting members of the implant of FIG. 55.

After the inner member 262 has been positioned to the desired location within the hollow sheath 258, the inner and outer members 254 and 262 can be secured to one another by a securing mechanism 268. As shown in FIG. 58, the securing member 268 includes a collar 270 of the spanning member 248 and a pair of slots 272 extending along the length of the hollow sheath 258. The collar 270 is configured to be disposed about the hollow sheath 258 of the outer member 254. As shown in FIG. 59, the collar 270 is disposed onto and shifted along the hollow sheath 258 in direction C, the collar 270 compresses the hollow shaft 258 thereby reducing the size of the slots 272, resulting in a friction fit connection between the hollow sheath 258 of the outer member 254 and the shaft 266 of the inner member 262, thereby securing the length of the spanning member 248. Further, as the collar 270 is shifted along the hollow sheath 258 away from the sheath distal ends 259 in direction D, the distal ends 259 tend to flex outwardly due to the restrictive collar 270 not locally reducing the size of the distal ends 259. As a result, the outwardly flexed distal ends 259 restrict the movement of the collar 270 toward the distal ends 259.

Alternatively, the securing mechanism 268 can include a set screw, ratchet mechanism, or a locking ball bearing collar (described below).

The hooks 250 each include a seat 274 for engaging one of the upper and lower surfaces 92 and 96 of the adjacent spinous processes 6 and 8. The seat 274 is configured to conform to the geometries of the spinous processes 6 and 8.

The hooks 250 are connected to the rod 252 by a throughbore 276 extending through the hook body 278. The heads 280 of the rod 252 each include a throughbore 282 corresponding to the hook body throughbore 276. As shown in FIGS. 58 and 63-65, a securing mechanism 284, such as a pin 286 and cap 287, secures the hook body 278 to the rod head portion 280 while permitting the hook body 278 to pivot about the pin 286. As a result, the hooks 250 can be adjusted relative to the rod 252 about the pin 286 based on the spinal geometry. Further, the position of the hooks 250 need not be fixed prior to insertion as they position themselves as the length of the rod 252 is reduced and the collar 270 is locked into the final position.

As shown, the interspinous implant member 246 and the spanning member 248 of the implant device 244 can be inserted using a unilateral posterior approach.

Figure 66:
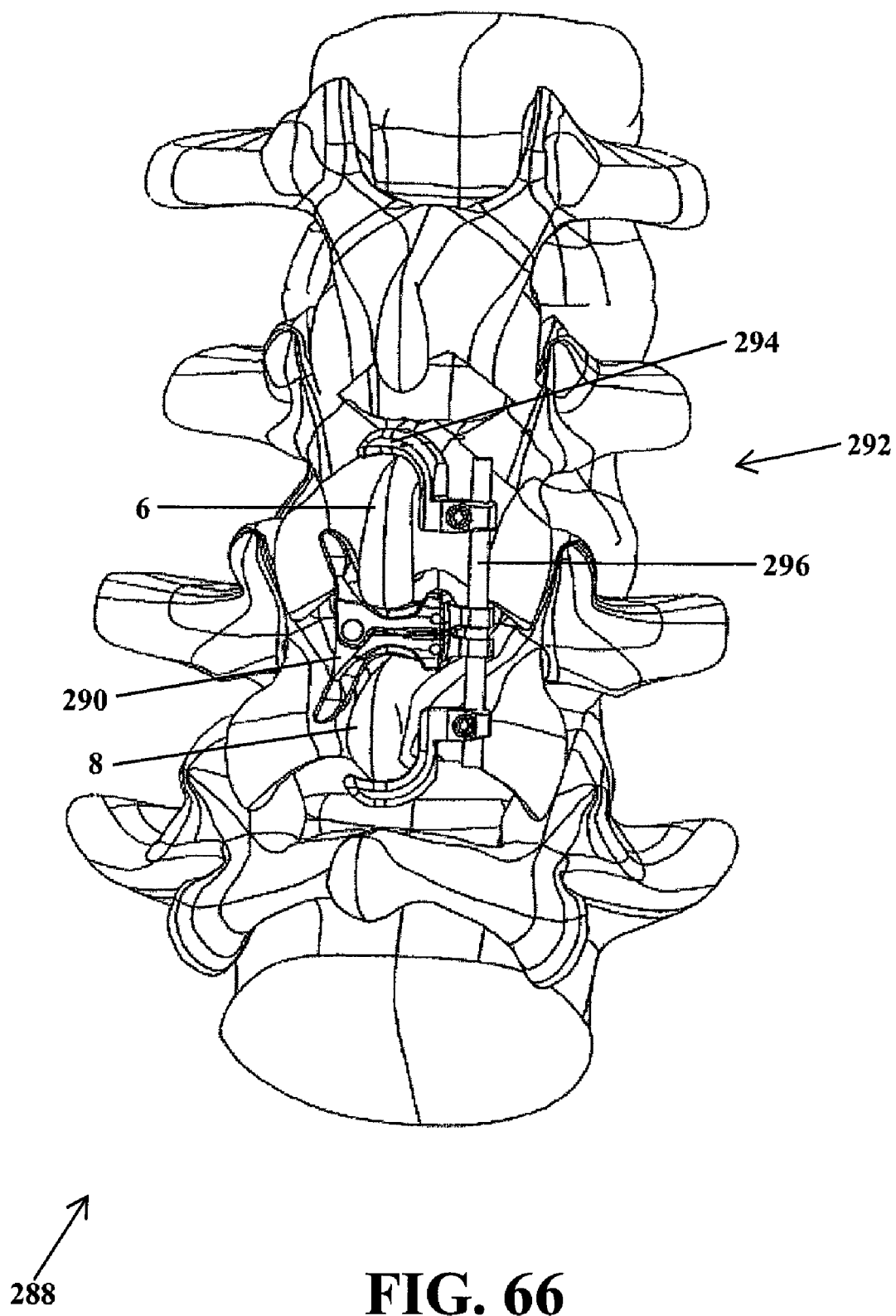
FIG. 66 is a posterior aspect prospective view of an implant in accordance with another aspect of the invention showing an interspinous insertion member in the implanted orientation positioned between adjacent spinous processes, a spanning member connected to the interspinous member, and a pair of connecting hook members engaging the adjacent spinous processes.

An implant 288 in accordance with another aspect of the invention is shown in FIGS. 66-75. As shown in FIG. 66, the implant device 288 includes an interspinous spacer 290 configured to be positioned between adjacent vertebrae 6 and 8. While other interspinous spacers can be utilized, the interspinous spacer 290 as shown in FIGS. 66-75 is similar to the interspinous spacers described above, with any differences discussed below.

The implant device 288 includes an interspinous spacer 290 positioned between and distracting adjacent spinous processes 6 and 8. A spanning member 292 further secures the spinous processes 6 and 8 with a pair of hooks 294 configured to engage about the spinous processes 6 and 8 generally opposite the upper and lower seat portions of the spanning member 292. This further acts to maintain the secure engagement of the spinous processes 6 and 8 and the spacer 290 thereby locking or securing the spacer 290 in the implanted orientation 22. The hooks 294 are connected to one another via a rod 296, which is further connected to the interspinous spacer 290. The implant device 288 can be implanted using a unilateral posterior approach.

Figure 67:
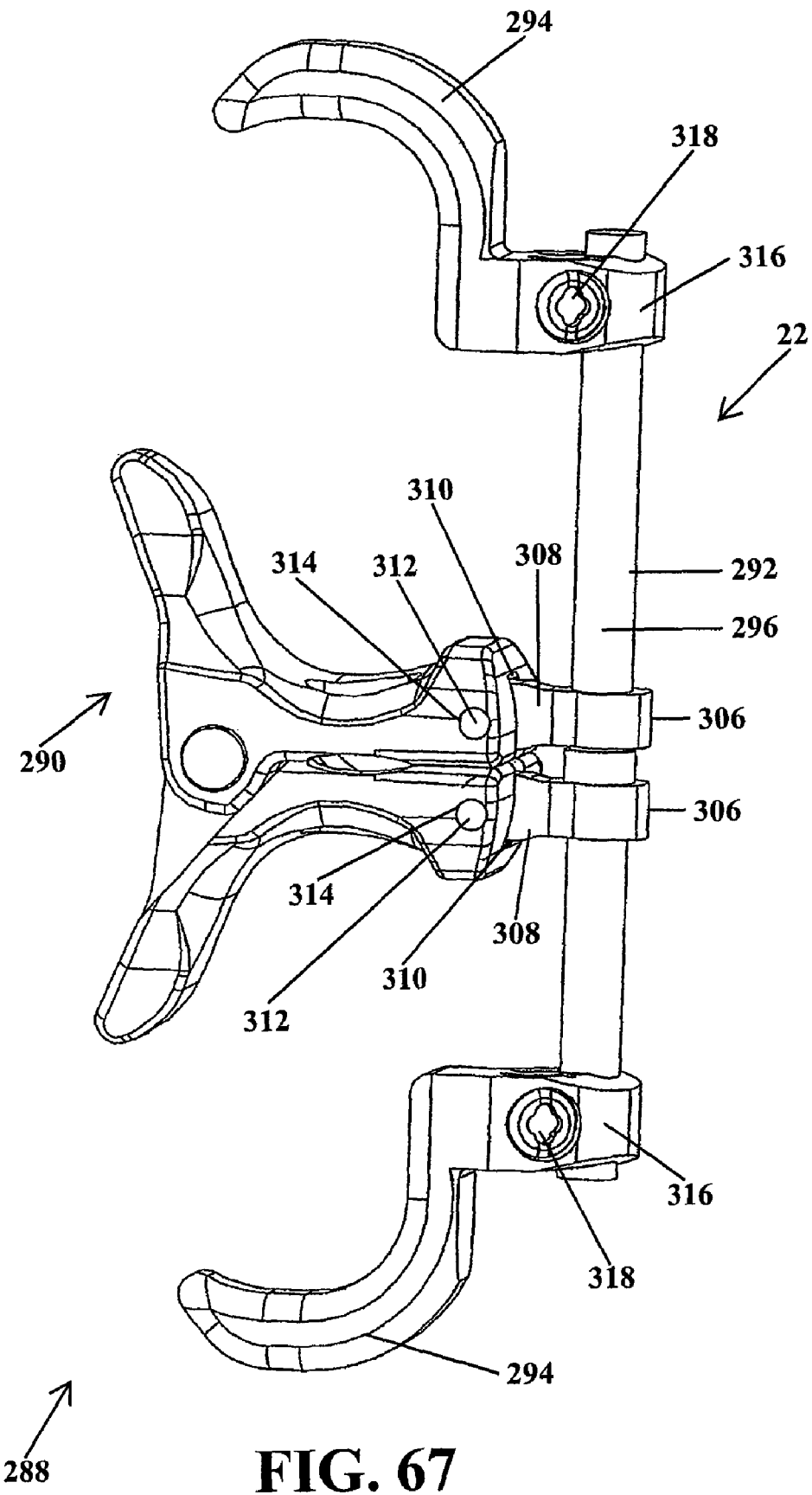
FIG. 67 is a perspective view of the implant of FIG. 66.
Figure 68:
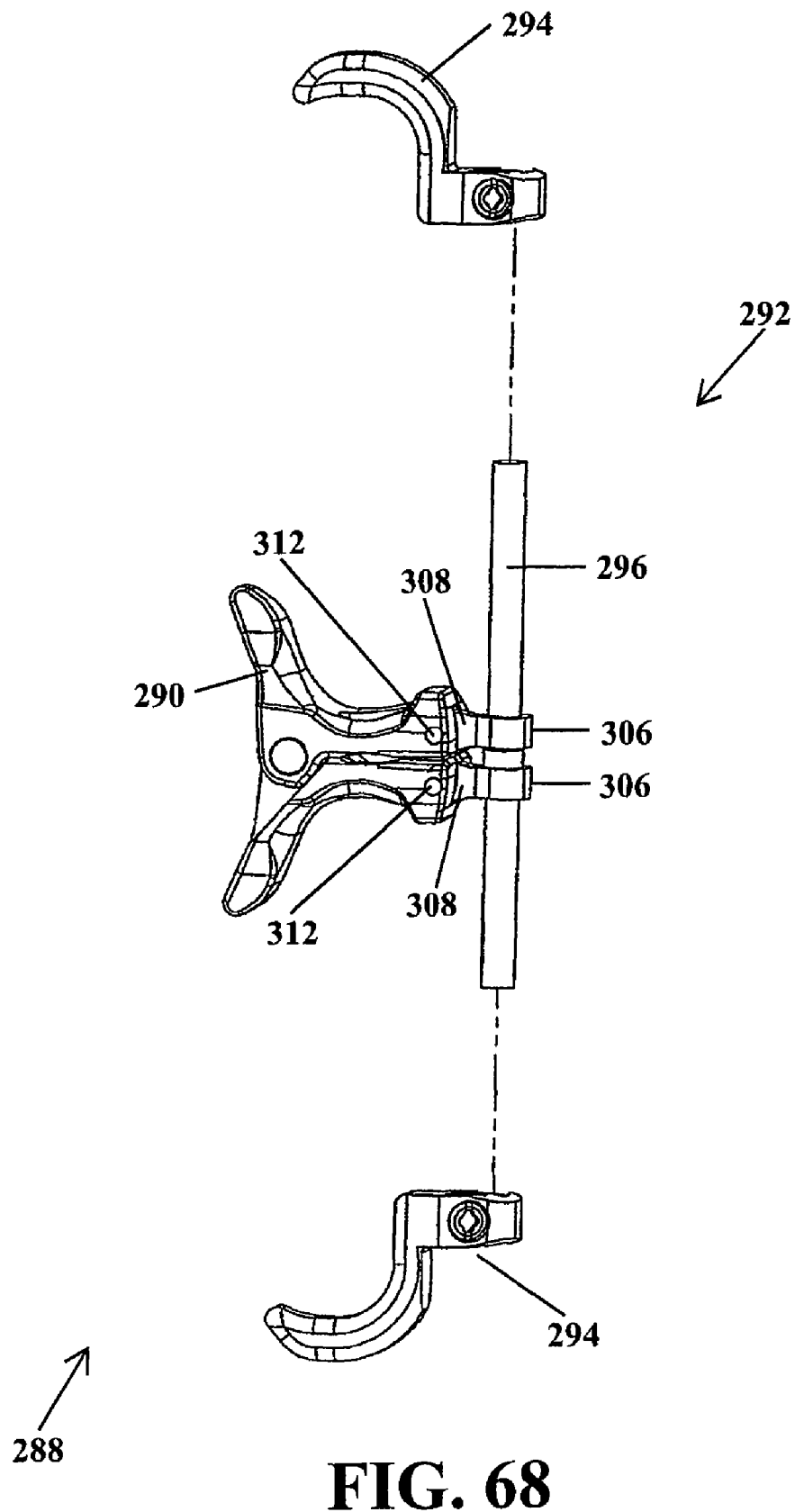
FIG. 68 is an exploded view of the implant of FIG. 66 showing the connecting hook members removed from the spanning rod member.
Figure 69:
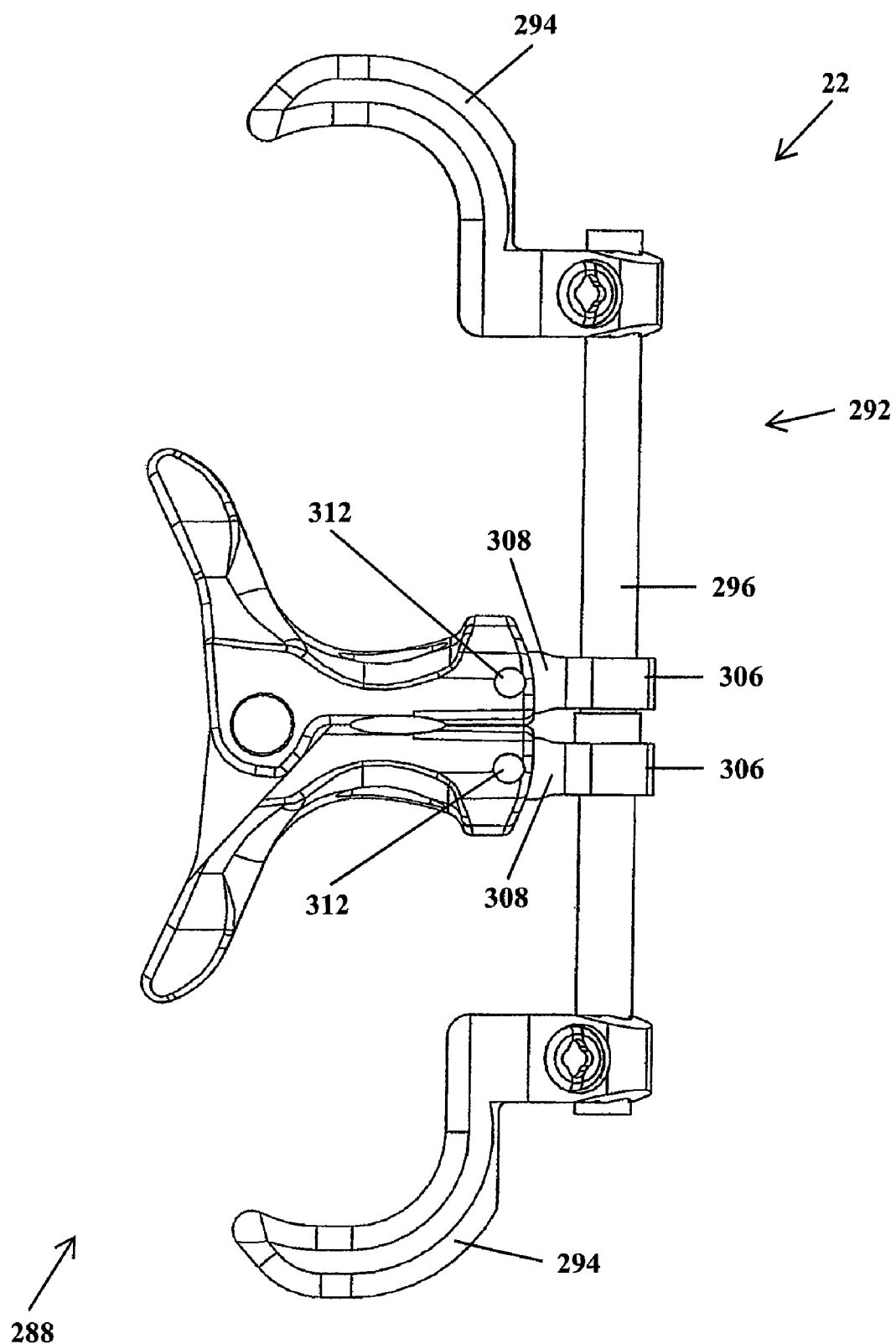
FIG. 69 is a front elevational view of the implant of FIG. 66.
Figure 70:
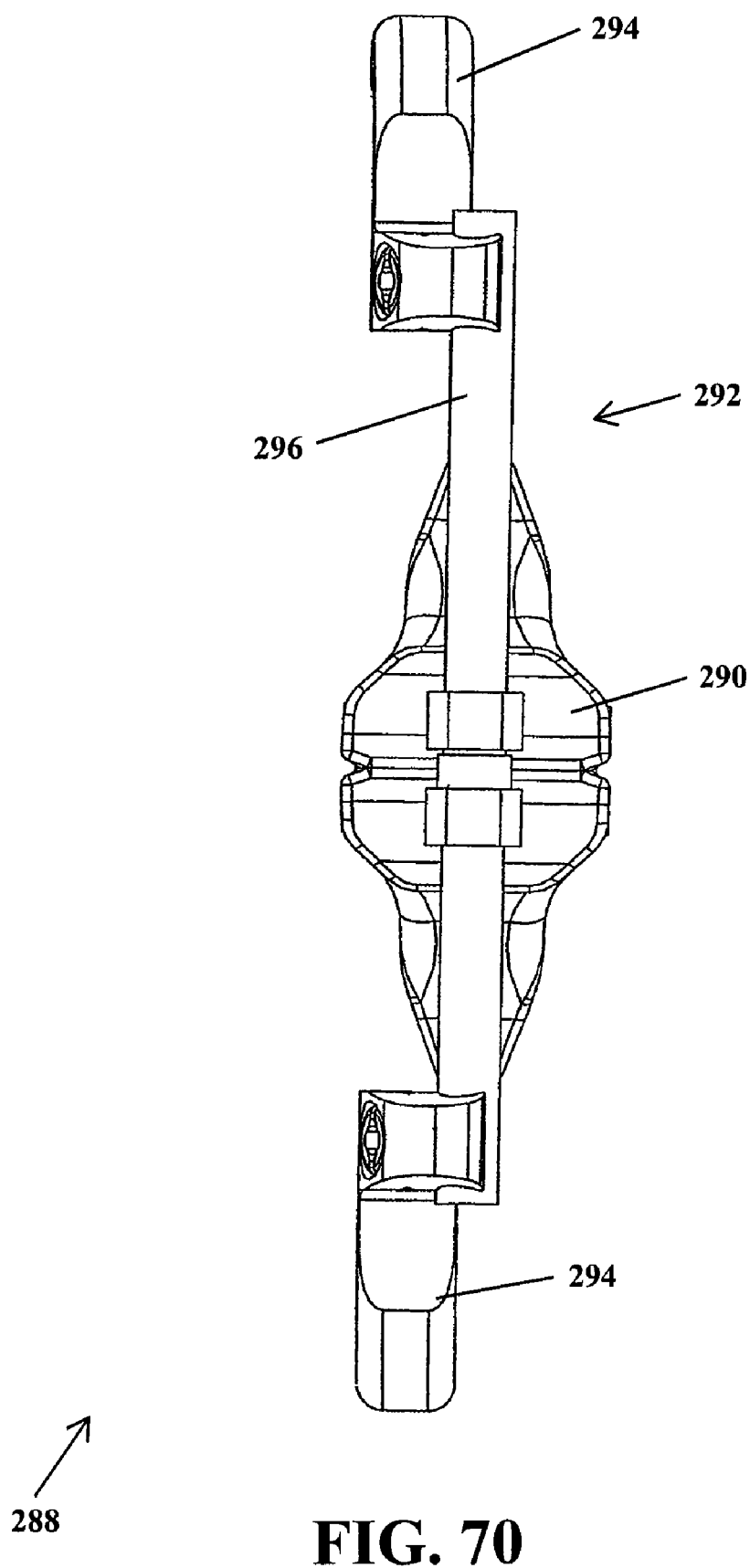
FIG. 70 is a right side elevational view of the implant of FIG. 66 showing the hooks offset from the rod.
Figure 71:
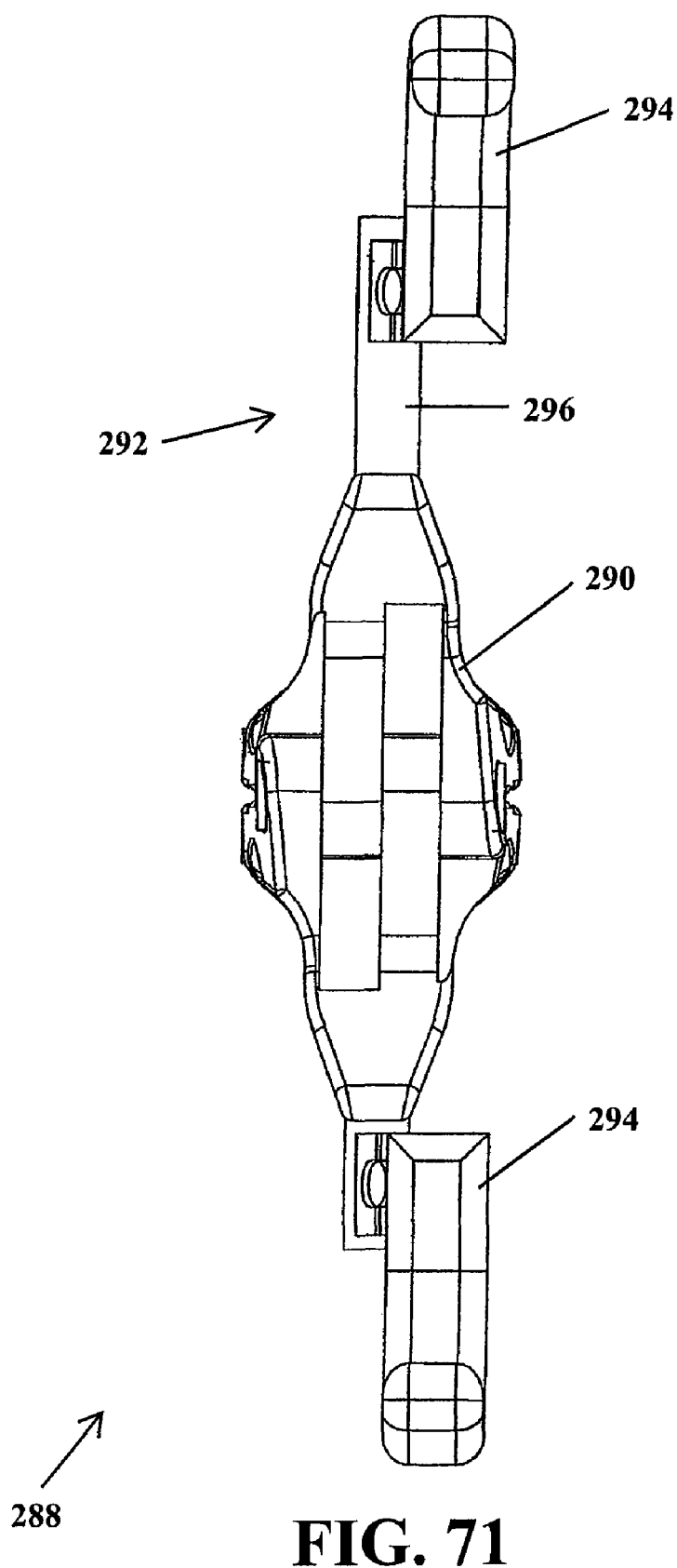
FIG. 71 is a left side elevational view of the implant of FIG. 66.
Figure 72:
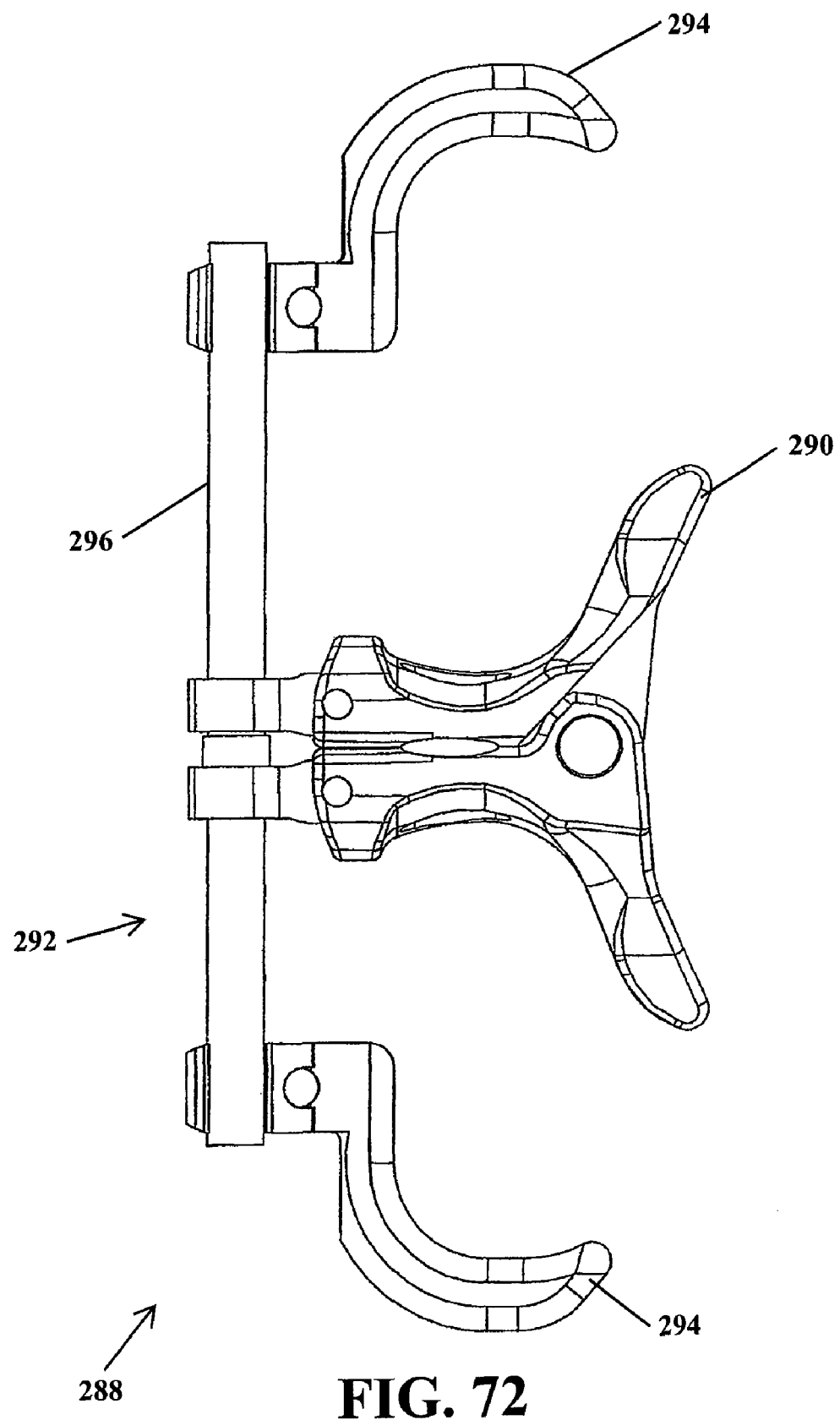
FIG. 72 is a back elevational view of the implant of FIG. 66.
Figure 73:
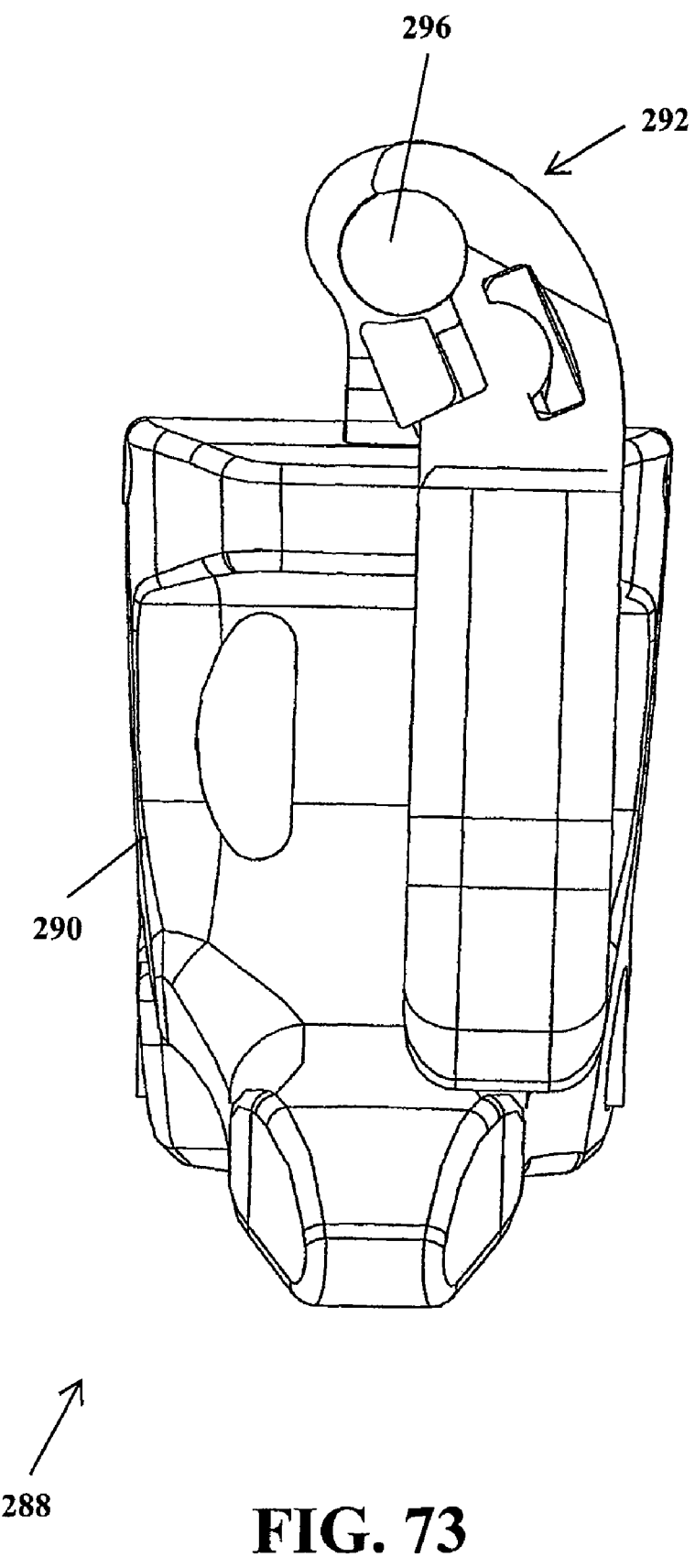
FIG. 73 is a bottom view of the implant of FIG. 66.

The collar 306 includes a linkage 308 extending therefrom. The interspinous spacer 290 includes a pair of openings 310 therein configured to receive the linkages 308 therein. As shown in FIGS. 67-69, the linkages 308 are secured within the openings 310 by pins 312 extending through corresponding throughbores 314 in the interspinous spacer 290 and the collar linkage 308.

Figure 66A:
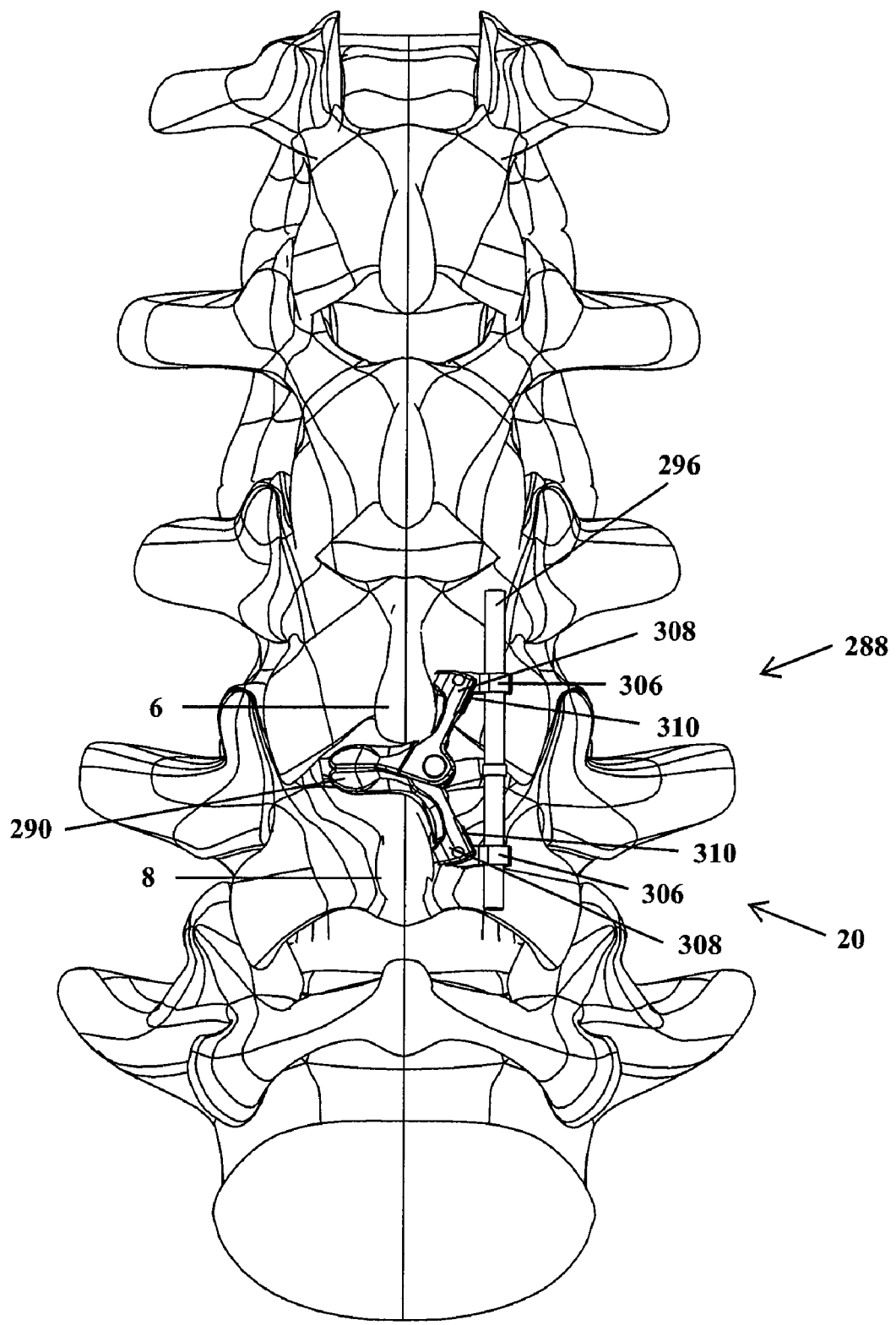
FIG. 66A is a front elevational view of the implant of FIG. 66 positioned between adjacent spinous process with the interspinous insertion member in the insertion orientation.

As shown in FIG. 66A, the linkages 308 can be connected to the interspinous spacer 290 with the spacer 290 in the insertion orientation 20. The openings 310 can be configured to permit the linkages 308 to pivot about the pins 312 while the collars 306 shift along the rod 296. As such, the implant 288 can be inserted as a single piece and secured in place after insertion.

Figure 74:
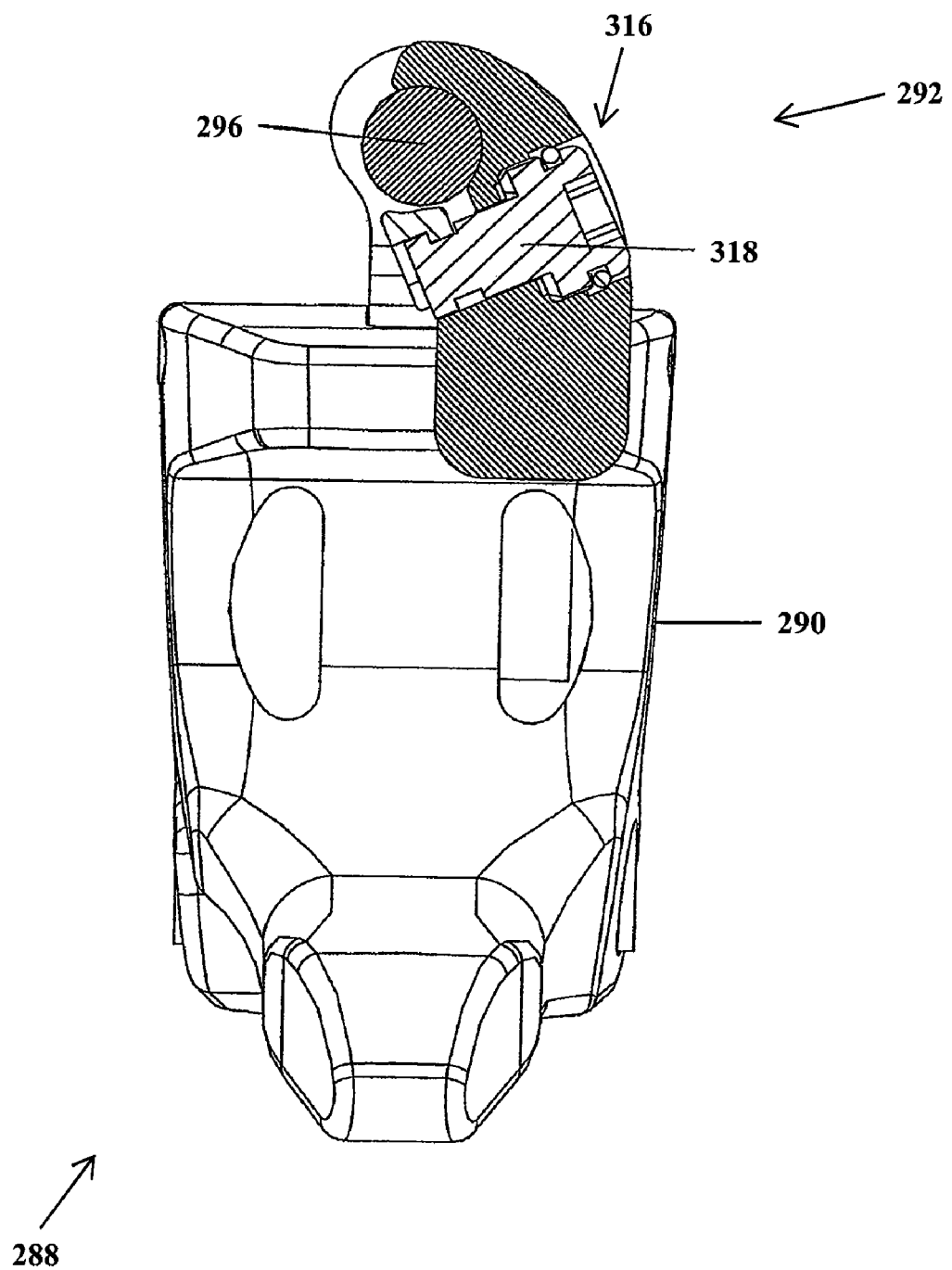
FIG. 74 is a bottom sectional view of the implant of FIG. 66 showing the connection between the hook and rod.
Figure 75:
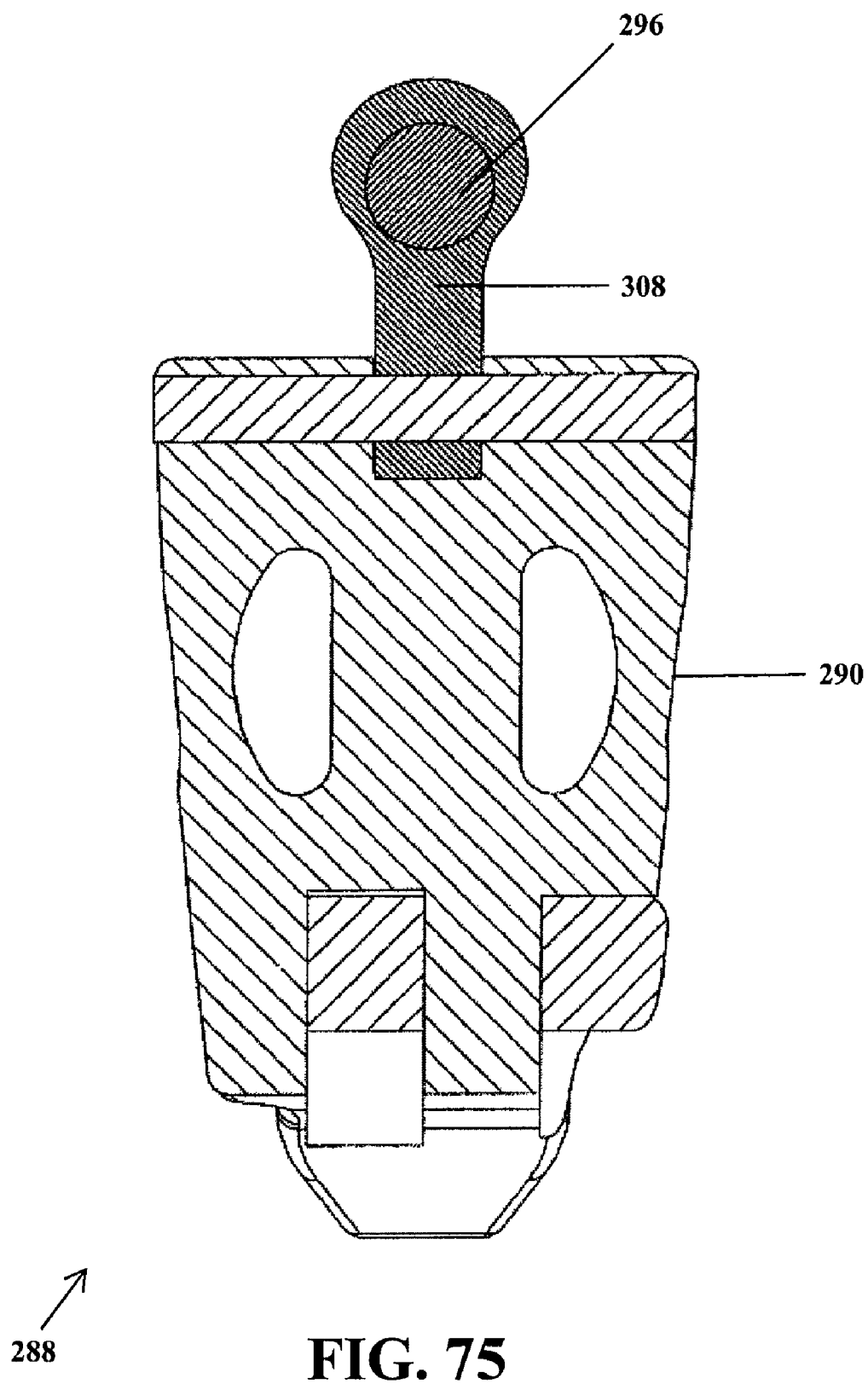
FIG. 75 is a bottom sectional view of the implant of FIG. 66 showing the linkage of the spanning member and the interspinous member.

The hooks 294 can be connected to the rod 296 by any known method. As shown in FIGS. 67 and 74, the hook bodies 294 are secured to the rod 296 via a cross link member 316 as described in U.S. patent application Ser. No. 10/692,460, titled CROSSLINK FOR SECURING SPINAL RODS, which is incorporated herein by reference in its entirety. The crosslink apparatus 316 developed for connecting spinal rods together can be used to quickly and easily securing the hooks 294 to the rod 296 as shown in FIG. 74. The crosslink apparatus 316 is configured to attach to a generally cylindrical shape so that the hooks bodies 294 with the crosslink apparatus 316 can attach to the rod 296 of the spanning member 292. The crosslink apparatus 316 can be secured in final position by rotating a cam member 318, such as a screw, such that the cross link 316 engages the rod 296 securing the hook 294 onto the rod 296.

Figure 76:
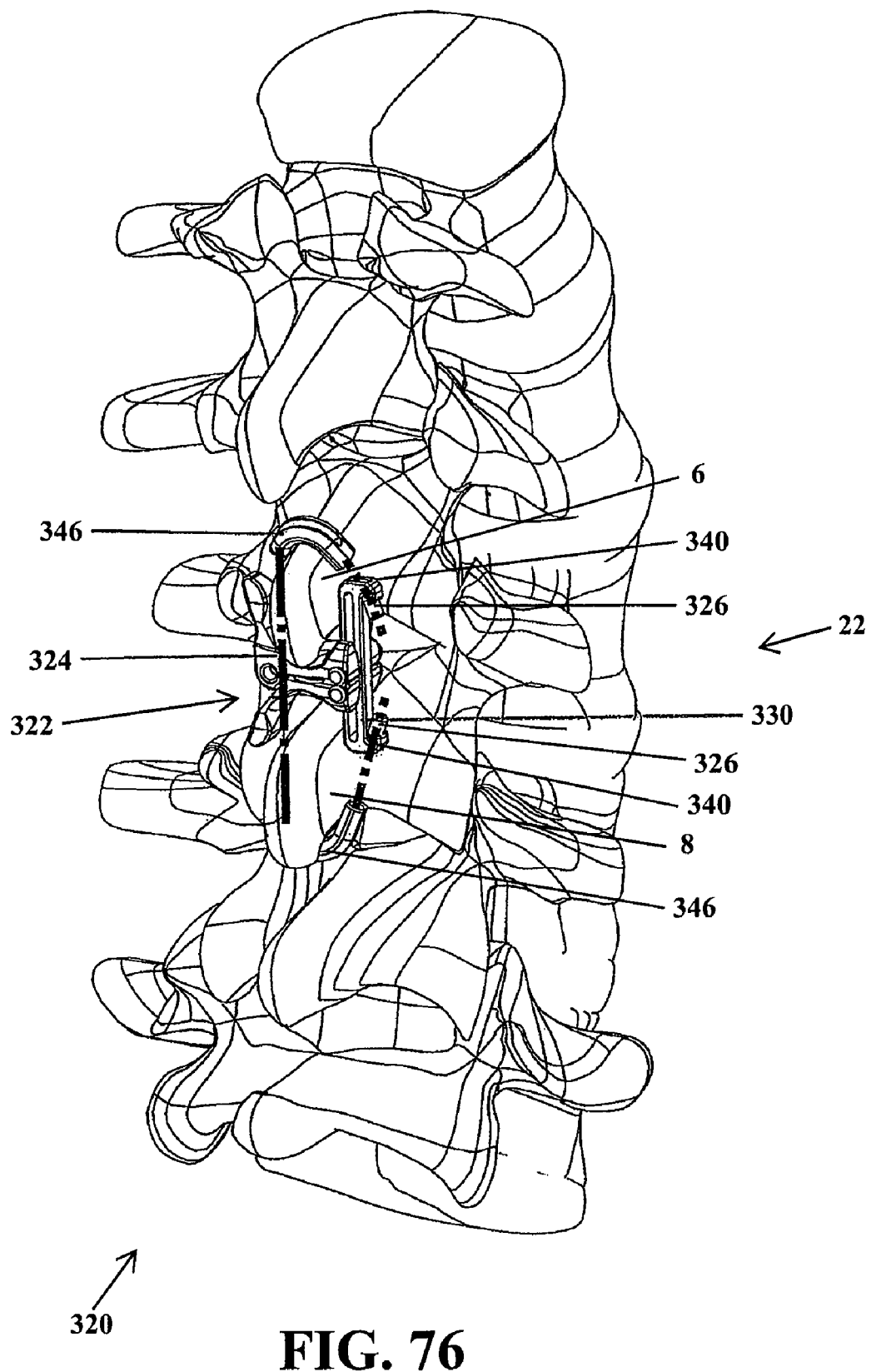
FIG. 76 is a posterior aspect prospective view of an implant in accordance with another aspect of the invention showing the interspinous insertion member, a spanning member connected to the insertion member, upper and lower grommets, and a cable extending from the either end of the spanning member and about the spinous processes.
Figure 77:
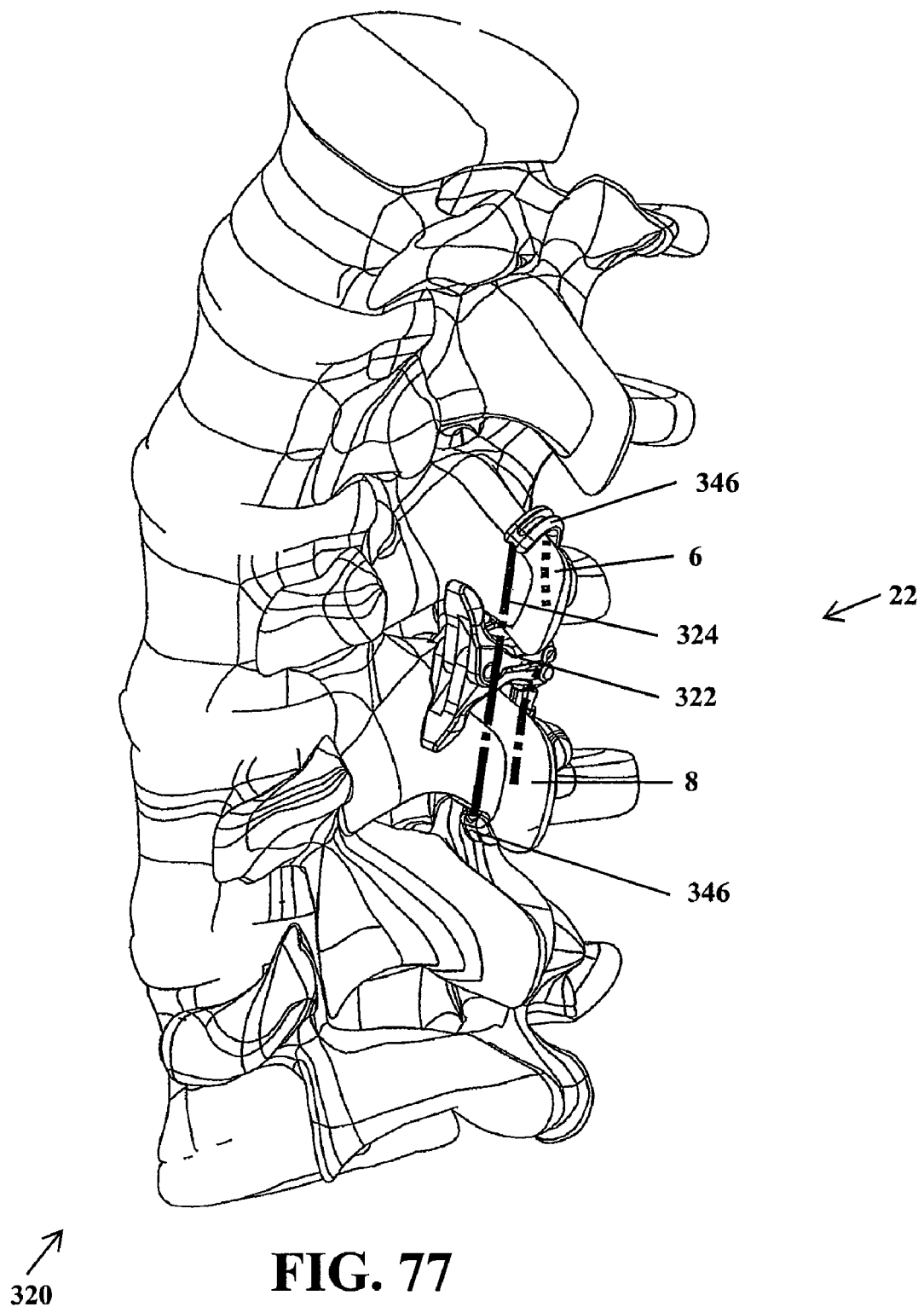
FIG. 77 is a posterior aspect prospective view of the implant of FIG. 76.

An implant 320 in accordance with another aspect of the invention is shown in FIGS. 76-97. As shown in FIG. 76, the implant device 320 includes an interspinous spacer 322 configured to be positioned between adjacent vertebrae 6 and 8. While other interspinous spacers can be utilized, the interspinous spacer 322 as shown in FIGS. 76-97 is similar to the interspinous spacers described above, with any differences discussed below.

As shown in FIGS. 76-81, the implant device 320 includes an interspinous implant member 322 for being positioned between and distracting adjacent vertebrae 6 and 8. A locking cable 324 extends about the adjacent vertebrae 6 and is connected to the interspinous spacer 322. More particularly, the cable 324 is secured to the spacer 322 by a pair of cable crimps 326.

Figure 78:
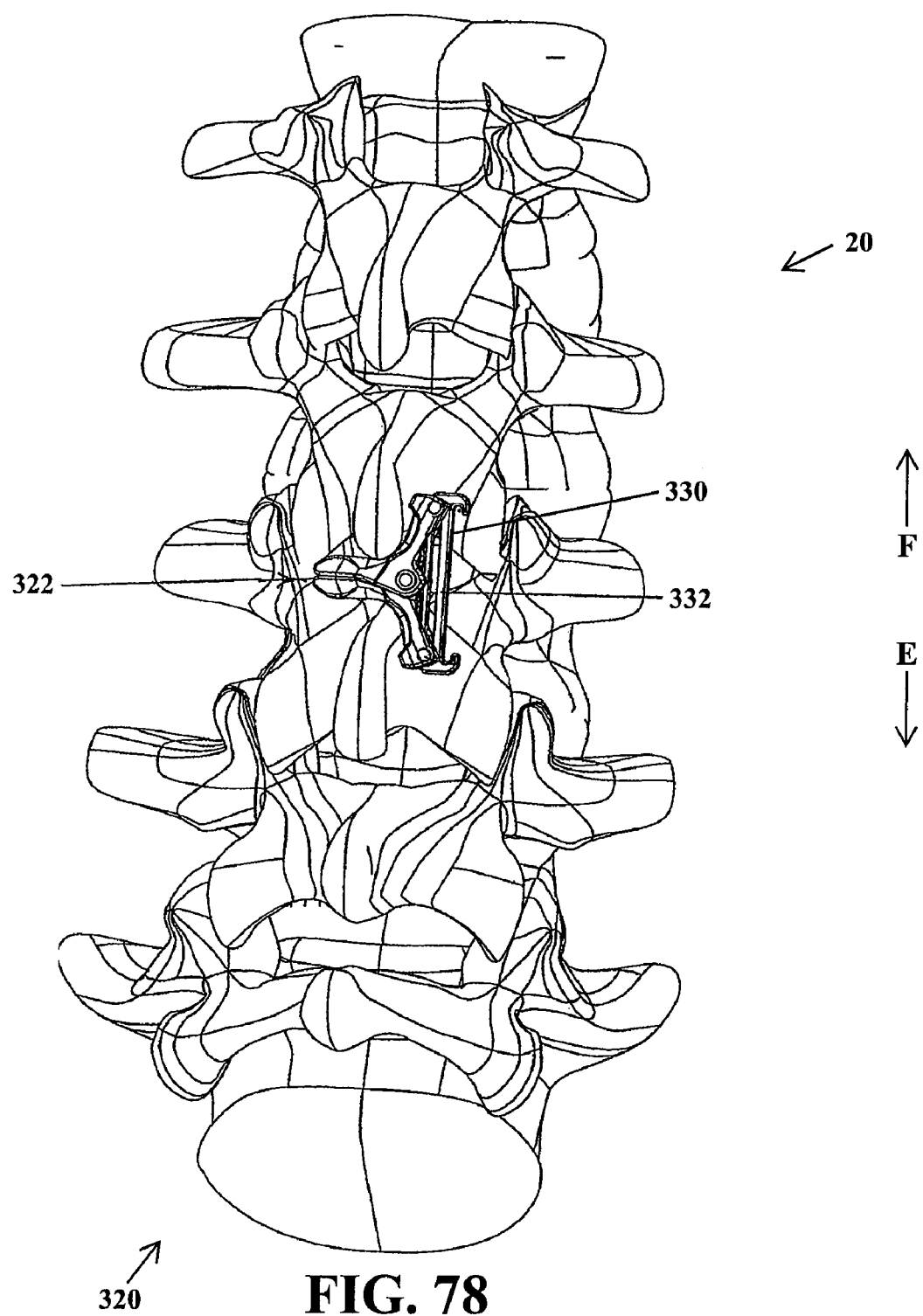
FIG. 78 is a posterior aspect prospective view of the interspinous member and spanning member of the implant of FIG. 76 with the interspinous member in the insertion orientation.
Figure 79:
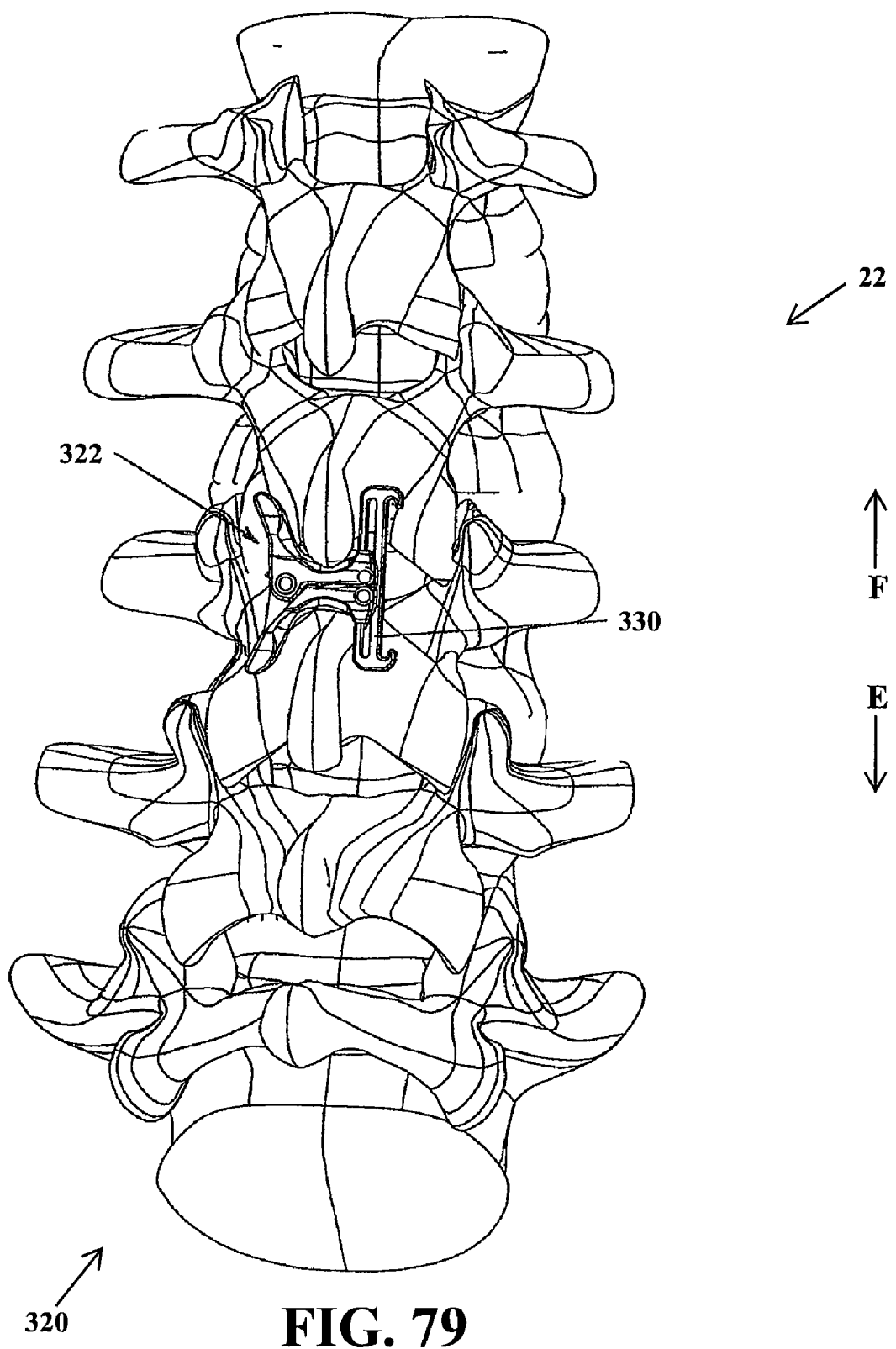
FIG. 79 is a posterior aspect prospective view of the interspinous member and spanning member of the implant of FIG. 76 with the interspinous member in the implanted orientation.
Figure 80:
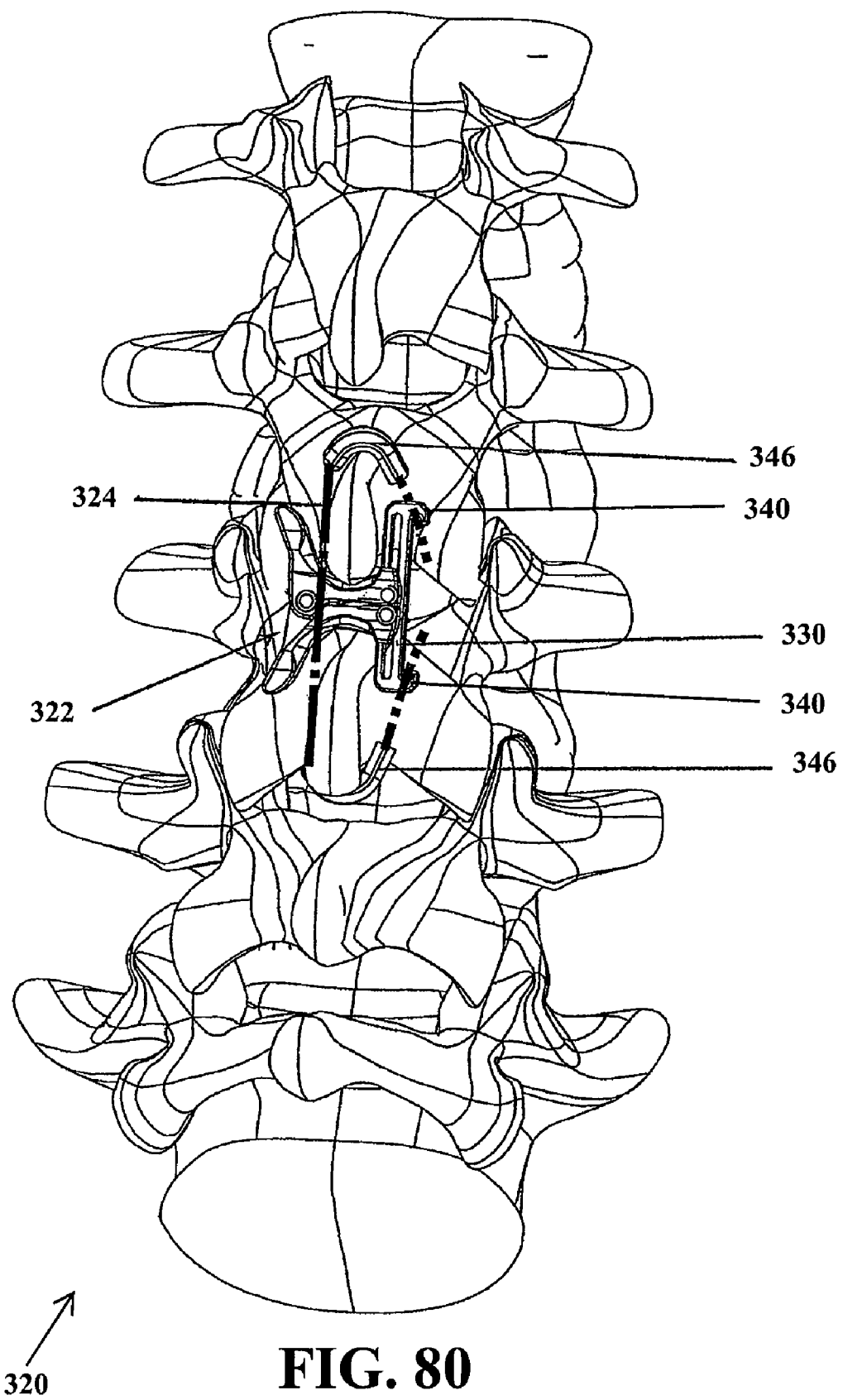
FIG. 80 is a posterior aspect prospective view of the implant of FIG. 76 showing the interspinous member in the implanted orientation, the grommets positioned on the spinous processes and the cable extending about the spinous processes and between the ends of the spanning member.
Figure 81:
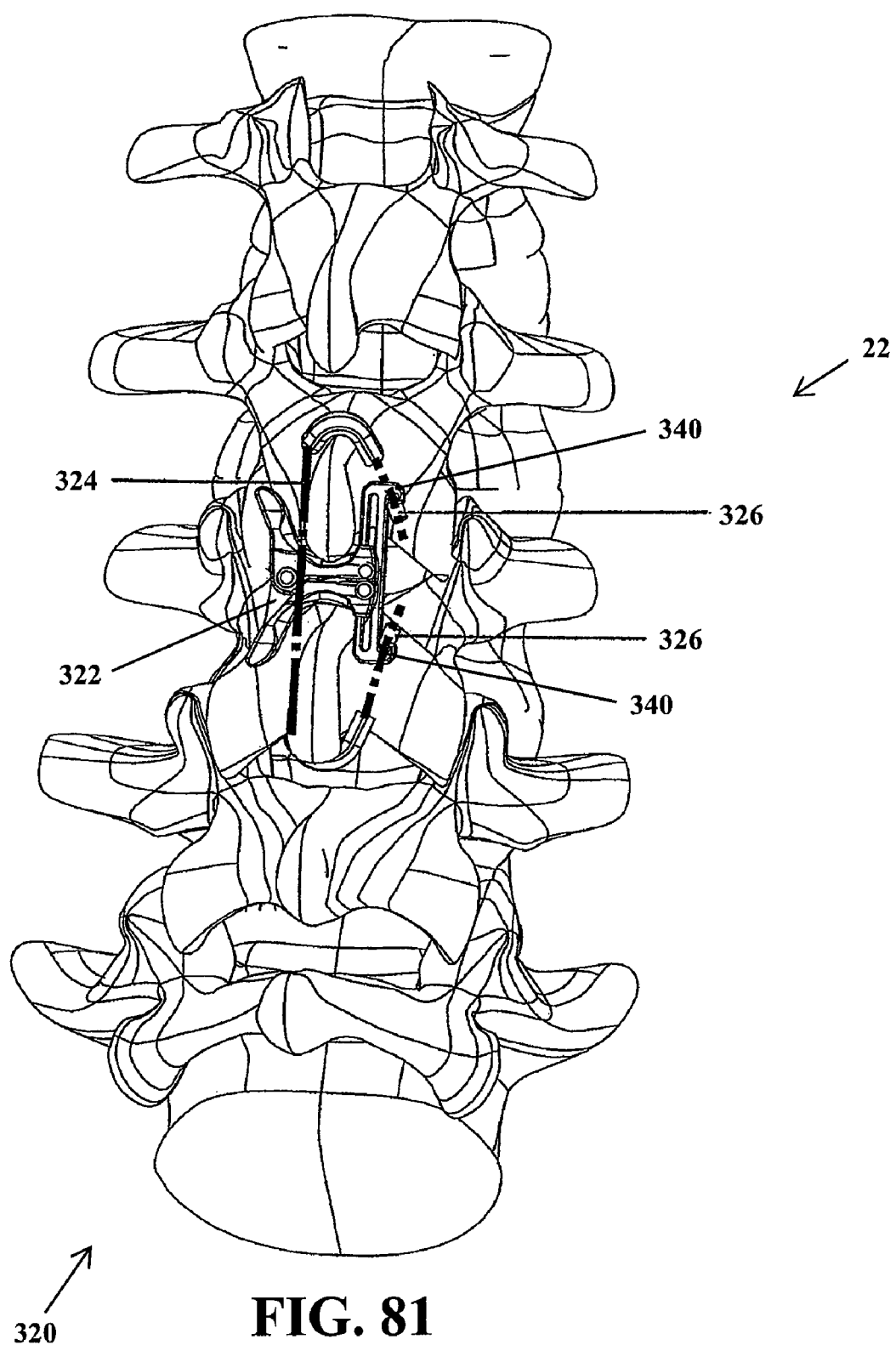
FIG. 81 is a posterior aspect prospective view of the implant of FIG. 76 showing the cable secured to the spanning member by crimps.
Figure 82:
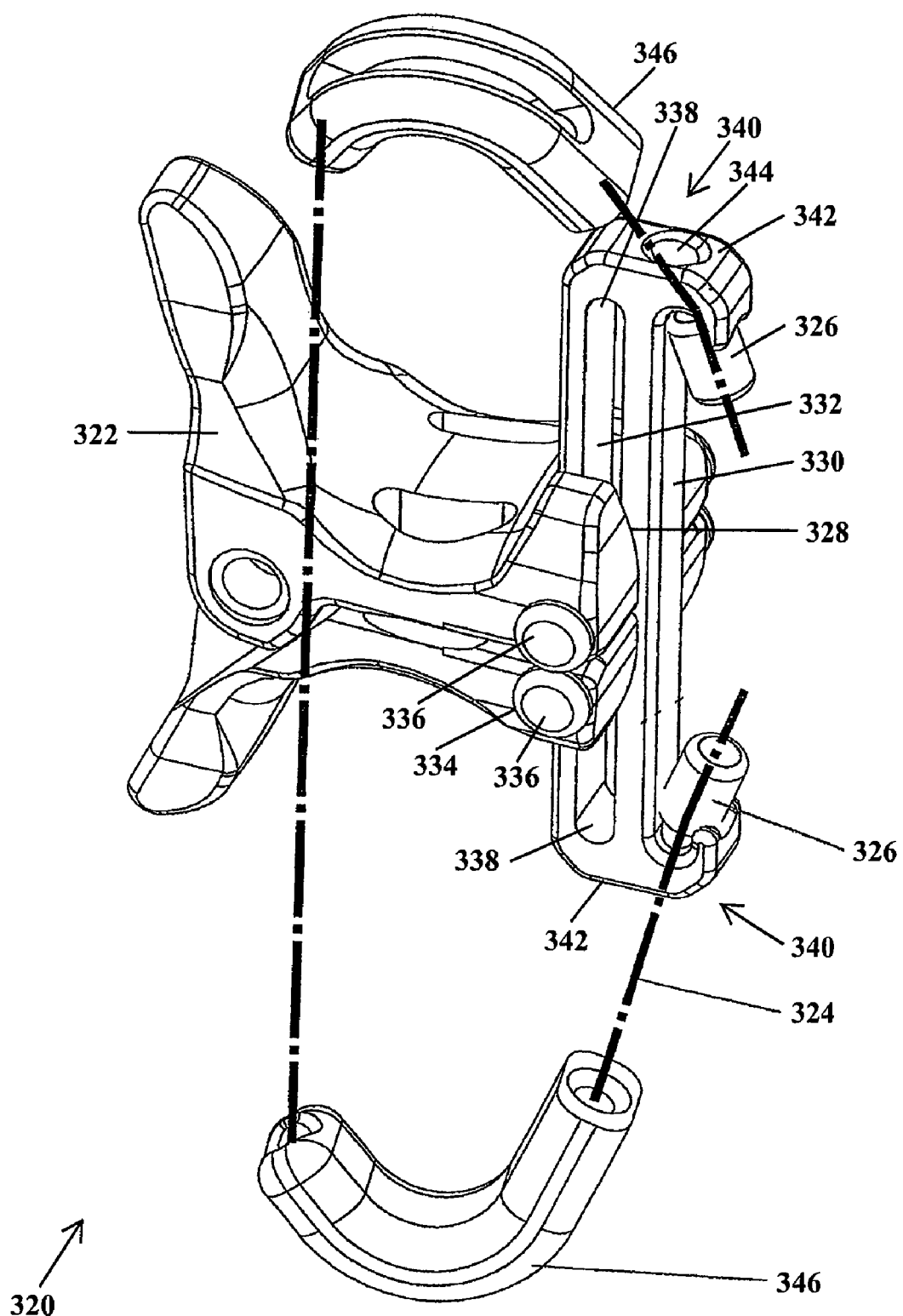
FIG. 82 is a perspective view of the implant of FIG. 76.
Figure 83:
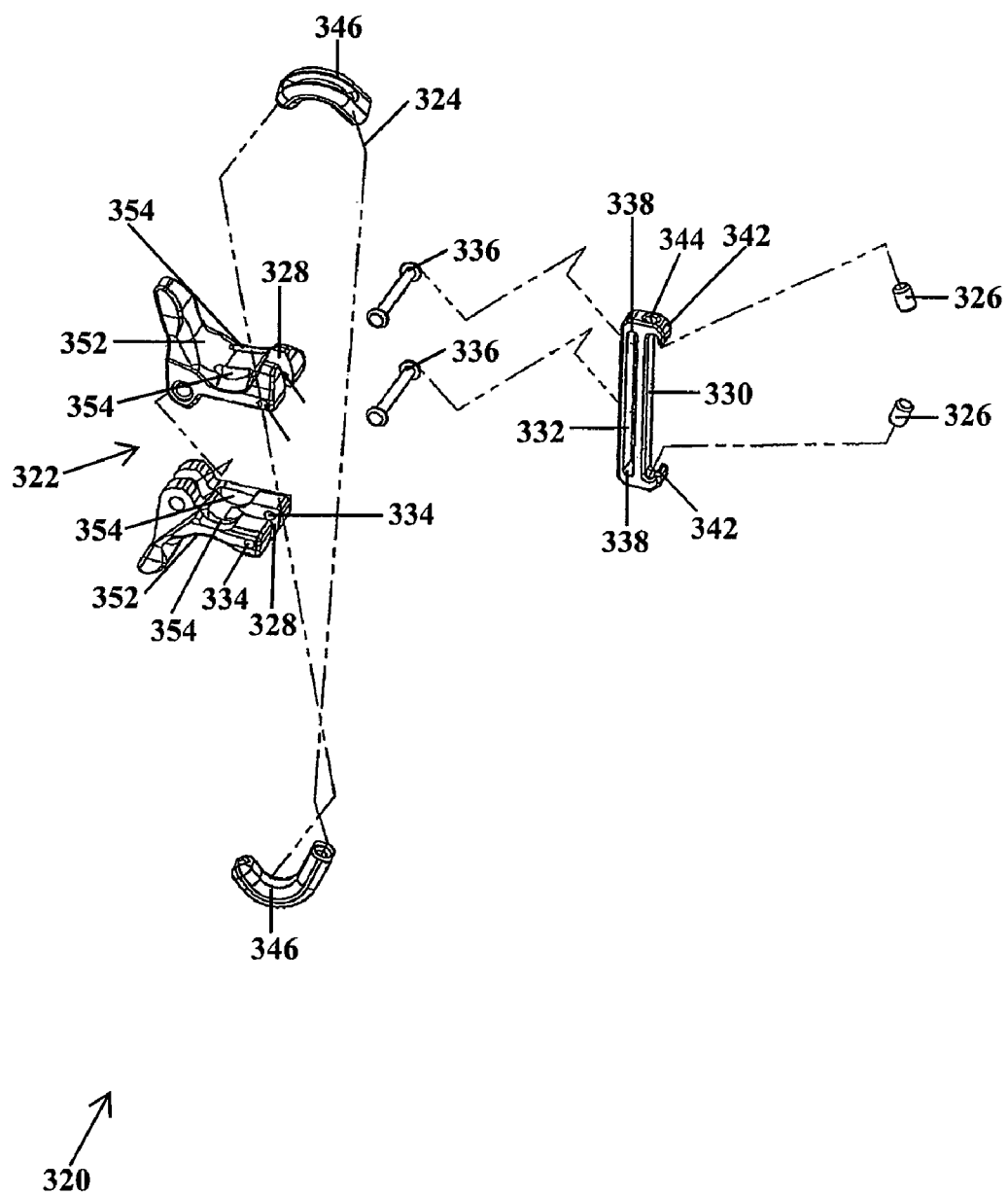
FIG. 83 is an exploded view of the implant of FIG. 76.
Figure 84:
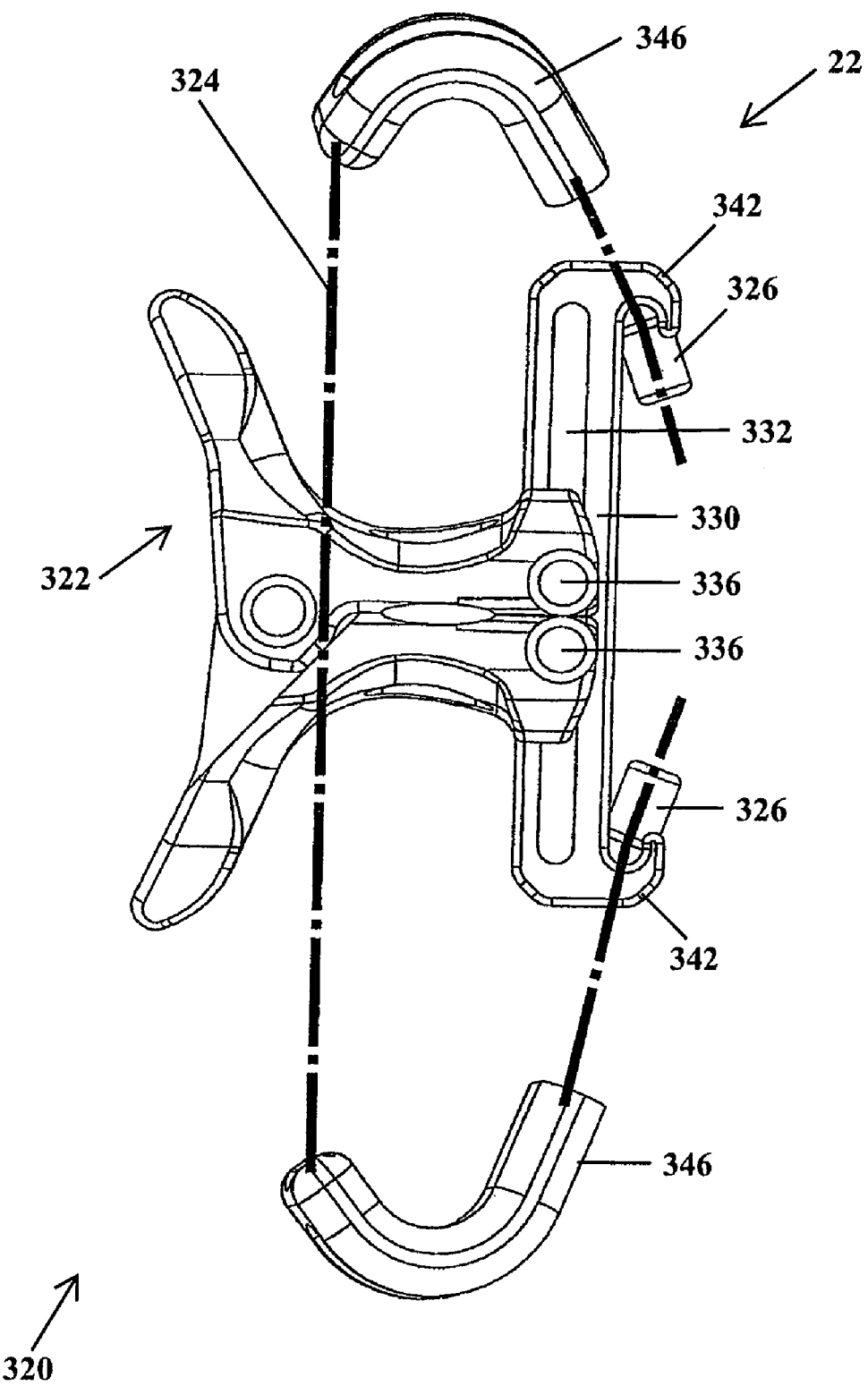
FIG. 84 is a front elevational view of the implant of FIG. 76.

As shown in FIGS. 82 and 83, the interspinous spacer 322 includes a slotted end 328 for receiving a spanning member 330 therein. The spanning member 330 includes an elongate slot 332 extending along its length. As shown in FIGS. 82-84, the interspinous member 322 includes a series of throughbores 334 for receiving pivot pins 336 therethrough. The pins 336 are configured to extend through the throughbores 334 and the elongate slot 332 of the spanning member 330. As shown in FIGS. 78 and 79, the pins 336 shift along the elongate slot 332 in directions E and F as the interspinous member 322 is pivoted between the compact orientation 20, wherein the pins 336 are shifted away from each other and toward the ends 338 of the slot 332, and the implanted orientation 22, wherein the pins 336 are shifted toward one another. As a result, the pins 336 maintain a mechanical connection with both the spanning member 330 and the interspinous spacer 322 while the interspinous spacer 322 is shifted from the insertion orientation 20 to the implanted orientation 22.

The cable 324 is connected to either end 340 of the spanning member 330 and extends about the spinous processes 6 and 8 as shown in FIGS. 77, 78 and 80-82. The cable 324 is configured to apply force to the spinous processes 6 and 8 to limit or prevent flexion of the mechanically engaged vertebrae 6 and 8. The force further acts to maintain the engagement of the vertebrae 6 and 8 and the spacer 322 thereby securing or locking the spacer 322 in the implanted orientation 22. The cable 324 preferably includes of braided stainless steel or cobalt chrome surgical or cerclage cable as describe in U.S. Pat. No. 6,605,091 with Ser. No. 09/608,536 filed Jun. 30, 2000 and titled SURGICAL CABLE ASSEMBLY AND METHOD which is incorporated herein by reference in its entirety. Alternatively, the cable 324 can be made from other biocompatible materials such as titanium, or synthetic polymer fibers such as polyglycolic acid (P.G.A.) or polydioxanone (PDS) in monofilament or braided configurations. However, even gut sutures could be used.

Figure 85:
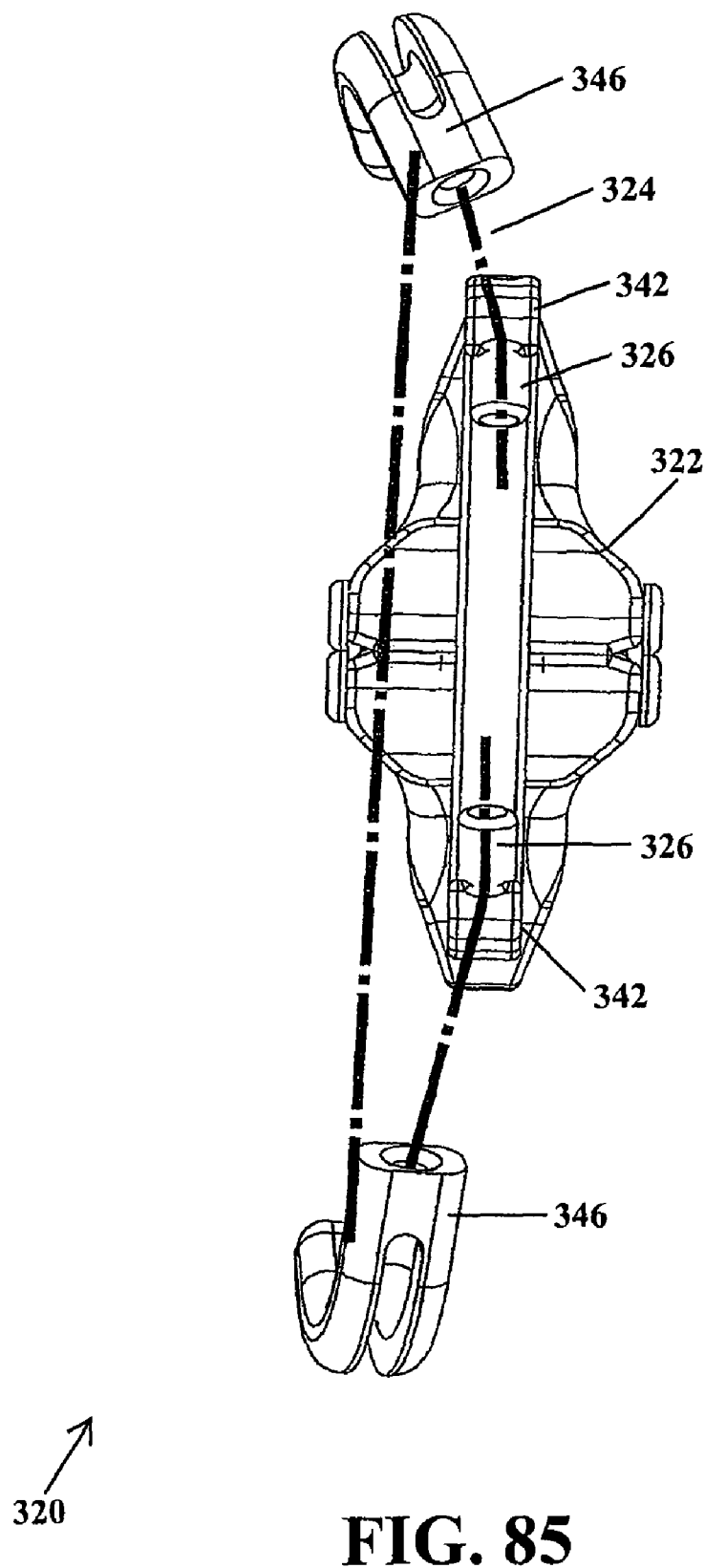
FIG. 85 is a right side elevational view of the implant of FIG. 76 showing the grommets offset from the spanning member.
Figure 86:
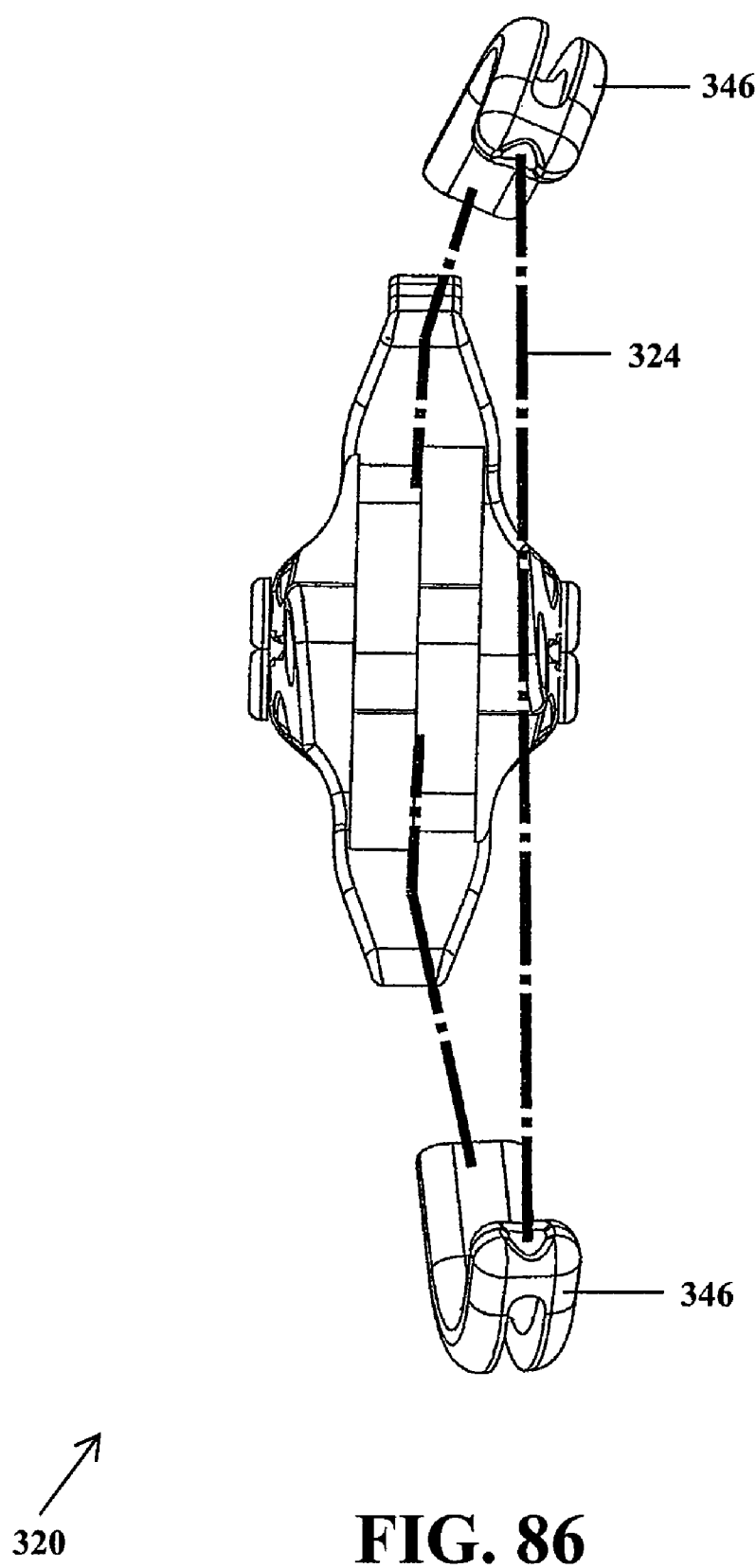
FIG. 86 is a left side elevational view of the implant of FIG. 76.
Figure 87:
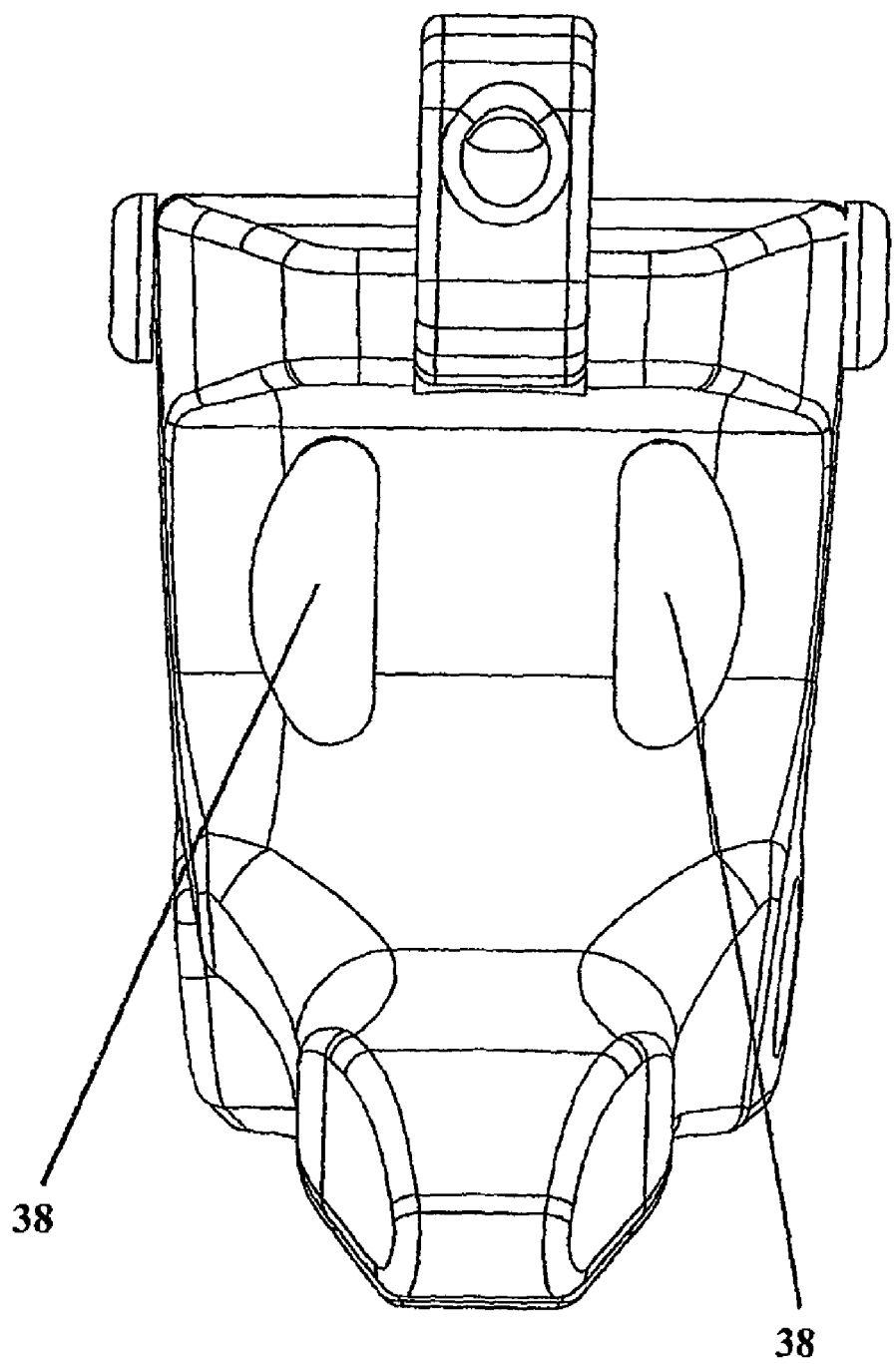
FIG. 87 is a bottom view of the implant of FIG. 76 showing a pair of openings in the interspinous member seat for receiving bone growth material.
Figure 88:
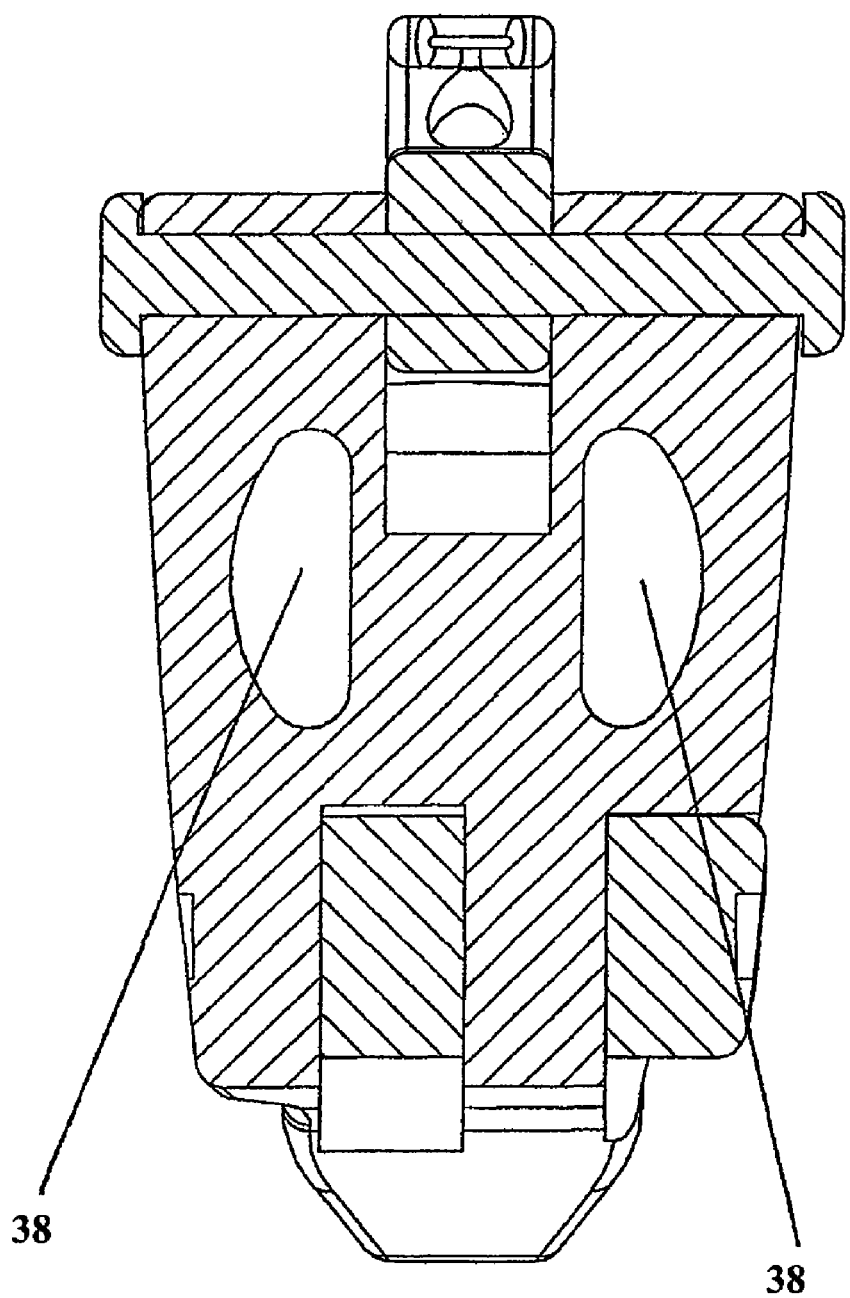
FIG. 88 is a bottom sectional view of the implant of FIG. 76 showing the pin extending through the interspinous member and the spanning member.
Figure 89:
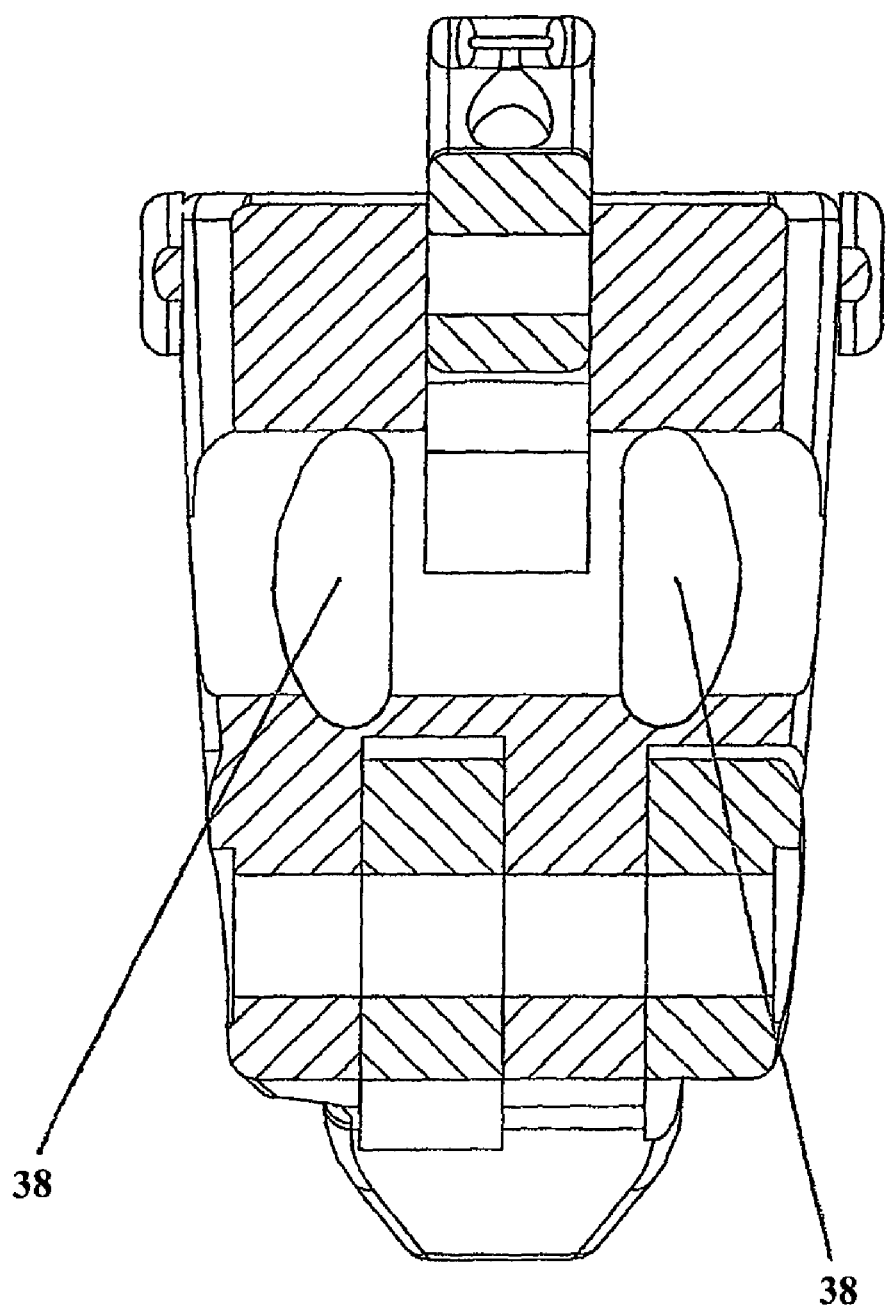
FIG. 89 is a bottom sectional view of the implant of FIG. 76.
Figure 90:
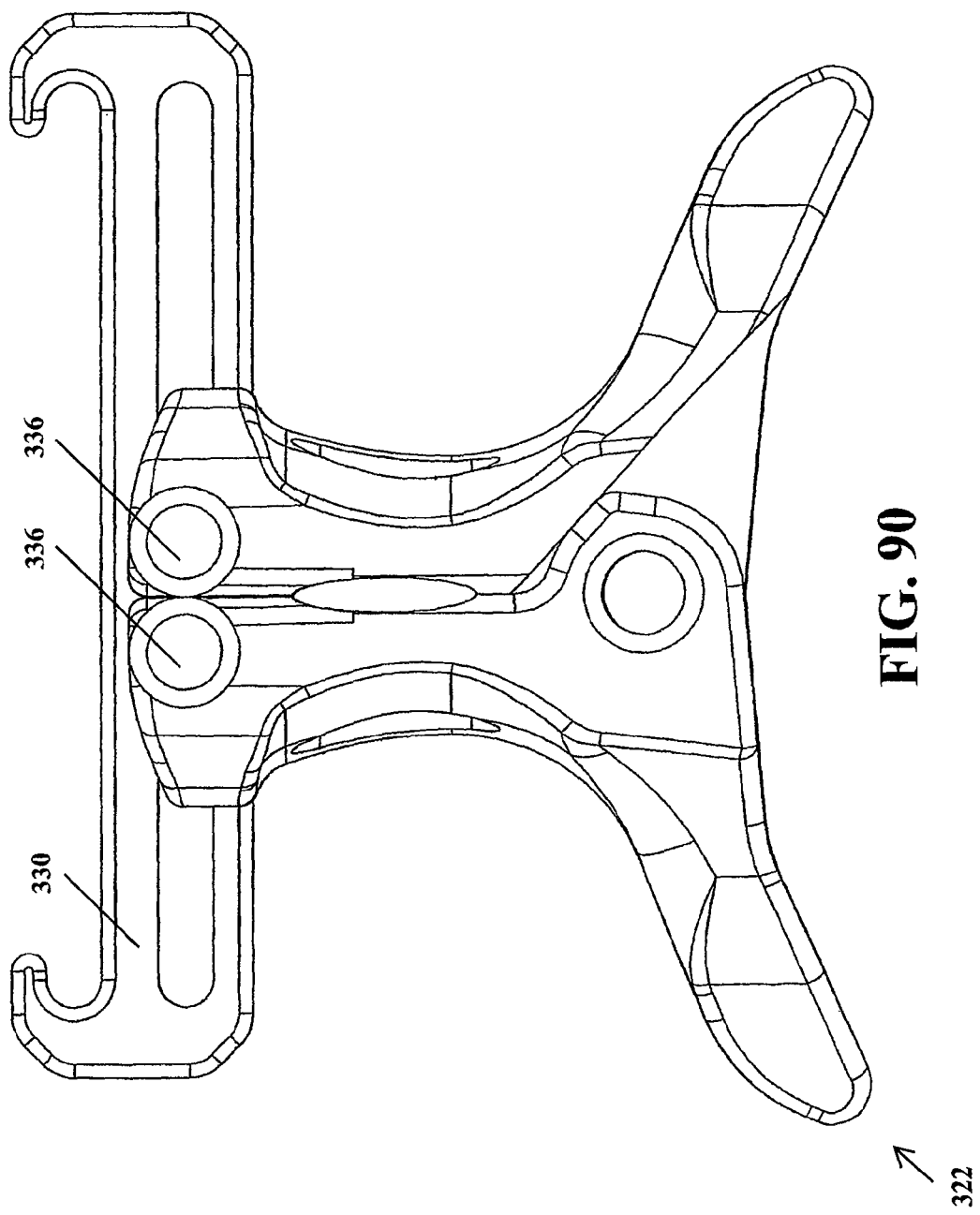
FIG. 90 is a front elevational view of the implant of FIG. 76 showing the interspinous member in the implanted orientation.
Figure 91:
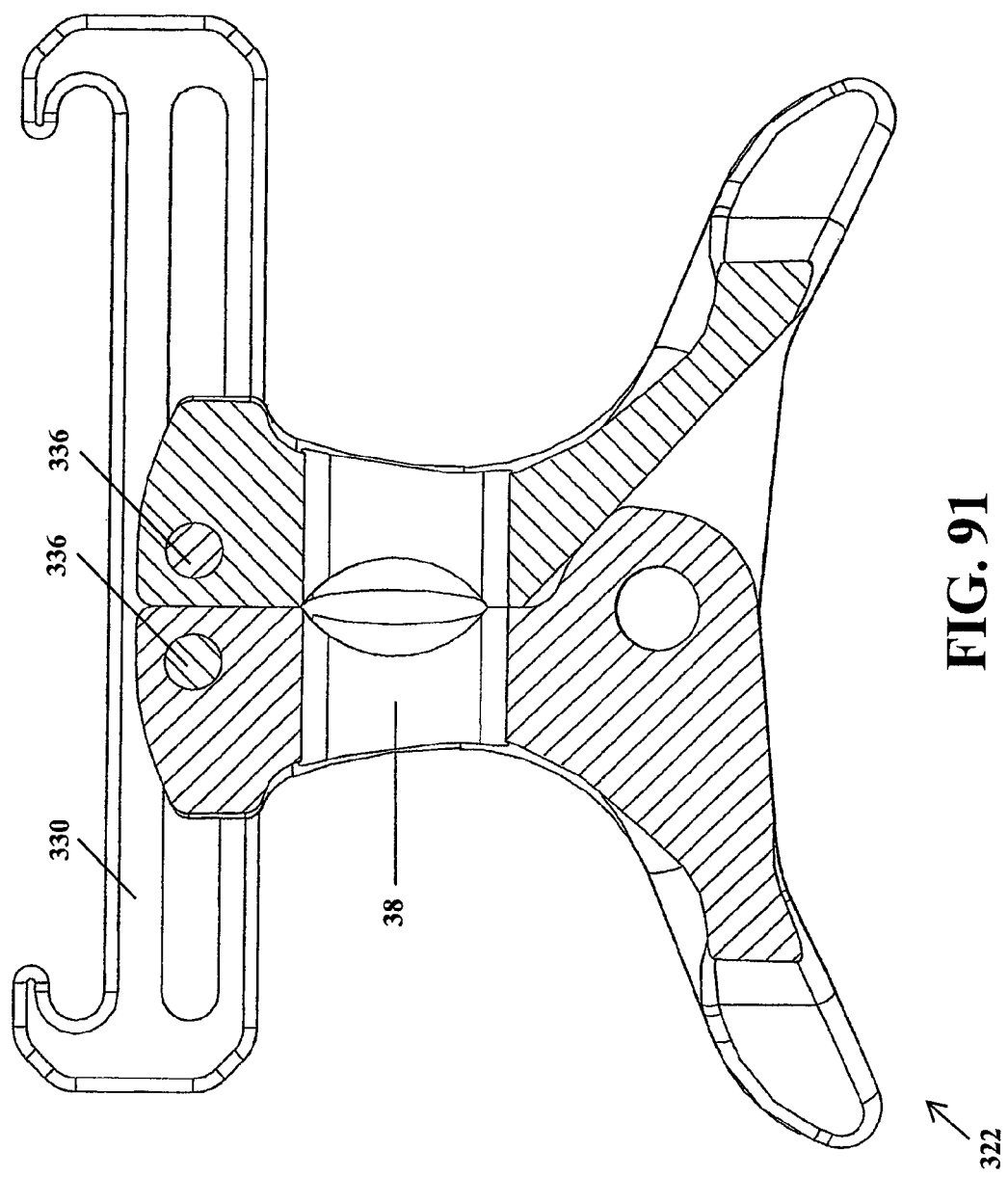
FIG. 91 is a front sectional view of the implant of FIG. 76 showing the openings extending through the seat of the interspinous member.
Figure 92:
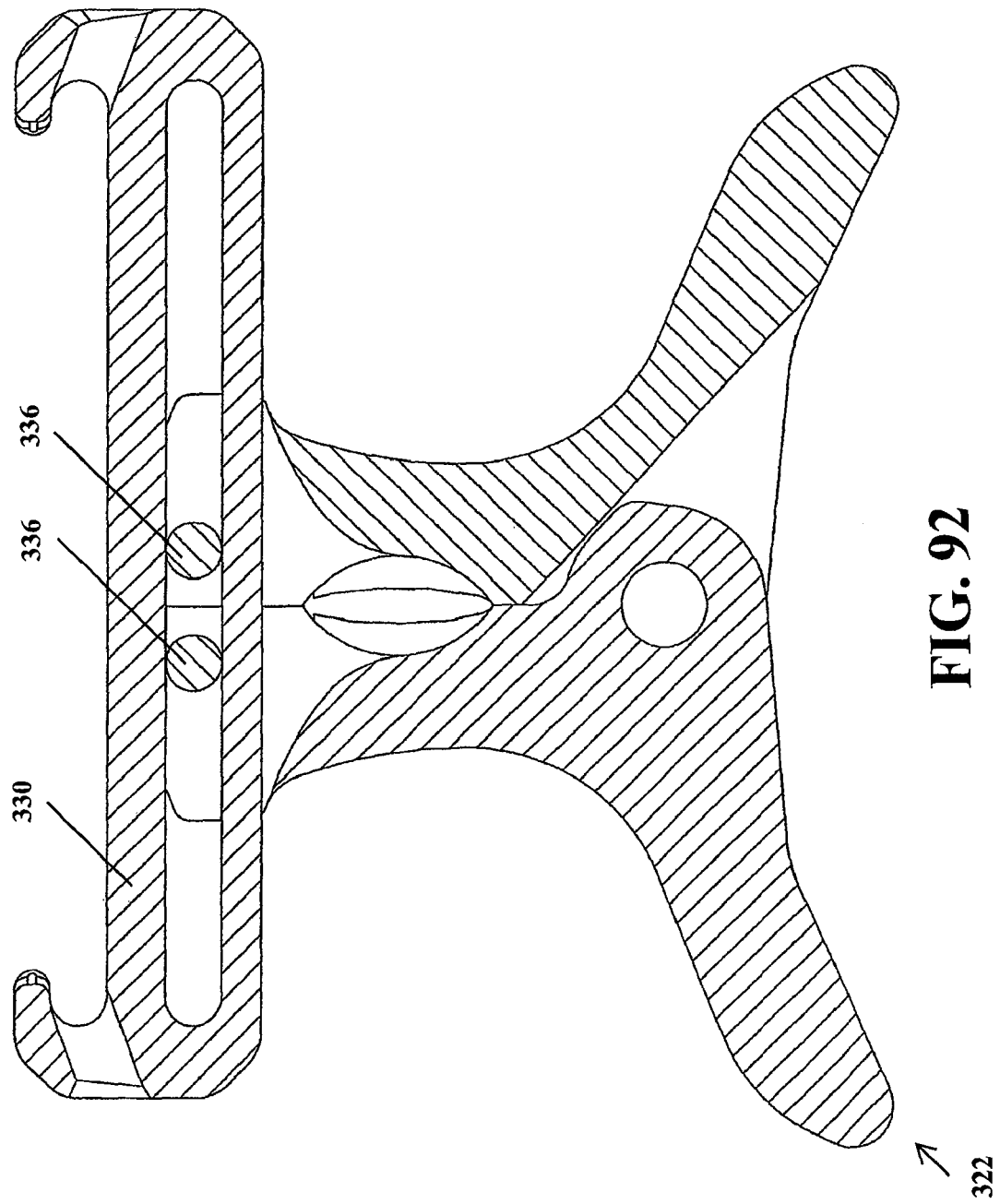
FIG. 92 is a front sectional view of the implant of FIG. 76.
Figure 93:
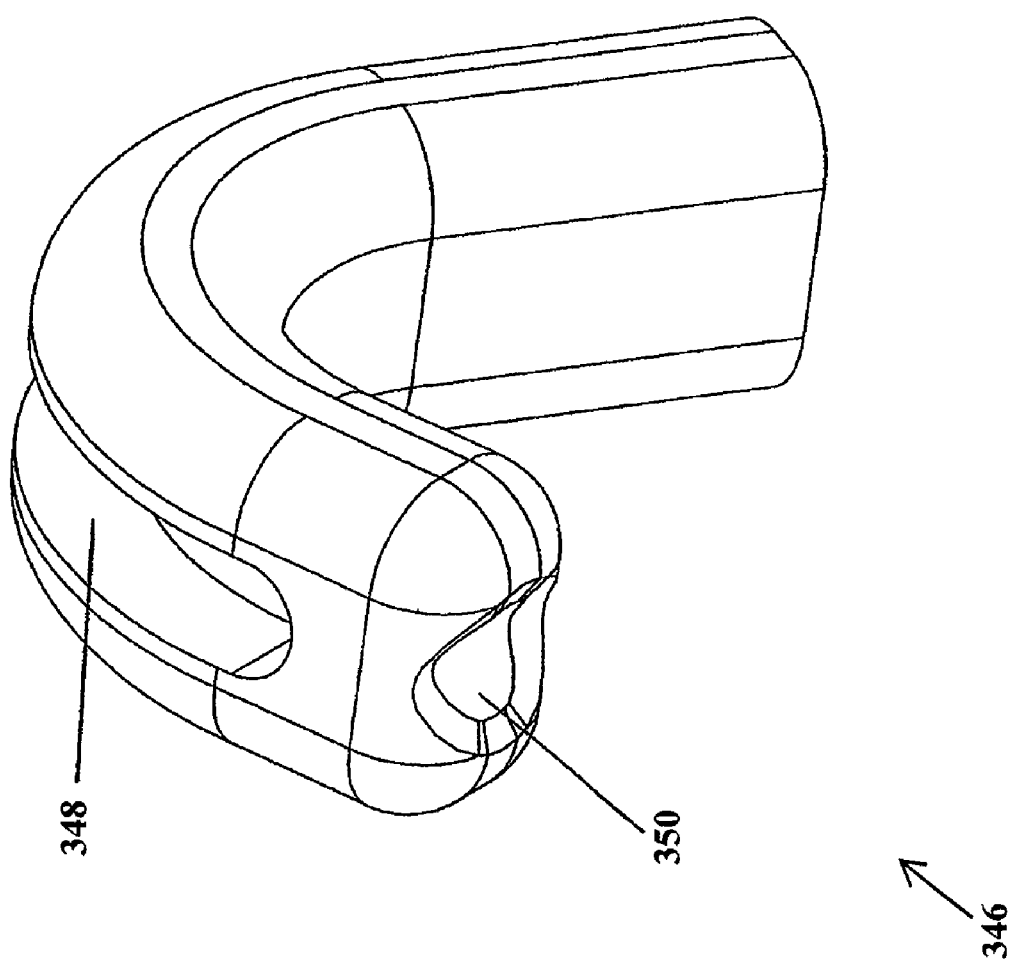
FIG. 93 is a perspective view of the grommet of the implant of FIG. 76 showing the groove and opening for positioning the cable.
Figure 94:
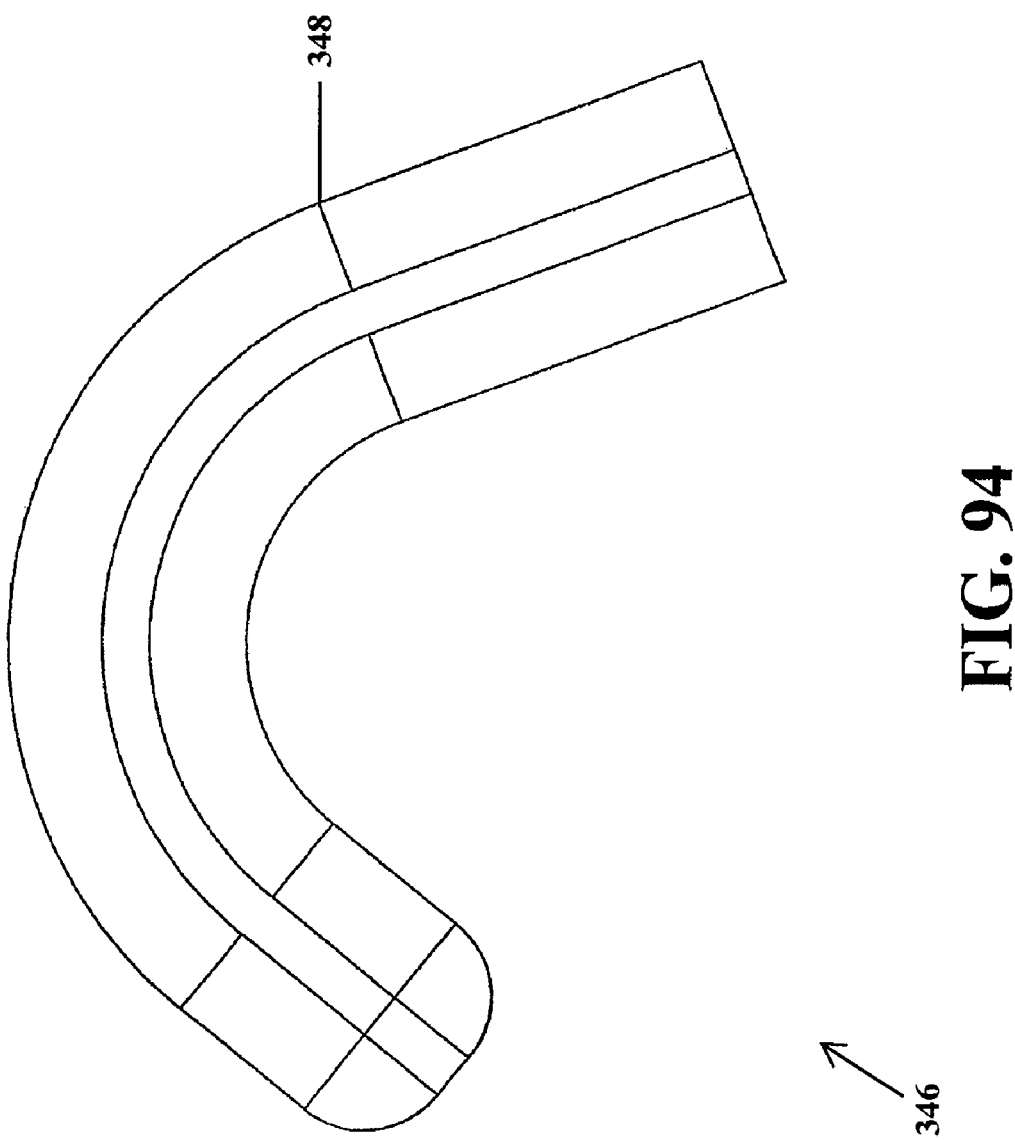
FIG. 94 is a front elevational view of the grommet of the implant of FIG. 76.
Figure 95:
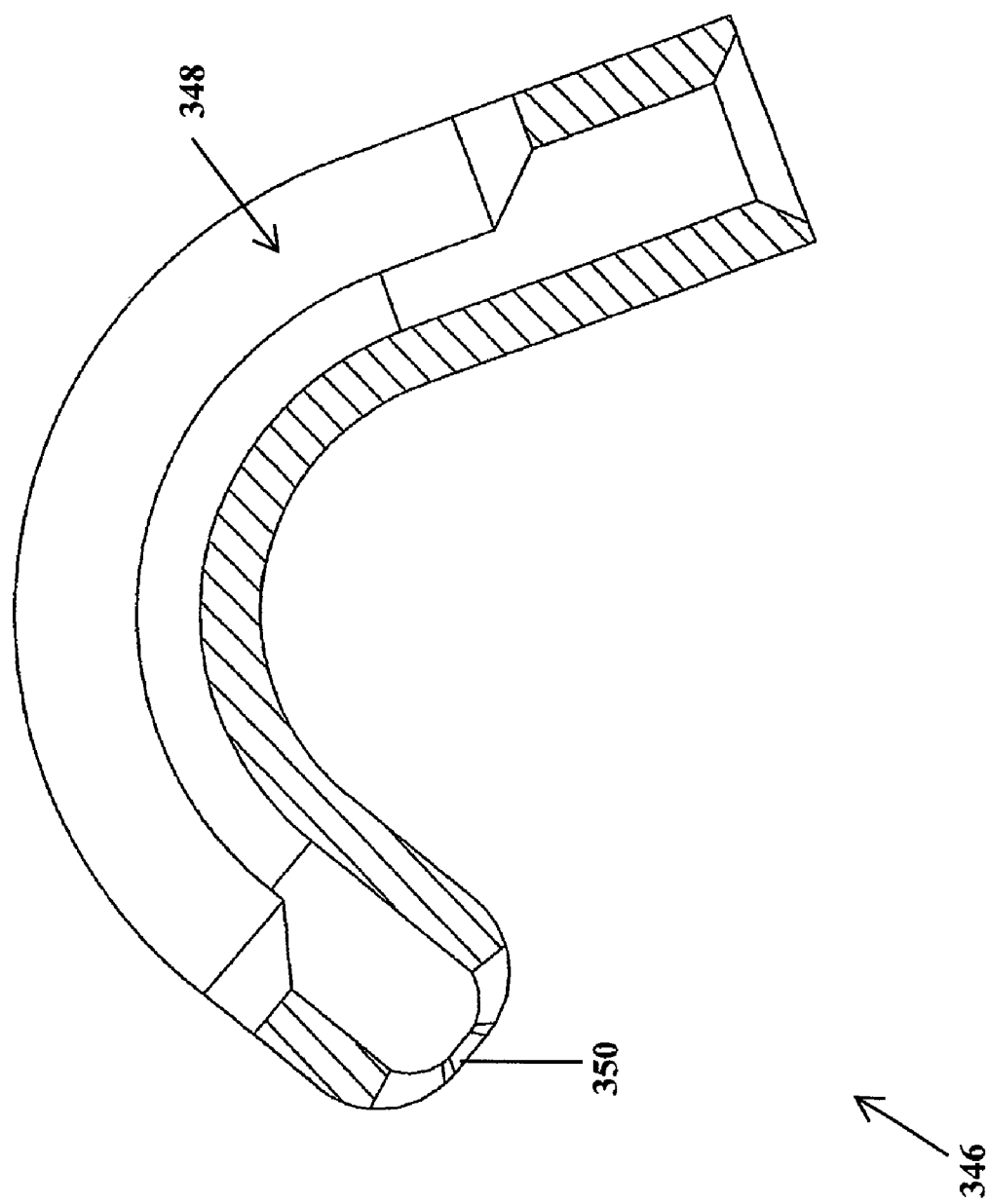
FIG. 95 is a front sectional view of the grommet of the implant of FIG. 76.
Figure 96:
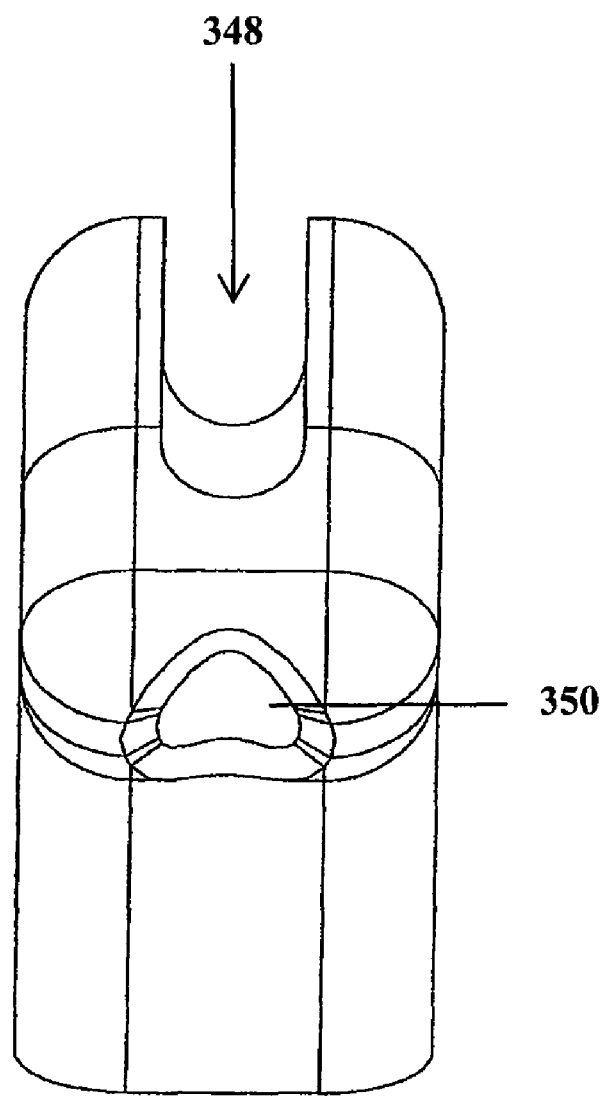
FIG. 96 is a side elevational view of the grommet of the implant of FIG. 76.
Figure 97:
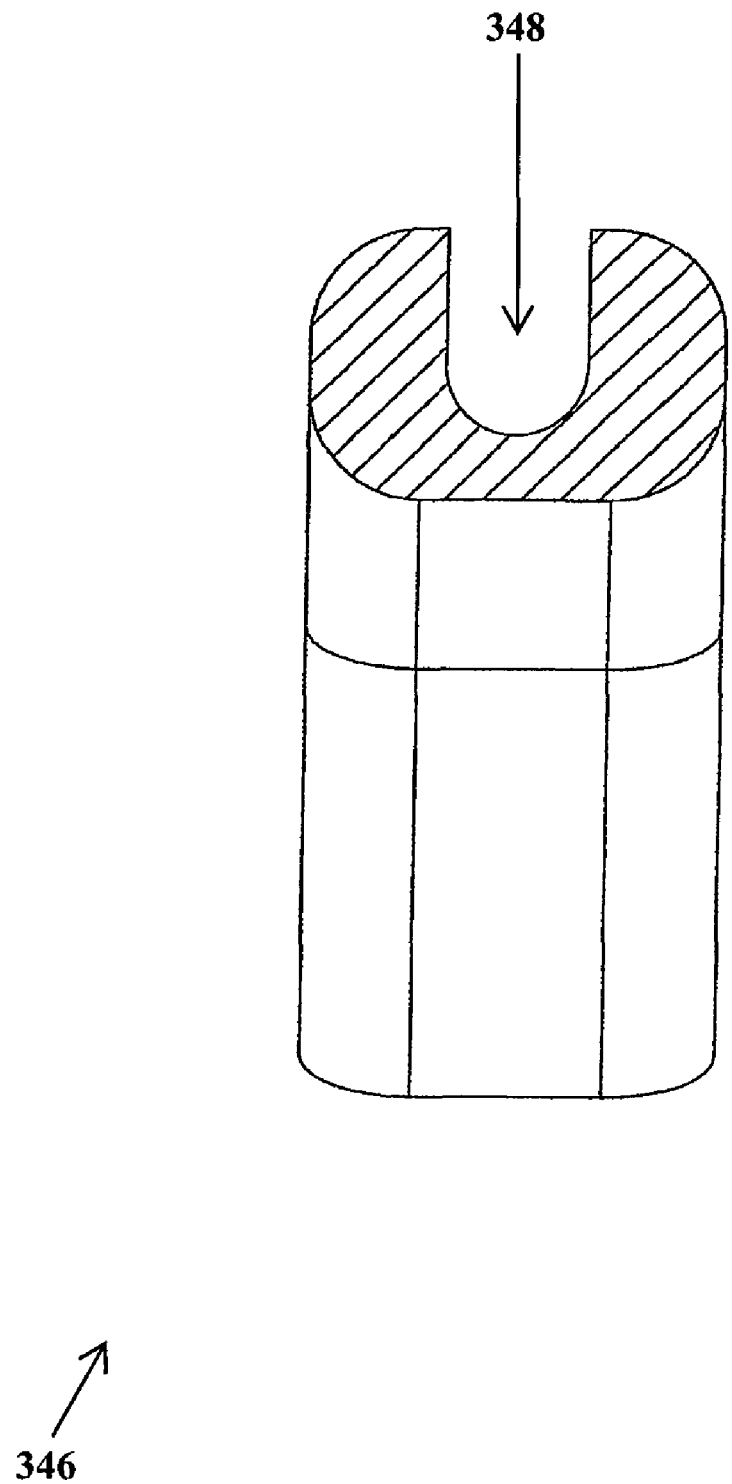
FIG. 97 is a side sectional view of the grommet of the implant of FIG. 76.

As shown in FIG. 82-85, the spanning member 330 includes a flange 342 at either end 340. The flanges 342 each include openings 344 for the cable 324 to extend therethrough. As shown in FIGS. 82 and 85, the flanges 342 are configured to house a crimp 326 which secures the cable 324. The crimps 326 can include those crimps discussed above with references to the embodiment shown in FIGS. 1-33.

As shown in FIGS. 76-82, the implant device 320 can further include sleeves 346 positioned on one or both of the spinous processes 6 and 8. The sleeve 346 is configured to limit or prevent the cable 324 from cutting or wearing against the spinous process 6 and 8. As shown in FIGS. 82 and 93-97, the sleeve 346 includes a channel 348 to seat the cable 324 therein. The sleeve 346 can further include eyelets 350 to limit or prevent slippage of the cable 324 out from the channel 348. The sleeve 346 is preferably made of deformable and biocompatible materials such as PEEK or titanium to allow the sleeve to deform to conform to the exact shape of the patient's anatomy, i.e. the spinous process 6 and 8. Alternatively, the sleeve 346 can be made from materials such as stainless steel or other biocompatible materials.

As shown in FIG. 83, the implant member seat 352 includes throughbores 354 within which bone void filler can be inserted. The fixation of the spinous processes 6 and 8 and presence of bone void filler therebetween allows bone to grow between the spinous processes 6 and 8.

The implant device 320 can be implanted by a surgeon unilaterally from a posterior approach. While not necessary, the unilateral approach allows for minimally invasive surgery to minimize the amount of trauma to adjacent tissue because only one side of the spinal erector muscles need be disrupted. In particular, the cable 324 is threaded through the sleeves 346 and the spanning member 330 and looped around the adjacent spinous processes 6 and 8 within the adjacent interspinous process 6 and 8. Finally, the crimps 326 are attached to the cable 324 and crimped to lock the implant device 320 in the final position. The threading and crimping of the cable 324 follows standard, conventional surgical procedures.

Figure 98:
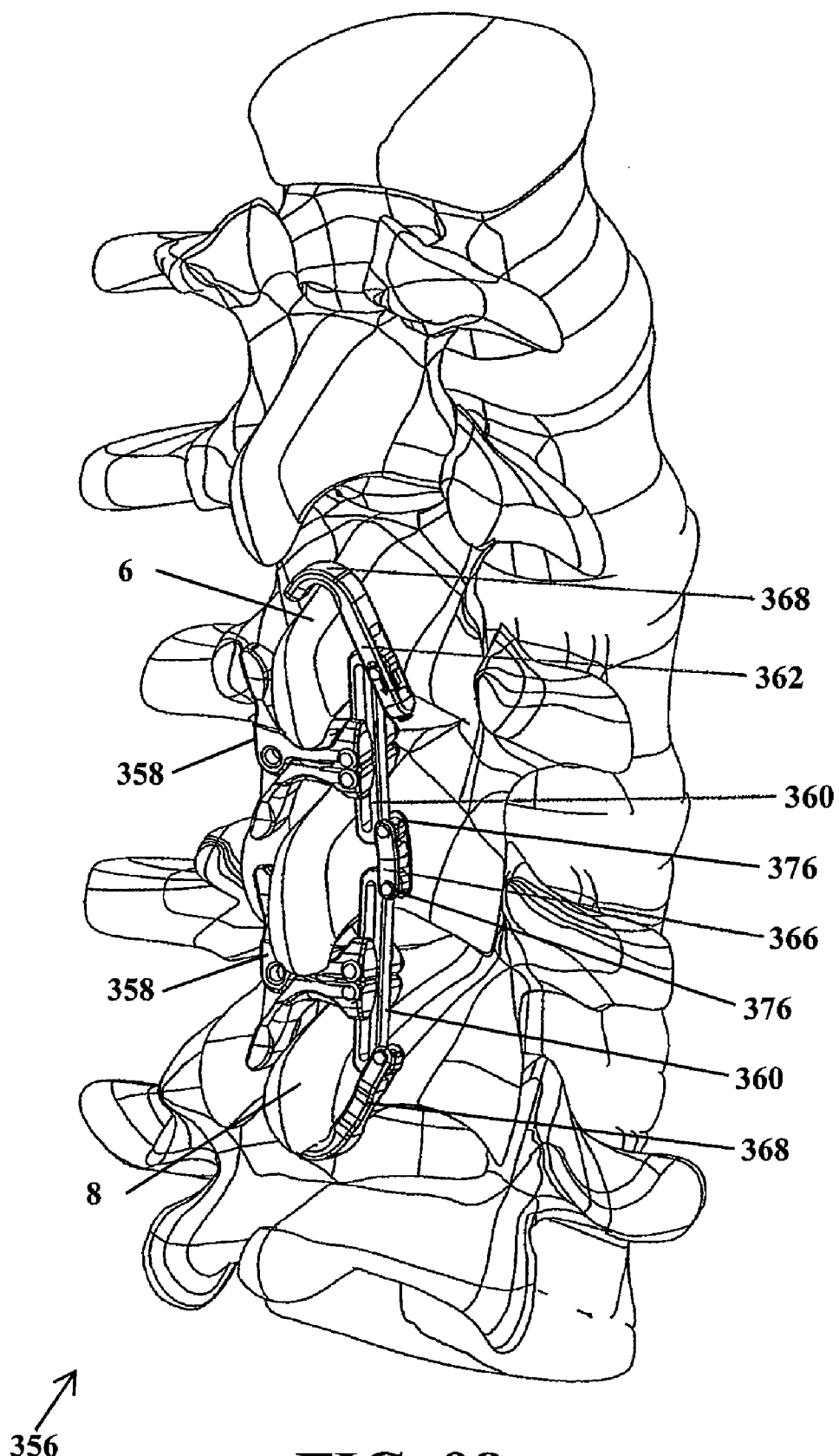
FIG. 98 is a posterior aspect prospective view of an implant in accordance with another aspect of the invention showing a pair of interspinous insertion members, a spanning member of each of the insertion members, a linkage connecting the spanning members and a connecting hook extending from each of the spanning members and engaging a spinous process.

An implant 356 in accordance with another aspect of the invention is shown in FIGS. 98-112. As shown in FIG. 98, the implant device 356 includes an interspinous spacer 358 configured to be positioned between adjacent vertebrae 6 and 8. While other interspinous spacers can be utilized, the interspinous spacer 358 as shown in FIGS. 98-112 is similar to the interspinous spacers described above, with any differences discussed below.

In particular, the interspinous spacer 358 and locking or spanning member 360 of the implant device 356 are similar to the interspinous spacer 320 and spanning member 330 of FIGS. 76-97. The only significant difference between the two is the flange configuration 362 of the spanning member 360, which does not include an opening for cable 364 to extend therethrough.

Figure 99:
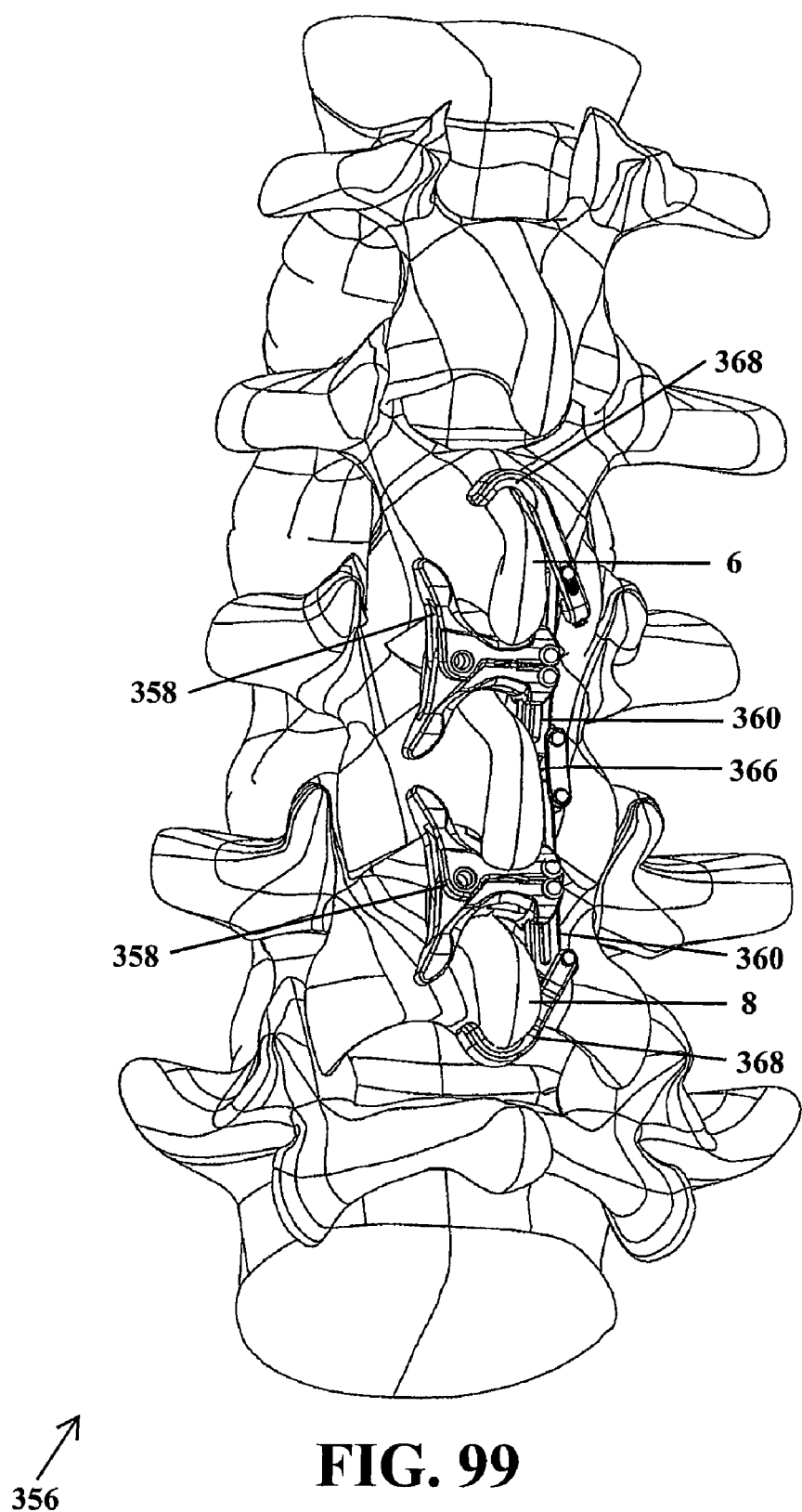
FIG. 99 is a posterior aspect prospective view of the implant of FIG. 98.

As shown in FIGS. 98 and 99, the implant device 356 includes at least two interspinous implants 358 with spanning members 360 attached thereto. The spanning members 360 are connected to one another by a linkage 366. Further, hook members 368 connect to and extend from the spanning members 360 and engage about the adjacent spinous processes 6 and 8 generally opposite the seat portions of the interspinous implants 358, thereby locking or securing the interspinous implants 358 in the implanted orientation 22.

As shown in FIGS. 98-102, the linkage 366 includes spaced arms 370 with a pin 372 extending between the distal arm ends 374. The pin 372 is configured to engage the flange 362 of the spanning member 360 and provide a pivot connection 376 therebetween. As shown in FIGS. 103-105 and 108-112, the linkage 366 can include a crooked configuration 378 to accommodate spinal geometries.

Figure 100:
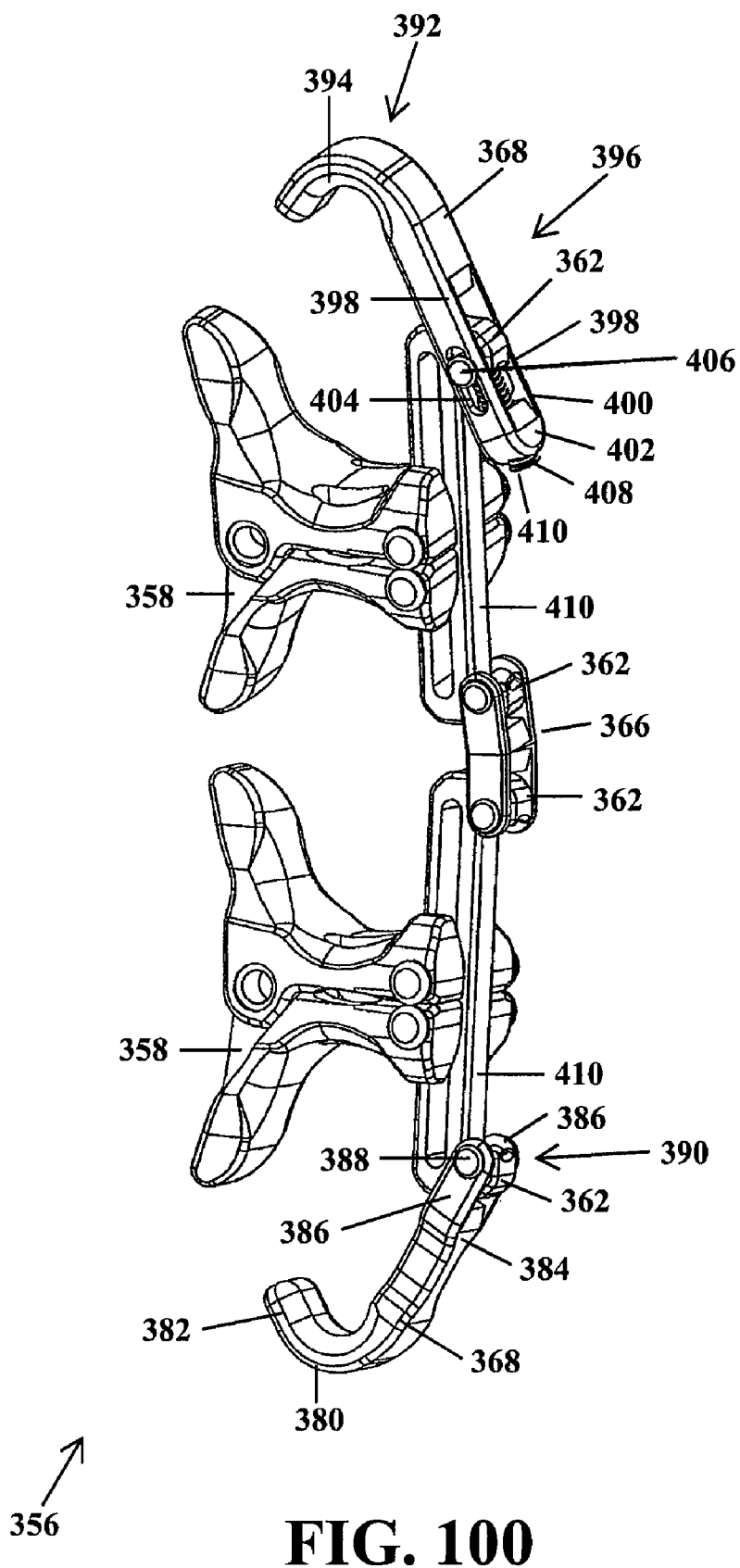
FIG. 100 is a perspective view of the implant of FIG. 98.
Figure 101:
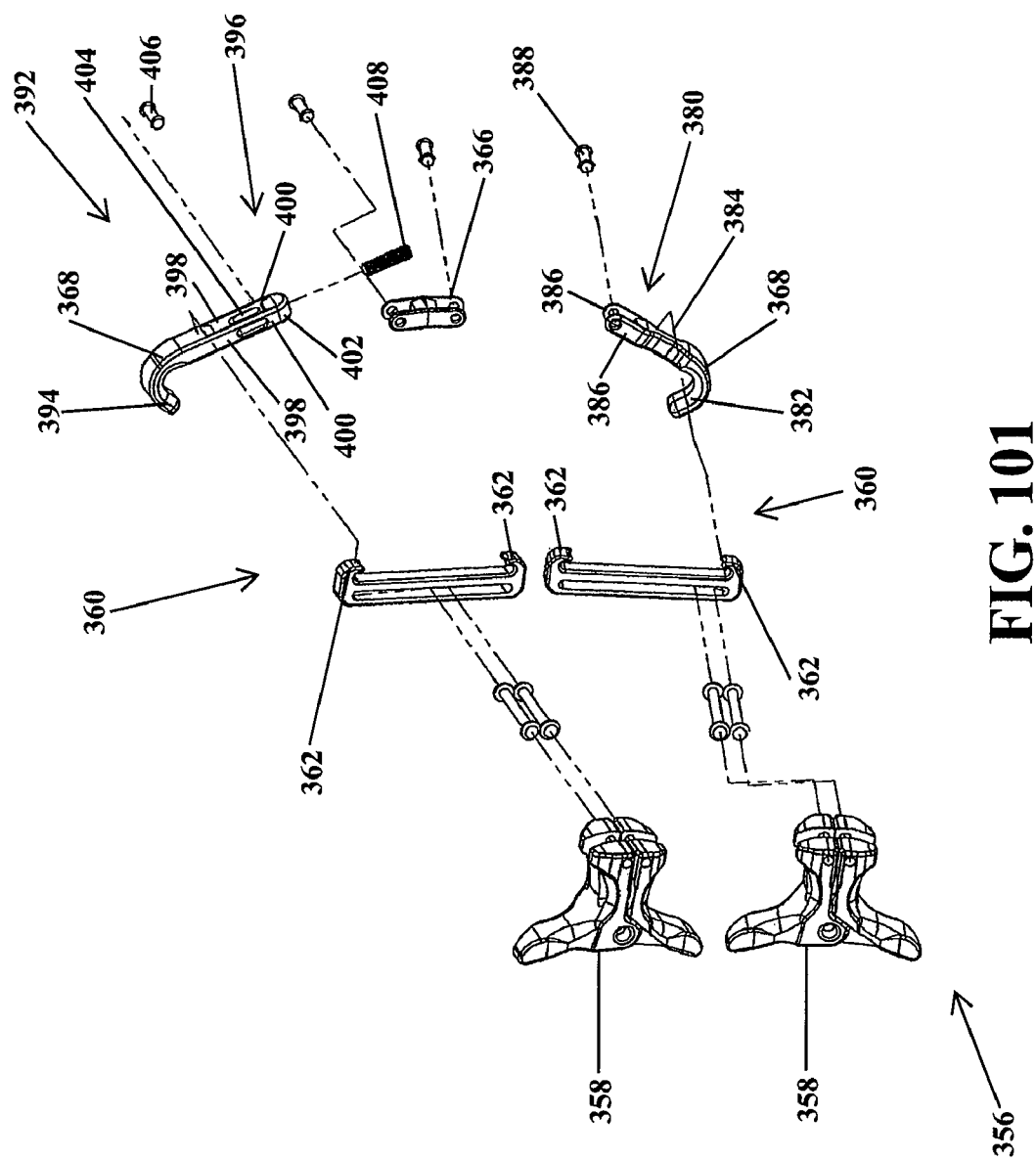
FIG. 101 is an exploded view of the implant of FIG. 98.
Figure 102:
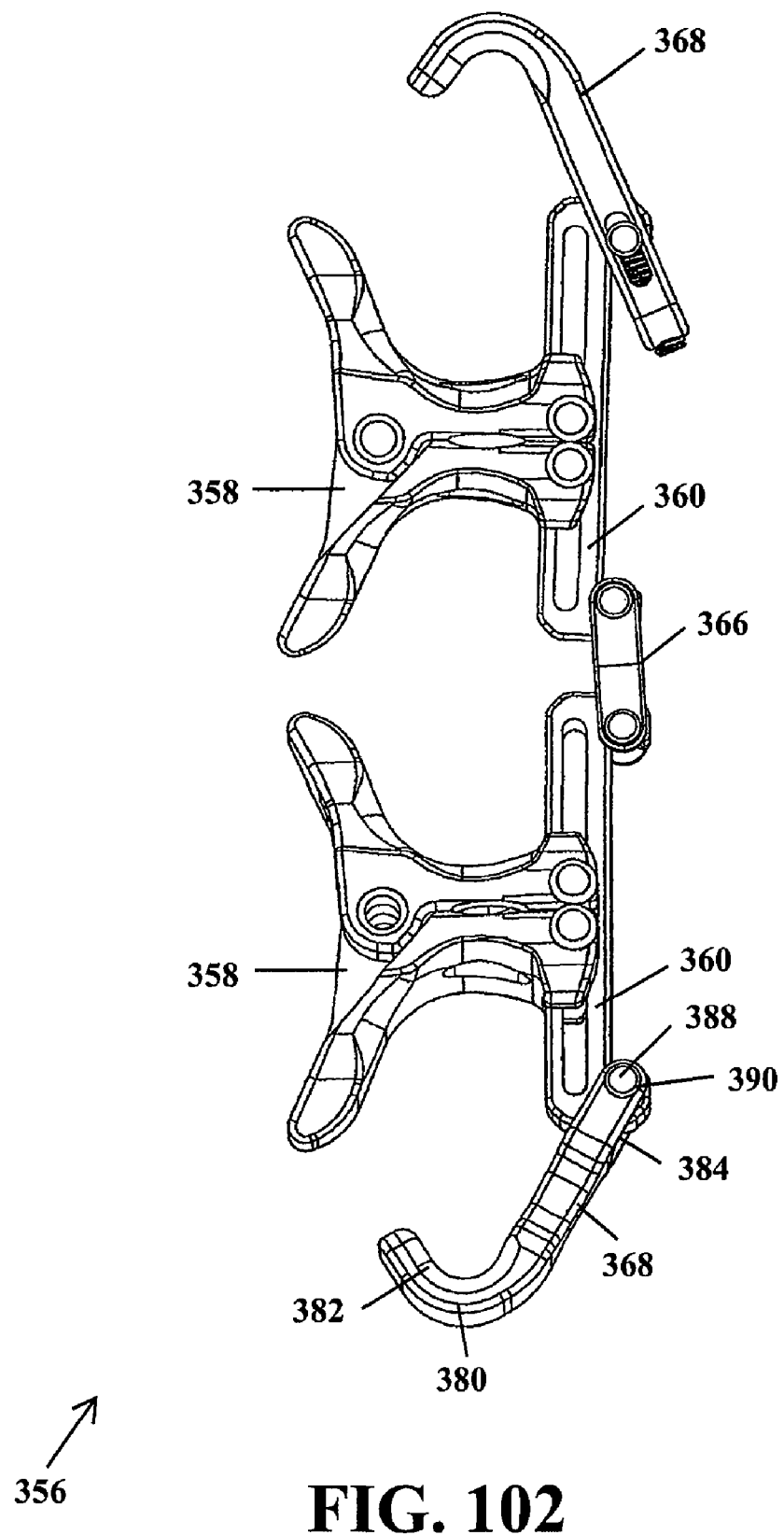
FIG. 102 is a front elevational view of the implant of FIG. 98.
Figure 103:
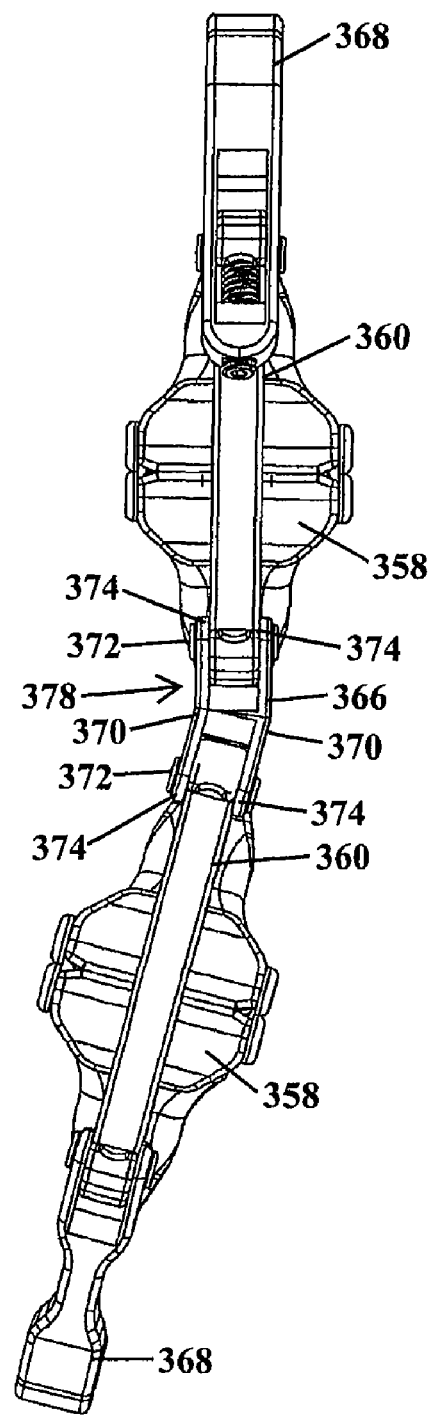
FIG. 103 is a right side elevational view of the implant of FIG. 98 showing the offset configuration of the linkage.
Figure 104:
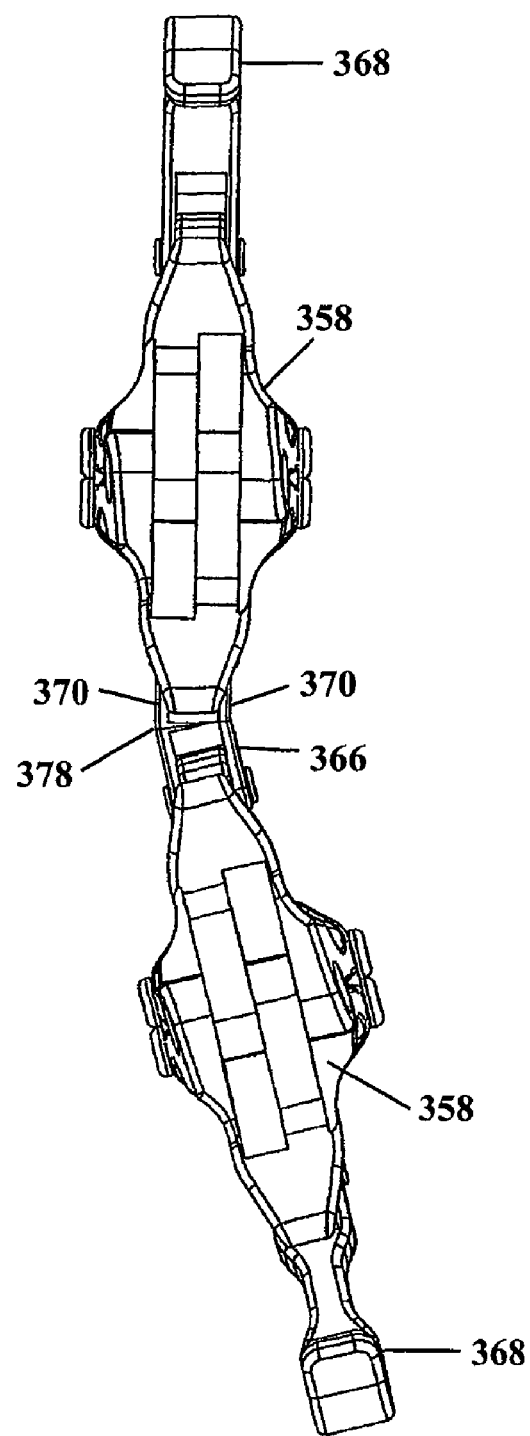
FIG. 104 is a left side elevational view of the implant of FIG. 98.
Figure 105:
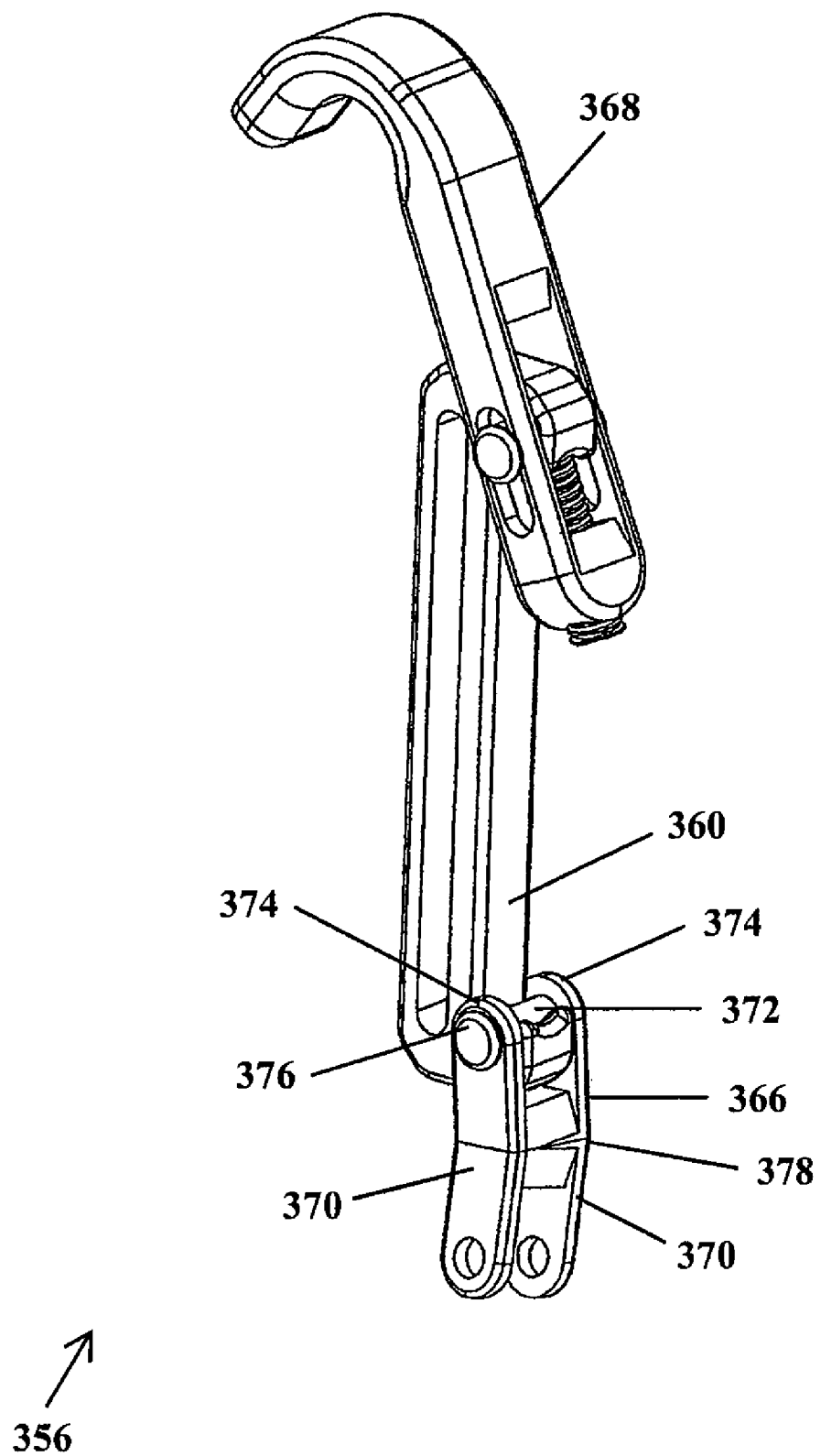
FIG. 105 is a perspective of one of the spanning members, one of the connecting members and the linkage of the implant of FIG. 98.
Figure 106:
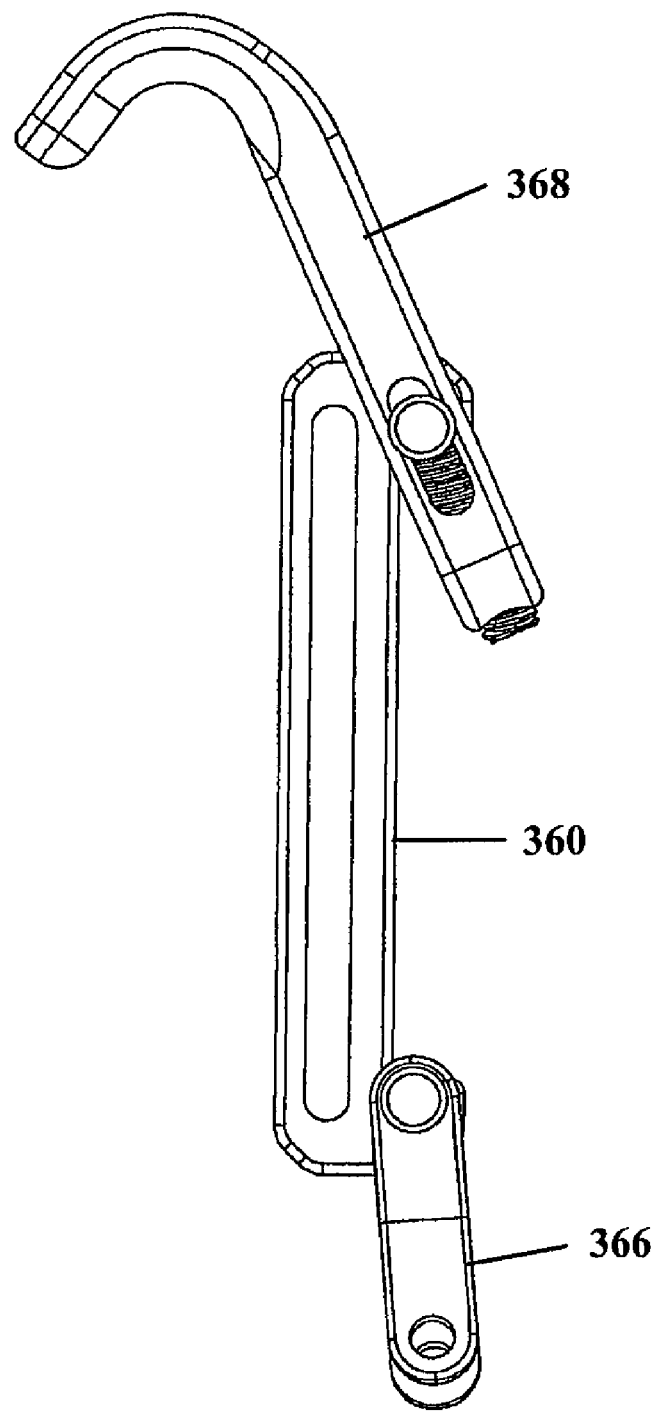
FIG. 106 is a front elevational view of one of the spanning members, one of the connecting members and the linkage of the implant of FIG. 98.
Figure 107:
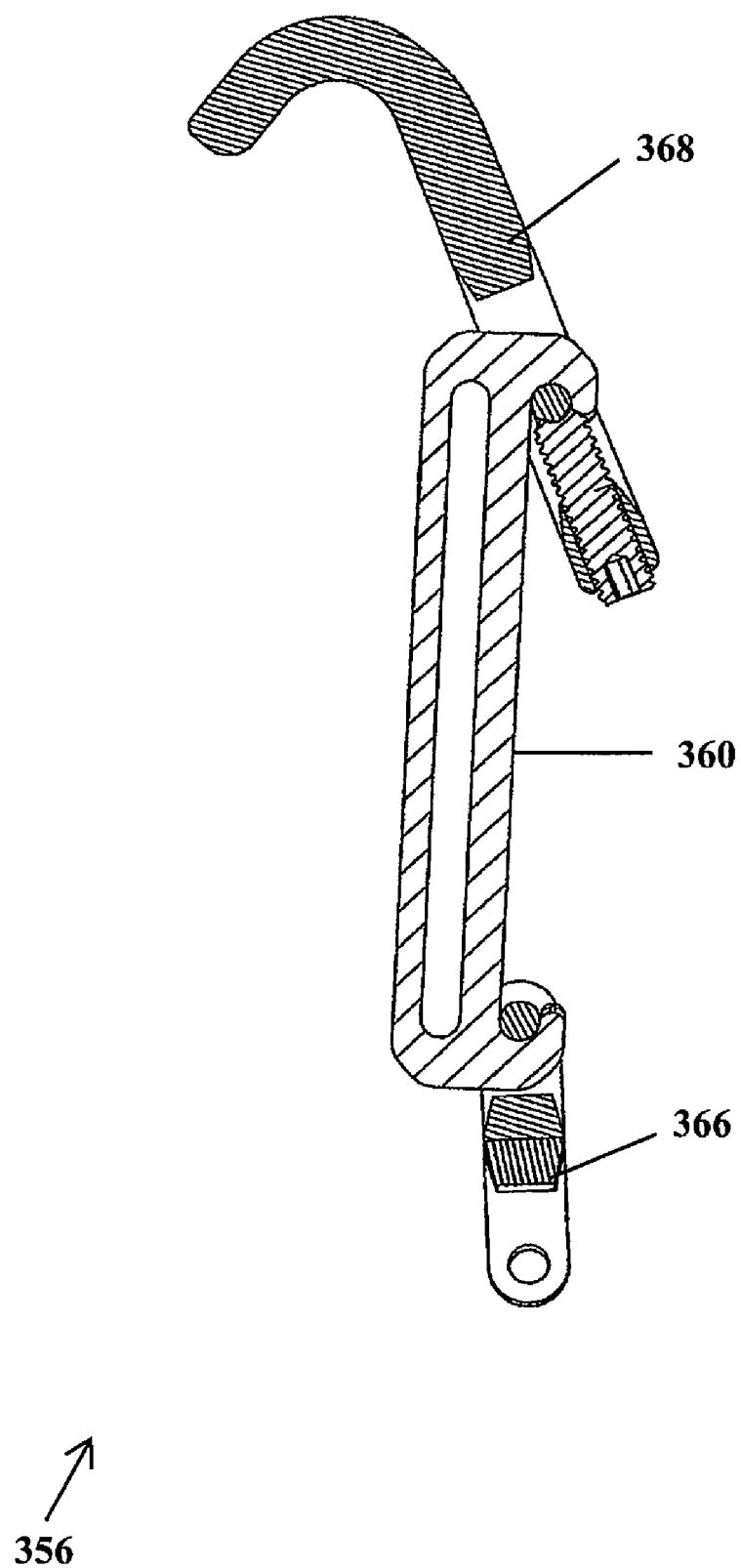
FIG. 107 is a front sectional view of one of the spanning members, one of the connecting members and the linkage of the implant of FIG. 98.
Figure 108:
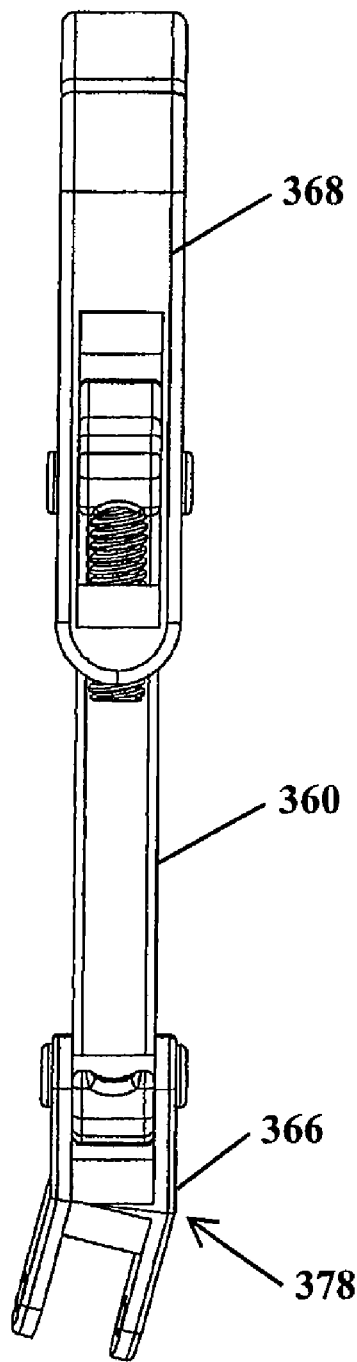
FIG. 108 is a right side view of one of the spanning members, one of the connecting members and the linkage of the implant of FIG. 98.
Figure 109:
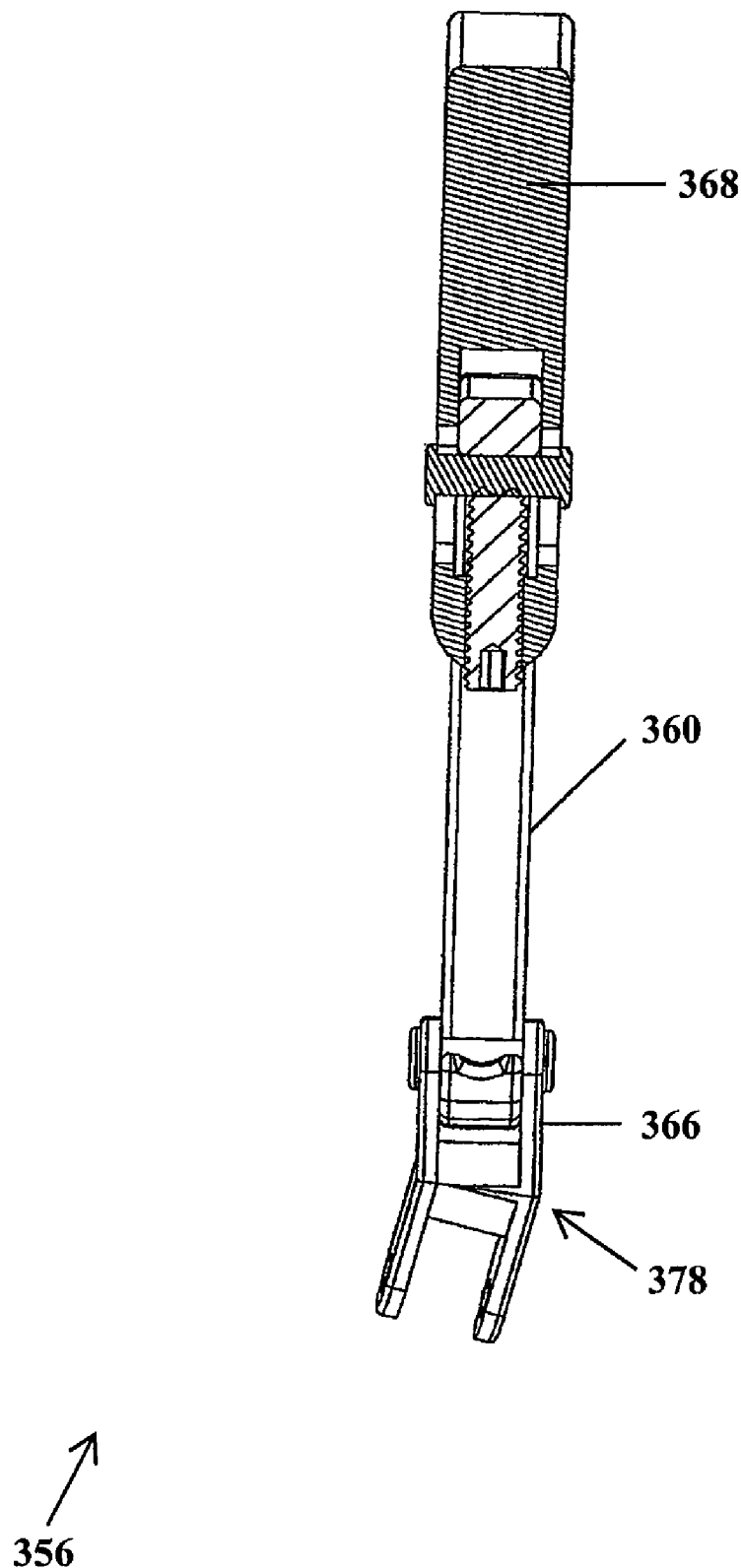
FIG. 109 is a right side sectional view of one of the spanning members, one of the connecting members and the linkage of the implant of FIG. 98.
Figure 110:
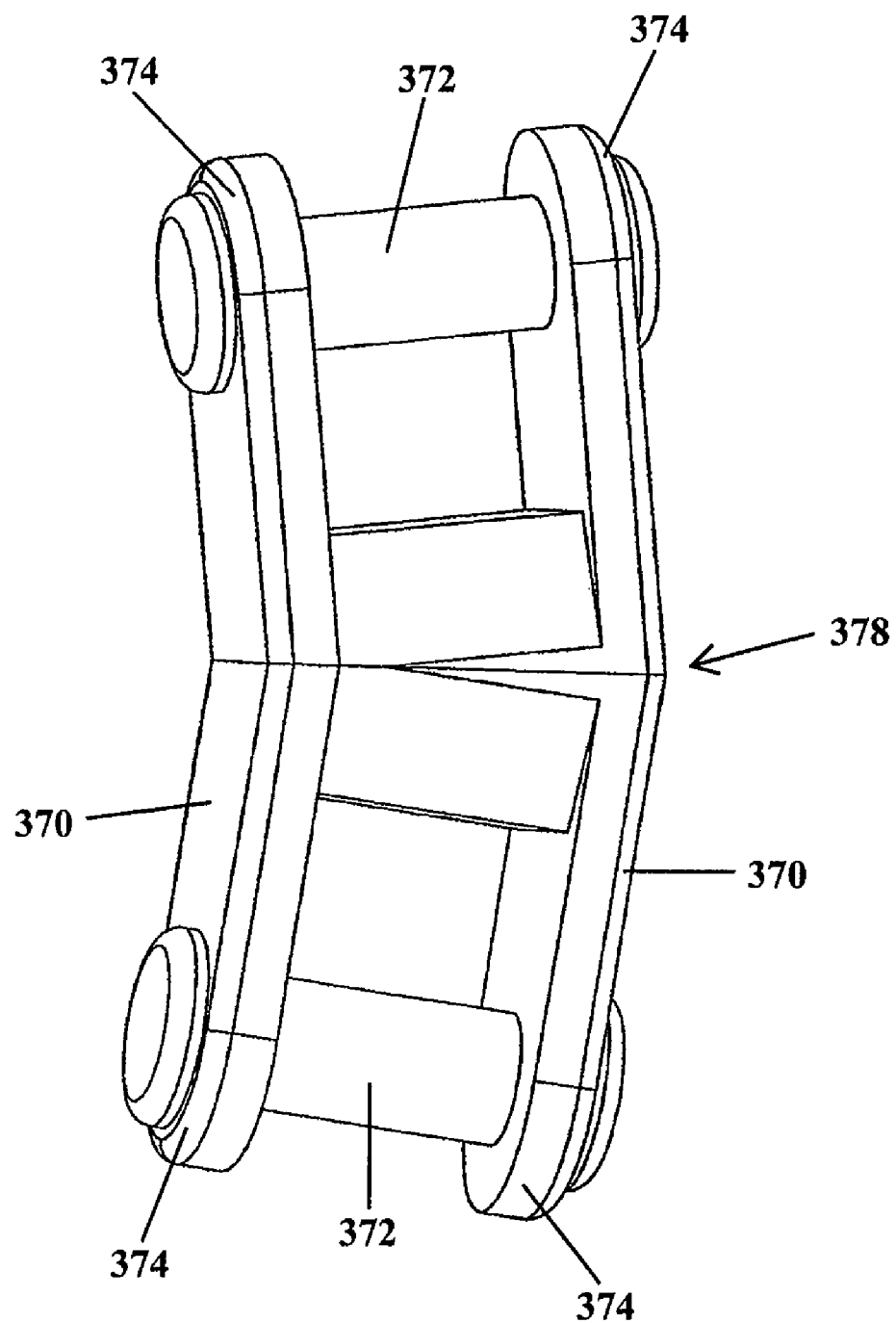
FIG. 110 is a perspective view of the linkage of the implant of FIG. 98.
Figure 111:
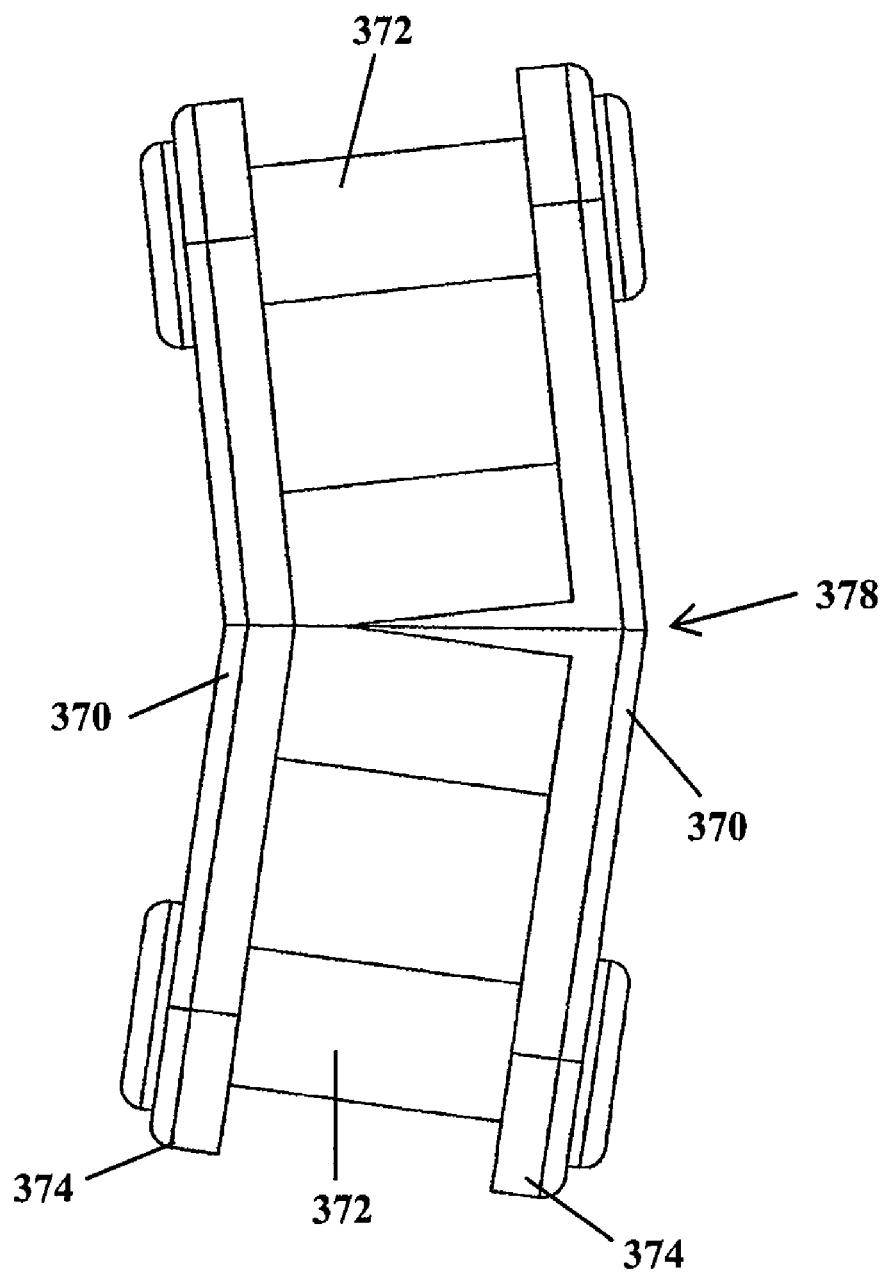
FIG. 111 is a front elevational view of the linkage of the implant of FIG. 98.
Figure 112:
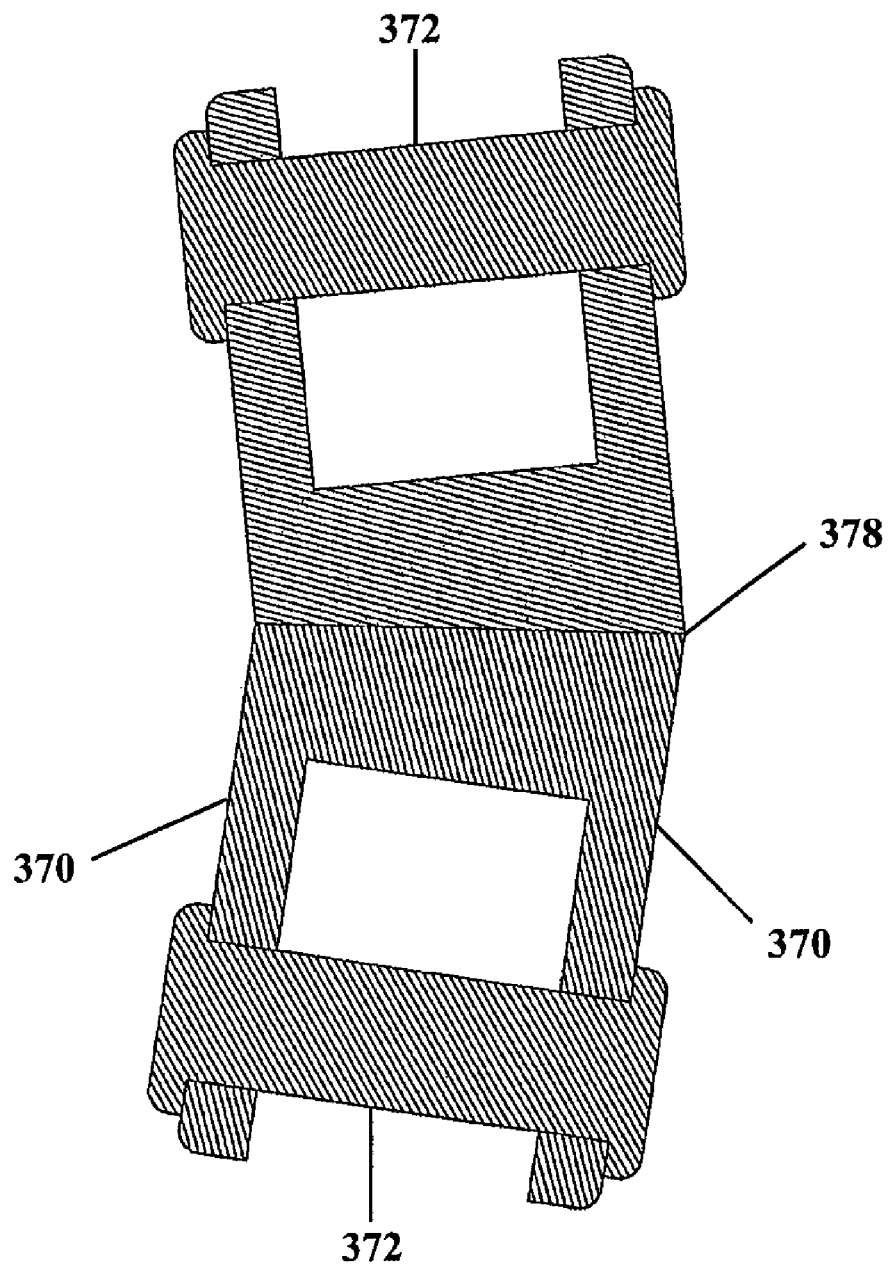
FIG. 112 is a front sectional view of the linkage of the implant of FIG. 98.

The implant device 356 can include any type of known hook 368. As shown in FIGS. 100-102, the implant device includes two different hooks. A fixed hook 380 includes spinous process engaging portion 382 and a body portion 384. The body portion 384 includes a pair of spaced arms 386 and a pin 388 extending therebetween. The pin 388 and spaced arms 386 are configured to engage a spanning member flange 362 and create a pivot connection 390 therebetween.

A variable hook 392, as shown in FIGS. 100-102, provides for a variable connection location, allowing a surgeon to vary the length of the hook 392 extending from the spanning member 360 based on spinal geometries. The hook 392 includes a spinous process engaging portion 394 and a hook body 396. The hook body 396 includes a pair of spaced arms 398 for receiving the spanning member flange 362. The spaced arms 398 are connected at their distal ends 400 by an arm connection portion 402. A slot 404 is formed along either arm 398 for a pin 406 to extend through, the pin 406 engagable by the spanning flange 362 and shiftable along the slot 404.

As shown in FIGS. 100-101, the pin 406 is secured in place by a set screw 408 extending through an aperture 410 in the arm connection portion 402 which engages the pin 406. As the variable hook 392 is implanted on the superior edge 92 of the vertebral body 6, gravity maintains the location of the pivot pin 406 against the set screw 408.

As shown, the interspinous implant member 358 and the spanning member 360 of the implant device 356 can be inserted using a unilateral posterior approach.

Figure 113:
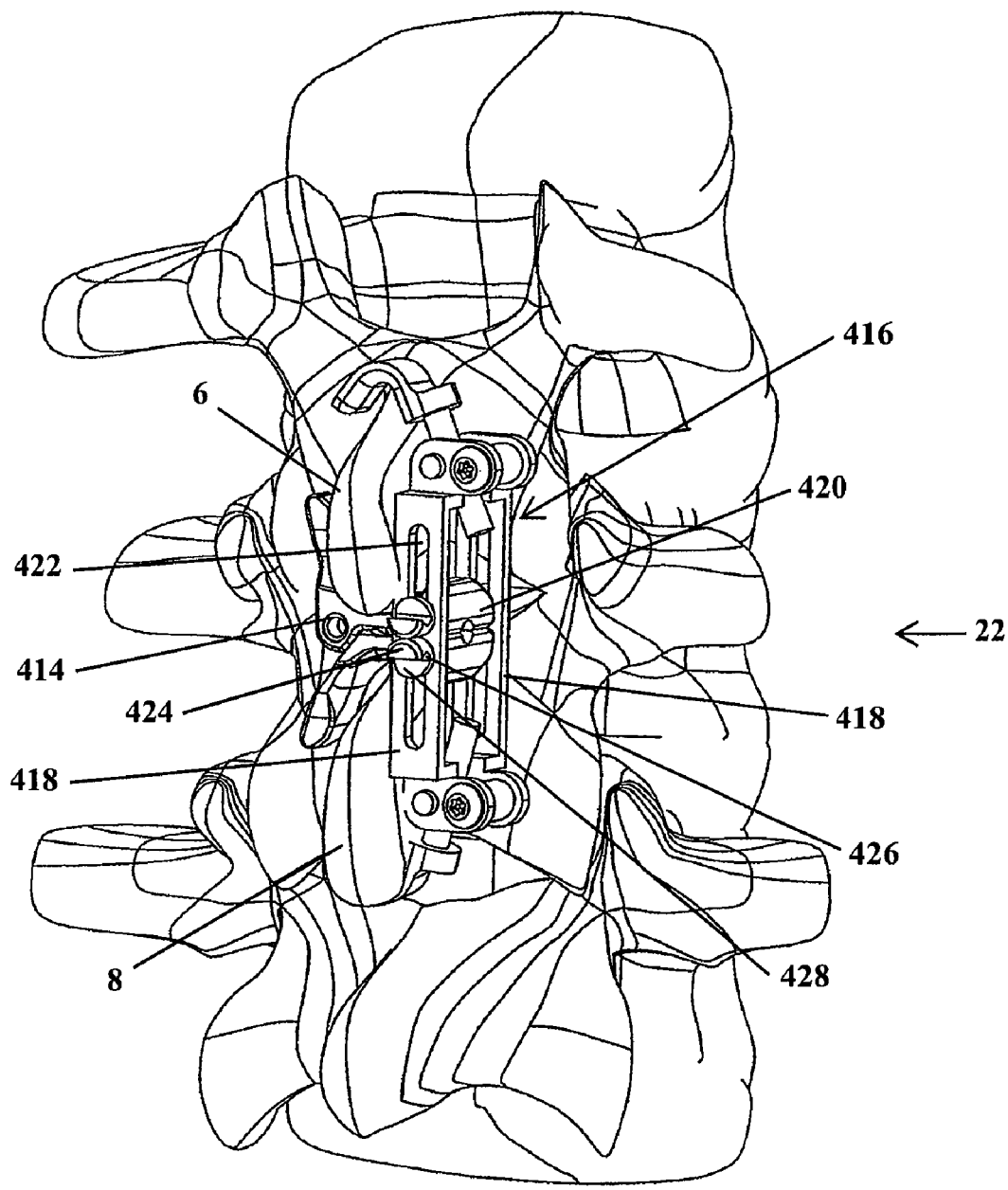
FIG. 113 is a posterior aspect prospective view of an implant in accordance with another aspect of the invention showing the interspinous member, the spanning member connected to the interspinous member, and hook connecting members extending from either end of the spanning member and engaging the spinous processes.

An implant 412 in accordance with another aspect of the invention is shown in FIGS. 113-122. As shown in FIG. 113, the implant device 412 includes an interspinous spacer 414 configured to be positioned between adjacent vertebrae 6 and 8. While other interspinous spacers can be utilized, the interspinous spacer 414 as shown in FIGS. 113-122 is similar to the interspinous spacers described above, with any differences discussed below.

Figure 114:
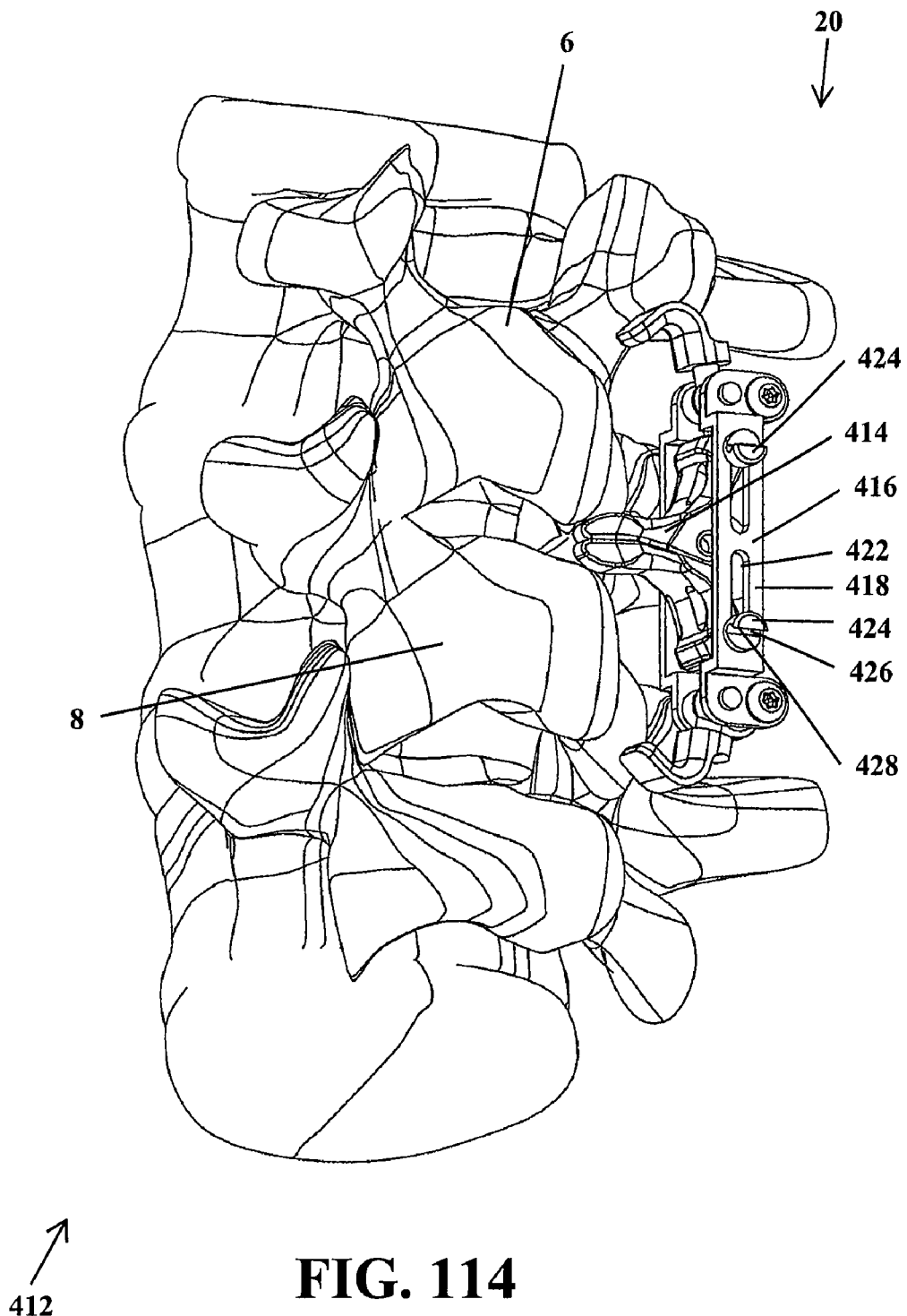
FIG. 114 is a posterior aspect prospective view of the implant of FIG. 113 showing the interspinous insertion member in the insertion orientation.
Figure 115:
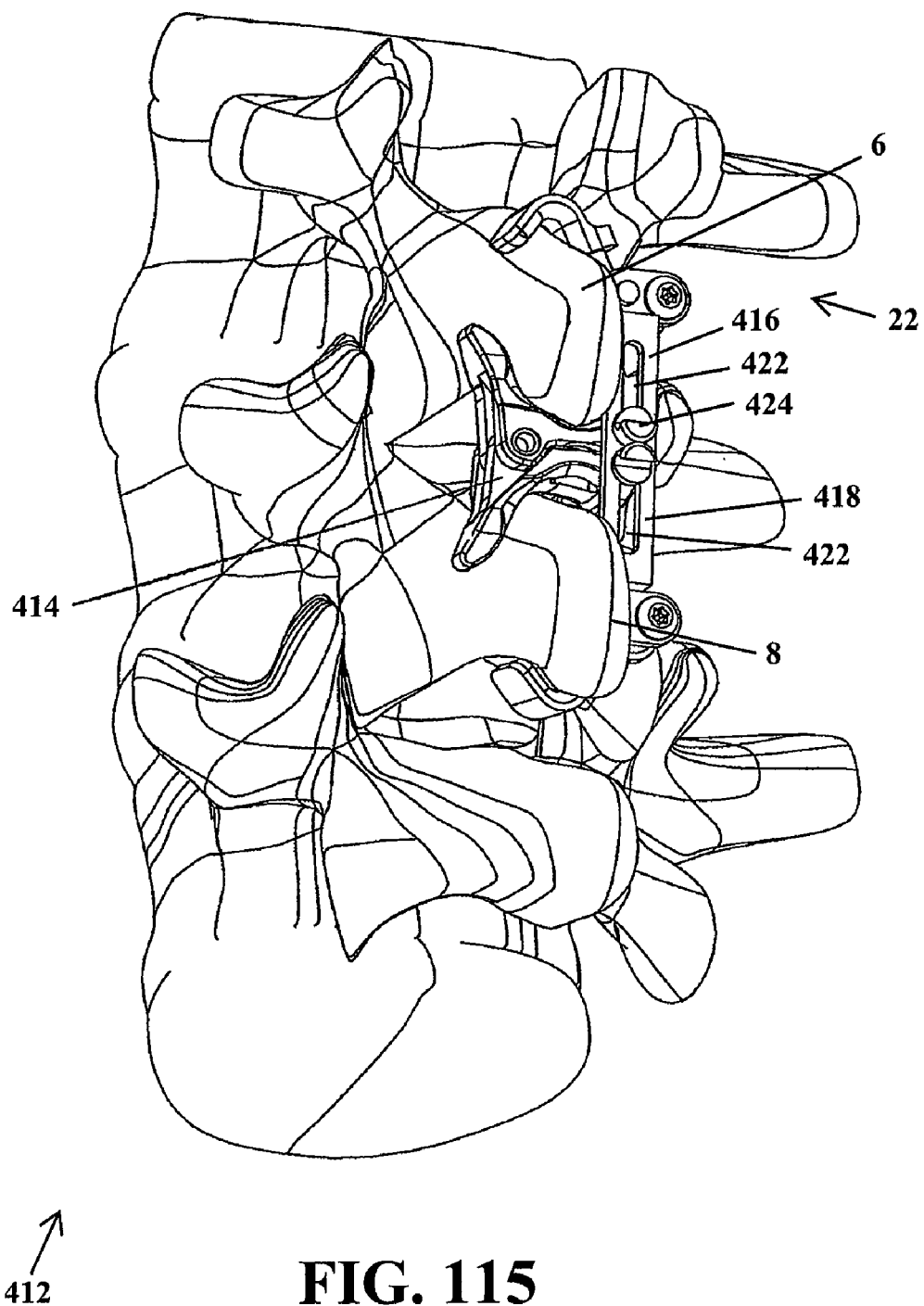
FIG. 115 is a posterior aspect prospective view of the implant of FIG. 113 showing the interspinous insertion member in the implanted orientation.
Figure 116:
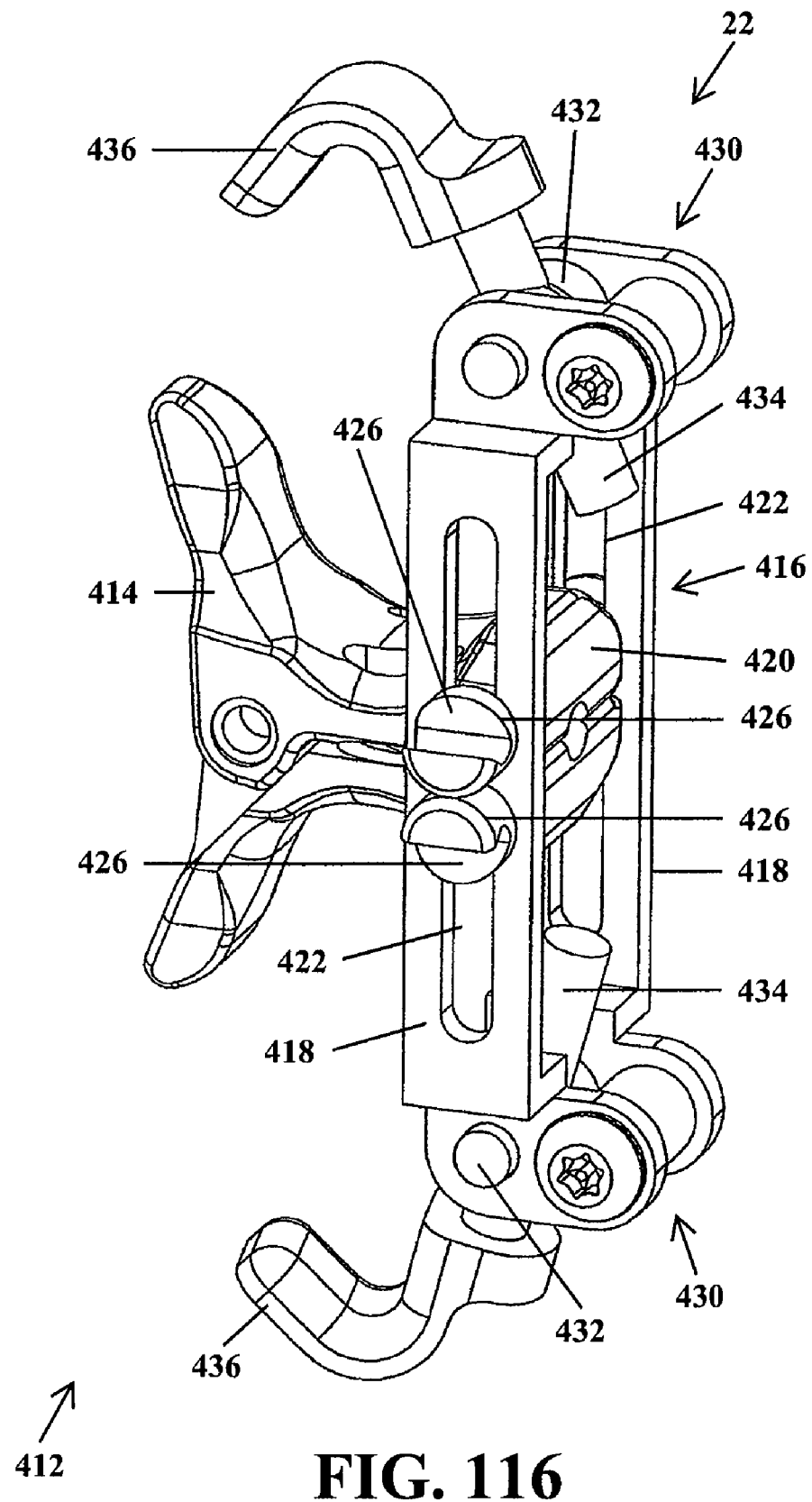
FIG. 116 is a perspective view of the implant of FIG. 113.
Figure 117:
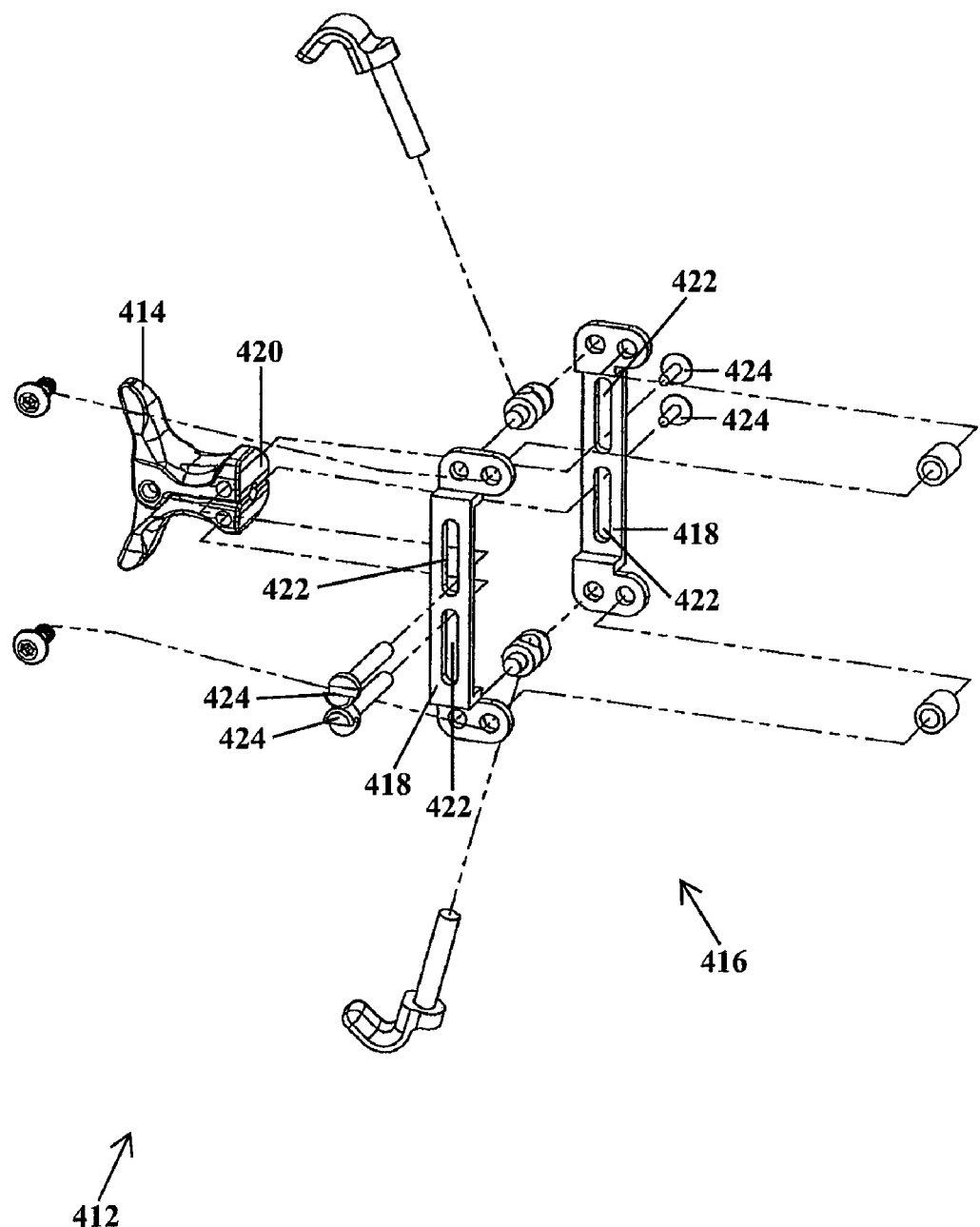
FIG. 117 is an exploded view of the implant of FIG. 113.
Figure 118:
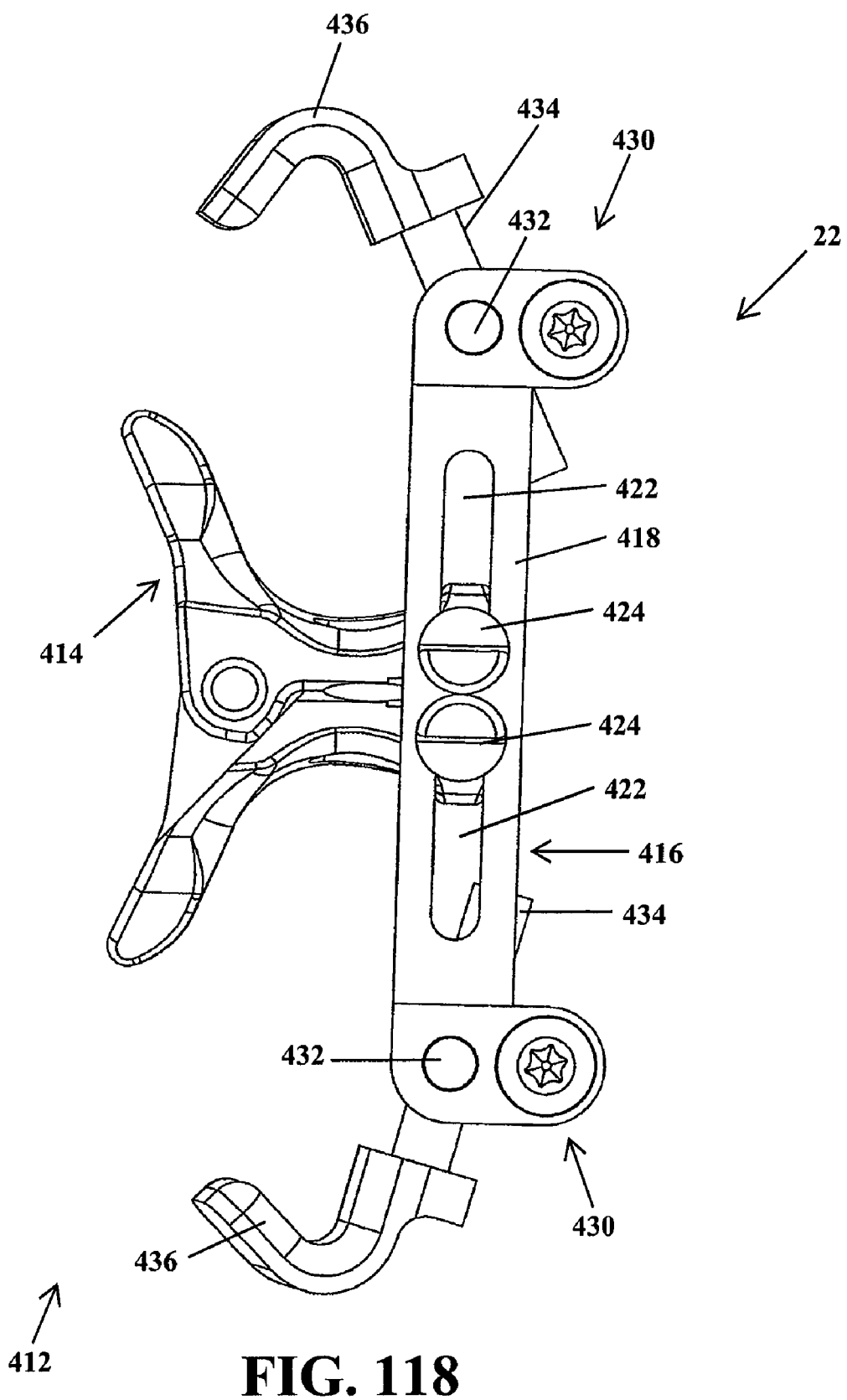
FIG. 118 is a front elevational view of the implant of FIG. 113.
Figure 119:
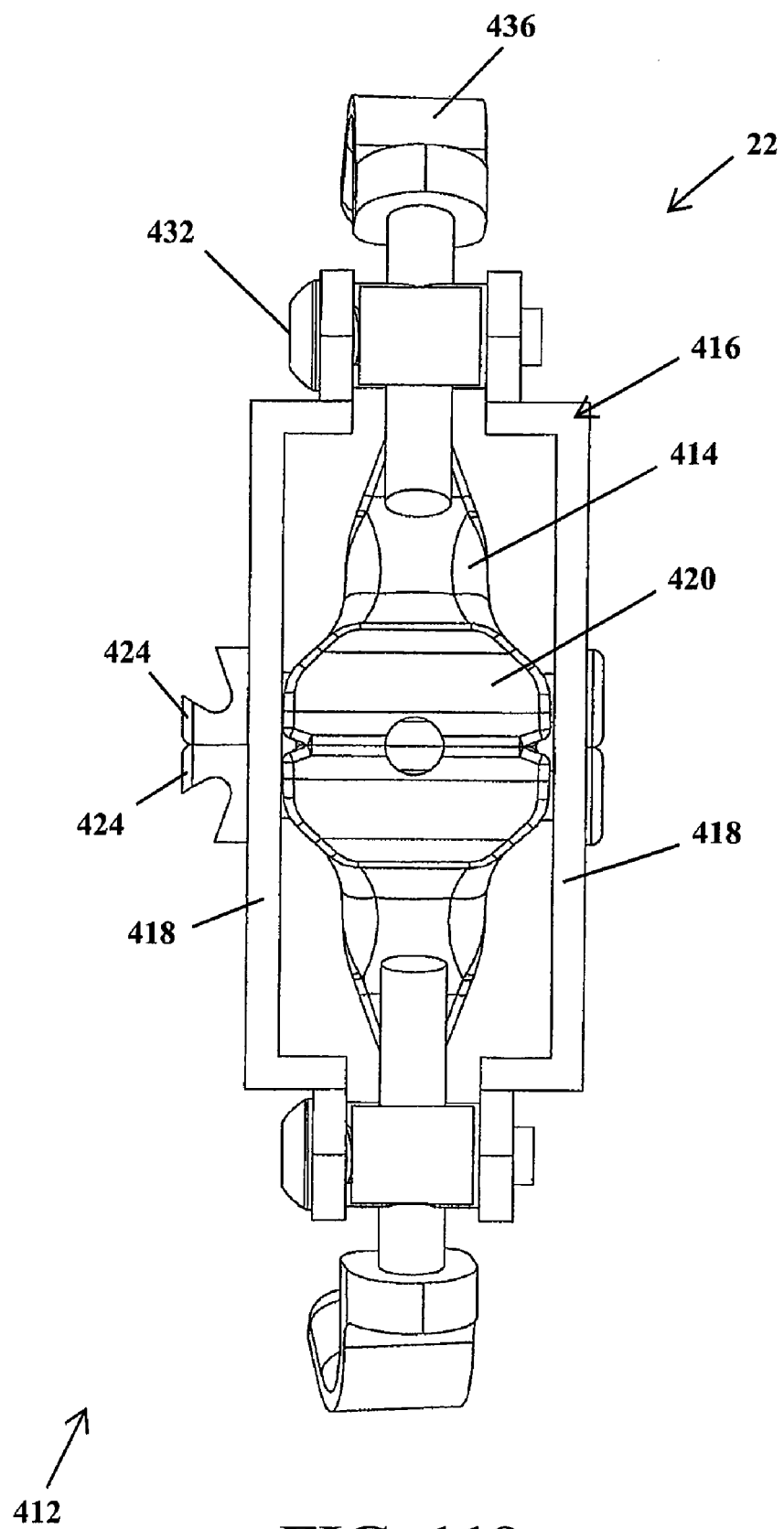
Figure 120:
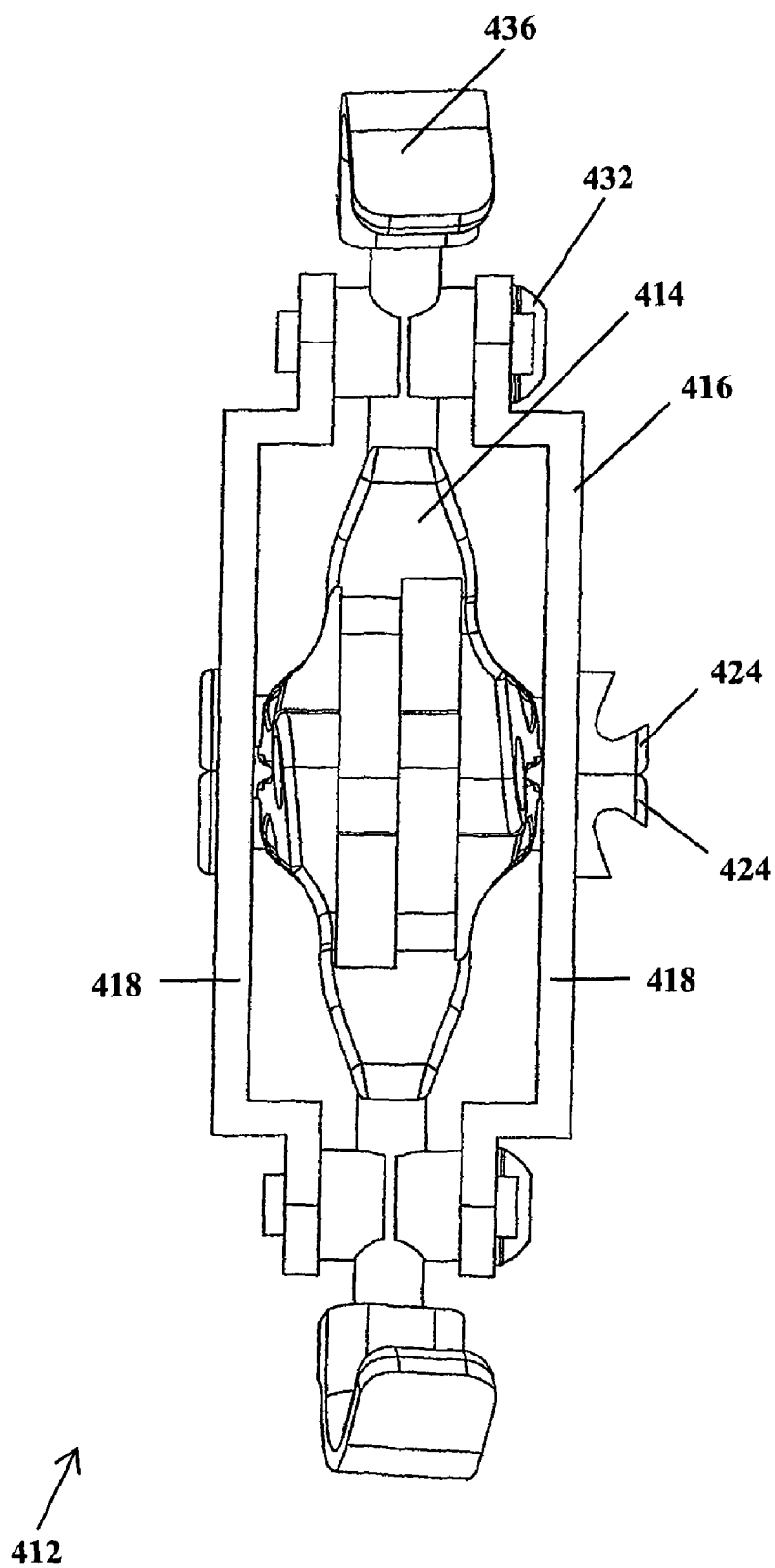
Figure 121:
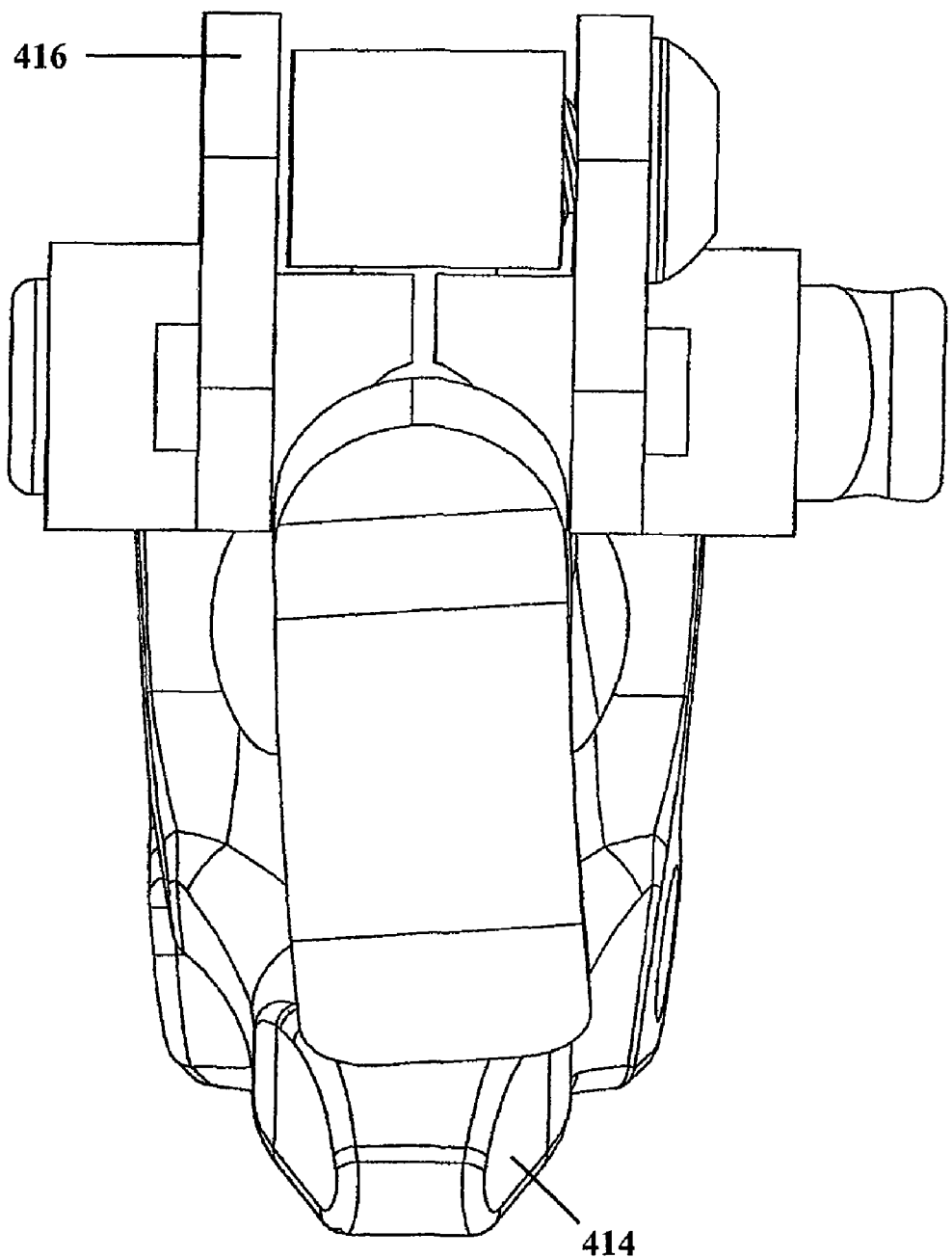
Figure 122:
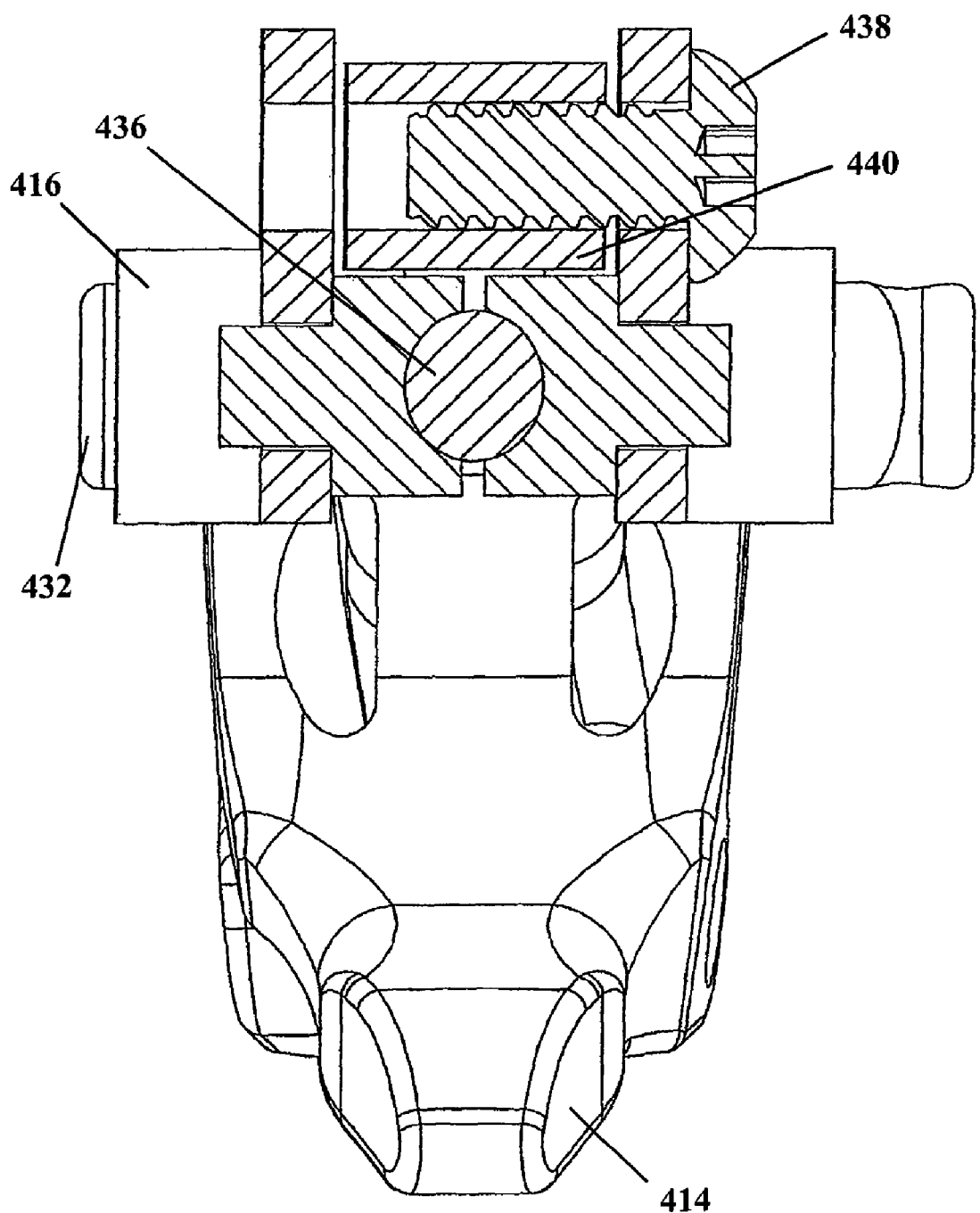

As shown in FIGS. 113-118, the implant device 412 includes a single assembly such that all the components are connected to one another and installed as one unit. The implant device 412 includes an interspinous spacer 414 for being positioned between adjacent spinous processes 6 and 8. A spanning member 416 includes a pair of sidewalls 418 spaced to receive an end 420 of the interspinous spacer 414 therebetween. The sidewalls 418 each include a slot 422 configured to receive spacer end bosses 424 extending from the ends of the spacer 414. The spacer end bosses 424 are configured to shift along the sidewalls slots 422 as the interspinous spacer 414 is shifted between an insertion orientation 20 and implanted orientation 22. As shown in FIGS. 113-114, the spacer bosses 424 include cut-out portions 426 which provide a tool engagement surface 428 for installing the device 412 and shifting the interspinous spacer 414 from the insertion orientation 20 to the implanted orientation 22.

The spanning member 416 further includes a flange 420 extending from either end thereof. The flange 430 provides a pivot connection 432 with a rod portion 434 of a hook member 436. Adjacent the pivot connection 432 is a screw 438 which, when tightened, causes the screw sheath 440 to expand into a frictional engagement with the pivot connection 432, thereby securing the hook member 436 in a given orientation. The hooks 436 are configured to engage the adjacent spinous processes 6 and 8 and urge them toward the implant member 414. This force further acts to maintain the engagement of the spinous processes 6 and 8 and the spacer implant member 414 thereby securing or locking the spacer implant member 414 in the implanted orientation 22

As shown, the interspinous implant member 414 and the spanning member 416 of the implant device 412 can be inserted using a unilateral posterior approach.

Unlike the other embodiments, the implant device 412 can be implanted in two different manners. The first option includes deploying the interspinous spacer 414 from the compact orientation 20 to the implanted orientation 22 and then tensioning and setting the hooks 436 in place. The second option includes tensioning and setting the hooks 436 in place and then deploying the interspinous spacer 414 from the insertion orientation 20 to the implanted orientation 22.

As discussed above, the interspinous implant members 4, 138, 202, 246, 290, 322, 358 and 414 can include seat cavity openings which, when the interspinous implant member is in the implanted orientation 22, extend between the adjacent spinous processes 6 and 8. More particularly, the cavity openings of the upper and lower members are configured to be aligned with one another with the implant members in the implanted orientation. These openings or bores can be filled with bone void filler. Fusion of the adjacent spinous processes 6 and 8 can be facilitated by filing the openings or bores of the seat by with allograft or autograft material, such as demineralized bone matrix (hereinafter DBM). The actual materials used in demineralized bone matrix (hereinafter DBM) is based on the surgeon's preference, but is typically a paste formed from the patient's blood and demineralized bone powder. DBM itself is a soft powder and has no structural properties. Bone void fillers instigate bone growth or bone fusion between the spinous processes in which the implant member 1101 is inserted.

The implant members 4, 138, 202, 246, 290, 322, 358 and 414 can be made from any suitable, structurally strong material. The structural portions and other components are constructed of suitable materials which are compatible with the uses and environments into which the apparatus will be utilized. Preferably, the implant member 4, 138, 202, 246, 290, 322, 358 and 414 is principally constructed of PEEK with the locking mechanisms constructed of metallic materials such as 17-4 stainless steel, or titanium. PEEK also includes any polymer of the poly-aryl-ether-ketone family such as, but not limited to, poly-ether-ketone (PEK) and poly-ether-ketone-ether-ketone-ketone (PEKEKK). Alternatively, the implant member 4, 138, 202, 246, 290, 322, 358 and 414 can be made of a composite of PEEK and metallic materials such as titanium.

The implant members 4, 138, 202, 246, 290, 322, 358 and 414 are made using standard lathes and milling machines. Alternatively, other standard manufacturing processes such as casting can be used. The insertion tool 40 is also preferably made of metallic materials such as 17-4 stainless steel and made using standard lathes and milling machines.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. An implant apparatus comprising:
    an upper implant member having a seat portion configuration for engaging an upper vertebral bone portion;
    a lower implant member having a seat portion configured for engaging a lower vertebral bone portion;
    a pivot connection between the upper and lower implant members to allow the implant members to be pivoted from an insertion orientation to an implanted orientation so that in the implanted orientation the seat portions are pivoted to face in generally opposite, upward and downward directions for secure engagement with the respective upper and lower vertebral bone portions; and
    a locking mechanism operable to keep the upper and lower implant members in the implanted orientation thereof, the locking mechanism and the upper and lower implant members having a connection mechanism therebetween, the connection mechanism including a pivot connection between a linkage of the locking mechanism with one of the upper and lower implant members and a releasable connection between the linkage and the other implant member.

2. The implant apparatus of claim 1 wherein the implant members are configured so that in the insertion orientation the seat portions generally face in the same direction transverse to the upward and downward directions.

3. The implant of claim 1 wherein the implant members each pivot at least approximately 40 degrees between the insertion and implanted orientations.

4. The implant apparatus of claim 1 wherein the locking mechanism includes a flexible member extending about the vertebral bone portions and connected to the upper and lower implant members.

5. The implant apparatus of claim 4 wherein the flexible member is a cable.

6. The implant apparatus of claim 1 wherein the upper and lower implant members each include a cavity opening to the corresponding seat portion so that the cavities are aligned with the implant members pivoted to the implanted orientation to receive bone void filler therein and promote bone growth therethrough.

7. An implant apparatus comprising:
    an upper implant member having a seat portion configuration for engaging an upper vertebral bone portion;
    a lower implant member having a seat portion configured for engaging a lower vertebral bone portion;
    a pivot connection between the upper and lower implant members to allow the implant members to be pivoted from an insertion orientation to an implanted orientation so that in the implanted orientation the seat portions are pivoted to face in generally opposite, upward and downward directions for secure engagement with the respective upper and lower vertebral bone portions; and
    a locking mechanism operable to keep the upper and lower implant members in the implanted orientation thereof, the locking mechanism including a linkage operable to interconnect and keep the upper and lower implant members in the implanted orientation thereof against pivoting back to the implanted orientation, wherein the linkage has a pivot connection to one of the upper and lower implant members at one end thereof, the other of the implant members has an engagement portion, and the linkage has a projection at its other end that is pivoted about the linkage pivot connection into secure engagement with the engagement portion with the implant members in the implanted orientation.

8. An implant apparatus comprising:
    an upper implant member having a seat portion configuration for engaging an upper vertebral bone portion;
    a lower implant member having a seat portion configured for engaging a lower vertebral bone portion;
    a pivot connection between the upper and lower implant members to allow the implant members to be pivoted from an insertion orientation to an implanted orientation so that in the implanted orientation the seat portions are pivoted to face in generally opposite, upward and downward directions for secure engagement with the respective upper and lower vertebral bone portions; and
    a locking mechanism operable to keep the upper and lower implant members in the implanted orientation thereof, the locking mechanism and the upper and lower implant members having a connection mechanism therebetween, the locking mechanism includes a pair of hooks configured to engage the upper and lower bone portions and connected to a rod device extending along the spinous processes;
    a collar member of the connection mechanism for being disposed about the rod device; and
    a projection of the collar member extending toward the implant members and having a secured connection therewith.

9. An implant device comprising:
a vertebral spacer device for being inserted between adjacent vertebrae;
a pivot connection of the vertebral spacer device for shifting portions of the vertebral spacer device between an insertion orientation and an implanted orientation;
an elongate tensioning member secured to the vertebral spacer device and sized to extend about bone portions of the adjacent vertebrae and tensioned to keep the vertebral spacer device portions in the implanted orientation thereof,
wherein the vertebral spacer device includes a rigid guide member for securing the elongate tensioning member thereto, and the rigid guide member and upper and lower implant members have a slide connection therebetween.

10. The implant device of claim 9 wherein the vertebral spacer device further includes a linkage cooperating with the tensioning member to secure the vertebral spacer device in the implanted orientation.

11. The implant device of claim 9 wherein the vertebral spacer device includes crimps for receiving and securing the elongate tensioning member therein.

12. The implant device of claim 9 wherein the elongate tensioning member comprises a cable extending about the adjacent vertebrae.

13. An implant device comprising:
an upper implant member and lower implant member for being positioned between adjacent spinous processes;
a pivot connection between the upper and lower members for pivoting the members between an insertion orientation and an implanted orientation;
a tool engagement extension portion connected to one of the upper and lower members configured for being engaged by an insertion tool;
a tool engagement end portion of the other of the upper and lower members configured for being engaged by the insertion tool; and
a pivot pin pivotably connecting the one member and the tool engagement extension portion such that the tool engagement extension portion is pivotable about the pin to be received by the tool engagement end portion with the members pivoted to the implanted orientation to keep the members from pivoting back toward the insertion orientation thereof,
wherein the tool engagement extension portion includes a pair of bosses for being engaged by the insertion tool and the tool engagement end portion includes corresponding slots to receive the bosses therein.

14. The implant device of claim 13 including a flexible elongate tensioning member sized for extending about the spinous processes, and the tool engagement extension portion has an attachment member configured to be connected to the elongate tensioning member to maintain secure contact between the spinous processes and the implant members pivoted to the implanted orientation.

15. The implant device of claim 14 wherein the attachment member comprises a crimp member having a throughbore through which the cable is advanced to tension the cable about the spinous processes with the crimp member being deformable to maintain the tension on the cable.

16. A method of securing adjacent spinous processes including:
pivoting an implant device about an implant device pivot connection to a insertion orientation;
inserting the implant device between adjacent spinous processes;
pivoting the implant device about the pivot connection to an implanted orientation; and
securing the implant device in the implanted orientation after the implant device has been pivoted to the implanted orientation, wherein securing the implant device includes providing a plate member having a cut-out opening formed therein; and
shifting the plate member so that the implant device is received in the plate member cut-out opening.

* * * * *